(12) United States Patent
Dhugga

(10) Patent No.: US 7,462,759 B2
(45) Date of Patent: Dec. 9, 2008

(54) BRITTLE STALK 2 GENE FAMILY AND RELATED METHODS AND USES

(75) Inventor: Kanwarpal Singh Dhugga, Johnston, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 30 days.

(21) Appl. No.: 11/347,780

(22) Filed: Feb. 3, 2006

(65) Prior Publication Data

US 2007/0186310 A1 Aug. 9, 2007

(51) Int. Cl.
*A01H 1/00* (2006.01)
*C07H 21/04* (2006.01)
*C07K 14/415* (2006.01)
*C12N 15/29* (2006.01)

(52) U.S. Cl. .................. 800/295; 435/6; 435/69.1; 435/468; 435/419; 530/370; 536/23.6; 800/278

(58) Field of Classification Search .......... 435/6, 435/69.1, 468, 419, 252.3, 320.1; 530/370; 536/23.6; 800/278, 295

See application file for complete search history.

(56) References Cited

U.S. PATENT DOCUMENTS 6,803,498 B2 10/2004 Dhugga et al.
6,930,225 B2 8/2005 Dhugga et al.

FOREIGN PATENT DOCUMENTS

WO 02/070723 A 9/2002

OTHER PUBLICATIONS

UniProt 12.1 database, Accession No. A2XFQ1, Yu et al., PLoS Biol., 3:E:38-E38, 2005, result 2.*
Database Uniprot, Nov. 23, 2004, Roothairless 3., XP002386156, EBI Accession No. Uniprot: Q5YLM2 & Wen Tsui-Jung et al., Analyses of Mutants of Three Genes That Influence Root Hair Development In Zea Mays (Gramineae) Suggest that Root Hairs are Dispensable, American Journal of Botany vol. 81(7):833-842, 1994.
Dilbag S Multani et al., Loss of an MDR Transporter in Compact Stalks of Maize BR2 and Sorghum DW3 Mutants, Science, vol. 302(5642):81-84, 2003.
Kanwarpal S. Dhugga, Plant Golgi Cell Wall Synthesis: From Genes to Enzyme Activities, Proceedings of the National Academy of Sciences, vol. 102(6):1815-1816, 2005.
Database Uniprot, Mar. 1, 2003, Cell Wall Protein-Like, XP002386157, EBI Accession No. Uniprot:Q8H3Y9.
Akira Kokubo et al., Culm Brittleness of Barley (Hordeum Vulgare L.) Mutants is Caused by Smaller Number of Cellulose Molecules in Cell Wall, Plant Physiol., vol. 97:509-514, 1991.
Qian Qian et al., Isolation and Genetic Characterization of a Fragile Plant Mutant in Rice (Oryza Sativa L.), Chinese Science Bulletin, vol. 46(24):2082-2085, 2001.
Yunhai Li et al., Brittle CULM1, Which Encodes a Cobra-Like Protein, Affects the Mechanical Properties of Rice Plants, the Plant Cell, vol. 15:2020-2031, 2003.
D. G. Lamgham, Estacion Experimental, MNL, vol. 14:21-22, 1940.
Neil G. Taylor et al., Interactions Among Three Distinct CESA Proteins Essential for Cellulose Synthesis, PNAS, vol. 100(3):1450-1455, 2003.
National Center for Biotechnology Information General Identifier No. 34733385, Accession No. AAQ81633, Oct. 5, 2004, T.-J. Wen et al., Analyses of Mutants of Three Genes That Influence Root Hair Development in Zea Mays (Graminese) Suggest that Root Hairs are Dispensable.
National Center for Biotechnology Information General Identifier No. 30090026, Accession No. AA017706, May 5, 2003, L. Yan et al., Positional Cloning of Wheat Vernalization Gene VRN1.
National Center for Biotechnology Information General Identifier No. 52076665, Accession No. BAD45565, Sep. 15, 2004, T. Sasaki et al., Oryza Sativa Nipponbare (GA2) Genomic DNA, Chromosome 6, PAC Clone:P0009H10.
National Center for Biotechnology Information General Identifier No. 50939113, Accession No. XP_479084, Nov. 9, 2004.
National Center for Biotechnology Information General Identifier No. 34898176, Accession No. NP_910434, Nov. 9, 2004.
National Center for Biotechnology Information General Identifier No. 50927043, Accession No. XP_473354, Nov. 9, 2004.
Neta Holland et al., A Comparative Analysis of the Plant Cellulose Synthase (CESA) Gene Family, Plant Physiology, vol. 123:1313-1323, 2000.
Kanwarpal S. Dhugga, Building the Wall: Genes and Enzyme Complexes for Polysaccharide Synthases, Current Opinion in Plant Biology, vol. 4:488-493, 2001.
Laura Appenzeller et al., Cellulose Synthesis in Maize: Isolation and Expression Analysis of the Cellulose Synthase (CESA) Gene Family, Cellulose, vol. 11:287-299, 2004.
S. M. Brady et al., Combining Expression and Comparative Evolutionary Analysis. The *Cobra* Gene Family. Plant Physiology, Jan. 2007, vol. 143, pp. 172-187.

* cited by examiner

*Primary Examiner*—Phuong T Bui

(57) ABSTRACT

This invention relates to isolated polynucleotides encoding BRITTLE STALK 2-like (Bk2L) family polypeptides. The invention also relates to the construction of a chimeric gene encoding all or a portion of a Bk2L polypeptide, in sense or antisense orientation, wherein expression of the chimeric gene results in production of altered levels of the Bk2L polypeptide in a transformed host cell.

6 Claims, 13 Drawing Sheets

```
                    +----+----+----+----+----+----+
                    10        20        30        40        50        60
                    +----+----+----+----+----+----+
  1 ---------------------------------------------------------ACCSVA  ZmBk2  (SEQ ID NO2) 450 AA).pro
  1 MTMG----LRVRD-----SSALLALAVAL----------------------------PDPGCNGI ZmBk2L1 (SEQ ID NO4) 667 AA).pro
  1 MAG-SVAP----HAVVLGLLLAGLAAAQRATTPAAAAPA------------------SA-PTA  ZmBk2L3 (SEQ ID NO6) 448 AA).pro
  1 MAAS-------GRSVACCAAALLAAALLL----------------------------SA-PTT  ZmBk2L4 (SEQ ID NO8) 449 AA).pro
  1 MAAG-------GRSIACFAAVLIAAALLL----------------------------SA-PTT  ZmBk2L5 (SEQ ID NO10) 678 AA).pro
  1 MVMAAPVPLRRRALLVVATLLAVVTAAMAQDYKDGGGDDYEEDEKKKPQFKAQEACNGV ZmBk2L6 (SEQ ID NO12) 460 AA).pro
  1 MAPPPL--LPAREVAA-SVALLAVAFSS-----------------------------SL-TRP ZmBk2L7 (SEQ ID NO14) 447 AA).pro
  1 ME------PRR-----SVLLLALAVAA-----------------------------A--LSV ZmBk2L8 (SEQ ID NO16) 654 AA).pro
  1 MAMLPVVV-----RMAAMPFIFLVLLAH------TASAQ------------------PDAGCNGI ZmBk2L9 (SEQ ID NO18) 444 AA).pro
  1 MGR---------------FVFVLL-----IL-------------------------MCCSSS +----+----+----+----+----+----+
                    70        80        90       100       110       120
                    +----+----+----+----+----+----+
 27 --------------------------VVAYDPLDPNGNITIKWDVI------------  ZmBk2  (SEQ ID NO2) 450 AA).pro
 44 QLTYNFVDRTKIRPFVSDKNKQPYAFRANVTVLNSGTRPLKSWAALVTFGYGEILVGVDG ZmBk2L1 (SEQ ID NO4) 667 AA).pro
 28 ----------------------TEAYDSLDPNGNITIKWDIM----------------  ZmBk2L3 (SEQ ID NO6) 448 AA).pro
 28 ----------------------TEAYDSLDPNGNITIKWDIM----------------  ZmBk2L4 (SEQ ID NO8) 449 AA).pro
 61 FLTYTFMERAKEYPHLKKAAAQPYAFKATATVLNTMTEDLKAWQMFVGFQHKEILVSVGG ZmBk2L5 (SEQ ID NO10) 678 AA).pro
 31 --------------------------SGAYDPLDPNGNITIKWDVI------------  ZmBk2L6 (SEQ ID NO12) 460 AA).pro
 21 --------------------------AVAYDPLDPNGNITIKWDIM------------  ZmBk2L7 (SEQ ID NO14) 447 AA).pro
 37 LLTYTLQRRDKIRPHVAAPNSQPYSFSASATVVNAGTRPLRSWALLLTFVHGEILVSVDG ZmBk2L8 (SEQ ID NO16) 654 AA).pro
 18 --------------------------RFTGAYDPIDPNGNITIVWDFQ-----------  ZmBk2L9 (SEQ ID NO18) 444 AA).pro
```

FIG. 1A

```
             130       140       150       160       170       180
        +---------+---------+---------+---------+---------+---------+
 47     ------------------------SWTPDG---Y------------------------VAMVT----  ZmBk2  (SEQ ID NO2)  450 AA).pro
104     AVLTGGGDLPYNTTEDAGNA----TSFSGYPHTDLLTPIATAGDLSQIQASVGIVGTLFA          ZmBk2L1 (SEQ ID NO4)  667 AA).pro
 48     ------------------------QWTPDG---Y------------------------VAVVT----  ZmBk2L3 (SEQ ID NO6)  448 AA).pro
 48     ------------------------QWTPDG---Y------------------------VAVVT----  ZmBk2L4 (SEQ ID NO8)  449 AA).pro
121     AVLLDGSDLPANVSGGAT------FAGYPMADLLNSIETAGEPSLIESKIEITGTQFG            ZmBk2L5 (SEQ ID NO10) 678 AA).pro
 51     ------------------------QWTADG---Y------------------------VAVVS----  ZmBk2L6 (SEQ ID NO12) 460 AA).pro
 41     ------------------------SWTPDG---Y------------------------VAVVT----  ZmBk2L7 (SEQ ID NO14) 447 AA).pro
 97     AVLTSGAAALPYNTTAGDAAGRPTPTSFTGYPQTDLLTPIATAGDPAKTQATVSLVGTLFA          ZmBk2L8 (SEQ ID NO16) 654 AA).pro
 40     ------------------------SLDVAGMTPY------------------------TVMVS----  ZmBk2L9 (SEQ ID NO18) 444 AA).pro 190       200       210       220       230       240
        +---------+---------+---------+---------+---------+---------+
 59     -----GPGPFVPLPTALSLDDP-AYACPAATNVTARV--LSTCCVLTPEAEANATAIDANTTDPT     ZmBk2  (SEQ ID NO2)  450 AA).pro
160     ----------------------------------------------------------------     ZmBk2L1 (SEQ ID NO4)  667 AA).pro
 60     ----------------------------------------------------------------     ZmBk2L3 (SEQ ID NO6)  448 AA).pro
 60     ----------------------------------------------------------------     ZmBk2L4 (SEQ ID NO8)  449 AA).pro
173     VKAPGKPMPKTIKLTNPVGFRCPAPNH---------KDRKFKAKKANST                     ZmBk2L5 (SEQ ID NO10) 678 AA).pro
 63     ----------------------------------------------------------------     ZmBk2L6 (SEQ ID NO12) 460 AA).pro
 53     ----------------------------------------------------------------     ZmBk2L7 (SEQ ID NO14) 447 AA).pro
157     GPEPYVPLPSFLSLADP-SYTCPPATNATSSPTNLTTCCVFTAGGDPTGGLVES----            ZmBk2L8 (SEQ ID NO16) 654 AA).pro
 55     ----------------------------------------------------------------     ZmBk2L9 (SEQ ID NO18) 444 AA).pro
```

FIG. 1B

```
                250       260       270       280       290       300
       ----+----|----+----|----+----|----+----|----+----|----+----|
 59    ---------------------------------MSNYQMYRHI-MA----------PGWTLGWSWAKKEVIWSIVG  ZmBk2  (SEQ ID NO2)  450 AA).pro
217    KDFLPRGTGDLVITYDVLQAYPSSYLALVTLENNAKLGRLDNWRLSWEWRRGEFIYSMKG                  ZmBk2L1 (SEQ ID NO4)  667 AA).pro
 60    ---------------------------------MFNYQQFRHI-GA----------PGWQLGWTWAKKEVIWSMVG  ZmBk2L3 (SEQ ID NO6)  448 AA).pro
 60    ---------------------------------MFNYQQFRHI-GA----------PGWQLGWTWAKKEVIWSMVG  ZmBk2L4 (SEQ ID NO8)  449 AA).pro
223    R-YQTRRKADLTFAYDVLQANTNNYQVQVTIDNWSPISRLDNWNLTWEWKRGEFIYSMKG                  ZmBk2L5 (SEQ ID NO10) 678 AA).pro
 63    ---------------------------------LYNYQQYRHIQAP----------PGWRLGWVWAKKEVIWAMTG  ZmBk2L6 (SEQ ID NO12) 460 AA).pro
 53    ---------------------------------INNFQTYRQI-TA----------PGWTVGWTWAKREVIWSMVG  ZmBk2L7 (SEQ ID NO14) 447 AA).pro
210    -GFLPRRTGDLVITYDVLQSYDTTYLALVTLENDALLGRLDAWQLSWRWEHGEFISSMRG                  ZmBk2L8 (SEQ ID NO16) 654 AA).pro
 55    ---------------------------------IHNYQMYRHIER----------PGWRLSWSWAGKEVIWSTTG   ZmBk2L9 (SEQ ID NO18) 444 AA).pro 310       320       330       340       350       360
       ----+----|----+----|----+----|----+----|----+----|----+----|
 91    AQAT--EQGDC------SKF-KGG-IPHC---CKRTPAVVDLLPGVPYNQQIAN----CCKA  ZmBk2  (SEQ ID NO2)  450 AA).pro
277    AHPSEVDTSGCICGAPGQYYQSLDFSQ-VLNCDRKPVILDLPLSRYNDTQIGKIDNCCRN    ZmBk2L1 (SEQ ID NO4)  667 AA).pro
 92    AQTT--EQGDC------SKF-KSSP-PHC---CKKDPTIVDLLPGTPYNMQIAN----CCKA  ZmBk2L3 (SEQ ID NO6)  448 AA).pro
 92    AQTT--EQGDC------SKF-KGNT-PHC---CKKDPTIVDLLPGTPYNMQIAN----CCKA  ZmBk2L4 (SEQ ID NO8)  449 AA).pro
282    AYTLLKEGPACIYSPAAGYYKDMDFT-PVYNCEKRPVIVDLPPEREKDDAVGNLPFCCKN    ZmBk2L5 (SEQ ID NO10) 678 AA).pro
 96    GQAT--EQGDC------SRF-KASVLPHC---CRRDPEVVDLLPGTPYNTQTAN----CCRG  ZmBk2L6 (SEQ ID NO12) 460 AA).pro
 85    AQAT--EQGDC------SRF-KAN-IPHC---CKRTPAVVDLLPGVPYNQQIAN----CCRG  ZmBk2L7 (SEQ ID NO14) 447 AA).pro
269    AYPREVDTAECLYGPQGQYYKDLDFSKAVLNCDRRPVVHDLPPSRANDTEIGRIDHCCRN    ZmBk2L8 (SEQ ID NO16) 654 AA).pro
 87    AETT--EQGDC------SRVGSGGSRPHC---CQKRPVMVDLPPGTPYNMQVAN----CCRG  ZmBk2L9 (SEQ ID NO18) 444 AA).pro
```

FIG. 1C

```
                 370       380       390       400       410       420
       ----------+---------+---------+---------+---------+---------+
       ----------+---------+---------+---------+---------+---------+
136 GVVSAYGQDPAGSVSAFQVSVGL----AGTTNKTVKLPRNFTLMGPG-----LGYTCGPAA  ZmBk2  (SEQ ID NO2) 450 AA).pro
336 GTILPKSMDEAQSKSAFQMQV--FKMPPDLNRTKLFPPANFKIVGASS-LNPDYACGQPV  ZmBk2L1 (SEQ ID NO4) 667 AA).pro
137 GVVNTFNQDPANAASSFQISVGL-----AGTTNKTVKVPRNFTLKTPG-----PGYTCGRAI  ZmBk2L3 (SEQ ID NO6) 448 AA).pro
137 GVINTFNQDPANAASSFQISVGL-----AGTTNKTVKVPKNFTLKTPG-----PGYTCGRAI  ZmBk2L4 (SEQ ID NO8) 449 AA).pro
341 GTLLPPTMDPSKSRAMFQMQV--YKLPPDLNRTALYPPQNWKISGK---LNPQYACGPPV  ZmBk2L5 (SEQ ID NO10) 678 AA).pro
142 GVLASWAQDPSDAVASFQVSVGQ-----AGSTNRTVKVPRNFTLLAPG-----PGYTCGAAK  ZmBk2L6 (SEQ ID NO12) 460 AA).pro
130 GVVSAYGQDPATAVAAFQVSVGQ-----AGTTNRTVKVPKNFTLLGPG-----PGYTCGPGK  ZmBk2L7 (SEQ ID NO14) 447 AA).pro
329 GTILPKSMDVARSKSAFQMVV--YKMPPDLNRTKLYPPTGFNVTGAASALNPEYACDPPI  ZmBk2L8 (SEQ ID NO16) 654 AA).pro
134 GVLSSLVQSDLTSAAAFQMVVGEFALARDSGGKEPEKPWQFDM--GV-----PGYTCSNAT  ZmBk2L9 (SEQ ID NO18) 444 AA).pro 430       440       450       460       470       480
       ----------+---------+---------+---------+---------+---------+
       ----------+---------+---------+---------+---------+---------+
188 VVPSTVYWTPDHRRRTQAL-------MTWTVTCTYSQQLASRYPSCCVSFSFYNSTIV  ZmBk2  (SEQ ID NO2) 450 AA).pro
393 PVSPTAFPDPSGLDST-------TLAVATWQVVCNITT-TKGAKPKCCVTFSAYYNDSVI  ZmBk2L1 (SEQ ID NO4) 667 AA).pro
189 VGRPTKFFTADGRRATQAL-------MTWNVTCTYSQFLAQKTPSCCVSLSSFYNDTIV  ZmBk2L3 (SEQ ID NO6) 448 AA).pro
189 VGRPTKFFSADGRRVTQAL-------MTWNVTCTYSQFLAQKTPSCCVSLSSFYNDTIV  ZmBk2L4 (SEQ ID NO8) 449 AA).pro
396 RVSPQEFPDPTGLMST-------TPAVASWQVACNITR-PKKRASKCCVSFSAYYNDSVV  ZmBk2L5 (SEQ ID NO10) 678 AA).pro
194 LVKPTKFMSQDGRRSTQAH-------MTWNVTCTYSQFLAQRSPTCCVSLSSFYNDTIV  ZmBk2L6 (SEQ ID NO12) 460 AA).pro
182 VVPSTVFLTPDRRRKTQAL-------MTWNVTCTYSQHLASKYPSCCVSFSSFYNDTIV  ZmBk2L7 (SEQ ID NO14) 447 AA).pro
387 SVSPSEYPDPSGLTSI-------TVAVATWQVVCNITT-SPKKPPRCCVSFSFYNESVV  ZmBk2L8 (SEQ ID NO16) 654 AA).pro
188 TVAPTRI-KVDKNRYVQALQDRAELRAVTWQVTCSYSQYRASAAPSCCVSMTTFYSETIV  ZmBk2L9 (SEQ ID NO18) 444 AA).pro
```

FIG. 1D

```
          ----+----|----+----|----+----|----+----|----+----|----+----|
              490       500       510       520       530       540
          ----+----|----+----|----+----|----+----|----+----|----+----|
240 PCARCACGCGGHGGH--AGPGG-CIEGDSKRALSAGVNTP--------RKDGQALLQCT  ZmBk2  (SEQ ID NO2)  450 AA).pro
445 PCSTCACGCPANRRGPTCSTTAQSMLLPPEALLVPFDNRSQKALAWAELKHYNVPRPMPC  ZmBk2L1 (SEQ ID NO4)  667 AA).pro
241 NCPTCSCGCQNPSGSN-------CVNED--S--------PNLQAAIDGPGKWTGQPLVQCT ZmBk2L3 (SEQ ID NO6)  448 AA).pro
241 NCPTCSCGCQNPSGSN-------CVNED--S--------PNLQAAIDGPGKWTGQPLVQCT ZmBk2L4 (SEQ ID NO8)  449 AA).pro
448 PCNTCACGCGDD--TATCDPDKRAMLLPPEALLVPFDNRSAKARAWAKIKHWRVPNPMPC  ZmBk2L5 (SEQ ID NO10) 678 AA).pro
246 SCPACSCGCQNNNSSSTAAPGS-CVEGSRRS------PYLASVVNDPSKNSLAPLVQCT   ZmBk2L6 (SEQ ID NO12) 460 AA).pro
234 PCAKCACGCEHKT---------CVQGDSKRLAVTGKHAHTAAAVRGQHRDKEAPLLQCT   ZmBk2L7 (SEQ ID NO14) 447 AA).pro
439 PCRTCACGCPSS--APTCSTTAPAMLLPPQALLMPFDRRASEALEWADQKHLGVPKPMPC  ZmBk2L8 (SEQ ID NO16) 654 AA).pro
247 DCPRCSCGCQGSPPSPQ-----CVSVDQQ--------QPWLPAVGDDEP--SSAPIVWCS  ZmBk2L9 (SEQ ID NO18) 444 AA).pro ----+----|----+----|----+----|----+----|----+----|----+----|
              550       560       570       580       590       600
          ----+----|----+----|----+----|----+----|----+----|----+----|
288 PHMCPIRVHWHVKLNYKDYWRAKIAITNYNYRMNYTQW-TLVAQHPNLDNVTEVFSFQYK  ZmBk2   (SEQ ID NO2)  450 AA).pro
505 GDFCGVSINWHVSTDYNKGWSARVTLFNWE-DVDMANWFAAIVMDKAYDGFEKAYSFNGT ZmBk2L1 (SEQ ID NO4)  667 AA).pro
285 SHMCPIRIHWHVKLNYKDYWRVKITITNENFRMNYTQW-NLVAQHPNEDNITQLFSFNYK ZmBk2L3 (SEQ ID NO6)  448 AA).pro
285 SHMCPIRIHWHVKLNYKEYWRVKITITNFNFRMNYTQW-NLVAQHPNFDNITQLFSFNYK ZmBk2L4 (SEQ ID NO8)  449 AA).pro
506 SDNCGVSINWHVINNYKSGWSARMTIFNWQ-DYTFKDWFAAVTMGSHFSGYENVYSFNGT ZmBk2L5 (SEQ ID NO10) 678 AA).pro
298 SHMCPVRVHWHVHVKVSYKEYWRVKITVTNFNYRMNYSQW-NLVAQHPNFDNLTTIFSFNYR ZmBk2L6 (SEQ ID NO12) 460 AA).pro
284 THMCPVRVHWHVKLNYKEYWRAKIAITNFNYHMNYTQW-TLVAQHPNLDNITEVFSFGYK ZmBk2L7 (SEQ ID NO14) 447 AA).pro
497 GDFCGVSVNWHVATDFTGGWSARLTLFNWD-GTDMPDWFTAIVMDKAYDGFEQAYSFNAT ZmBk2L8 (SEQ ID NO16) 654 AA).pro
292 EHMCPIRVHWHVKTNYRKYWRVKVTVSNYNLARNYSDW-NLVLQHPNLRSLTQLFSFNYR ZmBk2L9 (SEQ ID NO18) 444 AA).pro
```

FIG. 1E

```
              610       620       630       640       650       660
       +---------+---------+---------+---------+---------+---------+
       +---------+---------+---------+---------+---------+---------+
347 PLQPYGS-INDTGMFYGLKFYNDELMEAGPFGNVQSEV------LMRKDARTFTFSM ZmBk2  (SEQ ID NO2)  450 AA).pro
564 AV---G---KNTIFMQGLEGLNYLVKQTN-MSGSDYLVPGKQQSVLSFTKKLTPGLNVVA ZmBk2L1 (SEQ ID NO4)  667 AA).pro
344 PLTPYGGGINDTAMFWGVKFYNDLLMQAGKLGNVQSEL------LLRKDSRTFTFEK ZmBk2L3 (SEQ ID NO6)  448 AA).pro
344 PLTPYGGGINDTAMFWGVKFYNDLLMQAGKLGNVQSEL------LLRKDSRTFTFEK ZmBk2L4 (SEQ ID NO8)  449 AA).pro
565 RM---GAPFNNTIFMQGVPGLAYLEPITDAKTTSEPRLPGKQQSVISFTRKDAPNVNIPR ZmBk2L5 (SEQ ID NO10) 678 AA).pro
357 PLNPYGV-INDTAMLWGIKYYNDLLMTAGPDGNVQSEL------LFRKEPSTFTFHK ZmBk2L6 (SEQ ID NO12) 460 AA).pro
343 PVVSYGS-INDTAMFYGLKYFNDHLMQAGPYGNVQSEV------LMRKDASTFTFRQ ZmBk2L7 (SEQ ID NO14) 447 AA).pro
556 GV---G---NSTIFVRGAQGLNEFLLGERN-MSGVDYPVPGKQQSVFSFTKKKTPGIDIIA ZmBk2L8 (SEQ ID NO16) 654 AA).pro
351 PLVEYGA-YNDTGMFWGLRYNEMLLQDG---NVQSEM------ILEKESD-FTYSG ZmBk2L9 (SEQ ID NO18) 444 AA).pro 670       680       690       700       710       720
       +---------+---------+---------+---------+---------+---------+
       +---------+---------+---------+---------+---------+---------+
397 GWAFPRKIYFNGDECKMPPPDSYPYLPNAA-PVVASQLVLSAAASAFLLLL-LLV------A ZmBk2  (SEQ ID NO2)  450 AA).pro
617 GDGFPTKVFFNGDECAMP--QRIPISTGFSTRLSSGLALVPFLVASAFLLLQ------Q ZmBk2L1 (SEQ ID NO4)  667 AA).pro
395 GWAFPRRVYFNGDNCVMPSPENYPWLPNA-SPLTK-PLAIPFLVF-WVALAALLA---YA ZmBk2L3 (SEQ ID NO6)  448 AA).pro
395 GWAFPRRVYFNGDNCVMPSPENYPWLPNA-SPLITKQALTLPLLIF-WVALAVLLA---YA ZmBk2L4 (SEQ ID NO8)  449 AA).pro
622 GEGFPKRIYFDGEECALP--DRIPKVSS-ARRRAGTASLGQIAMAAALVMIVALVDSLCL ZmBk2L5 (SEQ ID NO10) 678 AA).pro
407 GWAFPRRVYFNGDNCVMPPPDAYPWLPNAASPRLSPSLLLPLVAAAWTAFAVL------S ZmBk2L6 (SEQ ID NO12) 460 AA).pro
393 GWAFPRKVYFNGDECQMPPPDAYPYLPNSA-PPTAAASIGGAAAAAVVLLGMIV-----A ZmBk2L7 (SEQ ID NO14) 447 AA).pro
609 GDGFPSKVFFNGDECAMP--LRIPSQ---GTSVVVPMQLC--LLVSAFMILL------L ZmBk2L8 (SEQ ID NO16) 654 AA).pro
397 GWAFPRRVYFNGQECVMPPADQYPVLPNGASALRGHFCFL------LLLFFV---VV ZmBk2L9 (SEQ ID NO18) 444 AA).pro
```

F I G. 1F

| | 1 | 2 | 3 | 4 | 5 | 6 | 7 | 8 | 9 | |
|---|---|---|---|---|---|---|---|---|---|---|
| 1 |  | 18.2 | 63.4 | 62.4 | 17.3 | 58.0 | 71.8 | 18.7 | 42.6 | 1 | ZmBk2 SEQ ID NO:2 |
| 2 | 195.1 |  | 20.3 | 20.7 | 45.1 | 19.6 | 18.3 | 60.6 | 14.4 | 2 | ZmBk2L1 SEQ ID NO:4 |
| 3 | 41.5 | 185.8 |  | 95.3 | 19.4 | 64.1 | 61.5 | 17.9 | 43.2 | 3 | ZmBk2L3 SEQ ID NO:6 |
| 4 | 43.4 | 190.3 | 4.1 |  | 18.9 | 64.1 | 62.2 | 19.4 | 43.2 | 4 | ZmBk2L4 SEQ ID NO:8 |
| 5 | 174.5 | 80.3 | 180.7 | 177.5 |  | 18.3 | 18.8 | 41.7 | 15.8 | 5 | ZmBk2L5 SEQ ID NO:10 |
| 6 | 51.2 | 198.0 | 38.7 | 38.9 | 184.8 |  | 61.1 | 17.6 | 45.3 | 6 | ZmBk2L6 SEQ ID NO:12 |
| 7 | 28.7 | 177.4 | 46.1 | 45.6 | 168.5 | 46.4 |  | 15.0 | 41.7 | 7 | ZmBk2L7 SEQ ID NO:14 |
| 8 | 174.6 | 46.7 | 188.7 | 187.2 | 90.4 | 195.0 | 172.9 |  | 16.4 | 8 | ZmBk2L8 SEQ ID NO:16 |
| 9 | 70.3 | 194.5 | 70.5 | 69.1 | 196.7 | 69.1 | 77.3 | 185.7 |  | 9 | ZmBk2L9 SEQ ID NO:18 |
| | 1 | 2 | 3 | 4 | 5 | 6 | 7 | 8 | 9 | | |

Percent Identity / Divergence

FIG. 2

|  | Bk2 | Bk2L1 | Bk2L3 | Bk2L4 | Bk2L5 | Bk2L6 | Bk2L7 | Bk2L8 | Bk2L9 |
|---|---|---|---|---|---|---|---|---|---|
| Bk2 | 1 | | | | | | | | |
| Bk2L1 | -0.0419 | 1 | | | | | | | |
| Bk2L3 | 0.459845 | 0.116365 | 1 | | | | | | |
| Bk2L4 | -0.0901 | 0.176403 | -0.13152 | 1 | | | | | |
| Bk2L5 | -0.0284 | -0.04545 | -0.06143 | 0.001596 | 1 | | | | |
| Bk2L6 | -0.05068 | -0.07715 | -0.04007 | -0.05498 | -0.01307 | 1 | | | |
| Bk2L7 | 0.012058 | 0.189464 | 0.105736 | 0.216614 | -0.0215 | -0.05006 | 1 | | |
| Bk2L8 | 0.035109 | -0.04871 | -0.02495 | -0.16562 | -0.03156 | -0.00536 | -0.12083 | 1 | |
| Bk2L9 | -0.01188 | 0.118807 | 0.025835 | -0.05263 | -0.01152 | -0.02682 | -0.03955 | -0.03345 | 1 |
| CesA1 | 0.322327 | 0.16084 | 0.679585 | 0.120328 | -0.06545 | -0.07823 | 0.291059 | -0.0153 | -0.04382 |
| CesA2 | 0.405233 | 0.044683 | 0.626191 | -0.17099 | -0.03841 | -0.04896 | -0.10262 | 0.038295 | 0.047804 |
| CesA3 | -0.10914 | 0.127964 | -0.15748 | 0.349026 | -0.0643 | -0.00339 | 0.106751 | -0.22135 | 0.062293 |
| CesA4 | 0.513933 | 0.012704 | 0.466216 | -0.15059 | -0.03912 | -0.07568 | -0.08647 | 0.205215 | 0.080826 |
| CesA5 | -0.18637 | 0.082161 | -0.23031 | 0.019721 | -0.04781 | 0.073704 | -0.10004 | 0.04946 | 0.05898 |
| CesA6 | 0.084407 | 0.097012 | 0.150658 | 0.241203 | -0.0484 | -0.06771 | 0.218979 | -0.1567 | -0.08357 |
| CesA7 | 0.617685 | -0.01927 | 0.706381 | -0.04471 | -0.05094 | -0.09761 | 0.086805 | 0.061506 | 0.000664 |
| CesA8 | 0.33504 | 0.1304 | 0.675267 | -0.09824 | -0.04103 | -0.08054 | 0.013196 | -0.03984 | -0.00451 |
| CesA9 | 0.06077 | 0.122298 | 0.122457 | -0.11313 | -0.01729 | -0.04026 | -0.0662 | 0.292937 | -0.00959 |
| CesA10 | 0.823773 | 0.006947 | 0.447201 | -0.0874 | -0.0298 | -0.06283 | 0.135322 | 0.014205 | -0.01491 |
| CesA11 | 0.765139 | 0.027053 | 0.392839 | -0.09231 | -0.02576 | -0.0511 | 0.041589 | 0.058995 | -0.01943 |
| CesA12 | 0.813525 | -0.00557 | 0.449179 | -0.11075 | -0.02793 | -0.05538 | 0.057295 | 0.081381 | -0.0288 |

FIG. 5A

|  | CesA1 | CesA2 | CesA3 | CesA4 | CesA5 | CesA6 | CesA7 | CesA8 | CesA9 | CesA10 | CesA11 | CesA12 |
|---|---|---|---|---|---|---|---|---|---|---|---|---|
| Bk2 |  |  |  |  |  |  |  |  |  |  |  |  |
| Bk2L1 |  |  |  |  |  |  |  |  |  |  |  |  |
| Bk2L3 |  |  |  |  |  |  |  |  |  |  |  |  |
| Bk2L4 |  |  |  |  |  |  |  |  |  |  |  |  |
| Bk2L5 |  |  |  |  |  |  |  |  |  |  |  |  |
| Bk2L6 |  |  |  |  |  |  |  |  |  |  |  |  |
| Bk2L7 |  |  |  |  |  |  |  |  |  |  |  |  |
| Bk2L8 |  |  |  |  |  |  |  |  |  |  |  |  |
| Bk2L9 |  |  |  |  |  |  |  |  |  |  |  |  |
| CesA1 | 1 |  |  |  |  |  |  |  |  |  |  |  |
| CesA2 | 0.466423 | 1 |  |  |  |  |  |  |  |  |  |  |
| CesA3 | -0.01079 | -0.28298 | 1 |  |  |  |  |  |  |  |  |  |
| CesA4 | 0.379045 | 0.475271 | -0.23983 | 1 |  |  |  |  |  |  |  |  |
| CesA5 | -0.07235 | -0.17617 | 0.279237 | -0.17944 | 1 |  |  |  |  |  |  |  |
| CesA6 | 0.327738 | -0.08471 | 0.160041 | -0.03737 | -0.03637 | 1 |  |  |  |  |  |  |
| CesA7 | 0.639066 | 0.586787 | -0.14422 | 0.561724 | -0.16896 | 0.121807 | 1 |  |  |  |  |  |
| CesA8 | 0.600142 | 0.666353 | -0.19674 | 0.479992 | -0.14746 | 0.053083 | 0.569269 | 1 |  |  |  |  |
| CesA9 | 0.20546 | 0.16037 | -0.11553 | 0.359446 | 0.160147 | -0.04269 | 0.23704 | 0.27599 | 1 |  |  |  |
| CesA10 | 0.424086 | 0.318652 | -0.11428 | 0.441978 | -0.14457 | 0.169571 | 0.567287 | 0.33819 | 0.053266 | 1 |  |  |
| CesA11 | 0.43014 | 0.341054 | -0.11502 | 0.478683 | -0.04722 | 0.22327 | 0.468309 | 0.387391 | 0.096179 | 0.857814 | 1 |  |
| CesA12 | 0.467707 | 0.35157 | -0.10216 | 0.495846 | -0.08321 | 0.21885 | 0.562321 | 0.387474 | 0.072621 | 0.897501 | 0.945678 | 1 |

FIG. 5B

BRITTLE STALK 2 GENE FAMILY AND RELATED METHODS AND USES

FIELD OF THE INVENTION

The field of invention relates to plant molecular biology, and in particular, to BRITTLE STALK 2-like genes, BRITTLE STALK 2-like polypeptides, and uses thereof.

BACKGROUND OF THE INVENTION

Plant primary growth is mainly driven by an enlargement of the cells, which occurs through the irreversible yielding of the primary cell wall to turgor pressure inside the cell. Although cell division is required to produce new cells, the growth results from the expansion of these cells, not simply from their division. Cellulose microfibrils, which are embedded in a matrix of hemicellulose and lignin in the wall, are the main determinants of tensile strength (Appenzeller et al., *Cellulose* 11:287-299 (2004)). A cell usually expands along the axis that is perpendicular to the orientation of the microfibrils. For example, radial deposition of microfibrils favors cell expansion along the longitudinal axis.

Secondary wall differs from primary wall in that it is richer in cellulose and lignin and its deposition commences toward the end of cell expansion. Modulation of primary cell wall synthesis has applications in altering growth rate and size (stature) of a plant whereas that of secondary wall can be useful in improving biomass accumulation and tissue strength (Appenzeller et al., *Cellulose* 11:287-299 (2004)).

Cellulose in general is the major wall constituent in mature plant cells forming vegetative tissues. The paracrystalline structure of cellulose that results from energy minimization by the formation of inter- and intra-chain hydrogen bonds makes it mechanically one of the strongest organic molecule known on density basis. It is natural then that cellulose is the primary determinant of strength in structural tissues.

Plant mechanical strength is one of the most important agronomic traits. Plant mutants that are defective in stem strength have been isolated and characterized. Barley brittle culm (bc) mutants were first described based on the physical properties of the culms, which have an 80% reduction in the amount of cellulose and a twofold decrease in breaking strength compared with those of wildtype plants (Kokubo et al., *Plant Physiol.* 97:509-514 (1991)). Rice brittle culm1 (bc1) mutants show a reduction in cell wall thickness and cellulose content (Qian et al., *Chi. Sci. Bull.* 46:2082-2085 (2001)). Li et al. described the identification of rice BRITTLE CULM1 (BC1), a gene that encodes a COBRA-like protein (*The Plant Cell* 15(9):2020-2031 (2003)). Their findings indicated that BC1 functions in regulating the biosynthesis of secondary cell walls to provide the main mechanical strength for rice plants.

The stalks of maize brittle stalk 2 (bk2) mutant exhibit a dramatically reduced mechanical strength compared to their wild type counterparts (Langham, M N L 14:21-22 (1940)). Maize bk2 mutants have stalk and leaves that are very brittle and break easily. The main chemical constituent deficient in the mutant stalk is cellulose. Therefore, stalk mechanical strength appears to be dependent primarily on the amount of cellulose in a unit length of the stalk below the ear.

Furthermore, genes encoding cellulose synthase catalytic subunits (CesA) have been implicated in cell wall synthesis and are represented by a large family in plants. Ten genes were identified in Arabidopsis after complete genome sequencing and twelve genes have been isolated from maize by EST sequencing (U.S. Pat. Nos. 6,803,498 and 6,930,225).

Three of the CesA genes from each Arabidopsis and maize have been reported to make secondary wall whereas the rest apparently make primary wall (Taylor et al., *Proc. Natl. Acad. Sci. U.S.A.* 100:1450-1455 (2003)). Mutations in three of the CesA genes from Arabidopsis resulted in collapsed xylem and reduced mechanical strength of the stem-like peduncle. When related CesA genes from rice were mutated the culms became brittle, indicating the role of these genes in secondary wall formation. In each case, reduced mechanical strength was correlated with diminished cellulose content.

In general, mutations in the CesA genes involved in primary wall formation cause severe phenotypic alterations whereas those in secondary wall-forming genes do not alter the visual phenotype as much as they affect mechanical strength (Appenzeller et al., *Cellulose* 11:287-299 (2004)).

As insufficient stalk strength is a major problem in corn breeding, it is desirable to provide compositions and methods for manipulating cellulose concentration in the cell wall and thereby alter plant stalk strength and/or quality for improved standability or silage quality.

SUMMARY OF THE INVENTION

The present invention includes:

In one embodiment, an isolated polynucleotide comprising (a) a nucleotide sequence encoding a polypeptide associated with stalk mechanical strength, wherein said polypeptide has an amino acid sequence of at least 80%, 85%, 90%, 95%, 96%, 97%, 98%, 99% or 100% sequence identity, or any integer in between 80% and 100%, based on the Clustal V method of alignment, when compared to SEQ ID NOs:16 or 18, or (b) a complement of the nucleotide sequence, wherein the complement and the nucleotide sequence consist of the same number of nucleotides and are 100% complementary.

In another embodiment, a method of altering (preferably increasing) stalk mechanical strength in a plant comprising (a) introducing into a regenerable plant cell a recombinant DNA construct to produce transformed plant cells, said recombinant DNA construct comprising a promoter that is functional in a plant operably linked to (i) a polynucleotide encoding a polypeptide having an amino acid sequence of at least 80% sequence identity, based on the Clustal V method of alignment, when compared to SEQ ID NOs:4, 6, 8, 10, 12, 14, 16, and 18, or (b) a full-length complement of said polynucleotide of (a) (i); and (b) regenerating a transgenic plant from said transformed plant cell, wherein said transgenic plant comprises in its genome said recombinant DNA construct and wherein said transgenic plant exhibits an alteration (preferably an increase) in stalk mechanical strength, when compared to a control plant not comprising said recombinant DNA construct. The method may further comprise (c) obtaining a progeny plant derived from said transgenic plant, wherein said progeny plant comprises in its genome the recombinant DNA construct.

In another embodiment, a method of evaluating stalk mechanical strength in a plant comprising (a) introducing into a regenerable plant cell a recombinant DNA construct to produce transformed plant cells, said recombinant DNA construct comprising a promoter that is functional in a plant operably linked to (i) a polynucleotide encoding a polypeptide having an amino acid sequence of at least 80% sequence identity, based on the Clustal V method of alignment, when compared to SEQ ID NOs:4, 6, 8, 10, 12, 14, 16, and 18, or (b) a full-length complement of said polynucleotide of (a) (i); (b) regenerating a transgenic plant from said transformed plant cell; and (c) evaluating said transgenic plant for stalk mechanical strength. The method may further comprise (d)

obtaining a progeny plant derived from said transgenic plant; and (e) evaluating said progeny plant for stalk mechanical strength.

In another embodiment, a method of evaluating stalk mechanical strength in a plant, comprising (a) introducing into a regenerable plant cell a recombinant DNA construct to produce transformed plant cells, said recombinant DNA construct comprising a promoter that is functional in a plant operably linked to (i) a polynucleotide encoding a polypeptide having an amino acid sequence of at least 80% sequence identity, based on the Clustal V method of alignment, when compared to SEQ ID NOs:4, 6, 8, 10, 12, 14, 16, and 18, or (b) a full-length complement of said polynucleotide of (a) (i); (b) regenerating a transgenic plant from said transformed plant cell; (c) obtaining a progeny plant derived from said transgenic plant; and (d) evaluating said progeny plant for stalk mechanical strength.

The present invention also includes:

In one embodiment, a plant comprising in its genome: (a) a first recombinant DNA construct comprising at least one promoter that is functional in a plant operably linked to at least one of a first isolated polynucleotide selected from the group consisting of (i) a polynucleotide encoding a polypeptide having an amino acid sequence of at least 80% sequence identity, based on the Clustal V method of alignment, when compared to SEQ ID NOs:2, 4, 6, 8, 10, 12, 14, 16, and 18; (ii) a polynucleotide having a nucleic acid sequence of at least 60% sequence identity, based on the Clustal V method of alignment, when compared to SEQ ID NOs:1, 3, 5, 7, 9, 11, 13, 15, and 17; and (iii) a full-length complement of the polynucleotide of (a) (i) or (a) (ii); and (b) a second recombinant DNA construct comprising at least one promoter that is functional in a plant operably linked to at least one of a second isolated polynucleotide selected from the group consisting of (iv) a polynucleotide encoding a polypeptide having an amino acid sequence of at least 80% sequence identity, based on the Clustal V method of alignment, when compared to SEQ ID NOs:20, 22, 24, 26, 28, 30, 32, 34, 36, 38, 40, and 42; (v) a polynucleotide having a nucleic acid sequence of at least 60% sequence identity, based on the Clustal V method of alignment, when compared to SEQ ID NOs:21, 23, 25, 27, 29, 31, 33, 35, 37, 39, and 41; and (vi) a full-length complement of the polynucleotide of (b) (iv) or (b) (v).

In another embodiment, a plant comprising in its genome at least one regulatory sequence operably linked to: (a) at least one isolated polynucleotide selected from the group consisting of (i) a polynucleotide encoding a polypeptide having an amino acid sequence of at least 80% sequence identity, based on the Clustal V method of alignment, when compared to SEQ ID NOs:2, 4, 6, 8, 10, 12, 14, 16, and 18; (ii) a polynucleotide having a nucleic acid sequence of at least 60% sequence identity, based on the Clustal V method of alignment, when compared to SEQ ID NOs:1, 3, 5, 7, 9, 11, 13, 15, and 17; and (iii) a full-length complement of the polynucleotide of (a) (i) or (a) (ii); and (b) at least one isolated polynucleotide selected from the group consisting of (i) a polynucleotide encoding a polypeptide having an amino acid sequence of at least 80% sequence identity, based on the Clustal V method of alignment, when compared to SEQ ID NOs:20, 22, 24, 26, 28, 30, 32, 34, 36, 38, 40, and 42; (ii) a polynucleotide having a nucleic acid sequence of at least 60% sequence identity, based on the Clustal V method of alignment, when compared to SEQ ID NOs:21, 23, 25, 27, 29, 31, 33, 35, 37, 39, and 41; and (iii) a full-length complement of the polynucleotide of (b) (i) or (b) (ii), and wherein said plant exhibits increased cell wall cellulose content or enhanced growth rate when compared to a control plant not comprising said at least one regulatory sequence operably linked to said (a) and (b).

In another embodiment, a plant comprising in its genome a suppression DNA construct comprising a promoter functional in a plant operably linked to (a) all or part of (i) a nucleic acid sequence encoding a polypeptide having an amino acid sequence of at least 50% sequence identity, or any integer from 51% up to and including 100% sequence identity, based on the Clustal V method of alignment, when compared to SEQ ID NOs:2, 4, 6, 8, 10, 12, 14, 16, and 18, or (ii) a full-length complement of the nucleic acid sequence of (a) (i); or (b) a region derived from all or part of a sense strand or antisense strand of a target gene of interest, or any integer from 51% up to and including 100% sequence identity, said region having a nucleic acid sequence of at least 50% sequence identity, based on the Clustal V method of alignment, when compared to said all or part of a sense strand or antisense strand from which said region is derived, and wherein said target gene of interest encodes a polypeptide selected from the group consisting of Bk2, Bk2L1, Bk2L3, Bk2L4, Bk2L5, Bk2L6, Bk2L7, Bk2L8 and Bk2L9, and wherein said plant exhibits reduced stalk mechanical strength when compared to a control plant not comprising said suppression DNA construct.

In another embodiment, a plant comprising in its genome a suppression DNA construct comprising a promoter functional in a plant operably linked to (a) all or part of (i) a nucleic acid sequence encoding a polypeptide having an amino acid sequence of at least 50% sequence identity, or any integer from 51% up to and including 100% sequence identity, based on the Clustal V method of alignment, when compared to SEQ ID NO:6, or (ii) a full-length complement of the nucleic acid sequence of (a) (i); or (b) a region derived from all or part of a sense strand or antisense strand of a target gene of interest, said region having a nucleic acid sequence of at least 50% sequence identity, or any integer from 51% up to and including 100% sequence identity, based on the Clustal V method of alignment, when compared to said all or part of a sense strand or antisense strand from which said region is derived, and wherein said target gene of interest encodes a Bk2L3 polypeptide, and wherein said plant exhibits reduced plant height and/or reduced organ size when compared to a control plant not comprising said suppression DNA construct.

In another embodiment, a plant comprising in its genome a suppression DNA construct comprising a promoter functional in a plant operably linked to (a) all or part of (i) a nucleic acid sequence encoding a polypeptide having an amino acid sequence of at least 50% sequence identity, or any integer from 51% up to and including 100% sequence identity, based on the Clustal V method of alignment, when compared to SEQ ID NO:10, or (ii) a full complement of the nucleic acid sequence of (a) (i); or (b) a region derived from all or part of a sense strand or antisense strand of a target gene of interest, said region having a nucleic acid sequence of at least 50% sequence identity, or any integer from 51% up to and including 100% sequence identity, based on the Clustal V method of alignment, when compared to said all or part of a sense strand or antisense strand from which said region is derived, and wherein said target gene of interest encodes a Bk2L5 polypeptide, and wherein said plant exhibits male sterility when compared to a control plant not comprising said suppression DNA construct.

BRIEF DESCRIPTION OF THE FIGURES AND SEQUENCE LISTINGS

The invention can be more fully understood from the following detailed description and the accompanying drawings and Sequence Listing which form a part of this application.

FIGS. 1A-1F show a Clustal V alignment, using default parameters, of the amino acid sequences of the Bk2 and Bk2-like proteins set forth in SEQ ID NOs:2, 4, 6, 8, 10, 12, 14, 16 and 18.

FIG. 2 shows a chart setting forth a comparison of the percent identity (and percent divergence in the lower half triangle), using the Clustal V alignment method, between the nine amino acid sequences shown in FIGS. 1A-1F.

FIGS. 5A-5B show the correlation among the expression level of all the different Bk2 and CesA genes from maize as studied from Solexa MPSS™.

Figure 6A:
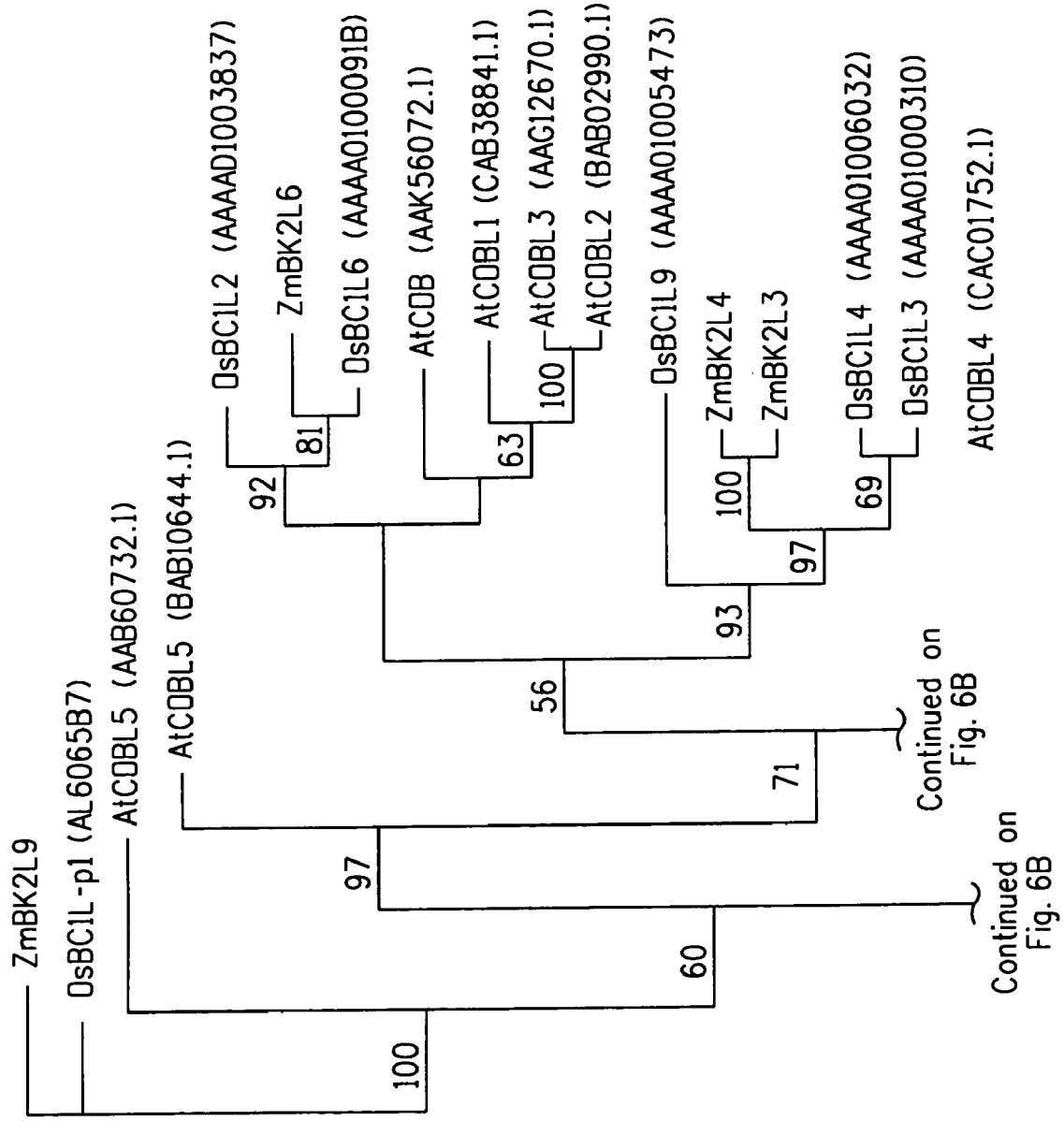
Figure 6B:
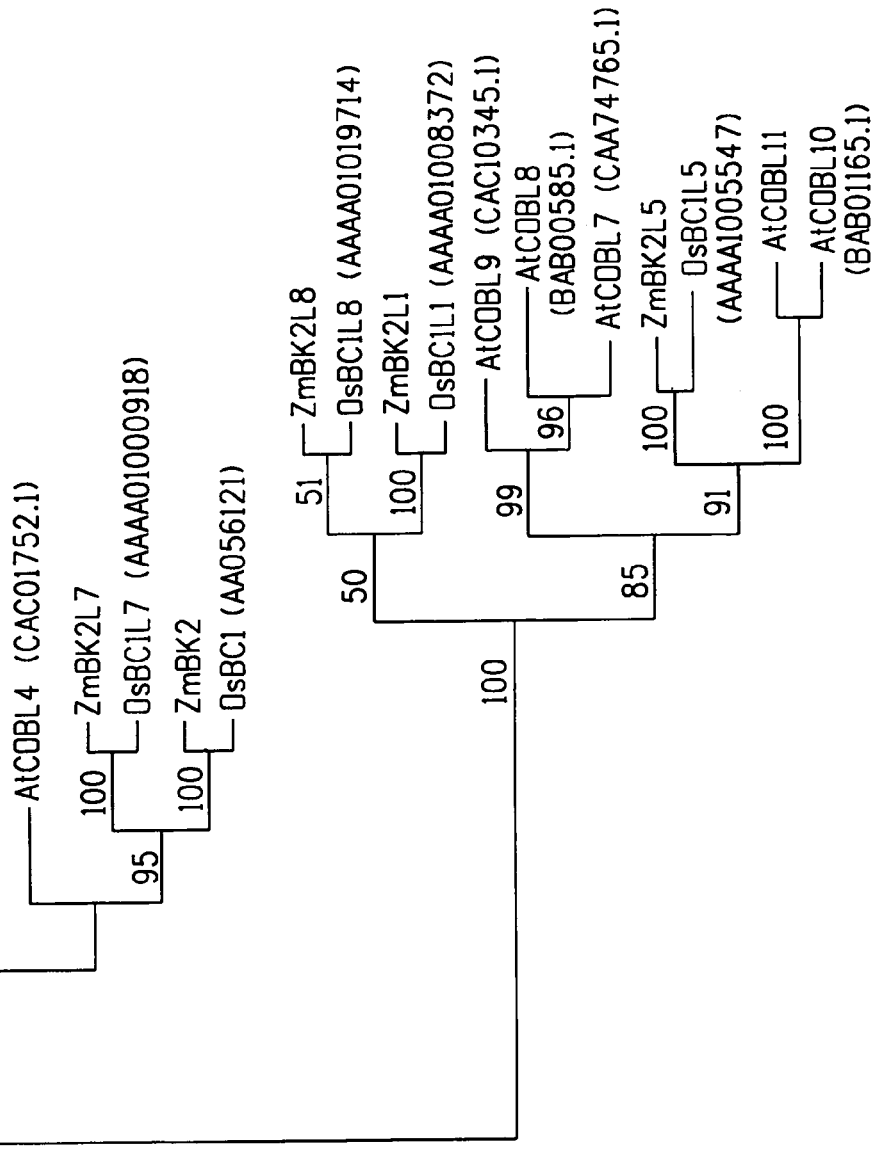

FIG. 6 shows the phylogenetic analysis of the Bk2L proteins from maize, BC1L proteins from rice, and COBL proteins from Arabidopsis (NCBI Accession Nos. are in parenthesis). The numbers along the branches are the bootstrap values obtained from a heuristic search over 5,000 replications. The bootstrap values for only the monophyletic groups that were supported >50% of the time are shown. The branch lengths are proportional to the inferred amino acid differences.

SEQ ID NO:1 is the 1784 bp nucleotide sequence containing the open reading frame (ORF) (nucleotides 89-1438) of the BRITTLE STALK 2 (Bk2) gene from maize flanked by additional untranslated regions (UTR) 5' (nucleotides 1-88) and 3' (nucleotides 1439-1784) to this ORF region.

SEQ ID NO:2 is the deduced amino acid sequence of a maize BRITTLE STALK 2 (Bk2) polypeptide derived from the ORF of the nucleotide sequence set forth in SEQ ID NO:1.

SEQ ID NO:3 is the 3152 bp nucleotide sequence containing the ORF (nucleotides 586-2586) of the BRITTLE STALK 2-Like1 (Bk2L1) gene from maize flanked by additional UTR regions 5' (nucleotides 1-585) and 3' (nucleotides 2587-3152) to this ORF region.

SEQ ID NO:4 is the deduced amino acid sequence of a maize BRITTLE STALK 2-Like1 (Bk2L1) polypeptide derived from ORF of the nucleotide sequence set forth in SEQ ID NO:3.

SEQ ID NO:5 is the 2094 bp nucleotide sequence containing the ORF (nucleotides 281-1624) of the BRITTLE STALK 2-Like3 (Bk2L3) gene from maize flanked by additional UTR regions 5' (nucleotides 1-280) and 3' (nucleotides 1625-2094) to this ORF region.

SEQ ID NO:6 is the deduced amino acid sequence of a maize BRITTLE STALK 2-Like3 (Bk2L3) polypeptide derived from the ORF of the nucleotide sequence set forth in SEQ ID NO:5.

SEQ ID NO:7 is the 2102 bp nucleotide sequence containing the ORF (nucleotides 326-1672) of the BRITTLE STALK 2-Like4 (Bk2L4) gene from maize flanked by additional UTR regions 5' (nucleotides 1-325) and 3' (nucleotides 1673-2102) to this ORF region.

SEQ ID NO:8 is the deduced amino acid sequence of a maize BRITTLE STALK 2-Like4 (Bk2L4) polypeptide derived from the ORF of the nucleotide sequence set forth in SEQ ID NO:7.

SEQ ID NO:9 is the 2422 bp nucleotide sequence containing the ORF (nucleotides 216-2249) of the BRITTLE STALK 2-Like5 (Bk2L5) gene from maize flanked by additional UTR regions 5' (nucleotides 1-215) and 3' (nucleotides 2250-2422) to this ORF region.

SEQ ID NO:10 is the deduced amino acid sequence of a maize BRITTLE STALK 2-Like5 (Bk2L5) polypeptide derived from the ORF of the nucleotide sequence set forth in SEQ ID NO:9.

SEQ ID NO:11 is the 1845 bp nucleotide sequence containing the ORF (nucleotides 184-1563) of the BRITTLE STALK 2-Like6 (Bk2L6) gene from maize flanked by additional UTR regions 5' (nucleotides 1-183) and 3' (nucleotides 1564-1845) to this ORF region.

SEQ ID NO:12 is the deduced amino acid sequence of a maize BRITTLE STALK 2-Like6 (Bk2L6) polypeptide derived from the ORF of the nucleotide sequence set forth in SEQ ID NO:11.

SEQ ID NO:13 is the 1644 bp nucleotide sequence containing the ORF (nucleotides 85-1425) of the BRITTLE STALK 2-Like7 (Bk2L7) gene from maize flanked by additional UTR regions 5' (nucleotides 1-84) and 3' (nucleotides 1426-1644) to this ORF region.

SEQ ID NO:14 is the deduced amino acid sequence of a maize BRITTLE STALK 2-Like7 (Bk2L7) polypeptide derived from the ORF of the nucleotide sequence set forth in SEQ ID NO:13.

SEQ ID NO:15 is the 2108 bp nucleotide sequence containing the ORF (nucleotides 144-2105) of the BRITTLE STALK 2-Like8 (Bk2L8) gene from maize flanked by additional UTR regions 5' (nucleotides 1-143) and 3' (nucleotides 2106-2108) to this ORF region.

SEQ ID NO:16 is the deduced amino acid sequence of a maize BRITTLE STALK 2-Like8 (Bk2L8) polypeptide derived from the ORF of the nucleotide sequence set forth in SEQ ID NO:15.

SEQ ID NO:17 is the 1335 bp nucleotide sequence containing the ORF (nucleotides 1-1332) of the BRITTLE STALK 2-Like9 (Bk2L9) gene from maize flanked by additional UTR regions 5' (nucleotides 0) and 3' (nucleotides 1963-1965) to this ORF region.

SEQ ID NO:18 is the deduced amino acid sequence of a maize BRITTLE STALK 2-Like9 (Bk2L9) polypeptide derived from the nucleotide sequence set forth in SEQ ID NO:17.

SEQ ID NO:19 is the 3780 bp nucleotide sequence containing the ORF (nucleotides 201-3428) of the CesA1 gene from maize flanked by additional UTR regions 5' (nucleotides 1-200) and 3' (nucleotides 3429-3780) to this ORF region.

SEQ ID NO:20 is the deduced amino acid sequence of a maize CesA1 polypeptide derived from the ORF of the nucleotide sequence set forth in SEQ ID NO: 19.

SEQ ID NO:21 is the 3725 bp nucleotide sequence containing the ORF (nucleotides 179-3403) of the CesA2 gene from maize flanked by additional UTR regions 5' (nucleotides 1-178) and 3' (nucleotides 3404-3725) to this ORF region.

SEQ ID NO:22 is the deduced amino acid sequence of a maize CesA2 polypeptide derived from the ORF of the nucleotide sequence set forth in SEQ ID NO:21.

SEQ ID NO:23 is the 2830 bp nucleotide sequence containing the ORF (nucleotides 3-2468) of the CesA3 gene from maize flanked by additional UTR regions 5' (nucleotides 1-2) and 3' (nucleotides 2469-2830) to this ORF region.

SEQ ID NO:24 is the deduced amino acid sequence of a maize CesA3 polypeptide derived from the ORF of the nucleotide sequence set forth in SEQ ID NO:23.

SEQ ID NO:25 is the 3773 bp nucleotide sequence containing the ORF (nucleotides 338-3571) of the CesA4 gene from maize flanked by additional UTR regions 5' (nucleotides 1-337) and 3' (nucleotides 3572-3773) to this ORF region.

SEQ ID NO:26 is the deduced amino acid sequence of a maize CesA4 polypeptide derived from the ORF of the nucleotide sequence set forth in SEQ ID NO:25.

SEQ ID NO:27 is the 3704 bp nucleotide sequence containing the ORF (nucleotides 272-3502) of the CesA5 gene from maize flanked by additional UTR regions 5' (nucleotides 1-271) and 3' (nucleotides 3503-3704) to this ORF region.

SEQ ID NO:28 is the deduced amino acid sequence of a maize CesA5 polypeptide derived from the ORF of the nucleotide sequence set forth in SEQ ID NO:27.

SEQ ID NO:29 is the 3568 bp nucleotide sequence containing the ORF (nucleotides 63-3242) of the CesA6 gene from maize flanked by additional UTR regions 5' (nucleotides 1-62) and 3' (nucleotides 3243-3568) to this ORF region.

SEQ ID NO:30 is the deduced amino acid sequence of a maize CesA6 polypeptide derived from the ORF of the nucleotide sequence set forth in SEQ ID NO:29.

SEQ ID NO:31 is the 3969 bp nucleotide sequence containing the ORF (nucleotides 144-3404) of the CesA7 gene from maize flanked by additional UTR regions 5' (nucleotides 1-143) and 3' (nucleotides 3405) to this ORF region.

SEQ ID NO:32 is the deduced amino acid sequence of a maize CesA7 polypeptide derived from the ORF of the nucleotide sequence set forth in SEQ ID NO:31.

SEQ ID NO:33 is the 3813 bp nucleotide sequence containing the ORF (nucleotides 215-3499) of the CesA8 gene from maize flanked by additional UTR regions 5' (nucleotides 1-214) and 3' (nucleotides 3500-3813) to this ORF region.

SEQ ID NO:34 is the deduced amino acid sequence of a maize CesA8 polypeptide derived from the ORF of the nucleotide sequence set forth in SEQ ID NO:33.

SEQ ID NO:35 is the 3799 bp nucleotide sequence containing the ORF (nucleotides 238-3477) of the CesA9 gene from maize flanked by additional UTR regions 5' (nucleotides 1-237) and 3' (nucleotides 3478-3799) to this ORF region.

SEQ ID NO:36 is the deduced amino acid sequence of a maize CesA9 polypeptide derived from the ORF of the nucleotide sequence set forth in SEQ ID NO:35.

SEQ ID NO:37 is the 3470 bp nucleotide sequence containing the ORF (nucleotides 29-3265) of the CesA10 gene from maize flanked by additional UTR regions 5' (nucleotides 1-28) and 3' (nucleotides 3266-3470) to this ORF region.

SEQ ID NO:38 is the deduced amino acid sequence of a maize CesA10 polypeptide derived from the ORF of the nucleotide sequence set forth in SEQ ID NO:37.

SEQ ID NO:39 is the 3231 bp nucleotide sequence containing the ORF (nucleotides 21-3044) of the CesA11 gene from maize flanked by additional UTR regions 5' (nucleotides 1-20) and 3' (nucleotides 3045-3231) to this ORF region.

SEQ ID NO:40 is the deduced amino acid sequence of a maize CesA11 polypeptide derived from the ORF of the nucleotide sequence set forth in SEQ ID NO:39.

SEQ ID NO:41 is the 3028 bp nucleotide sequence containing the ORF (nucleotides 52-2835) of the CesA12 gene from maize flanked by additional UTR regions 5' (nucleotides 1-51) and 3' (nucleotides 2836-3028) to this ORF region.

SEQ ID NO:42 is the deduced amino acid sequence of a maize CesA12 polypeptide derived from the ORF of the nucleotide sequence set forth in SEQ ID NO:41.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219(2):345-373 (1984) which are herein incorporated by reference. The symbols and format used for nucleotide and amino acid sequence data comply with the rules set forth in 37 C.F.R. §1.822. The sequence descriptions and Sequence Listing attached hereto comply with the rules governing nucleotide and/or amino acid sequence disclosures in patent applications as set forth in 37 C.F.R. §1.821-1.825.

DETAILED DESCRIPTION OF THE INVENTION

All patents, patent applications, and publications cited throughout the application are hereby incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms shall be utilized.

"Transgenic" includes any cell, cell line, callus, tissue, plant part or plant, the genome of which has been altered by the presence of a heterologous nucleic acid, such as a recombinant DNA construct, including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. Different alleles of a gene differ in their DNA sequence. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

"Contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well-established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

The term "amplified" means the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

The term "chromosomal location" includes reference to a length of a chromosome which may be measured by reference to the linear segment of DNA which it comprises. The chromosomal location can be defined by reference to two unique DNA sequences, i.e., markers.

The term "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

Sequence alignments and percent identity calculations may be determined using a variety of comparison methods designed to detect homologous sequences including, but not limited to, the Megalign program of the LASARGENE bioinformatics computing suite (DNASTAR Inc., Madison, Wis.). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Unless otherwise stated, "BLAST" sequence identity/similarity values provided herein refer to the value obtained using the BLAST 2.0 suite of programs using default parameters (Altschul et al., *Nucleic Acids Res.* 25:3389-3402 (1997)). Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=$^-$4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

As used herein, "any integer from 51% up to and including 100%" means 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%".

As used herein, "any integer from 61% up to and including 100%" means 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%".

As used herein, "any integer from 81% up to and including 100%" means 81%, 82%, 83%, 84%, 85%, 86%, 87%, 88%, 89%, 90%, 91%, 92%, 93%, 94%, 95%, 96%, 97%, 98%, 99%, or 100%".

As used herein, "80%, 85%, 90%, 95%, 96%, 97%, 98%, 99% or 100% sequence identity, or any other integer in between 80% and 100%" means 80%, 81%, 82%, 83%, 84%, 85%, 86%, 87%, 88%, 89%, 90%, 91%, 92%, 93%, 94%, 95%, 96%, 97%, 98%, 99%, or 100%.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning Now to Preferred Embodiments

Preferred embodiments include isolated polynucleotides and polypeptides, recombinant DNA constructs, compositions (such as plants or seeds) comprising these recombinant DNA constructs, and methods utilizing these recombinant DNA constructs.

Preferred Isolated Polynucleotides and Polypeptides

The present invention includes the following preferred isolated polynucleotides and polypeptides:

In one preferred embodiment, an isolated polynucleotide comprises (a) a nucleotide sequence encoding a polypeptide associated with stalk mechanical strength, wherein said polypeptide has an amino acid sequence of at least 80%, 85%, 90%, 95%, 96%, 97%, 98%, 99% or 100% sequence identity, or any other integer in between 80% and 100%, based on the Clustal V method of alignment, when compared to SEQ ID NOs:2, 4, 6, 8, 10, 12, 14, 16 or 18; or (b) a complement of the nucleotide sequence of (a), wherein the complement and the nucleotide sequence consist of the same number of nucleotides and are 100% complementary (i.e., a full-length complement of the nucleotide sequence of (a)). Preferably, the polypeptide is associated with maize stalk mechanical strength, and the amino acid sequence of the polypeptide is compared to SEQ ID NOs:16 or 18.

In another preferred embodiment, an isolated polynucleotide comprises (a) a nucleic acid sequence of at least 60% sequence identity, or any integer from 61% up to and including 100% sequence identity, based on the Clustal V method of alignment, when compared to SEQ ID NOs:1, 3, 5, 7, 9, 11, 13, 15, and 17, or (b) a full-length complement of said nucleic acid sequence of (a).

In another preferred embodiment, an isolated polypeptide associated with stalk mechnical strength comprises an amino acid sequence of at least 80%, 85%, 90%, 95%, 96%, 97%, 98%, 99% or 100% sequence identity, or any other integer in between 80% and 100%, based on the Clustal V method of alignment, when compared to SEQ ID NOs:2, 4, 6, 8, 10, 12, 14, 16 or 18.

Several methods may be used to measure the stalk mechanical strength of plants. Preferably, the mechanical strength may be measured with an electromechanical test system. In the case of maize stalk mechanical strength, in a preferred method, the internodes below the ear may be subjected to a three-point bend test using an Instron, Model 4411 (Instron Corporation, 100 Royall Street, Canton, Mass. 02021), with a span-width of 200 mm between the anchoring points and a speed of 200 mm/minute of the third point attached to a load cell; the load needed to break the internode can be used as a measure of mechanical strength (hereinafter "the three-point bend test"). Internodal breaking strength has been shown to be highly correlated with the amount of cellulose per unit length of the maize stalk (see U.S. Patent Application No. 2004068767 A1, herein incorporated by reference).

A polypeptide is "associated with stalk mechanical strength" in that the absence of the polypeptide in a plant results in a reduction of stalk mechanical strength of the plant when compared to a control plant that expresses the polypeptide.

A polypeptide is "associated with maize stalk mechanical strength" in that the absence of the polypeptide in a maize plant results in a reduction of stalk mechanical strength of the maize plant when compared to a control maize plant that expresses the polypeptide.

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Preferred Recombinant DNA Constructs and Suppression DNA Constructs

The present invention also includes a recombinant DNA construct comprising at least one polynucleotide operably linked to at least one regulatory sequence (e.g., preferably, a promoter that is functional in said plant), wherein said polynucleotide comprises any isolated polynucleotide of the present invention.

In one preferred embodiment, a recombinant DNA construct comprises a promoter that is functional in a plant operably linked to (a) a polynucleotide encoding a polypeptide having an amino acid sequence of at least 80% sequence identity, or any integer from 81% up to and including 100% sequence identity, based on the Clustal V method of alignment, when compared to SEQ ID NOs:2, 4, 6, 8, 10, 12, 14, 16, and 18, or (b) a full-length complement of said polynucleotide of (a).

In anther preferred embodiment, a recombinant DNA construct comprises a promoter that is functional in a plant operably linked to (a) a polynucleotide having a nucleic acid sequence of at least 60% sequence identity, or any integer from 61% up to and including 100% sequence identity, based on the Clustal V method of alignment, when compared to SEQ ID NOs:1, 3, 5, 7, 9, 11, 13, 15, and 17, or (b) a full-length complement of said polynucleotide of (a).

The present invention also includes a suppression DNA construct.

In one preferred embodiment, a suppression DNA construct comprises a promoter functional in a plant operably linked to (a) all or part of (i) a nucleic acid sequence encoding a polypeptide having an amino acid sequence of at least 50% sequence identity, or any integer from 51% up to and including 100% sequence identity, based on the Clustal V method of alignment, when compared to SEQ ID NOs:2, 4, 6, 8, 10, 12, 14, 16, and 18, or (ii) a full-length complement of the nucleic acid sequence of (a) (i); or (b) a region derived from all or part of a sense strand or antisense strand of a target gene of interest, said region having a nucleic acid sequence of at least 50% sequence identity, or any integer from 51% up to and including 100% sequence identity, based on the Clustal V method of alignment, when compared to said all or part of a sense strand or antisense strand from which said region is derived, and wherein said target gene of interest encodes a polypeptide selected from the group consisting of Bk2, Bk2L1, Bk2L3, Bk2L4, Bk2L5, Bk2L6, Bk2L7, Bk2L8 and Bk2L9.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50% or any integer between 51% and 100% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target protein. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al. (1998) *Plant J.* 16:651-659; and Gura (2000) *Nature* 404:804-808).

Another variation describes the use of plant viral sequences to direct the suppression of proximal mRNA encoding sequences (PCT Publication WO 98/36083 published on Aug. 20, 1998).

Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression see Wesley, S. V. et al. (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (WO 99/61632 published on Dec. 2, 1999).

The use of poly-T and poly-A sequences to generate the stem in the stem-loop structure has also been described (WO 02/00894 published Jan. 3, 2002).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication WO 02/00904, published 03 Jan. 2002.

RNA interference refers to the process of sequence-specific post-transcriptional gene silencing in animals mediated by short interfering RNAs (siRNAs) (Fire et al., *Nature* 391: 806 1998). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 1999). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein et al., *Nature* 409:363 (2001)). Short interfering RNAs derived from dicer activity are typically about 21 to about 23 nucleotides in length and comprise about 19 base pair duplexes (Elbashir et al., *Genes Dev.* 15:188 (2001)). Dicer has also been implicated in the excision of 21- and 22-nucleotide small temporal RNAs (stRNAs) from precursor RNA of conserved structure that are implicated in translational control (Hutvagner et al., *Science* 293:834 (2001)). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir et al., *Genes Dev.* 15:188 (2001)). In addition, RNA interference can also involve small RNA (e.g., miRNA) mediated gene silencing, presumably through cellular mechanisms that regulate chromatin structure and thereby prevent transcription of target gene sequences (see, e.g., Allshire, *Science* 297:1818-1819 (2002); Volpe et al., *Science* 297:1833-1837 (2002); Jenuwein, *Science* 297: 2215-2218 (2002); and Hall et al., *Science* 297:2232-2237 (2002)). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (*Nature* 391:806 (1998)) were the first to observe RNAi in *C. elegans*. Wianny and Goetz (*Nature Cell BioL* 2:70 (1999))

describe RNAi mediated by dsRNA in mouse embryos. Hammond et al. (*Nature* 404:293 (2000)) describe RNAi in Drosophila cells transfected with dsRNA. Elbashir et al., (*Nature* 411:494 (2001)) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

It is thought that sequence complementarity between small RNAs and their RNA targets helps to determine which mechanism, RNA cleavage or translational inhibition, is employed. It is believed that siRNAs, which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level. Again, without being held to a particular theory on the mechanism of action, a general rule is emerging that perfect or near-perfect complementarity causes RNA cleavage, whereas translational inhibition is favored when the miRNA/target duplex contains many mismatches. The apparent exception to this is microRNA 172 (miR172) in plants. One of the targets of miR172 is APETALA2 (AP2), and although miR172 shares near-perfect complementarity with AP2 it appears to cause translational inhibition of AP2 rather than RNA cleavage.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures. In animals, the enzyme involved in processing miRNA precursors is called Dicer, an RNAse III-like protein (Grishok et al., *Cell* 106:23-34 2001; Hutvagner et al., *Science* 293:834-838 (2001); Ketting et al., *Genes. Dev.* 15:2654-2659 (2001)). Plants also have a Dicer-like enzyme, DCL1 (previously named CARPEL FACTORY/SHORT INTEGUMENTS1/SUSPENSOR1), and recent evidence indicates that it, like Dicer, is involved in processing the hairpin precursors to generate mature miRNAs (Park et al., *Curr. Biol.* 12:1484-1495 (2002); Reinhart et al., *Genes. Dev.* 16:1616-1626 (2002)). Furthermore, it is becoming clear from recent work that at least some miRNA hairpin precursors originate as longer polyadenylated transcripts, and several different miRNAs and associated hairpins can be present in a single transcript (Lagos-Quintana et al., *Science* 294:853-858 (2001); Lee et al., *EMBO J* 21:46634670 2002). Recent work has also examined the selection of the miRNA strand from the dsRNA product arising from processing of the hairpin by DICER (Schwartz, et al. *Cell* 115:199-208(2003)). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

MicroRNAs appear to regulate target genes by binding to complementary sequences located in the transcripts produced by these genes. In the case of lin-4 and let-7, the target sites are located in the 3' UTRs of the target mRNAs (Lee et al., *Cell* 75:843-854 (1993); Wightman et al., *Cell* 75:855-862 (1993); Reinhart et al., *Nature* 403:901-906 (2000); Slack et al., *Mol. Cell* 5:659-669 (2000)), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, *Dev. Biol.* 216:671-680 (1999)). On the other hand, recent evidence suggests that miRNAs can in some cases cause specific RNA cleavage of the target transcript within the target site, and this cleavage step appears to require 100% complementarity between the miRNA and the target transcript (Hutvagner and Zamore, *Science* 297:2056-2060 (2002); Llave et al., *Plant Cell* 14:1605-1619 (2002)). It seems likely that miRNAs can enter at least two pathways of target gene regulation: Protein downregulation when target complementarity is<100%, and RNA cleavage when target complementarity is 100%. MicroRNAs entering the RNA cleavage pathway are analogous to the 21-25 nt short interfering RNAs (siRNAs) generated during RNA interference (RNAi) in animals and posttranscriptional gene silencing (PTGS) in plants (Hamilton and Baulcombe (1999); Hammond et al., (2000); Zamore et al., (2000); Elbashir et al., (2001)), and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al., *Plant Cell* 14:1605-1619 (2002); Park et al., *Curr. Biol.* 12:1484-1495 (2002); Rhoades et al., *Cell* 110:513-520 (2002)), and thus it appears that plant miRNAs have higher overall complementarity with their putative targets than do animal miRNAs. Most of these predicted target transcripts of plant miRNAs encode members of transcription factor families implicated in plant developmental patterning or cell differentiation.

Preferred regulatory elements of recombinant DNA constructs and suppression DNA constructs.

A number of promoters can be used in recombinant DNA constructs and suppression DNA constructs of the present invention. The promoters can be selected based on the desired outcome, and may include constitutive, tissue-specific, inducible, or other promoters for expression in the host organism.

High level, constitutive expression of the candidate gene under control of the 35S promoter may have pleiotropic affects. However, tissue specific and/or stress-specific expression may eliminate undesirable affects but retain the ability to enhance drought tolerance. This affect has been observed in Arabidopsis (Kasuga et al., Nature Biotechnol.

17:287-91 (1999)). As such, candidate gene efficacy may be tested when driven by different promoters.

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter. A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

A preferred stalk-specific promoter is the alfalfa stalk-specific S2A gene (Abrahams et al., *Plant Mol. Biol.* 27:513-528 (1995))

Promoters which are seed or embryo specific and may be useful in the invention include soybean Kunitz trysin inhibitor (Kti3, Jofuku and Goldberg, Plant Cell 1:1079-1093 (1989)), patatin (potato tubers) (Rocha-Sosa et al., EMBO J. 8:23-29 (1989)), convicilin, vicilin, and legumin (pea cotyledons) (Rerie, W. G., et al. *Mol. Gen. Genet* 259:149-157 (1991); Newbigin, E. J., et al., *Planta* 180:461-470 (1990); Higgins, T. J. V., et al., *Plant Mol. Biol.* 11:683-695 (1988)), zein (maize endosperm) (Schemthaner, J. P., et al., *EMBO J.* 7:1249-1255 (1988)), phaseolin (bean cotyledon) (Segupta-Gopalan, C., et al., *Proc. Natl. Acad. Sci.* U.S.A. 82:3320-3324 (1985)), phytohemagglutinin (bean cotyledon) (Voelker, T. et al., *EMBO J.* 6:3571-3577 (1987)), B-conglycinin and glycinin (soybean cotyledon) (Chen, Z-L, et al., *EMBO J.* 7:297-302 (1988)), glutelin (rice endosperm), hordein (barley endosperm) (Marris, C., et al., *Plant Mol. Biol.* 10:359-366 (1988)), glutenin and gliadin (wheat endosperm) (Colot, V., et al., *EMBO J.* 6:3559-3564 (1987)), and sporamin (sweet potato tuberous root) (Hattori, T., et al., *Plant Mol. Biol.* 14:595-604 (1990)). Promoters of seed-specific genes operably linked to heterologous coding regions in chimeric gene constructions maintain their temporal and spatial expression pattern in transgenic plants. Such examples include Arabidopsis thaliana 2S seed storage protein gene promoter to express enkephalin peptides in Arabidopsis and Brassica napus seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J.* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters which are timed to stress include the following: 1) the RD29A promoter (Kasuga et al., *Nature Biotechnol.* 17:287-291 (1991)); 2) barley promoter, B22E; expression of B22E is specific to the pedicel in developing maize kernels ("Primary Structure of a Novel Barley Gene Differentially Expressed in Immature Aleurone Layers". Klemsdae, S. S. et al., *Mol. Gen. Genet* 228(1/2):9-16 (1991)); and 3) maize promoter, Zag2 ("Identification and molecular characterization of ZAG1, the maize homolog of the Arabidopsis floral homeotic gene AGAMOUS", Schmidt, R. J. et al., *Plant Cell* 5(7):729-737 (1993)). Zag2 transcripts can be detected 5 days prior to pollination to 7 to 8 DAP, and directs expression in the carpel of developing female inflorescences and CimI which is specific to the nucleus of developing maize kernels. CimI transcript is detected 4 to 5 days before pollination to 6 to 8 DAP. Other useful promoters include any promoter which can be derived from a gene whose expression is maternally associated with developing female florets.

Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B., *Biochemistry of Plants* 15:1-82 (1989).

Particularly preferred promoters may include: alfalfa stalk-specific S2A gene promoter, RIP2, mLIP15, ZmCOR1, Rab17, CaMV 35S, RD29A, SAM synthetase, ubiquitin, CaMV 19S, nos, Adh, sucrose synthase, R-allele, or root cell promoter. Other preferred promoters include any of the CesA10, CesA11, and CesA12 promoters disclosed in United States Patent Publication 2005/0086712A1, which is hereby incorporated by reference in its entirety.

Recombinant DNA constructs and suppression DNA constructs of the present invention may also include other regulatory sequences, including but not limited to, translation leader sequences, introns, and polyadenylation recognition sequences. In another preferred embodiment of the present invention, a recombinant DNA construct of the present invention further comprises an enhancer or silencer.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395-4405 (1988); Callis et al., *Genes Dev.* 1:1183-1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

A translation leader sequence is a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Molecular Biotechnology* 3:225 (1995)).

Any plant can be selected for the identification of regulatory sequences and genes to be used in creating recombinant DNA constructs and suppression DNA constructs of the present invention. Examples of suitable plant targets for the isolation of genes and regulatory sequences would include but are not limited to alfalfa, apple, apricot, Arabidopsis, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly preferred plants for the identification of regulatory sequences are Arabidopsis, corn, wheat, soybean, and cotton.

In another preferred embodiment of the present invention, a recombinant DNA construct of the present invention further comprises an enhancer.

Preferred Compositions

A preferred composition of the present invention is a plant comprising in its genome any of the recombinant DNA constructs of the present invention (such as those preferred constructs discussed above).

Another preferred composition is a plant whose genome comprises a disruption (e.g., an insertion, such as a transposable element, or sequence mutation) of at least one gene (which may be heterologous or endogenous to the genome) selected from the group consisting of Bk2, Bk2L1, Bk2L3, Bk2L4, Bk2L5, Bk2L6, Bk2L7, Bk2L8 and Bk2L9.

Still another preferred composition is a plant whose genome comprises other recombinant DNA constructs as discussed below (e.g., constructs involving nucleic acid sequences and amino acid sequences relating to SEQ ID NOs:20-42).

Preferred compositions also include any progeny of the plant, and any seed obtained from the plant or its progeny. Progeny includes subsequent generations obtained by self-pollination or out-crossing of a plant. Progeny also includes hybrids and inbreds.

Preferably, in hybrid seed propagated crops, mature transgenic plants can be self-crossed to produce a homozygous inbred plant. The inbred plant produces seed containing the newly introduced recombinant DNA construct. These seeds can be grown to produce plants that would contain the recombinant DNA construct in its genome and exhibit the associated phenotype(s) as described herein, or used in a breeding program to produce hybrid seed, which can be grown to produce plants that would contain the recombinant DNA construct and exhibit the associated phenotype(s) as described herein. Preferably, the seeds are maize.

Preferably, the plant is a monocotyledonous or dicotyledonous plant, more preferably, a maize or soybean plant, even more preferably a maize plant, such as a maize hybrid plant or a maize inbred plant. The plant may also be sunflower, sorghum, canola, wheat, alfalfa, cotton, rice, barley or millet.

Preferably, any recombinant DNA construct is stably integrated into the genome of the plant.

Particularly preferred embodiments include:

1. A plant (preferably maize) comprising in its genome a recombinant DNA construct comprising at least one regulatory element operably linked to (a) a nucleotide sequence encoding a polypeptide associated with stalk mechanical strength, wherein said polypeptide has an amino acid sequence of at least 80%, 85%, 90%, 95%, 96%, 97%, 98%, 99% or 100% sequence identity, or any other integer in between 80% and 100%, based on the Clustal V method of alignment, when compared to SEQ ID NOs:16 or 18; or (b) a complement of the nucleotide sequence, wherein the complement and the nucleotide sequence consist of the same number of nucleotides and are 100% complementary (i.e., a full length complement of the nucleotide sequence of (a)). Preferably, the at least one regulatory element is a promoter that is functional in a plant.

2. A plant (preferably maize) comprising in its genome (a) a first recombinant DNA construct comprising at least one promoter that is functional in a plant operably linked to at least one of a first isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NOs:2, 4, 6, 8, 10, 12, 14, 16, and 18; (ii) a polynucleotide having a nucleic acid sequence of at least 60% sequence identity, or any integer from 61% up to and including 100% sequence identity, based on the Clustal V method of alignment, when compared to SEQ ID NOs:1, 3, 5, 7, 9, 11, 13, 15, and 17; and (iii) a full-length complement of the polynucleotide of (a) (i) or (a) (ii); and (b) a second recombinant DNA construct comprising at least one promoter that is functional in a plant operably linked to at least one of a second isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NOs:20, 22, 24, 26, 28, 30, 32, 34, 36, 38, 40, and 42; (ii) a polynucleotide having a nucleic acid sequence of at least 60% sequence identity, or any integer from 61% up to and including 100% sequence identity, based on the Clustal V method of alignment, when compared to SEQ ID NOs:21, 23, 25, 27, 29, 31, 33, 35, 37, 39, and 41; and (iii) a full-length complement of the polynucleotide of (b) (i) or (b) (ii). Preferably, the plant exhibits increased cell wall cellulose content and/or enhanced growth rate when compared to a control plant not comprising said first recombinant DNA construct and said second recombinant DNA construct.

3. A plant (preferably maize) comprising in its genome at least one regulatory sequence operably linked to (a) at least one isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NOs:2, 4, 6, 8, 10, 12, 14, 16, and 18; (ii) a polynucleotide having a nucleic acid sequence of at least 60% sequence identity, or any integer from 61% up to and including 100% sequence identity, based on the Clustal V method of alignment, when compared to SEQ ID NOs:1, 3, 5, 7, 9, 11, 13, 15, and 17; and (iii) a full-length complement of the polynucleotide of (a) (i) or (a) (ii); and (b) at least one isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NOs:20, 22, 24, 26, 28, 30, 32, 34, 36, 38, 40, and 42; (ii) a polynucleotide having a nucleic acid sequence of at least 60% sequence identity, or any integer from 61% up to and including 100% sequence identity, based on the Clustal V method of alignment, when compared to SEQ ID NOs:21, 23, 25, 27, 29, 31, 33, 35, 37, 39, and 41; and (iii) a full-length complement of the polynucleotide of (b) (i) or (b) (ii). Preferably, the plant exhibits increased cell wall cellulose content and/or enhanced growth rate when compared to a control plant not comprising said at least one regulatory sequence operably linked to said (a) and (b).

4. A plant (preferably maize) comprising in its genome at least one regulatory sequence operably linked to (a) at least one isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NO:2; (ii) a polynucleotide having a nucleic acid sequence of at least 60% sequence identity, or any integer from 61% up to and including 100% sequence identity, based on the Clustal V method of alignment, when compared to SEQ ID NO:1; and (iii) a full-length complement of the polynucleotide of (a) (i) or (a) (ii); and (b) at least one isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NOs:38, 40, and 42; (ii) a polynucleotide having a nucleic acid sequence of at least 60% sequence identity, or any integer from 61% up to and including 100% sequence identity, based on the Clustal V method of alignment, when compared to SEQ ID NOs:37, 39, and 41; and (iii) a full-length complement of the polynucleotide of (b) (i) or (b) (ii). Preferably, the plant exhibits increased cell wall cellulose content when compared to a control plant not comprising said at least one regulatory sequence operably linked to said (a) and (b).

5. A plant (preferably maize) comprising in its genome at least one regulatory sequence operably linked to (a) at least one isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NO:6; (ii) a polynucleotide having a nucleic acid sequence of at least 60% sequence identity, or any integer from 61% up to and including 100% sequence identity, based on the Clustal V method of alignment, when compared to SEQ ID NO:5; and (iii) a full-length complement of the polynucleotide of (a) (i) or (a) (ii); and (b) at least one isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NOs:20, 32, and 34; (ii) a polynucleotide having a nucleic acid sequence of at least 60% sequence identity, or any integer from 61% up to and including 100% sequence identity, based on the Clustal V method of alignment, when compared to SEQ ID NOs:19, 31, and 33; and (iii) a full-length complement of the polynucleotide of (b) (i) or (b) (ii). Preferably, the plant exhibits enhanced growth rate when compared to a control plant not comprising said at least one regulatory sequence operably linked to said (a) and (b).

6. A plant (preferably maize) comprising in its genome at least one regulatory sequence operably linked to at least two isolated polynucleotides selected from the group consisting of (a) a polynucleotide encoding a polypeptide having an amino acid sequence of at least 80% sequence identity, or any integer from 81% up to and including 100% sequence identity, based on the Clustal V method of alignment, when compared to SEQ ID NOs:2, 4, 6, 8, 10, 12, 14, 16, and 18; (b) a polynucleotide having a nucleic acid sequence of at least 60% sequence identity, or any integer from 61% up to and including 100% sequence identity, based on the Clustal V method of alignment, when compared to SEQ ID NOs:1, 3, 5, 7, 9, 11, 13, 15, and 17; and (c) a full-length complement of the polynucleotide of (a) or (b).

7. A plant (preferably maize) comprising in its genome a suppression DNA construct comprising a promoter functional in a plant operably linked to (a) all or part of (i) a nucleic acid sequence encoding a polypeptide having an amino acid sequence of at least 50% sequence identity, or any integer from 51% up to and including 100% sequence identity sequence identity, based on the Clustal V method of alignment, when compared to SEQ ID NOs:2, 4, 6, 8, 10, 12, 14, 16, and 18, or (ii) a full complement of the nucleic acid sequence of (a) (i); or (b) a region derived from all or part of a sense strand or antisense strand of a target gene of interest, said region having a nucleic acid sequence of at least 50% sequence identity, or any integer from 51% up to and including 100% sequence identity sequence identity, based on the Clustal V method of alignment, when compared to said all or part of a sense strand or antisense strand from which said region is derived, and wherein said target gene of interest encodes a polypeptide selected from the group consisting of BK2, Bk2L1, Bk2L3, Bk2L4, Bk2L5, Bk2L6, Bk2L7, Bk2L8 and Bk2L9. Preferably, the plant exhibits reduced stalk mechanical strength when compared to a control plant not comprising said suppression DNA construct. Preferably, the suppression DNA construct comprises a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

8. A plant (preferably maize) whose genome comprises a disruption of at least one gene encoding a polypeptide selected from the group consisting of BK2, Bk2L1, Bk2L3, Bk2L4, Bk2L5, Bk2L6, Bk2L7, Bk2L8 and Bk2L9. Preferably, the disruption results in said plant exhibiting reduced stalk mechanical strength when compared to a control plant not comprising said disruption. Preferably, the disruption comprises an insertion, such as a transposable element or sequence mutation.

9. A plant (preferably maize) comprising in its genome a suppression DNA construct comprising a promoter functional in a plant operably linked to (a) all or part of (i) a nucleic acid sequence encoding a polypeptide having an amino acid sequence of at least 50% sequence identity, or any integer from 51% up to and including 100% sequence identity sequence identity, based on the Clustal V method of alignment, when compared to SEQ ID NO:6, or (ii) a full complement of the nucleic acid sequence of (a) (i); or (b) a region derived from all or part of a sense strand or antisense strand of a target gene of interest, said region having a nucleic acid sequence of at least 50% sequence identity, or any integer from 51% up to and including 100% sequence identity, based on the Clustal V method of alignment, when compared to said all or part of a sense strand or antisense strand from which said region is derived, and wherein said target gene of interest encodes a Bk2L3 polypeptide. Preferably, the plant exhibits reduced plant height and/or reduced organ size when compared to a control plant not comprising said suppression DNA construct. Preferably, the suppression DNA construct comprises a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

10. A plant (preferably maize) whose genome comprises a disruption of at least one gene encoding a Bk2L3 polypeptide. Preferably, said disruption results in said plant exhibiting reduced plant height and/or reduced organ size when compared to a control plant not comprising said disruption. Preferably, the disruption comprises an insertion, such as a transposable element or sequence mutation.

11. A plant (preferably maize) comprising in its genome a suppression DNA construct comprising a promoter functional in a plant operably linked to (a) all or part of (i) a nucleic acid sequence encoding a polypeptide having an amino acid sequence of at least 50% sequence identity, or any integer from 51% up to and including 100% sequence identity sequence identity, based on the Clustal V method of alignment, when compared to SEQ ID NO:10, or (ii) a full complement of the nucleic acid sequence of (a) (i); or (b) a region derived from all or part of a sense strand or antisense strand of a target gene of interest, said region having a nucleic acid sequence of at least 50% sequence identity, or any integer from 51% up to and including 100% sequence identity, based on the Clustal V method of alignment, when compared to said all or part of a sense strand or antisense strand from which said region is derived, and wherein said target gene of interest encodes a Bk2L5 polypeptide. Preferably, the plant exhibits male sterility when compared to a control plant not comprising said suppression DNA construct. Preferably, the suppression DNA construct comprises a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

12. A plant (preferably maize) whose genome comprises a disruption of at least one gene encoding a BKL5 polypeptide. Preferably, the disruption results in said plant exhibiting male sterility when compared to a control plant not comprising said disruption. Preferably, the disruption comprises an insertion, such as a transposable element or sequence mutation.

13. Any progeny of the above plants, any seeds of the above plants, any seeds of progeny of the above plants, and cells from any of the above plants and progeny.

One of ordinary skill in the art would readily recognize a suitable control or reference plant for use in comparing or measuring relative to a plant comprising within its genome a recombinant DNA construct (or suppression DNA construct). For example, by way of non-limiting illustrations:

Progeny of a transformed plant which is hemizygous with respect to a recombinant DNA construct (or suppression DNA construct), such that the progeny are segregating into plants either comprising or not comprising the recombinant DNA construct (or suppression DNA construct): progeny comprising the recombinant DNA construct (or suppression DNA construct) would be typically measured relative to the progeny not comprising the recombinant DNA construct (or suppression DNA construct).

Introgression of a recombinant DNA construct (or suppression DNA construct) into an inbred line, such as in corn, or into a variety, such as in soybean: the introgressed line would typically be measured relative to the parent inbred or variety line.

Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line.

A plant comprising a recombinant DNA construct (or suppression DNA construct) in its genome (or a plant comprising a disruption of a gene in its genome): the plant may be measured relative to a control plant not comprising the recombinant DNA construct (or suppression DNA construct) in its genome (or to a control plant not comprising the disruption) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct or suppression DNA construct or disruption). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or Agrobacterium mediated transformation. Where multiple or stacked recombinant DNA constructs or isolated polynucleotides are desired to be integrated into the genome (e.g., to effect co-expression of two or more isolated polynucleotides), the individual isolated polynucleotides may be introduced into parent lines and crossed through traditional breeding techniques to provide the desired combination or stack in subsequent progeny plants.

Preferred techniques are set forth below in Example 3 for transformation of maize plant cells and in Example 8 for transformation of soybean plant cells.

Other preferred methods for transforming dicots, primarily by use of Agrobacterium tumefaciens, and obtaining transgenic plants include those published for cotton (U.S. Pat. No. 5,004,863, U.S. Pat. No. 5,159,135, U.S. Pat. No. 5,518, 908); soybean (U.S. Pat. No. 5,569,834, U.S. Pat. No. 5,416,011, McCabe et. al., BioITechnology 6:923 (1988), Christou et al., Plant Physiol. 87:671 674 (1988)); Brassica (U.S. Pat. No. 5,463,174); peanut (Cheng et al., Plant Cell Rep. 15:653 657 (1996), McKently et al., Plant Cell Rep. 14:699 703 (1995)); papaya; and pea (Grant et al., Plant Cell Rep. 15:254 258, (1995)).

Transformation of monocotyledons using electroporation, particle bombardment, and Agrobacterium have also been reported and are included as preferred methods, for example, transformation and plant regeneration as achieved in asparagus (Bytebier et al., Proc. Natl. Acad. Sci. (USA) 84:5354, (1987)); barley (Wan and Lemaux, Plant Physiol 104:37 (1994)); Zea mays (Rhodes et al., Science 240:204 (1988), Gordon-Kamm et al., Plant Cell 2:603 618 (1990), Fromm et al., BioITechnology 8:833 (1990), Koziel et al., BioITechnology 11: 194, (1993), Armstrong et al., Crop Science 35:550 557 (1995)); oat (Somers et al., BioITechnology 10: 15 89 (1992)); orchard grass (Horn et al., Plant Cell Rep. 7:469 (1988)); rice (Toriyama et al., TheorAppl. Genet. 205:34, (1986); Part et al., Plant Mol. Biol. 32:1135 1148, (1996); Abedinia et al., Aust. J. Plant Physiol. 24:133 141 (1997); Zhang and Wu, Theor. Appl. Genet. 76:835 (1988); Zhang et al. Plant Cell Rep. 7:379, (1988); Battraw and Hall, Plant Sci. 86:191 202 (1992); Christou et al., Bio/Technology 9:957 (1991)); rye (De la Pena et al., Nature 325:274 (1987)); sugarcane (Bower and Birch, Plant J. 2:409 (1992)); tall fescue (Wang et al., BioITechnology 10:691 (1992)), and wheat (Vasil et al., Bio/Technology 10:667 (1992); U.S. Pat. No. 5,631,152).

There are a variety of methods for the regeneration of plants from plant tissue. The particular method of regeneration will depend on the starting plant tissue and the particular plant species to be regenerated.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous isolated nucleic acid fragment that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art. Assays to detect proteins may be performed by SDS-polyacrylamide gel electrophoresis or immunological assays. Assays to detect levels of substrates or products of enzymes may be performed using gas chromatography or liquid chromatography for separation and UV or visible spectrometry or mass spectrometry for detection, or the like. Determining the levels of mRNA of the enzyme of interest may be accomplished using northern-blotting or RT-PCR techniques. Once plants have been regenerated, and progeny plants homozygous for the transgene have been obtained, plants will have a stable phenotype that will be observed in similar seeds in later generations.

Preferred Methods

The present invention also includes methods for altering stalk mechanical strength in a plant; methods for evaluating stalk mechanical strength in a plant; methods for evaluating cellulose content in plant; methods for altering cell wall cellulose content and/or growth rate in a plant, methods for conferring male sterility in a plant, and methods for reducing plant height and/or organ size in a plant. Preferably, the plant is a monocotyledonous or dicotyledonous plant, more preferably, a maize or soybean plant, even more preferably a maize plant. The plant may also be sunflower, sorghum, canola, wheat, alfalfa, cotton, rice, barley or millet.

A preferred method for altering (preferably increasing) stalk mechanical strength of a plant comprises (a) introducing a recombinant DNA construct into a regenerable plant cell to produce a transformed plant cell, the recombinant DNA construct comprising at least one regulatory element (preferably, a promoter that is functional in a plant) operably linked to (i) a nucleotide sequence encoding a polypeptide associated with stalk mechanical strength, wherein said polypeptide has an amino acid sequence of at least 80%, 85%, 90%, 95%, 96%, 97%, 98%, 99% or 100% sequence identity, or any other integer in between 80% and 100%, based on the Clustal V method of alignment, when compared to SEQ ID NOs:4, 6, 8, 10, 12, 14, 16 or 18, or (ii) a complement of the nucleotide sequence, wherein the complement and the nucleotide sequence consist of the same number of nucleotides and are 100% complementary; and (b) regenerating a transgenic plant from said transformed plant cell, wherein said transgenic plant comprises in its genome said recombinant DNA construct and wherein said transgenic plant exhibits an alteration (preferably an increase) in stalk mechanical strength, when compared to a control plant not comprising said recombinant DNA construct.

A preferred method of evaluating stalk mechanical strength in a plant comprises (a) introducing into a regenerable plant cell a recombinant DNA construct to produce transformed plant cells, said recombinant DNA construct comprising a promoter that is functional in a plant operably linked to (i) a polynucleotide encoding a polypeptide having an amino acid sequence of at least 80% sequence identity, or any integer from 81% up to and including 100% sequence identity, based on the Clustal V method of alignment, when compared to SEQ ID NOs:4, 6, 8, 10, 12, 14, 16, and 18, or (ii) a full-length complement of said polynucleotide of (a) (i); (b) regenerating a transgenic plant from said transformed plant cell; and (c) evaluating said transgenic plant for stalk mechanical strength. This method may further comprise (d) obtaining a progeny plant derived from said transgenic plant; and (e) evaluating said progeny plant for stalk mechanical strength.

Another preferred method of evaluating stalk mechanical strength in a plant comprises (a) introducing into a regenerable plant cell a recombinant DNA construct to produce transformed plant cells, said recombinant DNA construct comprising a promoter that is functional in a plant operably linked to (i) a polynucleotide encoding a polypeptide having an amino acid sequence of at least 80% sequence identity, or any integer from 81% up to and including 100% sequence identity, based on the Clustal V method of alignment, when compared to SEQ ID NOs:4, 6, 8, 10, 12, 14, 16, and 18, or (b) a full-length complement of said polynucleotide of (a) (i); (b) regenerating a transgenic plant from said transformed plant cell; (c) obtaining a progeny plant derived from said transgenic plant; and (d) evaluating said progeny plant for stalk mechanical strength.

A preferred method of evaluating cellulose content in a plant, comprises (a) introducing into a regenerable plant cell a recombinant DNA construct to produce transformed plant cells, said recombinant DNA construct comprising a polynucleotide operably linked to a promoter that is functional in a plant, wherein said polynucleotide encodes a polypeptide having an amino acid sequence of at least 80% sequence identity, or any integer from 81% up to and including 100% sequence identity, based on the Clustal V method of alignment, when compared to SEQ ID NOs:4, 6, 8, 10, 12, 14, 16, and 18; (b) regenerating a transgenic plant from said transformed plant cell; and (c) evaluating said transgenic plant for cellulose content. This method may further comprise (d) obtaining a progeny plant derived from said transgenic plant; and (e) evaluating said progeny plant for cellulose content.

Another preferred method of evaluating cellulose content in a plant comprises (a) introducing into a regenerable plant cell a recombinant DNA construct to produce transformed plant cells, said recombinant DNA construct comprising a polynucleotide operably linked to a promoter that is functional in a plant, wherein said polynucleotide encodes a polypeptide having an amino acid sequence of at least 80% sequence identity, or any integer from 81% up to and including 100% sequence identity, based on the Clustal V method of alignment, when compared to SEQ ID NOs:4, 6, 8, 10, 12, 14, 16, and 18; (b) regenerating a transgenic plant from said transformed plant cell; (c) obtaining a progeny plant derived from said transgenic plant; and (d) evaluating said progeny plant for cellulose content.

A preferred method for selecting a plant with altered cellulose content comprises (a) obtaining any plant of the present invention (such as any of the preferred embodiments discussed above); (b) evaluating the plant obtained in step (a) for cellulose content; and (c) selecting the evaluated plant of step (b) when its cellulose content is altered when compared to a control plant. Preferably, the evaluated plant is selected when its cellulose content is increased, even more preferably, when the cellulose content is at least 35%, 40%, 45%, 50%, 55%, or 60% and/or when the cellulose dry matter content is at least 100 mg/cm, 200 mg/cm, 300 mg/cm, 400 mg/cm, or 500 mg/cm. Preferred methods for measuring cellose content are set forth herein in Example 10.

A preferred method for altering (preferably increasing) cell wall cellulose content and/or for altering (preferably enhancing) growth rate in a plant comprises integrating (e.g., through transgenic techniques or a combination of transgenic techniques and traditional breeding) into the genome of a plant one or more recombinant DNA constructs such that the co-expression is obtained of (a) at least one isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NOs:2, 4, 6, 8, 10, 12, 14, 16, and 18; (ii) a polynucleotide having a nucleic acid sequence of at least 60% sequence identity, or any integer from 61% up to and including 100% sequence identity, based on the Clustal V method of alignment, when compared to SEQ ID NO s:1, 3, 5, 7, 9, 11, 13, 15, and 17; and (iii) a full-length complement of the polynucleotide of (a) (i) or (a) (ii); and (b) at least one isolated polynucleotide selected from the group consisting of (i) a polynucleotide encoding a polypeptide having an amino acid sequence of at least 81% sequence identity, or any integer up to and including 100% sequence identity, based on the Clustal V method of alignment, when compared to SEQ ID NOs:20, 22, 24, 26, 28, 30, 32, 34, 36, 38, 40, and 42; (ii) a polynucleotide having a nucleic acid sequence of at least 61% sequence identity, or any integer up to and including 100% sequence identity, based on the Clustal V method of alignment, when compared to SEQ ID NOs:21, 23, 25, 27, 29, 31, 33, 35, 37, 39, and 41; and (iii) a full-length complement of the polynucleotide of (b) (i) or (b) (ii).

Preferably, a method for increasing cell wall cellulose content in a plant comprises integrating into the genome of a plant one or more recombinant DNA constructs such that the co-expression is obtained of (a) at least one isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NO:2; (ii) a polynucleotide having a nucleic acid sequence of at least 60% sequence identity, or any integer from 61% up to and including 100% sequence identity, based on the Clustal V method of alignment, when compared to SEQ ID NO:1; and (iii) a full-length complement of the polynucleotide of (a) (i) or (a) (ii); and (b) at least one isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NOs:38, 40, and 42; (ii) a polynucleotide having a nucleic acid sequence of at least 60% sequence identity, or any integer from 61% up to and including 100% sequence identity, based on the Clustal V method of alignment, when compared to SEQ ID NOs:37, 39, and 41; and (iii) a full-length complement of the polynucleotide of (b) (i) or (b) (ii).

Preferably, a method for enhancing plant growth rate comprises integrating into the genome of a plant one or more recombinant DNA constructs such that the co-expression is obtained of (a) at least one isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NO:6; (ii) a polynucleotide having a nucleic acid sequence of at least 60% sequence identity, or any integer from 61% up to and including 100% sequence identity, based on the Clustal V method of alignment, when compared to SEQ ID NO:5; and (iii) a full-length complement of the polynucleotide of (a) (i) or (a) (ii); and (b) at least one isolated polynucleotide selected from the group consisting of (i) a polynucleotide encoding a polypeptide having an amino acid sequence of at least 80% sequence identity, or any integer from 81% up to and including 100% sequence identity, based on the Clustal V method of alignment, when compared to SEQ ID NOs:20, 32, and 34; (ii) a polynucleotide having a nucleic acid sequence of at least 60% sequence identity, or any integer from 61% up to and including 100% sequence identity, based on the Clustal V method of alignment, when compared to SEQ ID NOs:19, 31, and 33; and (iii) a full-length complement of the polynucleotide of (b) (i) or (b) (ii).

A preferred method of conferring male sterility in a plant comprises: (a) introducing into a regenerable plant cell a suppression DNA construct comprising a promoter functional in a plant operably linked to (i) all or part of (A) a nucleic acid sequence encoding a polypeptide having an amino acid sequence of at least 50% sequence identity, or any integer from 51% up to and including 100% sequence identity sequence identity, based on the Clustal V method of alignment, when compared to SEQ ID NO:10, or (B) a full complement of the nucleic acid sequence of (i) (A); or (ii) a region derived from all or part of a sense strand or antisense strand of a target gene of interest, said region having a nucleic acid sequence of at least 50% sequence identity, or any integer from 51% up to and including 100% sequence identity, based on the Clustal V method of alignment, when compared to said all or part of a sense strand or antisense strand from which said region is derived, and wherein said target gene of interest encodes a Bk2L5 polypeptide; and (b) regenerating a transgenic plant from said transformed plant cell, wherein said transgenic plant comprises in its genome said suppression DNA construct and wherein said transgenic plant exhibits reduced plant height and/or reduced organ size when compared to a control plant not comprising said suppression DNA construct. The method may further comprise: (c) obtaining a progeny plant derived from said transgenic plant, wherein said progeny plant comprises in its genome the suppression DNA construct.

A preferred method of reducing plant height and/or reducing organ size in a plant comprises: (a) introducing into a regenerable plant cell a suppression DNA construct comprising a promoter functional in a plant operably linked to (i) all or part of (A) a nucleic acid sequence encoding a polypeptide having an amino acid sequence of at least 50% sequence identity, or any integer from 51% up to and including 100% sequence identity sequence identity, based on the Clustal V method of alignment, when compared to SEQ ID NO:6, or (B) a full complement of the nucleic acid sequence of (i) (A); or (ii) a region derived from all or part of a sense strand or antisense strand of a target gene of interest, said region having a nucleic acid sequence of at least 50% sequence identity, or any integer from 51% up to and including 100% sequence identity, based on the Clustal V method of alignment, when compared to said all or part of a sense strand or antisense strand from which said region is derived, and wherein said target gene of interest encodes a Bk2L3 polypeptide; and (b) regenerating a transgenic plant from said transformed plant cell, wherein said transgenic plant comprises in its genome said suppression DNA construct and wherein said transgenic plant exhibits reduced plant height and/or reduced organ size when compared to a control plant not comprising said suppression DNA construct. The method may further comprise: (c) obtaining a progeny plant derived from said transgenic plant, wherein said progeny plant comprises in its genome the suppression DNA construct.

The isolated nucleic acids and proteins and any embodiments of the present invention can be used over a broad range of plant types, particularly monocots such as the species of the Family Graminiae including *Sorghum bicolor* and *Zea mays*. The isolated nucleic acid and proteins of the present invention can also be used in species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Triticum, Bambusa, Dendrocalamus,* and *Melocanna*.

EXAMPLES

The present invention is further illustrated in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Characterization of Maize cDNA Encoding Bk2-Like Proteins

The maize brittle stalk 2 (bk2) phenotype was first reported in 1940 (Langham, *MNL* 14:21-22 (1940)), and was mapped by phenotype to chr9L between the markers umc95 and bnl7.13 around the 100 centiMorgan region (Howell et al., *MNL* 65:52-53 (1991)). Previously, clone csc1c.pk005.k4:fis (SEQ ID NO:1) was shown to encode a BRITTLE STALK 2 polypeptide (SEQ ID NO:2) (International Application No. PCT/US2005/035450 which claims the benefit of U.S. Provisional Application No. 60/615,868, filed Oct. 6, 2004, the entire contents of which are herein incorporated by reference). Also disclosed were two other members of the Bk2 gene family (SEQ ID NOs:7 and 8 and SEQ ID NOs:13 and 14). In the instant disclosure these genes have been named as Bk2-like (Bk2L).

Search for additional maize cDNA sequences homologous at the nucleic acid and amino acid level to the maize BRITTLE STALK 2 (Bk2) sequence (SEQ ID NO:1) was conducted using BLASTN or TBLASTN algorithm provided by the National Center for Biotechnology Information (NCBI) against several databases, including, but not limited to, DuPont's internal proprietary database (Basic Local Alignment Search Tool; Altschul et al., *J. Mol. Biol.* 215:403-410 (1993); Altschul et al., *Nucleic Acids Res.* 25:3389-3402 (1997)) and publicly available Maize Genomic Survey Sequences (GSS) and TIGR Maize genomic assemblies (The TIGR Gene Index Databases, The Institute for Genomic Research, Rockville, Md. 20850; Quackenbush et al., *J. Nucleic Acids Res.* 28(1):141-145 (2000)). Six new members of the Bk2 gene family were isolated (Bk2L1, Bk2L3, Bk2L5, Bk2L6, Bk2L8 and Bk2L9). Table 1 lists all the Bk2-like proteins disclosed in the instant specification, in addition to Bk2 itself.

TABLE 1

Brittle Stalk 2-like Proteins

| Protein | SEQ ID NO: | |
|---|---|---|
| | Nucleotide | Amino Acid |
| Bk2 | 1 | 2 |
| Bk2L1 | 3 | 4 |
| Bk2L3 | 5 | 6 |
| Bk2L4 | 7 | 8 |
| Bk2L5 | 9 | 10 |

TABLE 1-continued

Brittle Stalk 2-like Proteins

| Protein | SEQ ID NO: | |
|---|---|---|
| | Nucleotide | Amino Acid |
| Bk2L6 | 11 | 12 |
| Bk2L7 | 13 | 14 |
| Bk2L8 | 15 | 16 |
| Bk2L9 | 17 | 18 |

FIGS. 1A-1F show a Clustal V alignment, using default parameters, of the amino acid sequences reported in Table 1. FIG. 2 is a chart setting forth a comparison of the percent identity (and percent divergence in the lower half triangle), using the Clustal V alignment method, between the nine amino acid sequences shown in FIGS. 1A-1F.

The possible function of the polypeptide encoded by each cDNA was further identified by conducting BLAST (Basic Local Alignment Search Tool; Altschul, S. F., et al., *J. Mol. Biol.* 215:403-410 (1993)) searches of the ESTs against public databases. The searches were conducted for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The sequences were analyzed for similarity using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J., *Nature Genetics* 3:266-272 (1993)) provided by the NCBI. Shown in Table 2 are the "Score" results obtained for the amino acid sequences of the entire Bk2-like proteins encoded by the entire cDNA inserts comprising the indicated cDNA clones. The data in Table 2 also presents the results obtained for the calculation of the percent identity of the amino acid sequences set forth in SEQ ID NOs:2, 4, 6, 8, 10, 12, 14, 16 and 18, with the sequences identified in the NCBI General Identifier No. column.

TABLE 2

BLAST Results for Sequences Encoding Polypeptides Homologous to Bk2-like Proteins

| Gene (SEQ ID NO:) | NCBI General Identifier No. (Accession No.) | Score (bits) | Percent Identity |
|---|---|---|---|
| Bk2L1 (SEQ ID NO: 3) | NCBI GI 34733385 (AAQ81633.1) | 1266 | 100% |
| Bk2L3 (SEQ ID NO: 5) | NCBI GI 30090026 (AAO17706.1) | 868 | 95% |
| Bk2L4 (SEQ ID NO: 7) | NCBI GI 30090026 (AAO17706.1) | 922 | 97% |
| Bk2L5 (SEQ ID NO: 9) | NCBI GI 52076665 (BAD45565.1) | 1079 | 79% |
| Bk2L6 (SEQ ID NO: 11) | NCBI GI 50939113 (XP_479084.1) | 742 | 81% |
| Bk2L7 (SEQ ID NO: 13) | NCBI GI 50939113 (XP_479085.1) | 751 | 82% |
| Bk2L8 (SEQ ID NO: 15) | NCBI GI 34898176 (NP_910434.1) | 838 | 65% |
| Bk2L9 (SEQ ID NO: 17) | NCBI GI 50927043 (XP_473354.1) | 597 | 63% |

FIG. 6 shows the phylogenetic analysis of the Bk2L proteins from maize, BC1L proteins from rice, and COBL proteins from Arabidopsis (NCBI Accession Nos. are in parenthesis). The numbers along the branches are the bootstrap values obtained from a heuristic search over 5,000 replications. The bootstrap values for only the monophyletic groups that were supported>50% of the time are shown. The branch lengths are proportional to the inferred amino acid differences.

Example 2

Gene Expression Analysis of Bk2-Like Proteins

The tissue specificity of expression of the Bk2-like gene family disclosed in Table 1 was examined using Solexa's Massively Parallel Signature Sequencing (MPSS™) technology (see Table 3) (Brenner et al., *Nat. Biotechnol.* 18:630-634 (2000); Brenner et al., *Proc. Natl. Acad. Sci. U.S.A.* 97:1665-1670 (2000)). MPSS™ involves the generation of seventeen base signature tags from mRNA samples that have been reverse transcribed. The tags are simultaneously sequenced and assigned to genes or ESTs. The abundance of these tags is given a number value that is normalized to parts per million (PPM) which then allows the tag expression, or tag abundance, to be compared across different tissues. Thus, the MPSS™ platform can be used to determine the expression pattern of a particular gene and its expression level in different tissues. The numbers are averages over multiple libraries for each tissue listed in the second column.

TABLE 3

Expression in PPM of the Bk2 Gene Family in Maize

| Tissue | Lib. # | Bk2 | Bk2L1 | Bk2L3 | Bk2L4 | Bk2L5 | Bk2L6 | Bk2L7 | Bk2L8 | Bk2L9 |
|---|---|---|---|---|---|---|---|---|---|---|
| anther | 3 | 1 | 73 | 49 | 51 | 0 | 0 | 0 | 9 | 1 |
| ear | 17 | 0 | 48 | 17 | 30 | 0 | 0 | 0 | 0 | 0 |
| embryo | 10 | 0 | 18 | 61 | 18 | 0 | 0 | 0 | 0 | 3 |
| endosperm | 26 | 0 | 18 | 48 | 23 | 0 | 4 | 1 | 3 | 0 |
| husk | 1 | 75 | 68 | 490 | 16 | 0 | 0 | 39 | 0 | 0 |
| kernel | 5 | 2 | 86 | 103 | 51 | 0 | 1 | 1 | 15 | 1 |
| leaf | 46 | 17 | 20 | 87 | 10 | 0 | 0 | 0 | 32 | 0 |
| meristem | 20 | 2 | 60 | 81 | 19 | 0 | 0 | 0 | 2 | 0 |
| pericarp | 6 | 4 | 16 | 290 | 54 | 0 | 0 | 0 | 2 | 0 |

TABLE 3-continued

Expression in PPM of the Bk2 Gene Family in Maize

| Tissue | Lib. # | Bk2 | Bk2L1 | Bk2L3 | Bk2L4 | Bk2L5 | Bk2L6 | Bk2L7 | Bk2L8 | Bk2L9 |
|---|---|---|---|---|---|---|---|---|---|---|
| pollen | 2 | 0 | 6 | 2 | 13 | 794 | 0 | 0 | 0 | 0 |
| root | 43 | 52 | 69 | 263 | 14 | 0 | 0 | 2 | 8 | 0 |
| seedling | 7 | 8 | 16 | 72 | 21 | 0 | 0 | 0 | 8 | 0 |
| silk | 9 | 0 | 36 | 69 | 47 | 29 | 0 | 2 | 0 | 0 |
| spikelet | 12 | 17 | 86 | 205 | 111 | 0 | 0 | 12 | 0 | 0 |
| stalk | 15 | 172 | 48 | 474 | 15 | 0 | 0 | 8 | 14 | 0 |
| tassel | 2 | 4 | 72 | 53 | 62 | 0 | 0 | 16 | 0 | 0 |
| vascular bundles | 2 | 182 | 56 | 117 | 11 | 0 | 0 | 0 | 7 | 0 |
| whorl | 7 | 152 | 9 | 126 | 33 | 0 | 0 | 0 | 2 | 2 |

Figure 3:
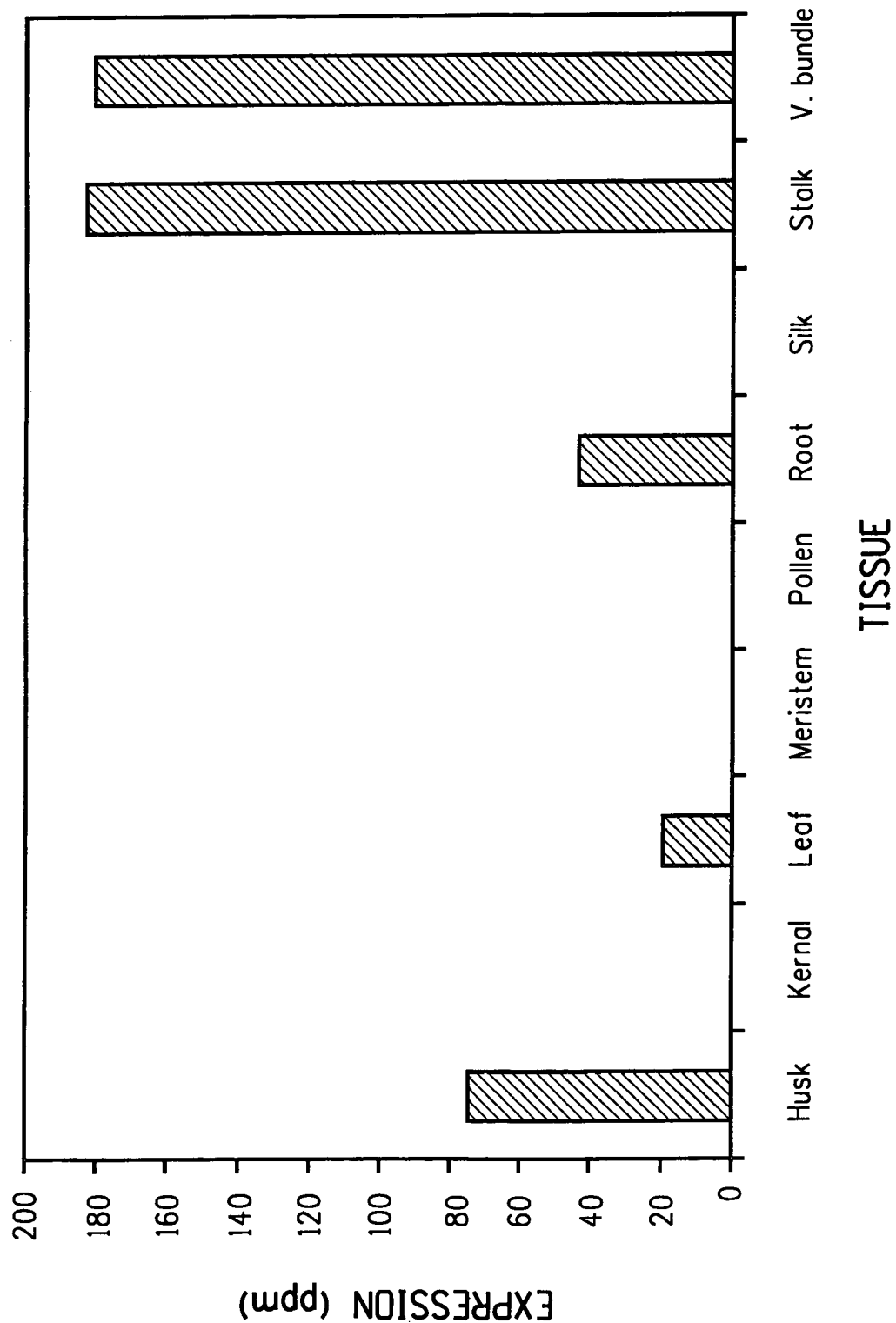
FIG. 3 shows Solexa MPSS™ gene expression analysis of gene Bk2.
Figure 4:
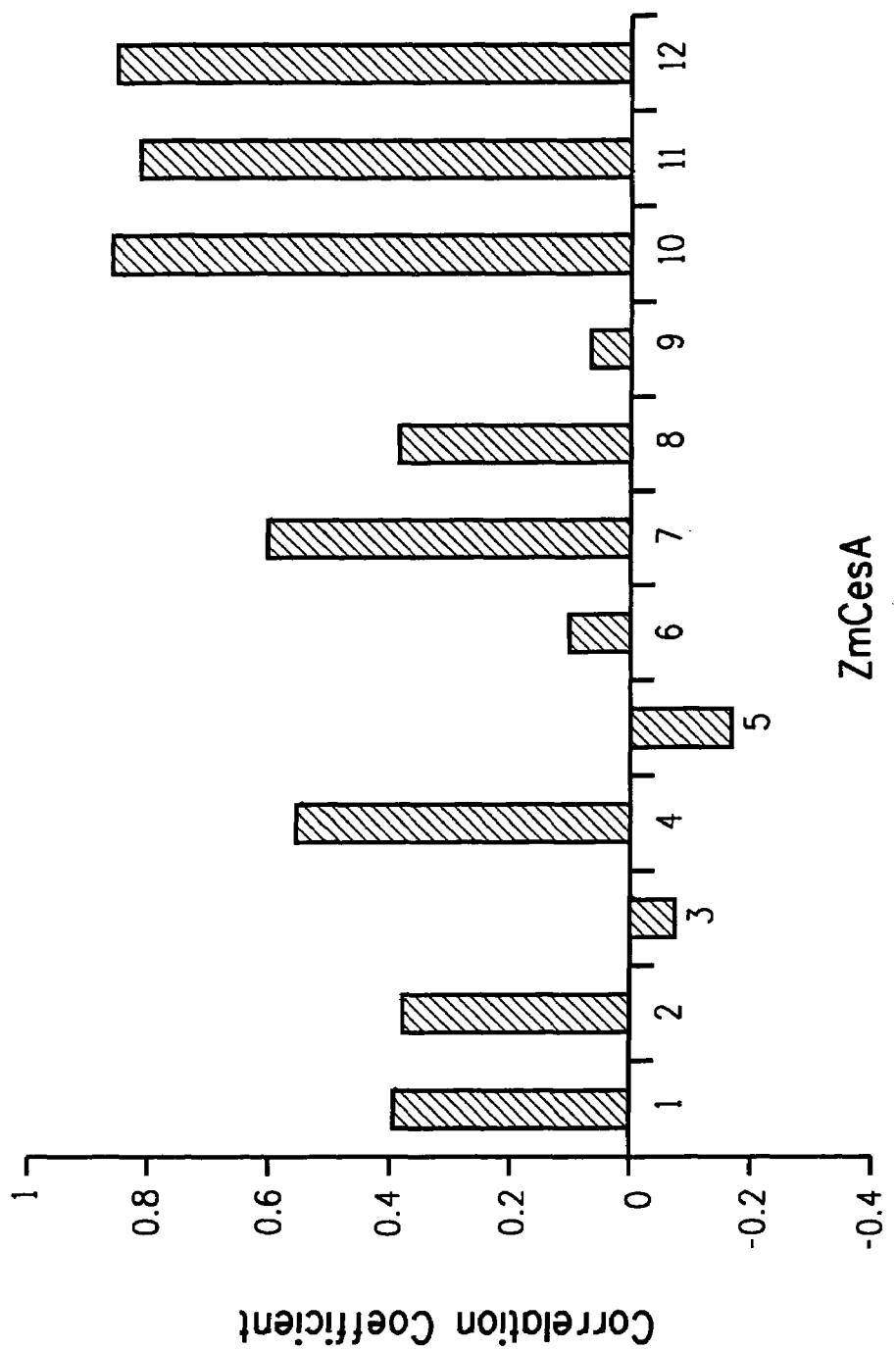
FIG. 4 shows the correlation of expression patterns of the Bk2 gene with members of the CesA gene family.

Bk2 (Table 3, column 3 and FIG. 3) is expressed in husk, leaf, root, stalk and isolated vascular bundles, but not in the kernel, meristem, pollen or silk tissues. This expression pattern is consistent with the role of the Bk2 gene in secondary wall formation as all the tissues it is expressed in contain at least some lignified cells. The correlation coefficient analysis of the expression level of Bk2 with the expression levels of the twelve maize CesA genes is shown in FIG. 4 (also see FIG. 5A, column 2). The expression pattern of the Bk2 gene is very similar to that of the previously disclosed secondary wall-forming CesA genes, CesA10, 11 and 12 (see FIG. 5 of U.S. Pat. No. 6,930,225, granted Aug. 16, 2005, the entire contents of which are herein incorporated by reference). More specifically, Bk2 shows a higher correlation coefficient, approximately>0.8, with each of the maize CesA10, 11, and 12 genes than with any other gene in this class. Since the three CesA genes are also co-expressed, it is likely that their corresponding proteins form a functional complex along with the Bk2 protein. Table 4 lists all the primary and secondary wall-forming CesA proteins known to date (U.S. Pat. No. 6,930,225, supra; U.S. Pat. No. 6,803,498, granted Oct. 12, 2004, the entire contents of which are herein incorporated by reference). The maize CesA10, 11, and 12 genes and their orthologs from Arabidopsis and rice have been implicated in secondary wall formation (Tanaka et al., *Plant Physiol.* 133: 73-83 (2003); Taylor et al., *Proc. Natl. Acad. Sci. U.S.A.* 100: 1450-1455 (2003); Appenzeller et al., *Cellulose* 11:287-299 (2004)). The co-expression of the Bk2 and secondary wall-forming CesA genes supports a role for Bk2 in secondary wall formation in maize.

TABLE 4

Primary and Secondary Wall-forming CesA Proteins

| | SEQ ID NO: | |
|---|---|---|
| Protein | (Nucleotide) | (Amino Acid) |
| CesA1 | 19 | 20 |
| CesA2 | 21 | 22 |
| CesA3 | 23 | 24 |
| CesA4 | 25 | 26 |
| CesA5 | 27 | 28 |
| CesA6 | 29 | 30 |
| CesA7 | 31 | 32 |
| CesA8 | 33 | 34 |
| CesA9 | 35 | 36 |
| CesA10 | 37 | 38 |
| CesA11 | 39 | 40 |
| CesA12 | 41 | 42 |

Another Bk2L gene that shows correlated expression with CesA genes is Bk2L3. The expression pattern of Bk2L3, is very similar to the CesA genes that were reported previously to be involved in primary wall formation (Holland et al., *Plant Physiol.* 123:1313-1323 (2000); Dhugga, *Curr. Opin. Plant Biol.* 4:488-493 (2001); Appenzeller et al., *Cellulose* 11:287-299 (2004)). Three genes in particular, CesA1, 7 and 8 appear to likely form a functional cellulose synthase complex for primary wall formation. The expression of the Bk2L3 gene is highly correlated with these three CesA genes that it appears that, analogous to the secondary wall cellulose synthase complex consisting of three CesA proteins and a Bk2 protein, these four proteins may form a functional cellulose synthase complex for primary wall formation.

Bk2L5 is expressed only in pollen. Some expression in silk most likely results from the pollen tube growing through it. Bk2L8 appears like is leaf-preferred and Bk2L6 is endosperm-specific.

Correlation among the expression level of all the different Bk2 and CesA genes from maize as studied from Solexa MPSS™ is shown in FIGS. 5A and 5B.

Example 3

Prophetic Example

Engineering Increased Stalk Strength by Overexpression of Maize Bk2-like Genes Under a Strong, Stalk-Specific Promoter A chimeric transgene is constructed to directly overexpress the Bk2 gene/polypeptide in a tissue specific manner. The transgene construct comprises a maize cDNA encoding Bk2L3 and/or Bk2L6 (e.g., SEQ ID NO:5 or SEQ ID NO:11) operably linked to the promoter from the alfalfa stalk-specific S2A gene (Abrahams et al., *Plant Mol. Biol.* 27:513-528 (1995)). The DNA containing the Bk2L3 or Bk2L6 ORF is then fused to the S2A promoter on the 5' end and pinII terminator on the 3' end to produce an expression cassette as illustrated in FIG. 3. The construct is then linked to a selectable marker cassette containing a bar gene driven by CaMV 35S promoter and a pinII terminator. It is appreciated that one skilled in the art could employ different promoters, 5' end sequences and/or 3' end sequences to achieve comparable expression results. Transgenic maize plants are produced by transforming immature maize embryos with this expression cassette using the Agrobacterium-based transformation method by Zhao (U.S. Pat. No. 5,981,840, issued Nov. 9, 1999; the contents of which are hereby incorporated by reference). While the method below is described for the transformation of maize plants with the S2A promoter-Bk2L3 (or Bk2L6) expression cassette, those of ordinary skill in the art recognize that this method can be used to produce transformed maize plants with any nucleotide construct or expression cassette that comprises a promoter linked to maize Bk2L3 (or Bk2L6) gene for expression in a plant.

Immature embryos are isolated from maize and the embryos contacted with a suspension of Agrobacterium, where the bacteria are capable of transferring the S2A promoter- Bk2L3 (or Bk2L6) expression cassette (illustrated above) to at least one cell of at least one of the immature embryos (step 1: the infection step). In this step, the immature embryos are immersed in an Agrobacterium suspension for the initiation of inoculation. The embryos are co-cultured for a time with the Agrobacterium (step 2: the co-cultivation step). The immature embryos are cultured on solid medium following the infection step. Following this co-cultivation period an optional "resting" step is included. In this resting step, the embryos are incubated in the presence of at least one antibiotic known to inhibit the growth of Agrobacterium without the addition of a selective agent for plant transformants (step 3: resting step). The immature embryos are cultured on solid medium with antibiotic, but without a selecting agent, for elimination of Agrobacterium and for a resting phase for the infected cells. Next, inoculated embryos are cultured on medium containing a selective agent and growing transformed calli are recovered (step 4: the selection step). Preferably, the immature embryos are cultured on solid medium with a selective agent resulting in the selective growth of transformed cells. The resulting calli are then regenerated into plants by culturing the calli on solid, selective medium (step 5: the regeneration step).

Example 4

Prophetic Example

Engineering Increased Stalk Strength by Transgenic Expression of Maize Bk2-Like Genes with an Enhancer Element in the Promoter Region Under a Strong, Stalk-Specific Promoter The expression of the Bk2L3 (or Bk2L6) gene is increased by placing a heterologous enhancer element in the promoter region of the native Bk2L3 (or Bk2L6) gene. An expression cassette is constructed comprising an enhancer element such as CaMV 35S fused to the native promoter of Bk2L3 (or Bk2L6) and the full-length cDNA. Transgenic maize plants can then be produced by transforming immature maize embryos with this expression cassette as described in Example #3.

Example 5

Prophetic Example

Engineering Increased Stalk Strength by Overexpression of Maize Bk2-Like and CesA Genes Whereas the secondary wall-forming genes mainly affect the mechanical strength of the plant tissues and not the morphological phenotype, the primary wall-forming genes can affect plant growth rate and thus their modulation can be employed to increase the rate of growth. The maize genes CesA1, 7, and 8 were previously shown to be co-expressed across multiple tissues, suggesting that they might form a functional enzyme complex. Bk2L3 is co-expressed with these three CesA genes, strongly suggesting that the protein products of all of these four genes form a functional enzyme complex. Simultaneous over-expression of these four genes as a single multi-gene construct or as separate constructs containing different combinations of these genes in maize driven by different promoters, preferably by the promoters of genes whole expression is associated with cell elongation, can be employed to produce transgenic plants with enhanced growth rate. Any of the other Bk2L genes can also be used in combination with the mentioned three CesA genes as described above to produce transgenic plants with enhanced growth rate.

Example 6

Prophetic Example

Engineering Increased Stalk Strength by Overexpression of Maize Bk2-Like and CesA Genes Aside from contributing to mechanical strength, secondary wall accounts for a majority of the biomass in plants. Whereas mechanical strength has applications in reducing in crop lodging, quality and amount biomass are important for many other applications, including ethanol production. The Bk2 gene along with the maize CesA10, 11, and 12 genes offers an avenue to increase the ratio of cellulose in the cell wall. The efficiency of ethanol production is directly related to the amount of cellulose in the biomass. Replacement of lignin with cellulose will also be useful in silage digestibility.

The Bk2 gene can be co-expressed with the CesA10, 11, and 12 genes as described in Example 5 for the primary wall-forming genes but under the control of secondary wall-specific promoters to produce transgenic plants with improved stalk strength and biomass quality.

Example 7

Prophetic Example

Engineering Down-Regulation of Maize Bk2-Like Genes

Since primary wall forming CesA genes contribute to cell expansion, their limited down-regulation can be employed to reduce plant height or organ size. In particular, the expression of the Bk2L3 gene is highly correlated with the primary wall-forming CesA genes. Whereas the overexpression of all the members of a functional enzyme complex may be required to increased enzyme activity, down-regulation of only one member may be sufficient to reduce activity. The down-regulation of Bk2L3, for example (and/or Bk2L5 for male sterility), can be accomplished by any of the technologies of co-suppression, RNAi, antisense RNA, or micro RNA resulting in dwarf transgenic plants. Height reduction has applications in some crop plants where harvest index is low and needs to be increased. Modern wheat and rice varieties, for example, are considerably shorter than their older counterparts. The ability to reduce plant height was mainly the cause of green revolution in each of these crops.

Example 8

Prophetic Example

Expression of Recombinant DNA Constructs in Dicot Cells Under a Strong, Stalk-Specific Promoter An expression cassette composed of the promoter from the alfalfa stalk-specific S2A gene (Abrahams et al., *Plant Mol.*

BioL 27:513-528 (1995)) 5-prime to the cDNA fragment can be constructed and be used for expression of the instant polypeptides in transformed soybean. The pinII terminator can be placed 3-prime to the cDNA fragment. Such construct may be used to overexpress the Bk2-like genes. It is realized that one skilled in the art could employ different promoters and/or 3-prime end sequences to achieve comparable expression results.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 9

Prophetic Example

Expression of Recombinant DNA Constructs in Microbial Cells Under a Strong, Stalk-Specific Promoter The cDNAs (SEQ ID NOs:1, 3, 5, 7, 9, 11, 13, 15 or 17) encoding the instant BRITTLE STALK 2-like polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 is constructed by first destroying the EcoRI and HindIII sites in pET-3a at their original positions. An oligonucleotide adaptor containing EcoRI and Hind III sites is inserted at the BamHI site of pET-3a. This creates pET-3aM with additional unique cloning sites for insertion of genes into the expression vector. Then, the NdeI site at the position of translation initiation is converted to an NcoI site using oligonucleotide-directed mutagenesis. The DNA sequence of pET-3aM in this region, 5'-CATATGG, is converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 10

Characteristics of the Stalk Tissue of the Wildtype (Bk2) and of the Brittle Stalk (bk2-ref) Mutant of Maize The maize stock containing the reference allele of bk2 (bk2-ref) was obtained from the Maize Genetics COOP Stock Center (USDA/ARS & Crop Sciences/UIUC, S-123 Turner Hall, 1102 S. Goodwin Avenue, Urbana, Ill. 61801-4798). Three greenhouse-grown plants each of the bk2-ref/bk2-ref and its wildtype sibling, Bk2/bk2-ref, both derived from seeds obtained from the same selfed ear, were evaluated for different traits approximately two weeks after flowering. Three internodes below the ear (internodes 3, 4, and 5, numbered from the ear node) were subjected to a three-point flexural test using a model 4411 Instron electromechanical testing device (Instron Corp., Canton, Mass.). The span width between the anchor points was 20 cm. The anvil was vertically driven at a constant speed of 20 cm/min against the internodal zone -3 cm above the node on a horizontally placed stalk until it collapsed or snapped. The maximum load to break was used as a measure of strength to differentiate the internodes and stalks.

Total dry matter was measured in the stalk portion below the ear node. Structural dry matter and cellulose contents were determined in duplicates on each of the three plants from the third and fourth internodes below the ear node by boiling the powdered stalk material twice with buffer (25 mM MOPS, pH 7) for 30 minutes. The remaining material was suspended in methanol/chloroform (3/1, v/v) for 1 hour, dried and weighed. Crystalline cellulose was determined by the Updegraff method (Updegraff, *Anal. Biochem.* 32:120-124 (1969)). Briefly, ground stalk material was place in a boiling water bath in an 8:2:1 mixture of acetic acid:water:nitric acid for 1 hour, the crystalline material washed three times with water and then with 95% ethanol followed by drying in a Speedvac. Klason lignin was determined by incubating the ground stalk material with 72% (w/w) sulfuric acid for 1 hour, washing twice with a 1:20 dilution of 72% sulfuric acid in water, heating at 65° C. for 30 minutes, washing once with water, and drying the residue at 80° C. overnight. Sugar composition was determined as described in (Appenzeller et al., *Cellulose* 11:287-299 (2004)).

In summary, reduction in mechanical strength in the stalk tissue was highly correlated with a reduction in the amount of cellulose and an uneven deposition of secondary cell wall material in the subepidermal and perivascular sclerenchyma fibers. Lower amount of cellulose and thinner walls of the mutant were reflected in reduced dry matter content per unit length of the stalk.

TABLE 5

Measurement of Stalk Composition and Mechanical Strength

| Trait | Wildtype | bk2-ref |
|---|---|---|
| ear height (cm) | 102.00 ± 8.8 | 106.33 ± 11.8 |
| stalk diameter (mm) | 23.84 ± 0.27 | 23.40 ± 0.46 |
| stalk dry mass (g) | 89.43 ± 3.39 | 62.08 ± 8.46 |
| moisture (%) | 79.20 ± 0.21 | 84.87 ± 1.04 |
| dry matter (g/cm) | 0.68 ± 0.04 | 0.43 ± 0.07 |
| displacement to break (mm) | 11.83 ± 0.46 | 6.51 ± 1.10 |
| load to break (kg) | 23.68 ± 2.25 | 9.04 ± 2.66 |
| insoluble dry matter (%) | 51.57 ± 1.00 | 45.20 ± 1.69 |
| cellulose (%) | 33.30 ± 0.56 | 23.76 ± 0.68 |
| lignin (%) | 9.07 ± 0.21 | 10.28 ± 0.63 |
| remainder cell wall (%) | 9.20 ± 1.68 | 11.16 ± 2.03 |
| cellulose (g/cm) | 0.24 ± 0.114 | 0.11 ± 0.019 |

What is claimed is:

1. An isolated polynucleotide comprising:
(a) a nucleotide sequence encoding a polypeptide that increases stalk mechanical strength of a transformed plant expressing said polypeptide when compared to an untransformed control plant, wherein said polypeptide has an amino acid sequence of at least 90% sequence identity, based on the Clustal V method of alignment, when compared to SEQ ID NO:16; or
(b) a complement of the nucleotide sequence, wherein the complement and the nucleotide sequence consist of the same number of nucleotides and are 100% complementary.

2. A recombinant DNA construct comprising the polynucleotide of claim 1 operably linked to a promoter that is functional in a plant.

3. A plant comprising in its genome the recombinant DNA construct of claim 2.

4. The isolated polynucleotide of claim 1, wherein said stalk mechanical strength is measured by the three-point bend test.

5. The isolated polynucleotide of claim 1, wherein the polypeptide has an amino acid sequence of at least 95% sequence identity, based on the Clustal V method of alignment, when compared to SEQ ID NO:16.

6. The isolated polynucleotide of claim 1, wherein the polypeptide comprises SEQ ID NO:16.

* * * * *

SEQUENCE LISTING

<160> NUMBER OF SEQ ID NOS: 42

<210> SEQ ID NO 1
<211> LENGTH: 1784
<212> TYPE: DNA
<213> ORGANISM: Zea mays

<400> SEQUENCE: 1

```
gatcggagct tgtgctgcta ctgctactat accagcgcta gctagcagca gccgccggcc      60
ggctcgcgca agctaaggaa gggtcgacat gacgatgggg ctccgcgtcc gcgactcctc     120
cgcgctgctg gctctggccg tcgcgctcgc ctgctgctcc gttgcagtgg tggcctacga     180 cccctggac ccgaacggca acatcaccat caagtgggac gtgatctcgt ggacgcccga     240
cgggtacgtg gcgatggtga cgatgagcaa ctaccagatg taccggcaca tcatggcgcc     300
```

-continued

```
cggtggacg ttgggtggt cgtgggccaa gaaggaggtg atctggtcca tcgtgggggc    360
gcaggccacg gagcagggg actgctccaa gttcaagggc ggcatccgc actgctgcaa    420 gcgcaccccg gccgtggtgg acctcctccc ggggtgccc tacaaccagc agatcgccaa    480
ctgctgcaag gccggcgtgg tgtcggcgta cgggcaggac ccggcgggt ccgtctccgc    540 gttccaggtc tccgtcggcc tggccggtac caccaacaag acggtgaagc tgcccaggaa    600
cttcacgctc atggggcccg ggctgggcta cctgcggg cccgccgccg tggtgccgtc    660
caccgtgtac tggacgcccg accaccggcg ccggacgcag gcgctcatga cgtggacggt    720
gacctgcacc tactcgcagc agctggcgtc ccggtacccg tcctgctgcg tctccttctc    780
ctccttctac aacagcacca tcgtgccgtg cgcccggtgc gcgtgcggct gcggcggcca    840
cggcggccac gcgggtccgg gcggctgcat cgagggggac tccaagcgcg cgctgtcggc    900
cggggtgaac acgccgcgca aggacggcca ggcgctgctg cagtgcacgc cgcacatgtg    960
ccccatccgg gtgcactggc acgtcaagct caactacaag gactactggc gcgccaagat   1020
cgccatcacc aactacaact acaggatgaa ctacacgcag tggacgctgg tggcgcagca   1080
ccccaacctg gacaacgtca ccgaggtctt cagcttccag tacaagccgc tgcaaccata   1140
cgggagcatc aatgacactg gcatgttcta cgggctcaag ttctacaacg actttctcat   1200
ggaggccggc ccgttcggca acgtgcagtc ggaggtgctc atgcgcaagg acgcaaggac   1260
cttcaccttc agcatgggct gggcgttccc gcgcaagatc tacttcaacg gcgacgagtg   1320
caagatgccg ccgccggact cctacccta cctgcccaac gccgcgcccg tcgtcgcctc   1380
gcagctggtc ctgtccgccg ccgcctcggc gttcctactg ttgctgctcc tggtggcatg   1440
accgtgaccg aaccaagggc aaggcctccg ttttgttttc ccgtctcgtc ccgtgggcag   1500
ggagcagact tcagtaggca gggcatttta tttggttttt ttgccaagga ttcaacactt   1560
gggttttcgt cagaggaaaa ctgtcgtgta tgtagtgtga gttgcaggtc gtcggatccc   1620
cacgtacaag acaatctttg gatctagaat atgcaaaacg tgaatcagca cgccaggatc   1680
atcgtctcct acaagattgg cagaaaaaaa atctcatgat gagtgatgtg tcaacagacc   1740
tatatatatg tgataatcac tggtttcaaa aaaaaaaaaa aaaa                    1784
```

<210> SEQ ID NO 2
<211> LENGTH: 450
<212> TYPE: PRT
<213> ORGANISM: Zea mays

<400> SEQUENCE: 2

```
Met Thr Met Gly Leu Arg Val Arg Asp Ser Ser Ala Leu Leu Ala Leu
1               5                   10                  15

Ala Val Ala Leu Ala Cys Cys Ser Val Ala Val Ala Tyr Asp Pro
            20                  25                  30

Leu Asp Pro Asn Gly Asn Ile Thr Ile Lys Trp Asp Val Ile Ser Trp
        35                  40                  45

Thr Pro Asp Gly Tyr Val Ala Met Val Thr Met Ser Asn Tyr Gln Met
    50                  55                  60

Tyr Arg His Ile Met Ala Pro Gly Trp Thr Leu Gly Trp Ser Trp Ala
65                  70                  75                  80

Lys Lys Glu Val Ile Trp Ser Ile Val Gly Ala Gln Ala Thr Glu Gln
                85                  90                  95

Gly Asp Cys Ser Lys Phe Lys Gly Gly Ile Pro His Cys Cys Lys Arg
            100                 105                 110
```

Thr Pro Ala Val Val Asp Leu Leu Pro Gly Val Pro Tyr Asn Gln Gln
        115                 120                 125

Ile Ala Asn Cys Cys Lys Ala Gly Val Val Ser Ala Tyr Gly Gln Asp
130                 135                 140

Pro Ala Gly Ser Val Ser Ala Phe Gln Val Ser Val Gly Leu Ala Gly
145                 150                 155                 160

Thr Thr Asn Lys Thr Val Lys Leu Pro Arg Asn Phe Thr Leu Met Gly
                165                 170                 175

Pro Gly Leu Gly Tyr Thr Cys Gly Pro Ala Ala Val Val Pro Ser Thr
            180                 185                 190

Val Tyr Trp Thr Pro Asp His Arg Arg Thr Gln Ala Leu Met Thr
        195                 200                 205

Trp Thr Val Thr Cys Thr Tyr Ser Gln Gln Leu Ala Ser Arg Tyr Pro
    210                 215                 220

Ser Cys Cys Val Ser Phe Ser Ser Phe Tyr Asn Ser Thr Ile Val Pro
225                 230                 235                 240

Cys Ala Arg Cys Ala Cys Gly Cys Gly Gly His Gly His Ala Gly
                245                 250                 255

Pro Gly Gly Cys Ile Glu Gly Asp Ser Lys Arg Ala Leu Ser Ala Gly
            260                 265                 270

Val Asn Thr Pro Arg Lys Asp Gly Gln Ala Leu Leu Gln Cys Thr Pro
        275                 280                 285

His Met Cys Pro Ile Arg Val His Trp His Val Lys Leu Asn Tyr Lys
    290                 295                 300

Asp Tyr Trp Arg Ala Lys Ile Ala Ile Thr Asn Tyr Asn Tyr Arg Met
305                 310                 315                 320

Asn Tyr Thr Gln Trp Thr Leu Val Ala Gln His Pro Asn Leu Asp Asn
                325                 330                 335

Val Thr Glu Val Phe Ser Phe Gln Tyr Lys Pro Leu Gln Pro Tyr Gly
            340                 345                 350

Ser Ile Asn Asp Thr Gly Met Phe Tyr Gly Leu Lys Phe Tyr Asn Asp
        355                 360                 365

Phe Leu Met Glu Ala Gly Pro Phe Gly Asn Val Gln Ser Glu Val Leu
    370                 375                 380

Met Arg Lys Asp Ala Arg Thr Phe Thr Phe Ser Met Gly Trp Ala Phe
385                 390                 395                 400

Pro Arg Lys Ile Tyr Phe Asn Gly Asp Glu Cys Lys Met Pro Pro Pro
                405                 410                 415

Asp Ser Tyr Pro Tyr Leu Pro Asn Ala Ala Pro Val Val Ala Ser Gln
            420                 425                 430

Leu Val Leu Ser Ala Ala Ala Ser Ala Phe Leu Leu Leu Leu Leu Leu
        435                 440                 445

Val Ala
    450

<210> SEQ ID NO 3
<211> LENGTH: 3152
<212> TYPE: DNA
<213> ORGANISM: Zea mays

<400> SEQUENCE: 3
cctgaacctc tcctcggcac atgcgcgggc cccactttac aagcgacagt agccccatcc      60
gcagccgtgc acgctagaat cggacggctt gccgcgcatc tcgcccgtcc gcggcgccgc     120
tgcccgaacc gaaccctacc gtttcaacca ggcgccgcct ctccgcgtcc gctgagtcac     180

```
tgcctcctgg gcccggaccc acacgcccct cgtcaatcaa catcaactca cgctcctcat    240
catccctcca ctggaaactg accccctcg tcgtctcgtc tcttttcctg ccggcgtcga     300
ttcccactcc gttttgttaa aaaccgatcg ttttctccat ttctttgtag ggactagtaa    360
tagatagaca gcagagggag agacgacagg cgtagctagc accagcactc aagctactac    420
gcacgcacgc cgccgctccc ccagttcaaa cccaccaccc cttccccctt catcttcctt    480
tcccagctgt gcacgcgctt tccgatcgct tcatctacct cgccaccgcg cttccgccca    540
gccccagtca ccagtccacc gcgcccgcgc cccgatccca gcgatatggc tggctccgta    600
gctccccacg ctgtggtcct cggtcttctc ctgctcgcgg ggctcgcggc ggcgcagagg    660
gcgacgacgc cggctgcggc ggccccgcgc ccgaccccg gctgcaacgg catccagctg     720
acctacaact tcgtggaccg caccaagatc cggcccttcg tcagcgacaa gaacaagcag    780
ccctacgcct tccgcgccaa cgtcaccgtg ctcaactccg gcacccgccc gctcaagtcc    840
tgggcggcac tcgtcacatt cggctacggc gagatcctcg tcggcgtcga cggcgccgtg    900
ctcacgggcg gcggcgacct gccgtacaac accacggagg acgccggcaa cgccaccctcg   960 ttctccgggt accgcatac agacctcctc acgcccatcg ccaccgccgg ggacctgtcg     1020
cagatccagg cctccgtcgg catcgtcggc acgctcttcg ccgggcccgg cccgttcgtg    1080
ccgctcccca ccgcgctgtc gctggacgac ccggcctacg cgtgcccggc ggcgaccaac    1140
gtcactgctc gggtgctgtc cacgtgctgc gtcctcacgc cggaggccga ggccaacgcc    1200
actgccatcg acgccaacac caccgacccg accaaggatt tcctgccgcg cggcaccggc    1260
gacctcgtca tcacctacga tgtgctccag gcctacccct ccagctacct tgcgctcgtc    1320
acgctcgaga caacgccaa gctcggccgc ctcgacaact ggcggctgtc gtgggagtgg    1380
cggcgtgggg agttcatcta ctcaatgaaa ggagctcacc catcagaggt ggacacctcg    1440
ggctgtatct gtggggcgcc tgggcagtac taccagagcc ttgattttc gcaggtgctc     1500 aattgtgacc gcaagccggt gatccttgac ctgcccctgt cccggtacaa cgacactcag    1560
attgggaaga ttgacaattg ctgcaggaat gggacaatct tgcccaagtc catggacgag    1620
gcacagtcga atctgcgttc cagatgcaa gttttcaaga tgccaccaga cctgaaccgg     1680
actaagctgt tcccccctgc taatttcaag atcgtgggtg catcatcgct gaacccggac    1740
tatgcctgtg gccagccggt gcctgtcagc ccaaccgcgt tcccagaccc gagcgggctt    1800
gactcgacga cgcttgctgt ggcaacatgg caggtggtgt gcaacattac cacgacaaag    1860
ggggccaagc ccaagtgttg tgtgaccttc tcggcgtact acaacgactc agtgatcccc    1920
tgcagcacct gcgcttgtgg gtgccctgca aacaggcgag ggccaacgtg cagcaccacc    1980
gcacaatcca tgctgctgcc accggaggcg ctgcttgtgc cattcgacaa ccggtcacag    2040
aaggcgttgg cgtgggctga gctgaagcat acaatgtgc cccggccgat gccttgcggt      2100 gactttgtg gcgtgagcat caattggcat gtctcaacgg actacaacaa gggctggagc      2160
gctcgggtga cattgttcaa ctgggaggat gtcgacatgg ccaattggtt tgctgccatc    2220
gtcatggaca aggcgtatga cggctttgag aaggcttact cgttcaacgg caccgcagtg    2280
ggcaagaaca cgatctttat gcagggtctg gaggggctta attacctggt gaagcagacc    2340
aacatgagtg ggtccgacta ccttgttcct ggcaagcaac agtcagtcct ctcattcacc    2400
aagaagctga ccccgggggtt aaatgttgtt gctggagatg gcttcccaac aaaggtcttc   2460
ttcaatggcg acgaatgcgc tatgccacag agaattccga tcagcactgg attcagcacc    2520
```

-continued

```
cgtctcagca gtggccttgc tctggttccg ttccttgttg cttcggcttt cctattgctc      2580
cagcaatgat ccacgggact ccaattcttt gattctttca ggtggtttgg tcgatgccat      2640
ttgtaagaaa gcctcttttt tttgtttctg tgattgcttt agtagattct acttagctgc      2700
tgtatgttag tcagatgaag cagcagctgt gaaacagtat gaatacttgg atagtgagag      2760
aaaaagtgag gaagcatttg ttgcgggttt gcaacattgg ttcctcgttc taatggcatt      2820
tacgaattgt ctcatgttct gtctgtcata cagaattttac tctgtgaatc cgttcatgtc      2880 ttgttttgt tgtttggtc acaaattcag gccttgtttg gttcctttag attgagtccg        2940
tggaatggtt tctagttcga atggtttact aatatgtgta accttaatga ggtggaatgg      3000
ttcctgggtc gaatcatggt tagctgaacg gaccgtcaaa ctgattggaa agggatcgaa      3060
ggggattaaa gacggatgag gggaatttga cttgttaggg atttagttcc ctcgttcttc      3120
tccaatcccc cttagatttg agatccgaat tc                                    3152
```

<210> SEQ ID NO 4
<211> LENGTH: 667
<212> TYPE: PRT
<213> ORGANISM: Zea mays

<400> SEQUENCE: 4

```
Met Ala Gly Ser Val Ala Pro His Ala Val Leu Gly Leu Leu Leu
1               5                  10                  15

Leu Ala Gly Leu Ala Ala Ala Gln Arg Ala Thr Thr Pro Ala Ala Ala
            20                  25                  30

Ala Pro Ala Pro Asp Pro Gly Cys Asn Gly Ile Gln Leu Thr Tyr Asn
        35                  40                  45

Phe Val Asp Arg Thr Lys Ile Arg Pro Phe Val Ser Asp Lys Asn Lys
    50                  55                  60

Gln Pro Tyr Ala Phe Arg Ala Asn Val Thr Val Leu Asn Ser Gly Thr
65                  70                  75                  80

Arg Pro Leu Lys Ser Trp Ala Ala Leu Val Thr Phe Gly Tyr Gly Glu
                85                  90                  95

Ile Leu Val Gly Val Asp Gly Ala Val Leu Thr Gly Gly Asp Leu
            100                 105                 110

Pro Tyr Asn Thr Thr Glu Asp Ala Gly Asn Ala Thr Ser Phe Ser Gly
        115                 120                 125

Tyr Pro His Thr Asp Leu Leu Thr Pro Ile Ala Thr Ala Gly Asp Leu
    130                 135                 140

Ser Gln Ile Gln Ala Ser Val Gly Ile Val Gly Thr Leu Phe Ala Gly
145                 150                 155                 160

Pro Gly Pro Phe Val Pro Leu Pro Thr Ala Leu Ser Leu Asp Asp Pro
                165                 170                 175

Ala Tyr Ala Cys Pro Ala Ala Thr Asn Val Thr Ala Arg Val Leu Ser
            180                 185                 190

Thr Cys Cys Val Leu Thr Pro Glu Ala Glu Ala Asn Ala Thr Ala Ile
        195                 200                 205

Asp Ala Asn Thr Thr Asp Pro Thr Lys Asp Phe Leu Pro Arg Gly Thr
    210                 215                 220

Gly Asp Leu Val Ile Thr Tyr Asp Val Leu Gln Ala Tyr Pro Ser Ser
225                 230                 235                 240

Tyr Leu Ala Leu Val Thr Leu Glu Asn Asn Ala Lys Leu Gly Arg Leu
                245                 250                 255

Asp Asn Trp Arg Leu Ser Trp Glu Trp Arg Arg Gly Glu Phe Ile Tyr
```

```
                260                 265                 270
Ser Met Lys Gly Ala His Pro Ser Glu Val Asp Thr Ser Gly Cys Ile
        275                 280                 285
Cys Gly Ala Pro Gly Gln Tyr Tyr Gln Ser Leu Asp Phe Ser Gln Val
        290                 295                 300
Leu Asn Cys Asp Arg Lys Pro Val Ile Leu Asp Leu Pro Leu Ser Arg
305                 310                 315                 320
Tyr Asn Asp Thr Gln Ile Gly Lys Ile Asp Asn Cys Cys Arg Asn Gly
                325                 330                 335
Thr Ile Leu Pro Lys Ser Met Asp Glu Ala Gln Ser Lys Ser Ala Phe
            340                 345                 350
Gln Met Gln Val Phe Lys Met Pro Pro Asp Leu Asn Arg Thr Lys Leu
            355                 360                 365
Phe Pro Pro Ala Asn Phe Lys Ile Val Gly Ala Ser Ser Leu Asn Pro
        370                 375                 380
Asp Tyr Ala Cys Gly Gln Pro Val Pro Val Ser Pro Thr Ala Phe Pro
385                 390                 395                 400
Asp Pro Ser Gly Leu Asp Ser Thr Thr Leu Ala Val Ala Thr Trp Gln
                405                 410                 415
Val Val Cys Asn Ile Thr Thr Thr Lys Gly Ala Lys Pro Lys Cys Cys
            420                 425                 430
Val Thr Phe Ser Ala Tyr Tyr Asn Asp Ser Val Ile Pro Cys Ser Thr
        435                 440                 445
Cys Ala Cys Gly Cys Pro Ala Asn Arg Arg Gly Pro Thr Cys Ser Thr
        450                 455                 460
Thr Ala Gln Ser Met Leu Leu Pro Pro Glu Ala Leu Leu Val Pro Phe
465                 470                 475                 480
Asp Asn Arg Ser Gln Lys Ala Leu Ala Trp Ala Glu Leu Lys His Tyr
                485                 490                 495
Asn Val Pro Arg Pro Met Pro Cys Gly Asp Phe Cys Gly Val Ser Ile
                500                 505                 510
Asn Trp His Val Ser Thr Asp Tyr Asn Lys Gly Trp Ser Ala Arg Val
        515                 520                 525
Thr Leu Phe Asn Trp Glu Asp Val Asp Met Ala Asn Trp Phe Ala Ala
        530                 535                 540
Ile Val Met Asp Lys Ala Tyr Asp Gly Phe Glu Lys Ala Tyr Ser Phe
545                 550                 555                 560
Asn Gly Thr Ala Val Gly Lys Asn Thr Ile Phe Met Gln Gly Leu Glu
                565                 570                 575
Gly Leu Asn Tyr Leu Val Lys Gln Thr Asn Met Ser Gly Ser Asp Tyr
            580                 585                 590
Leu Val Pro Gly Lys Gln Gln Ser Val Leu Ser Phe Thr Lys Lys Leu
        595                 600                 605
Thr Pro Gly Leu Asn Val Val Ala Gly Asp Gly Phe Pro Thr Lys Val
        610                 615                 620
Phe Phe Asn Gly Asp Glu Cys Ala Met Pro Gln Arg Ile Pro Ile Ser
625                 630                 635                 640
Thr Gly Phe Ser Thr Arg Leu Ser Ser Gly Leu Ala Leu Val Pro Phe
                645                 650                 655
Leu Val Ala Ser Ala Phe Leu Leu Leu Gln Gln
            660                 665

<210> SEQ ID NO 5
```

<211> LENGTH: 2094
<212> TYPE: DNA
<213> ORGANISM: Zea mays
<220> FEATURE:
<221> NAME/KEY: misc_feature
<222> LOCATION: (2087)..(2089)
<223> OTHER INFORMATION: n is a, c, g, or t

<400> SEQUENCE: 5

```
ctcgtgctgc tgcttccgct gcagtaaaat acggggaaga ggaggggagg gagacgcggc      60
cgctgcctgc cgcacatgct ttaagtccca ctccccacct ccccagatct ccgccctcct     120
ccccaccgcc cccattcctc ccctcggccg caaccgtagc cgccgcacta cggagcaaga     180
tcgtcgggta gacggacggg cgggcgggcg ggcgcggctc tgtatctatc tgtcggtggg     240
agaccgcgtg tgtcggttag gcggcgggtg gcaaggaaga atggcggcga gcggcagatc     300
cgtcgcgtgc tgtgccgccg cgctgctcgc ggccgcgttg ctcctctccg caccgactgc     360
aacagaggct tatgattcgc tggatccaaa tggcaacatc accataaaat gggatatcat     420
gcagtggact cctgatggat atgtcgctgt tgtcacaatg tttaattatc aacaatttcg     480
gcatatcggc gcacctggtt ggcagcttgg gtggacatgg gcaaagaagg aggttatatg     540
gtcaatggtt ggggctcaga ccactgaaca gggcgactgc tcaaagttca agagcagccc     600
accccattgc tgcaagaaag atccaacaat tgtcgattta cttccaggca ctccatacaa     660
catgcaaatt gccaattgct gcaaggcagg agttgtaaat acctttaacc aggacccagc     720
aaatgctgct tcctccttcc agatcagtgt tggtcttgct ggaactacca ataaaactgt     780
taaggtgccc aggaacttca ctcttaagac tccaggccct gggtacacat gtgggcgtgc     840
cattgttggc aggcctacga agtttttcac cgcggacggg cgcagggcaa cccaagctct     900
aatgacatgg aatgtgacct gcacatattc ccaatttctt gctcagaaga ctccatcctg     960
ctgtgtatct ctatcatcgt tttataatga cacaattgtg aactgcccaa catgctcatg    1020
tggctgccag aacccaagtg ggtcaaactg tgtgaatgag gattcaccta atctacaagc    1080
tgcaattgat ggccctggca aatggactgg tcagccccct gtacaatgca cttcccacat    1140
gtgcccgata agaatccact ggcatgtgaa gctcaactac aaggattact ggagagtgaa    1200
aatcactatc acaaacttca acttccgcat gaattacacg cagtggaact tagtagccca    1260
gcatccaaac tttgataata tcactcagtt gttcagcttc aactacaaac cacttactcc    1320
atatggtggt ggcataaatg atacggcaat gttctggggt gtaaaattct acaatgatct    1380
gctgatgcaa gccggcaaac ttgggaatgt gcaatcagag ctgcttctcc gcaaggactc    1440
ccggactttc actttcgaaa agggatgggc cttcccacgc cgagtttact tcaatggtga    1500
taattgtgtc atgccatctc ctgaaaatta tccatggctg ccgaatgcaa gccctctaac    1560
aaaaccattg gcactcccat tcttggtatt ctgggttgcc ttggctgctc tgttggctta    1620
tgcatgatta gtgggatcaa gaggtttagc aagtttcaag ttgatgtcag attccatgag    1680
gtgcactgca acaagtcatt tgttcattca attccatggt tgcacagaaa agatgaggcg    1740
atgccaagaa aaagtcgata tgtctatgtg tttaagttaa agggccaaaa tgtatttctt    1800
gtttggtata aacagcccct acaacacttt ggtgaactta gttactgcag attaggtaat    1860
tacagttgca cctttttgtat tttatagcaa acccagaatt tttcattgga ttctacgact    1920
gccctcttg tagtaaatgc aaggcttccc tgatactcct gtttaaagat ttgtggattg    1980
ggtgagacaa tggtgattga gataactaag ttctggggtc ttgatccatt tgmwgctggr    2040
aagawtattg atctaaattg ctaaaaaaaa acctcgtgcc gaattcnnng cctc           2094
```

<210> SEQ ID NO 6
<211> LENGTH: 448
<212> TYPE: PRT
<213> ORGANISM: Zea mays

<400> SEQUENCE: 6

```
Met Ala Ala Ser Gly Arg Ser Val Ala Cys Cys Ala Ala Leu Leu
1               5                   10                  15

Ala Ala Ala Leu Leu Ser Ala Pro Thr Ala Thr Glu Ala Tyr Asp
            20                  25                  30

Ser Leu Asp Pro Asn Gly Asn Ile Thr Ile Lys Trp Asp Ile Met Gln
        35                  40                  45

Trp Thr Pro Asp Gly Tyr Val Ala Val Thr Met Phe Asn Tyr Gln
    50                  55                  60

Gln Phe Arg His Ile Gly Ala Pro Gly Trp Gln Leu Gly Trp Thr Trp
65              70                  75                      80

Ala Lys Lys Glu Val Ile Trp Ser Met Val Gly Ala Gln Thr Thr Glu
                85                  90                  95

Gln Gly Asp Cys Ser Lys Phe Lys Ser Pro Pro His Cys Cys Lys
            100                 105                 110

Lys Asp Pro Thr Ile Val Asp Leu Leu Pro Gly Thr Pro Tyr Asn Met
            115                 120                 125

Gln Ile Ala Asn Cys Cys Lys Ala Gly Val Val Asn Thr Phe Asn Gln
        130                 135                 140

Asp Pro Ala Asn Ala Ala Ser Ser Phe Gln Ile Ser Val Gly Leu Ala
145                 150                 155                 160

Gly Thr Thr Asn Lys Thr Val Lys Val Pro Arg Asn Phe Thr Leu Lys
                165                 170                 175

Thr Pro Gly Pro Gly Tyr Thr Cys Gly Arg Ala Ile Val Gly Arg Pro
            180                 185                 190

Thr Lys Phe Phe Thr Ala Asp Gly Arg Arg Ala Thr Gln Ala Leu Met
        195                 200                 205

Thr Trp Asn Val Thr Cys Thr Tyr Ser Gln Phe Leu Ala Gln Lys Thr
210                 215                 220

Pro Ser Cys Cys Val Ser Leu Ser Ser Phe Tyr Asn Asp Thr Ile Val
225                 230                 235                 240

Asn Cys Pro Thr Cys Ser Cys Gly Cys Gln Asn Pro Ser Gly Ser Asn
                245                 250                 255

Cys Val Asn Glu Asp Ser Pro Asn Leu Gln Ala Ala Ile Asp Gly Pro
            260                 265                 270

Gly Lys Trp Thr Gly Gln Pro Leu Val Gln Cys Thr Ser His Met Cys
        275                 280                 285

Pro Ile Arg Ile His Trp His Val Lys Leu Asn Tyr Lys Asp Tyr Trp
290                 295                 300

Arg Val Lys Ile Thr Ile Thr Asn Phe Asn Phe Arg Met Asn Tyr Thr
305                 310                 315                 320

Gln Trp Asn Leu Val Ala Gln His Pro Asn Phe Asp Asn Ile Thr Gln
                325                 330                 335

Leu Phe Ser Phe Asn Tyr Lys Pro Leu Thr Pro Tyr Gly Gly Ile
            340                 345                 350

Asn Asp Thr Ala Met Phe Trp Gly Val Lys Phe Tyr Asn Asp Leu Leu
        355                 360                 365

Met Gln Ala Gly Lys Leu Gly Asn Val Gln Ser Glu Leu Leu Leu Arg
```

```
                 370                 375                 380
Lys Asp Ser Arg Thr Phe Thr Phe Glu Lys Gly Trp Ala Phe Pro Arg
385                 390                 395                 400

Arg Val Tyr Phe Asn Gly Asp Asn Cys Val Met Pro Ser Pro Glu Asn
                405                 410                 415

Tyr Pro Trp Leu Pro Asn Ala Ser Pro Leu Thr Lys Pro Leu Ala Leu
            420                 425                 430

Pro Phe Leu Val Phe Trp Val Ala Leu Ala Ala Leu Leu Ala Tyr Ala
        435                 440                 445

<210> SEQ ID NO 7
<211> LENGTH: 2102
<212> TYPE: DNA
<213> ORGANISM: Zea mays

<400> SEQUENCE: 7
```

| | | | | | |
|---|---|---|---|---|---|
| ggaaagcagc | gctgcggagc | agagtgtgtc | gcttcgctgt | aaaaacaggg | gagagggaga | 60 |
| cgcgcccgct | gccagtgcct | gccgcacacg | cgtttagcgt | ttaagttcca | ctcctcgccg | 120 |
| ccccagatct | ccgccctcct | caccactgcc | cctcattccc | cggcgcccag | cacccggcgg | 180 |
| ccgcaaccgc | cgcagtccgg | agcaagatcg | gcgggtagac | ggacggacgg | acgggcgaca | 240 |
| ggcgggcggg | cgcggctctg | tctgtatcta | tctgttggtg | ggagaccggt | tgtgtcggtt | 300 |
| aggcggcggc | gggtgggaag | gaagaatggc | ggcgggcggc | agatccatcg | cgtgctttgc | 360 |
| cgccgtgctg | ctcgcggccg | cgctgctcct | ctccgcaccg | accaccacag | aggcctacga | 420 |
| ttcgctggat | ccaaacggca | acatcactat | aaaatgggat | atcatgcagt | ggactcctga | 480 |
| cggatatgtc | gctgttgtca | caatgttcaa | ttatcaacaa | tttcggcaca | tcggggcacc | 540 |
| tggatggcag | cttgggtgga | catgggcaaa | aaaggaggtt | atatggtcaa | tggttgggggc | 600 |
| tcagaccact | gaacagggtg | actgctcaaa | gttcaagggc | aacaccccccc | attgctgcaa | 660 |
| gaaagatcca | acaattgttg | atttacttcc | aggcactcca | tacaacatgc | aaattgccaa | 720 |
| ttgctgcaag | gcaggagtta | taaatacctt | taaccaggac | ccagcaaatg | ctgcttcctc | 780 |
| cttccagatc | agtgttggtc | ttgctggaac | taccaataaa | actgttaagg | tgccgaagaa | 840 |
| tttcactctt | aagactccag | ccctgggta | cacatgtggg | cgtgctattg | ttggcaggcc | 900 |
| aacgaagttt | ttctctgcag | atgggcgcag | ggtaacccaa | gctctaatga | catggaatgt | 960 |
| gacctgcaca | tattcccaat | ttcttgctca | gaagactcca | tcctgctgtg | tatctctctc | 1020 |
| atcatttttat | aatgacacaa | ttgtgaactg | cccgacatgc | tcatgtggct | gccagaaccc | 1080 |
| aagtgggtca | aactgtgtga | acgaggattc | acctaatcta | caagccgcaa | ttgatggtcc | 1140 |
| tggtaaatgg | actggccagc | tcttgtaca | atgcacttct | cacatgtgcc | caataagaat | 1200 |
| ccactggcat | gtgaagctca | actacaagga | atactggaga | gtgaaaatca | ctatcacgaa | 1260 |
| cttcaacttc | cgcatgaatt | acacacagtg | aacttagtt | gctcagcatc | caaactttga | 1320 |
| taatatcact | cagttgttca | gcttcaacta | caaaccactt | actccatatg | ggggtggcat | 1380 |
| aaatgatacg | gcaatgttct | ggggtgtaaa | gttctacaat | gatttgctga | tgcaagccgg | 1440 |
| caaacttggg | aatgtgcaat | cagaactgct | tctccgcaag | gactcacgga | ctttcacatt | 1500 |
| cgaaaaggga | tgggccttcc | cacgccgagt | gtacttcaat | ggtgataatt | gtgtcatgcc | 1560 |
| atctcctgaa | aattatccat | ggctgccgaa | tgcaagccct | ctaacaaaac | aagcattgac | 1620 |
| actcccactc | ttgatattct | gggttgcctt | ggctgttctg | ttggcttatg | catgatgagt | 1680 |
| gggatcaaga | tgtttagcaa | gcttcaagtt | gatgtcggat | tccatgaggt | gcactgcaac | 1740 |

-continued

```
gggatattta ttcattcaat tccatagcgg cacaggagag atgaggcgaa gccaagaaaa    1800
agtggatgtg tgtgtgtgtg tgtttgtaag ttaaagggcc aaaatgtatt tcttgtctgg    1860
tagtatatag cagctctaca acactttggt gaacttagtt actgcaaatt aggcaattac    1920
agttgcacct tttgtatttt atagcaaacc cagacttcta ttggattcta tgactgcccc    1980
tcttgtagta aacgcaaggc ttcactggta ctcctgttta aagattggtc aaatagaaga    2040
gacgacggtg attgtcaaaa aaaaaaaaaa aaaaaaaaaa aaaaaaaaaa aaaaaaaaaa    2100
aa                                                                    2102
```

<210> SEQ ID NO 8
<211> LENGTH: 449
<212> TYPE: PRT
<213> ORGANISM: Zea mays

<400> SEQUENCE: 8

```
Met Ala Gly Gly Arg Ser Ile Ala Cys Phe Ala Ala Val Leu Leu
1               5                   10                  15

Ala Ala Ala Leu Leu Leu Ser Ala Pro Thr Thr Thr Glu Ala Tyr Asp
                20                  25                  30

Ser Leu Asp Pro Asn Gly Asn Ile Thr Ile Lys Trp Asp Ile Met Gln
            35                  40                  45

Trp Thr Pro Asp Gly Tyr Val Ala Val Thr Met Phe Asn Tyr Gln
    50                  55                  60

Gln Phe Arg His Ile Gly Ala Pro Gly Trp Gln Leu Gly Trp Thr Trp
65              70                  75                  80

Ala Lys Lys Glu Val Ile Trp Ser Met Val Gly Ala Gln Thr Thr Glu
                85                  90                  95

Gln Gly Asp Cys Ser Lys Phe Lys Gly Asn Thr Pro His Cys Cys Lys
            100                 105                 110

Lys Asp Pro Thr Ile Val Asp Leu Leu Pro Gly Thr Pro Tyr Asn Met
        115                 120                 125

Gln Ile Ala Asn Cys Cys Lys Ala Gly Val Ile Asn Thr Phe Asn Gln
    130                 135                 140

Asp Pro Ala Asn Ala Ala Ser Ser Phe Gln Ile Ser Val Gly Leu Ala
145                 150                 155                 160

Gly Thr Thr Asn Lys Thr Val Lys Val Pro Lys Asn Phe Thr Leu Lys
                165                 170                 175

Thr Pro Gly Pro Gly Tyr Thr Cys Gly Arg Ala Ile Val Gly Arg Pro
            180                 185                 190

Thr Lys Phe Phe Ser Ala Asp Gly Arg Arg Val Thr Gln Ala Leu Met
        195                 200                 205

Thr Trp Asn Val Thr Cys Thr Tyr Ser Gln Phe Leu Ala Gln Lys Thr
    210                 215                 220

Pro Ser Cys Cys Val Ser Leu Ser Ser Phe Tyr Asn Asp Thr Ile Val
225                 230                 235                 240

Asn Cys Pro Thr Cys Ser Cys Gly Cys Gln Asn Pro Ser Gly Ser Asn
                245                 250                 255

Cys Val Asn Glu Asp Ser Pro Asn Leu Gln Ala Ala Ile Asp Gly Pro
            260                 265                 270

Gly Lys Trp Thr Gly Gln Pro Leu Val Gln Cys Thr Ser His Met Cys
        275                 280                 285

Pro Ile Arg Ile His Trp His Val Lys Leu Asn Tyr Lys Glu Tyr Trp
    290                 295                 300
```

```
Arg Val Lys Ile Thr Ile Thr Asn Phe Asn Phe Arg Met Asn Tyr Thr
305                 310                 315                 320

Gln Trp Asn Leu Val Ala Gln His Pro Asn Phe Asp Asn Ile Thr Gln
            325                 330                 335

Leu Phe Ser Phe Asn Tyr Lys Pro Leu Thr Pro Tyr Gly Gly Gly Ile
            340                 345                 350

Asn Asp Thr Ala Met Phe Trp Gly Val Lys Phe Tyr Asn Asp Leu Leu
            355                 360                 365

Met Gln Ala Gly Lys Leu Gly Asn Val Gln Ser Glu Leu Leu Leu Arg
            370                 375                 380

Lys Asp Ser Arg Thr Phe Thr Phe Glu Lys Gly Trp Ala Phe Pro Arg
385                 390                 395                 400

Arg Val Tyr Phe Asn Gly Asp Asn Cys Val Met Pro Ser Pro Glu Asn
                405                 410                 415

Tyr Pro Trp Leu Pro Asn Ala Ser Pro Leu Thr Lys Gln Ala Leu Thr
            420                 425                 430

Leu Pro Leu Leu Ile Phe Trp Val Ala Leu Ala Val Leu Leu Ala Tyr
            435                 440                 445

Ala
```

<210> SEQ ID NO 9
<211> LENGTH: 2422
<212> TYPE: DNA
<213> ORGANISM: Zea mays

<400> SEQUENCE: 9

```
aaccatgcac ctcaattttta gcaacctcgc acaaaaactg catgcctaat tataccttct    60
tggcccctcc tcccccgctg gaacgcatgt gtttgcttcc catcgctcct ggcttccccg   120
tcgagcgagg gagccacatt cttgcttcca ttgttcgctc aaacgcttgg tagctcgatc   180
ggcgccgttg ttcttgggcc ggccggtcga gccgaatggt catggcagcg ccagtgccgc   240
tccggcggcg gcgggcgctc ctggtggtag cgacgttact cgccgtggtc accgcggcga   300
tggcgcagga ctataaagat ggtggcggcg acgactacga ggaggacgag aagaagaagc   360
cgcagttcaa ggcgcaggag gcgtgcaacg gcgtgttcct gacgtacacg ttcatggagc   420
gcgccaagga gtacccgcac ctgaagaagg cggcggcgca gccgtacgcg ttcaaggcca   480
cggcgacggt gctcaacacc atgaccgagg acctcaaggc gtggcagatg ttcgtgggct   540
tccagcacaa ggagatcctc gtgtccgtcg gcggcgccgt gctgctcgac ggctccgacc   600
tccccgccaa cgtgtccggt ggcgccacct tgcgggata cccaatggcc gacctcctca   660
actccatcga cggcgggc gagccgtccc tgatcgagag caagattgag atcaccggca   720
cccaattcgg cgtgaaggcc cccgggaagc ccatgcccaa gaccatcaag ttgaccaacc   780
ccgtgggctt ccggtgcccc gcccccaacc acaaagacag cgtgatgtac gtgtgctgcg   840
tcaaggaccg caagttcaag gcgaagaagg ctaacagcac gcggtaccag acacggcgga   900
aagcggacct gacgttcgcc tacgacgtgc tgcaggccaa caccaacaac taccaggtgc   960
aggtgaccat cgacaactgg agccccatca gccggctgga caactggaac ctcacctggg  1020
agtggaagcg cggcgagttc atctacagca tgaaggcgc ctacacgctg ctcaaggaag  1080
gccccgcctg catctacagc cccgcagcgg gctactacaa ggacatggac ttcaccccg  1140
tctacaactg cgagaagcgg cccgtcatcg tggacctccc gccggagcgg gagaaggacg  1200
acgccgtcgg gaacctcccc ttctgctgca agaacggcac gctgctgccg cccaccatgg  1260
```

-continued

```
acccgtccaa gtcgcgggcc atgttccaga tgcaggtgta caagctgccg ccggacctga      1320
accgcacggc gctgtacccg ccgcagaact ggaagatctc cggcaagctc aacccgcagt      1380
acgcgtgcgg gccgcccgtc cgcgtgagcc cccaggagtt cccggacccg acgggtctca      1440
tgtcgaccac ccccgccgtg gcgtcgtggc aggtggcgtg caacatcacg cggcccaaga      1500
agcgcgcctc caagtgctgc gtctccttct ccgcctacta caacgactcc gtggtgccgt      1560
gcaacacctg cgcctgcggc tgcggcgacg acaccgcgac gtgcgacccg acaagcgcg       1620 ccatgctgct gccaccggag gcgctgctcg tcccgttcga caaccggtcg gccaaggcac      1680
gggcgtgggc caagatcaag cactggcggg tgcccaaccc catgccgtgc agcgacaact      1740
gcggcgtcag catcaactgg cacgtcatca acaactacaa gtccggctgg tcggcgcgca      1800
tgaccatctt caactggcag gactacacct tcaaggattg gtttgccgca gtgaccatgg      1860
gcagccactt cagcggctac gagaacgtct actccttcaa cggcacgcgg atgggcgccc      1920
ccttcaacaa caccatcttc atgcaggggg tgccgggcct cgcttacctc gagcccatca      1980
ccgacgcgaa gacgacatcg gaacccaggc ttcccggcaa gcagcagtcg gtcatctcgt      2040
tcaccaggaa agacgcgccc aatgtcaaca ttcccagagg ggaaggcttc cccaagagga      2100
tctacttcga cggcgaggag tgcgcgctcc cggataggat acccaaggtg tcgagcgcgc      2160
gccggcgggc tgggaccgcg agcctgggtc agatagccat ggcggcggcg ctcgtgatga      2220
ttgtggcgct agtggattcc ttgtgcctat gatgactgaa aacttctttg gttcatagag      2280
gatttgactg acctagcgcg ctgcatttgt tgaacacttc attcattaac taggtacgtg      2340
cccgtgcgtt gctacggaag taaaaaaata gcgtacaaaa tatatacgaa gcgaaaaaca      2400
tcactatgat agtaaaaatc gt                                              2422
```

<210> SEQ ID NO 10
<211> LENGTH: 678
<212> TYPE: PRT
<213> ORGANISM: Zea mays

<400> SEQUENCE: 10

```
Met Val Met Ala Ala Pro Val Pro Leu Arg Arg Arg Ala Leu Leu
1               5                   10                  15

Val Val Ala Thr Leu Leu Ala Val Val Thr Ala Ala Met Ala Gln Asp
            20                  25                  30

Tyr Lys Asp Gly Gly Gly Asp Asp Tyr Glu Glu Asp Glu Lys Lys Lys
        35                  40                  45

Pro Gln Phe Lys Ala Gln Glu Ala Cys Asn Gly Val Phe Leu Thr Tyr
    50                  55                  60

Thr Phe Met Glu Arg Ala Lys Glu Tyr Pro His Leu Lys Lys Ala Ala
65                  70                  75                  80

Ala Gln Pro Tyr Ala Phe Lys Ala Thr Ala Thr Val Leu Asn Thr Met
                85                  90                  95

Thr Glu Asp Leu Lys Ala Trp Gln Met Phe Val Gly Phe Gln His Lys
            100                 105                 110

Glu Ile Leu Val Ser Val Gly Gly Ala Val Leu Leu Asp Gly Ser Asp
        115                 120                 125

Leu Pro Ala Asn Val Ser Gly Gly Ala Thr Phe Ala Gly Tyr Pro Met
    130                 135                 140

Ala Asp Leu Leu Asn Ser Ile Glu Thr Ala Gly Glu Pro Ser Leu Ile
145                 150                 155                 160
```

-continued

```
Glu Ser Lys Ile Glu Ile Thr Gly Thr Gln Phe Gly Val Lys Ala Pro
                165                 170                 175
Gly Lys Pro Met Pro Lys Thr Ile Lys Leu Thr Asn Pro Val Gly Phe
            180                 185                 190
Arg Cys Pro Ala Pro Asn His Lys Asp Ser Val Met Tyr Val Cys Cys
        195                 200                 205
Val Lys Asp Arg Lys Phe Lys Ala Lys Ala Asn Ser Thr Arg Tyr
    210                 215                 220
Gln Thr Arg Arg Lys Ala Asp Leu Thr Phe Ala Tyr Asp Val Leu Gln
225                 230                 235                 240
Ala Asn Thr Asn Asn Tyr Gln Val Gln Val Thr Ile Asp Asn Trp Ser
                245                 250                 255
Pro Ile Ser Arg Leu Asp Asn Trp Asn Leu Thr Trp Glu Trp Lys Arg
            260                 265                 270
Gly Glu Phe Ile Tyr Ser Met Lys Gly Ala Tyr Thr Leu Leu Lys Glu
        275                 280                 285
Gly Pro Ala Cys Ile Tyr Ser Pro Ala Ala Gly Tyr Tyr Lys Asp Met
    290                 295                 300
Asp Phe Thr Pro Val Tyr Asn Cys Glu Lys Arg Pro Val Ile Val Asp
305                 310                 315                 320
Leu Pro Pro Glu Arg Glu Lys Asp Asp Ala Val Gly Asn Leu Pro Phe
                325                 330                 335
Cys Cys Lys Asn Gly Thr Leu Leu Pro Pro Thr Met Asp Pro Ser Lys
            340                 345                 350
Ser Arg Ala Met Phe Gln Met Gln Val Tyr Lys Leu Pro Pro Asp Leu
        355                 360                 365
Asn Arg Thr Ala Leu Tyr Pro Pro Gln Asn Trp Lys Ile Ser Gly Lys
    370                 375                 380
Leu Asn Pro Gln Tyr Ala Cys Gly Pro Pro Val Arg Val Ser Pro Gln
385                 390                 395                 400
Glu Phe Pro Asp Pro Thr Gly Leu Met Ser Thr Pro Ala Val Ala
                405                 410                 415
Ser Trp Gln Val Ala Cys Asn Ile Thr Arg Pro Lys Lys Arg Ala Ser
            420                 425                 430
Lys Cys Cys Val Ser Phe Ser Ala Tyr Tyr Asn Asp Ser Val Val Pro
        435                 440                 445
Cys Asn Thr Cys Ala Cys Gly Cys Gly Asp Asp Thr Ala Thr Cys Asp
    450                 455                 460
Pro Asp Lys Arg Ala Met Leu Leu Pro Pro Glu Ala Leu Leu Val Pro
465                 470                 475                 480
Phe Asp Asn Arg Ser Ala Lys Ala Arg Ala Trp Ala Lys Ile Lys His
                485                 490                 495
Trp Arg Val Pro Asn Pro Met Pro Cys Ser Asp Asn Cys Gly Val Ser
            500                 505                 510
Ile Asn Trp His Val Ile Asn Asn Tyr Lys Ser Gly Trp Ser Ala Arg
        515                 520                 525
Met Thr Ile Phe Asn Trp Gln Asp Tyr Thr Phe Lys Asp Trp Phe Ala
    530                 535                 540
Ala Val Thr Met Gly Ser His Phe Ser Gly Tyr Glu Asn Val Tyr Ser
545                 550                 555                 560
Phe Asn Gly Thr Arg Met Gly Ala Pro Phe Asn Asn Thr Ile Phe Met
                565                 570                 575
Gln Gly Val Pro Gly Leu Ala Tyr Leu Glu Pro Ile Thr Asp Ala Lys
```

```
                 580                 585                 590
Thr Thr Ser Glu Pro Arg Leu Pro Gly Lys Gln Gln Ser Val Ile Ser
        595                 600                 605

Phe Thr Arg Lys Asp Ala Pro Asn Val Asn Ile Pro Arg Gly Glu Gly
610                 615                 620

Phe Pro Lys Arg Ile Tyr Phe Asp Gly Glu Glu Cys Ala Leu Pro Asp
625                 630                 635                 640

Arg Ile Pro Lys Val Ser Ser Ala Arg Arg Ala Gly Thr Ala Ser
                645                 650                 655

Leu Gly Gln Ile Ala Met Ala Ala Ala Leu Val Met Ile Val Ala Leu
            660                 665                 670

Val Asp Ser Leu Cys Leu
        675

<210> SEQ ID NO 11
<211> LENGTH: 1845
<212> TYPE: DNA
<213> ORGANISM: Zea mays

<400> SEQUENCE: 11
agaagagaga ggggaaagtt gcttctctct ctgacccgcc cactccctcc ttccctgctc      60
cggtcgcact ccgtagttcc tccgcgcact tacgtacagc agacagacac gagatcgagt     120
ggtacagggc ccgccagaaa cctcacgagc tagctgggtt cctgccgcgc cgccgatcca     180
cgcatggcgc gccgccgcct cctgcccgcg cgcttcgtcg ccgcctccgt cgcgctgctc     240
gccgtcgcct tctcctcctc tctaacgcgt ccgtcaggtg catacgatcc gctcgatccg     300
aacgggaaca taacaatcaa gtgggacgtg atacagtgga ctgcggatgg ctatgtggcc     360
gtcgtttcgc tatacaacta ccagcagtac cgccacatcc aggcgccgcc ggggtggagg     420
ctaggctggg tgtgggcgaa gaaggaggtg atctgggcga tgaccggcgg ccaggccacc     480
gagcagggcg actgctccag gttcaaggcc agcgtcctcc cccactgctg caggagggac     540
ccggaggtgg tggacctgct gcccgggact ccctacaaca cgcagaccgc caactgctgc     600
aggggaggag tgctcgcctc gtgggcgcag gaccctagcg acgccgtcgc ctcgttccag     660
gtcagcgttg gcaggctgg gtccaccaac aggaccgtca aggtgcccag gaacttcacc     720
ctgctggcgc ctggtcccgg gtacacctgc ggagccgcca gcttgtcaa gcctaccaag     780
ttcatgtctc aggatggcag agatcaact caagcgcaca tgacctggaa cgtgacgtgc     840
acgtactccc agttccttgc ccagagatct ccaacctgct gtgtctcgct ctcgtcgttc     900
tacaacgaca ccattgttag ctgcccagca tgctcctgcg gctgccagaa caacaacagc     960
agtagcaccg ccgcgccagg aagctgcgta gagggtagta gaaggtcgcc ctatctggct    1020
tccgtcgtca acgatcctag caagaacagc ttggcgccgc tagtccagtg cacctcacac    1080
atgtgcccgg taagggtgca ctggcacgtc aaggtcagct acaaggagta ctggagggtg    1140
aagatcacgg tcaccaactt caactaccgg atgaactact cgcagtggaa cctggtcgcg    1200
cagcacccca acttcgacaa cctcaccacc attttcagct tcaactacag acctctcaac    1260
ccctacggag tgatcaacga cacggcgatg ctatggggca tcaagtacta caacgatctg    1320
ctcatgacgg ccgggccaga cgggaacgtg cagtccgagc ttctgttccg gaaggagccg    1380
tccacgttca ccttccacaa aggatgggcc ttccccaggc gagtctactt caacggagac    1440
aactgcgtga tgccgccgcc ggacgcctac ccgtggctgc ccaacgccgc ctcgccgcgg    1500
ctgtcgcctt cgcttctcct cccgctcgtt gcggctgctt ggacagcatt cgcagtcctt    1560
```

```
tcgtgatggg cccatatgcg tagggaaggc aaggcaaggc acacaatgtc ccatgacaag      1620
ttctgacctg attcagcgtt gttgcttgct gctgatcatt agtcgatctg ttgcgaagtt      1680
ttatttggtg tcttgaatct tgattcagga acaggttcag atgtgcattc acgtactacc      1740
aagcatgtac attcccaata cttgtaaatt tctgcaaaga ctgactggca agtgacagta      1800 gaataatct gtttctctct ccgcatcagg aaagtttcgg ctcaa                      1845
```

<210> SEQ ID NO 12
<211> LENGTH: 460
<212> TYPE: PRT
<213> ORGANISM: Zea mays

<400> SEQUENCE: 12

```
Met Ala Pro Pro Leu Leu Pro Ala Arg Phe Val Ala Ala Ser Val
1               5                   10                  15

Ala Leu Leu Ala Val Ala Phe Ser Ser Ser Leu Thr Arg Pro Ser Gly
            20                  25                  30

Ala Tyr Asp Pro Leu Asp Pro Asn Gly Asn Ile Thr Ile Lys Trp Asp
        35                  40                  45

Val Ile Gln Trp Thr Ala Asp Gly Tyr Val Ala Val Ser Leu Tyr
    50                  55                  60

Asn Tyr Gln Gln Tyr Arg His Ile Gln Ala Pro Pro Gly Trp Arg Leu
65                  70                  75                  80

Gly Trp Val Trp Ala Lys Lys Glu Val Ile Trp Ala Met Thr Gly Gly
                85                  90                  95

Gln Ala Thr Glu Gln Gly Asp Cys Ser Arg Phe Lys Ala Ser Val Leu
            100                 105                 110

Pro His Cys Cys Arg Arg Asp Pro Glu Val Val Asp Leu Leu Pro Gly
        115                 120                 125

Thr Pro Tyr Asn Thr Gln Thr Ala Asn Cys Cys Arg Gly Gly Val Leu
    130                 135                 140

Ala Ser Trp Ala Gln Asp Pro Ser Asp Ala Val Ala Ser Phe Gln Val
145                 150                 155                 160

Ser Val Gly Gln Ala Gly Ser Thr Asn Arg Thr Val Lys Val Pro Arg
                165                 170                 175

Asn Phe Thr Leu Leu Ala Pro Gly Pro Gly Tyr Thr Cys Gly Ala Ala
            180                 185                 190

Lys Leu Val Lys Pro Thr Lys Phe Met Ser Gln Asp Gly Arg Arg Ser
        195                 200                 205

Thr Gln Ala His Met Thr Trp Asn Val Thr Cys Thr Tyr Ser Gln Phe
    210                 215                 220

Leu Ala Gln Arg Ser Pro Thr Cys Cys Val Ser Leu Ser Ser Phe Tyr
225                 230                 235                 240

Asn Asp Thr Ile Val Ser Cys Pro Ala Cys Ser Cys Gly Cys Gln Asn
                245                 250                 255

Asn Asn Ser Ser Ser Thr Ala Ala Pro Gly Ser Cys Val Glu Gly Ser
            260                 265                 270

Arg Arg Ser Pro Tyr Leu Ala Ser Val Val Asn Asp Pro Ser Lys Asn
        275                 280                 285

Ser Leu Ala Pro Leu Val Gln Cys Thr Ser His Met Cys Pro Val Arg
    290                 295                 300

Val His Trp His Val Lys Val Ser Tyr Lys Glu Tyr Trp Arg Val Lys
305                 310                 315                 320
```

```
Ile Thr Val Thr Asn Phe Asn Tyr Arg Met Asn Tyr Ser Gln Trp Asn
            325                 330                 335

Leu Val Ala Gln His Pro Asn Phe Asp Asn Leu Thr Thr Ile Phe Ser
        340                 345                 350

Phe Asn Tyr Arg Pro Leu Asn Pro Tyr Gly Val Ile Asn Asp Thr Ala
            355                 360                 365

Met Leu Trp Gly Ile Lys Tyr Tyr Asn Asp Leu Leu Met Thr Ala Gly
    370                 375                 380

Pro Asp Gly Asn Val Gln Ser Glu Leu Leu Phe Arg Lys Glu Pro Ser
385                 390                 395                 400

Thr Phe Thr Phe His Lys Gly Trp Ala Phe Pro Arg Arg Val Tyr Phe
                405                 410                 415

Asn Gly Asp Asn Cys Val Met Pro Pro Asp Ala Tyr Pro Trp Leu
            420                 425                 430

Pro Asn Ala Ala Ser Pro Arg Leu Ser Pro Ser Leu Leu Pro Leu
            435                 440                 445

Val Ala Ala Trp Thr Ala Phe Ala Val Leu Ser
    450                 455                 460

<210> SEQ ID NO 13
<211> LENGTH: 1644
<212> TYPE: DNA
<213> ORGANISM: Zea mays

<400> SEQUENCE: 13
tgcacgcccg atactgctag ccaaggccaa gccagtgcag gcgcggtggt gtgtgttgtt      60
ctcgtcgcgc actcgccggc agcgatggag ccccgccgct ccgtgctgct cctggccctc     120
gccgtcgccc ccgcgctctc cgtcgcagtg gcttacgacc cgttggaccc gaacgggaac     180
attaccatca agtgggacat catgtcgtgg acgcccgacg ctatgtcgc ggtggtgacc     240
atcaacaact ccagacgta ccggcagatc acggcgccgg gtggacggt ggggtggacg      300
tgggcgaagc gggaggtgat ctggtccatg gtgggcgcgc aggccacgga gcagggcgac     360
tgctcccgct tcaaggccaa catcccgcac tgctgcaagc gcaccccggc cgtcgtcgac     420
ctgctccccg gcgtgcccta caaccagcag atcgccaact gctgccgcgg cggcgtcgtc     480
agcgcctacg ccaggaccc ggccaccgcc gtcgccgcgt tccaggtcag cgtcggccag      540
gccggcacca ccaaccgcac cgtcaaggtg cccaagaact tcacgctgct ggggccgggg     600
ccaggataca cctgcggccc cggcaaggtc gtcccctcca ccgtcttcct cacgcccgac     660
cgccgacgca agacacaagc cctcatgacg tggaacgtga cgtgcaccta ctcgcagcac     720
ctggcgtcca gtaccccctc ctgctgcgtc tccttctcct ccttctacaa cgacaccatc     780
gtgccctgcg ccaagtgcgc ctgcggctgc gagcacaaga cctgcgtcca gggcgactcg     840
aagcggctgg cggtgacggg gaagcacgcg cacacggcgg cggcggtgcg cgggcagcac     900
cgggacaagg aggcgccgct gctgcagtgc acgacgcaca tgtgccccgt gcgcgtgcac     960
tggcacgtca agctcaacta caaggagtac tggcgcgcca agatcgccat caccaacttc    1020
aactaccaca tgaactacac gcagtggacg ctcgtcgcgc agcaccccaa cctcgacaac    1080
atcaccgagg tcttcagctt cggctacaag cccgtcgtct cctatggatc catcaatgac    1140
acggccatgt tctacgggct caagtacttc aacgaccacc tgatgcaggc ggggccgtac    1200
gggaacgtgc agtcggaggt gctcatgcgc aaggacgcca gcaccttcac cttcaggcag    1260
ggctgggcct tcccgcgcaa ggtctacttc aacggcgacg agtgccagat gccgccgccg    1320
```

-continued

```
gacgcctacc cctacttgcc caactccgcg ccgccgacag ccgcggcgtc gctgggcggc    1380
gcagcggcag cggccgtcgt ggtgctcttg ggcatgatcg tggcatgaga aaacacggga    1440
catcgatcga cctagtgcta ggaccggcac aggggaatgg aaaaaagacg ttgctttctt    1500
ctgtagatag agagaccaga gacctcggtt tgggtttcag gaatggtttg gaactttgga    1560
tgttttcttt tcagtgtaga tggacaagcc atgattttgc aaggaaaatt aacatgtgca    1620
aaaaaaaaaa aaaaaaaaa aaaa                                            1644
```

<210> SEQ ID NO 14
<211> LENGTH: 447
<212> TYPE: PRT
<213> ORGANISM: Zea mays

<400> SEQUENCE: 14

```
Met Glu Pro Arg Arg Ser Val Leu Leu Ala Leu Ala Val Ala Ala
1               5                   10                  15

Ala Leu Ser Val Ala Val Ala Tyr Asp Pro Leu Asp Pro Asn Gly Asn
            20                  25                  30

Ile Thr Ile Lys Trp Asp Ile Met Ser Trp Thr Pro Asp Gly Tyr Val
        35                  40                  45

Ala Val Val Thr Ile Asn Asn Phe Gln Thr Tyr Arg Gln Ile Thr Ala
    50                  55                  60

Pro Gly Trp Thr Val Gly Trp Thr Trp Ala Lys Arg Glu Val Ile Trp
65                  70                  75                  80

Ser Met Val Gly Ala Gln Ala Thr Glu Gln Gly Asp Cys Ser Arg Phe
                85                  90                  95

Lys Ala Asn Ile Pro His Cys Cys Lys Arg Thr Pro Ala Val Val Asp
            100                 105                 110

Leu Leu Pro Gly Val Pro Tyr Asn Gln Gln Ile Ala Asn Cys Cys Arg
        115                 120                 125

Gly Gly Val Val Ser Ala Tyr Gly Gln Asp Pro Ala Thr Ala Val Ala
    130                 135                 140

Ala Phe Gln Val Ser Val Gly Gln Ala Gly Thr Thr Asn Arg Thr Val
145                 150                 155                 160

Lys Val Pro Lys Asn Phe Thr Leu Leu Gly Pro Gly Pro Gly Tyr Thr
                165                 170                 175

Cys Gly Pro Gly Lys Val Val Pro Ser Thr Val Phe Leu Thr Pro Asp
            180                 185                 190

Arg Arg Arg Lys Thr Gln Ala Leu Met Thr Trp Asn Val Thr Cys Thr
        195                 200                 205

Tyr Ser Gln His Leu Ala Ser Lys Tyr Pro Ser Cys Cys Val Ser Phe
    210                 215                 220

Ser Ser Phe Tyr Asn Asp Thr Ile Val Pro Cys Ala Lys Cys Ala Cys
225                 230                 235                 240

Gly Cys Glu His Lys Thr Cys Val Gln Gly Asp Ser Lys Arg Leu Ala
                245                 250                 255

Val Thr Gly Lys His Ala His Thr Ala Ala Ala Val Arg Gly Gln His
            260                 265                 270

Arg Asp Lys Glu Ala Pro Leu Leu Gln Cys Thr Thr His Met Cys Pro
        275                 280                 285

Val Arg Val His Trp His Val Lys Leu Asn Tyr Lys Glu Tyr Trp Arg
    290                 295                 300

Ala Lys Ile Ala Ile Thr Asn Phe Asn Tyr His Met Asn Tyr Thr Gln
305                 310                 315                 320
```

Trp Thr Leu Val Ala Gln His Pro Asn Leu Asp Asn Ile Thr Glu Val
            325                 330                 335

Phe Ser Phe Gly Tyr Lys Pro Val Val Ser Tyr Gly Ser Ile Asn Asp
            340                 345                 350

Thr Ala Met Phe Tyr Gly Leu Lys Tyr Phe Asn Asp His Leu Met Gln
            355                 360                 365

Ala Gly Pro Tyr Gly Asn Val Gln Ser Glu Val Leu Met Arg Lys Asp
            370                 375                 380

Ala Ser Thr Phe Thr Phe Arg Gln Gly Trp Ala Phe Pro Arg Lys Val
385                 390                 395                 400

Tyr Phe Asn Gly Asp Glu Cys Gln Met Pro Pro Asp Ala Tyr Pro
            405                 410                 415

Tyr Leu Pro Asn Ser Ala Pro Pro Thr Ala Ala Ser Leu Gly Gly
            420                 425                 430

Ala Ala Ala Ala Ala Val Val Val Leu Leu Gly Met Ile Val Ala
            435                 440                 445

<210> SEQ ID NO 15
<211> LENGTH: 2108
<212> TYPE: DNA
<213> ORGANISM: Zea mays

<400> SEQUENCE: 15

| | | | | | |
|---|---|---|---|---|---|
| tcttcgtctt | cgtgtcatcg | tgcgtgtgtg | cgcttggacg | gaaacggcct | ctcatcctcc | 60 |
| gacgacccag | actcgatcca | ctcaccacca | ccggcttatt | cgtttatacg | gaaacagatt | 120 |
| cagcttctgt | gcctgcttca | gccatggcca | tgctgcccgt | cgtcgtccgc | atggccgcca | 180 |
| tgcccttcat | cttccttgtg | ctcctcgcgc | acaccgcctc | ggcacagccc | gacgccggct | 240 |
| gcaacgggat | cctcctcacc | tacacgctgc | agcgccggga | caagatcagg | cctcacgtgg | 300 |
| cggcgcccaa | ctcccagccc | tactccttca | gcgccagcgc | caccgtcgtc | aacgccggca | 360 |
| cccgcccgct | acgctcctgg | gcgctgctgc | tcaccttcgt | gcacggcgag | atcctcgtct | 420 |
| ccgtcgacgg | ggccgtgctc | acctcgggcg | ccgccctgcc | ctacaacacc | acggcggggg | 480 |
| acgccgccgg | caggcccacg | cccacgtcct | tcaccgggta | cccgcagacg | gacctcctca | 540 |
| ccccgatcgc | cacggccggg | gaccccgcca | agacacaggc | cacggtcagc | ctcgtaggca | 600 |
| cgctcttcgc | cgggccggag | ccctacgtcc | cgctcccctc | gtttctctcg | ctcgccgacc | 660 |
| cttcctacac | ctgcccgccg | gccaccaacg | ccacgtcgtc | gccgacgaac | ctcaccacct | 720 |
| gctgcgtgtt | cacggcgggt | ggggaccccca | ccggcggcct | ggtggagagt | ggcttcctcc | 780 |
| cgcgccgcac | cggcgacctg | gtcatcacct | acgacgtgct | ccagtcgtac | gacaccacct | 840 |
| acctagcgct | cgtcacgctg | gagaacgacg | cgctgctcgg | ccgcctcgac | gcctggcagc | 900 |
| tgtcgtggag | gtgggagcac | ggggagttca | tcagctccat | gcgaggcgcc | tacccgcggg | 960 |
| aggtggacac | ggccgaatgc | tctctacggtc | cccagggcca | gtactacaag | gacctcgact | 1020 |
| tctccaaggc | ggtgctcaac | tgcgaccgca | ggccgtcgt | ccacgacctg | ccgccgtcgc | 1080 |
| gggccaacga | cacggagatc | ggccggatcg | accactgctg | ccggaacggc | accatcctgc | 1140 |
| ccaagtccat | ggacgtcgcg | cgctccaagt | cggcgttcca | gatggtggtg | tacaagatgc | 1200 |
| cgcccgacct | caaccggacc | aagctctacc | cgccacagg | gttcaacgtc | accggcgccg | 1260 |
| cgtccgcgct | gaaccggag | tacgcgtgcg | acccacccat | ctcggtgagc | ccgtcggagt | 1320 |
| acccggaccc | cagcgggctc | acgtcgatca | cggtggccgt | ggcgacgtgg | caggtggtgt | 1380 |

-continued

```
gcaacatcac cacgtcgccc aagaagccgc ccaggtgctg cgtctccttc tcctccttct    1440
acaacgagtc ggtggtcccc tgccggacgt gcgcgtgcgg ctgccgcctcg tccgcgccga   1500 cctgcagcac cacggcgccg gcgatgctgc tgccgccgca ggcgctgctc atgccgttcg    1560
accggcgggc cagcgaggcg ctcgagtggg cggaccagaa gcacctcggc gtgcccaaac    1620
ccatgccctg cggcgacttc tgcggcgtca gcgtcaactg gcacgtcgcc accgacttca    1680
ccggaggatg gagcgcgcgc ctcacgctct tcaactggga cggcacggac atgccggact    1740
ggttcacggc catcgtcatg gacaaggcgt acgacggctt cgaacaggcc tactccttca    1800
acgccacggg cgtcgggaac agcaccatct tcgtcagggg cgcccagggc ctcaacttcc    1860
tgctcgggga gaggaacatg agcggcgtag attacccggt gcccgggaag cagcagtccg    1920
tcttctcctt caccaagaag aagacccccg gcatcgacat catcgccggg acggcttcc    1980 cgtccaaggt cttcttcaac ggcgacgagt gcgccatgcc attgaggatt ccgagccagg    2040
ggaccagtgt cgtcgtccct atgcagctgt gtttgcttgt ttccgctttc atgttattgc    2100
tgctgtaa                                                             2108
```

<210> SEQ ID NO 16
<211> LENGTH: 654
<212> TYPE: PRT
<213> ORGANISM: Zea mays

<400> SEQUENCE: 16

```
Met Ala Met Leu Pro Val Val Arg Met Ala Ala Met Pro Phe Ile
1               5                   10                  15

Phe Leu Val Leu Leu Ala His Thr Ala Ser Ala Gln Pro Asp Ala Gly
                20                  25                  30

Cys Asn Gly Ile Leu Leu Thr Tyr Thr Leu Gln Arg Arg Asp Lys Ile
            35                  40                  45

Arg Pro His Val Ala Ala Pro Asn Ser Gln Pro Tyr Ser Phe Ser Ala
        50                  55                  60

Ser Ala Thr Val Val Asn Ala Gly Thr Arg Pro Leu Arg Ser Trp Ala
65                  70                  75                  80

Leu Leu Leu Thr Phe Val His Gly Glu Ile Leu Val Ser Val Asp Gly
                85                  90                  95

Ala Val Leu Thr Ser Gly Ala Ala Leu Pro Tyr Asn Thr Thr Ala Gly
                100                 105                 110

Asp Ala Ala Gly Arg Pro Thr Pro Thr Ser Phe Thr Gly Tyr Pro Gln
            115                 120                 125

Thr Asp Leu Leu Thr Pro Ile Ala Thr Ala Gly Asp Pro Ala Lys Thr
        130                 135                 140

Gln Ala Thr Val Ser Leu Val Gly Thr Leu Phe Ala Gly Pro Glu Pro
145                 150                 155                 160

Tyr Val Pro Leu Pro Ser Phe Leu Ser Leu Ala Asp Pro Ser Tyr Thr
                165                 170                 175

Cys Pro Pro Ala Thr Asn Ala Thr Ser Ser Pro Thr Asn Leu Thr Thr
            180                 185                 190

Cys Cys Val Phe Thr Ala Gly Gly Asp Pro Thr Gly Gly Leu Val Glu
        195                 200                 205

Ser Gly Phe Leu Pro Arg Arg Thr Gly Asp Leu Val Ile Thr Tyr Asp
    210                 215                 220

Val Leu Gln Ser Tyr Asp Thr Thr Tyr Leu Ala Leu Val Thr Leu Glu
225                 230                 235                 240
```

-continued

```
Asn Asp Ala Leu Leu Gly Arg Leu Asp Ala Trp Gln Leu Ser Trp Arg
                245                 250                 255

Trp Glu His Gly Glu Phe Ile Ser Ser Met Arg Gly Ala Tyr Pro Arg
            260                 265                 270

Glu Val Asp Thr Ala Glu Cys Leu Tyr Gly Pro Gln Gly Gln Tyr Tyr
        275                 280                 285

Lys Asp Leu Asp Phe Ser Lys Ala Val Leu Asn Cys Asp Arg Arg Pro
    290                 295                 300

Val Val His Asp Leu Pro Pro Ser Arg Ala Asn Asp Thr Glu Ile Gly
305                 310                 315                 320

Arg Ile Asp His Cys Cys Arg Asn Gly Thr Ile Leu Pro Lys Ser Met
                325                 330                 335

Asp Val Ala Arg Ser Lys Ser Ala Phe Gln Met Val Val Tyr Lys Met
            340                 345                 350

Pro Pro Asp Leu Asn Arg Thr Lys Leu Tyr Pro Pro Thr Gly Phe Asn
        355                 360                 365

Val Thr Gly Ala Ala Ser Ala Leu Asn Pro Glu Tyr Ala Cys Asp Pro
    370                 375                 380

Pro Ile Ser Val Ser Pro Ser Glu Tyr Pro Asp Pro Ser Gly Leu Thr
385                 390                 395                 400

Ser Ile Thr Val Ala Val Ala Thr Trp Gln Val Val Cys Asn Ile Thr
                405                 410                 415

Thr Ser Pro Lys Lys Pro Pro Arg Cys Cys Val Ser Phe Ser Ser Phe
            420                 425                 430

Tyr Asn Glu Ser Val Val Pro Cys Arg Thr Cys Ala Cys Gly Cys Pro
        435                 440                 445

Ser Ser Ala Pro Thr Cys Ser Thr Thr Ala Pro Ala Met Leu Leu Pro
    450                 455                 460

Pro Gln Ala Leu Leu Met Pro Phe Asp Arg Arg Ala Ser Glu Ala Leu
465                 470                 475                 480

Glu Trp Ala Asp Gln Lys His Leu Gly Val Pro Lys Pro Met Pro Cys
                485                 490                 495

Gly Asp Phe Cys Gly Val Ser Val Asn Trp His Val Ala Thr Asp Phe
            500                 505                 510

Thr Gly Gly Trp Ser Ala Arg Leu Thr Leu Phe Asn Trp Asp Gly Thr
        515                 520                 525

Asp Met Pro Asp Trp Phe Thr Ala Ile Val Met Asp Lys Ala Tyr Asp
    530                 535                 540

Gly Phe Glu Gln Ala Tyr Ser Phe Asn Ala Thr Gly Val Gly Asn Ser
545                 550                 555                 560

Thr Ile Phe Val Arg Gly Ala Gln Gly Leu Asn Phe Leu Leu Gly Glu
                565                 570                 575

Arg Asn Met Ser Gly Val Asp Tyr Pro Val Pro Gly Lys Gln Gln Ser
            580                 585                 590

Val Phe Ser Phe Thr Lys Lys Thr Pro Gly Ile Asp Ile Ile Ala
        595                 600                 605

Gly Asp Gly Phe Pro Ser Lys Val Phe Asn Gly Asp Glu Cys Ala
    610                 615                 620

Met Pro Leu Arg Ile Pro Ser Gln Gly Thr Ser Val Val Pro Met
625                 630                 635                 640

Gln Leu Cys Leu Leu Val Ser Ala Phe Met Leu Leu Leu
                645                 650
```

<210> SEQ ID NO 17
<211> LENGTH: 1335
<212> TYPE: DNA
<213> ORGANISM: Zea mays

<400> SEQUENCE: 17

```
atggggcgct tcgtcttcgt cctgctaatc ctgatgtgct gttcctcctc ccgattcaca      60
ggtgcctacg accccataga tccgaacggg aacatcacga tcgtctggga ttttcagagt     120
ctcgacgtcg cgggcatgac cccgtacacg gtcatggtga gcatccacaa ctaccagatg     180
taccgacaca tcgagcgtcc ggggtggcgg ctgagctgga gctgggccgg caaggaggtc     240
atctggagca cgacgggcgc ggagacgacg gagcagggcg actgctcccg cgtcggcagc     300
gggggcagcc gcccgcattg ctgccagaag cggcccgtca tggtggacct gccgcctggc     360
acgccgtaca acatgcaggt cgccaactgc tgccggggcg gcgtgctgtc gtctctcgtc     420
cagagcgacc tgacgtccgc cgccgcgttc cagatggtgg tcggcgagtt cgccctcgcc     480
agggacagcg gcggcaagga gcccgagaag ccgtggcagt cgacatgggg cgtgccgggg     540
tacacctgca gcaacgcgac cacggtggcc ccgaccagga tcaaggtcga caagaaccgc     600
tacgtccagg cgctccagga tcgagctgaa ctccgtgcag tgacatggca ggtgacctgc     660
tcgtactcgc agtaccgggc gtcggcggcg ccgtcgtgct gcgtctccat gacgaccttc     720
tacagcgaga cgatcgtaga ttgcccgcgg tgcagctgcg gctgccaagg gtccccaccg     780
tcgccacaat gcgtcagcgt cgatcaacaa caaccatggt tgccggccgt cggcgacgac     840
gagccgtcgt cggcgccgat cgtctggtgc tccgagcaca tgtgcccgat ccgggtgcac     900
tggcacgtga agacgaacta ccgcaagtac tggcgggtga aggtgacggt gtccaactac     960
aacctggcga ggaactacag cgactggaac ctggtgctgc agcaccccaa cctgcggagc    1020
ctgacgcagc tgttcagctt caactacagg cctctcgtcg agtacggcgc ctacaacgac    1080
acggggatgt tctgggggtt acgttactac aacgagatgc tgctgcagga cgggaacgtg    1140
cagtcggaga tgatcctgga aaggagagc gacttcacct attccggtgg ctgggcgttc    1200
ccgcggaggg tctacttcaa cggccaagag tgcgtcatgc cgccggcgga ccagtacccc    1260
gtactgccca acggagcctc ggctttgcgg gggcattttt gcttcctgct gctactcttc    1320
ttcgttgtgg tgtag                                                     1335
```

<210> SEQ ID NO 18
<211> LENGTH: 444
<212> TYPE: PRT
<213> ORGANISM: Zea mays

<400> SEQUENCE: 18

Met Gly Arg Phe Val Phe Val Leu Leu Ile Leu Met Cys Cys Ser Ser
1               5                   10                  15

Ser Arg Phe Thr Gly Ala Tyr Asp Pro Ile Asp Pro Asn Gly Asn Ile
            20                  25                  30

Thr Ile Val Trp Asp Phe Gln Ser Leu Asp Val Ala Gly Met Thr Pro
        35                  40                  45

Tyr Thr Val Met Val Ser Ile His Asn Tyr Gln Met Tyr Arg His Ile
    50                  55                  60

Glu Arg Pro Gly Trp Arg Leu Ser Trp Ser Ala Gly Lys Glu Val
65                  70                  75                  80

Ile Trp Ser Thr Thr Gly Ala Glu Thr Thr Glu Gln Gly Asp Cys Ser
                85                  90                  95

```
Arg Val Gly Ser Gly Gly Ser Arg Pro His Cys Cys Gln Lys Arg Pro
            100                 105                 110
Val Met Val Asp Leu Pro Pro Gly Thr Pro Tyr Asn Met Gln Val Ala
            115                 120                 125
Asn Cys Cys Arg Gly Gly Val Leu Ser Ser Leu Val Gln Ser Asp Leu
        130                 135                 140
Thr Ser Ala Ala Ala Phe Gln Met Val Val Gly Glu Phe Ala Leu Ala
145                 150                 155                 160
Arg Asp Ser Gly Gly Lys Glu Pro Glu Lys Pro Trp Gln Phe Asp Met
                165                 170                 175
Gly Val Pro Gly Tyr Thr Cys Ser Asn Ala Thr Val Ala Pro Thr
            180                 185                 190
Arg Ile Lys Val Asp Lys Asn Arg Tyr Val Gln Ala Leu Gln Asp Arg
            195                 200                 205
Ala Glu Leu Arg Ala Val Thr Trp Gln Val Thr Cys Ser Tyr Ser Gln
    210                 215                 220
Tyr Arg Ala Ser Ala Ala Pro Ser Cys Cys Val Ser Met Thr Thr Phe
225                 230                 235                 240
Tyr Ser Glu Thr Ile Val Asp Cys Pro Arg Cys Ser Cys Gly Cys Gln
                245                 250                 255
Gly Ser Pro Pro Ser Pro Gln Cys Val Ser Val Asp Gln Gln Gln Pro
            260                 265                 270
Trp Leu Pro Ala Val Gly Asp Asp Glu Pro Ser Ser Ala Pro Ile Val
            275                 280                 285
Trp Cys Ser Glu His Met Cys Pro Ile Arg Val His Trp His Val Lys
    290                 295                 300
Thr Asn Tyr Arg Lys Tyr Trp Arg Val Lys Val Thr Val Ser Asn Tyr
305                 310                 315                 320
Asn Leu Ala Arg Asn Tyr Ser Asp Trp Asn Leu Val Leu Gln His Pro
                325                 330                 335
Asn Leu Arg Ser Leu Thr Gln Leu Phe Ser Phe Asn Tyr Arg Pro Leu
            340                 345                 350
Val Glu Tyr Gly Ala Tyr Asn Asp Thr Gly Met Phe Trp Gly Leu Arg
            355                 360                 365
Tyr Tyr Asn Glu Met Leu Leu Gln Asp Gly Asn Val Gln Ser Glu Met
    370                 375                 380
Ile Leu Glu Lys Glu Ser Asp Phe Thr Tyr Ser Gly Gly Trp Ala Phe
385                 390                 395                 400
Pro Arg Arg Val Tyr Phe Asn Gly Gln Glu Cys Val Met Pro Pro Ala
                405                 410                 415
Asp Gln Tyr Pro Val Leu Pro Asn Gly Ala Ser Ala Leu Arg Gly His
            420                 425                 430
Phe Cys Phe Leu Leu Leu Leu Phe Phe Val Val Val
        435                 440

<210> SEQ ID NO 19
<211> LENGTH: 3780
<212> TYPE: DNA
<213> ORGANISM: Zea mays

<400> SEQUENCE: 19
gtcgacccac gcgtccgcag cagcagaagc actgcgcggc attgcagcga tcgagcggga    60
ggaatttggg gcatggtggt cgccaacgcc gctcggatct agaggcccgc acgggccgat   120
tggtctccgc ccgcctcgtc ggtgttggtg tcgttggcgt gtggagccgt ctcggtggga   180
```

-continued

```
gcagcgggga gggagcggag atggcggcca acaaggggat ggtggcgggc tcgcacaacc    240
gcaacgagtt cgtcatgatc cgccacgacg gcgatgtgcc gggctcggct aagcccacaa    300
agagtgcgaa tggacaggtc tgccagattt gcggtgactc tgtgggtgtt tcagccactg    360
gtgatgtctt tgttgcctgc aatgagtgtg ccttccctgt ctgccgccca tgctatgagt    420
atgagcgcaa ggaggggaac caatgctgcc cccagtgcaa gactagatac aagagacaga    480
aaggtagccc tcgagttcat ggtgatgagg atgaggaaga tgttgatgac ctagacaatg    540
aattcaacta caagcaaggc agtgggaaag gcccagagtg gcaactgcaa ggagatgatg    600
ctgatctgtc ttcatctgct cgccatgagc cacatcatcg gattccacgc ctgacaagcg    660
gtcaacagat atctggagag attcctgatg cttcccctga ccgtcattct atccgcagtc    720
caacatcgag ctatgttgat ccaagcgtcc cagttcctgt gaggattgtg gaccccctcga    780
aggacttgaa ttcctatggg cttaatagtg ttgactggaa ggaaagagtt gagagctgga    840
gggttaaaca ggacaaaaat atgatgcaag tgactaataa atatccagag ctagaggag    900
gagacatgga ggggactggc tcaaatggag aagatatgca aatggttgat gatgcacggc    960
tacctttgag ccgtatcgtg ccaatttcct caaaccagct caacctttac cgggtagtga   1020
tcattctccg tcttatcatc ctgtgcttct tcttccagta tcgtgtcagt catccagtgc   1080
gtgatgctta tggattatgg ctagtatctg ttatctgcga ggtctggttt gccttgtctt   1140
ggcttctaga tcagttccca aaatggtatc caatcaaccg tgagacatat cttgacaggc   1200
ttgcattgag gtatgataga gagggagagc catcacagc ggctcccatt gatgtcttcg   1260
tcagtacagt ggatccattg aaggaacctc cactgatcac agccaacact gttttgtcca   1320
ttctttctgt ggattaccct gttgacaaag tgtcatgcta tgtttctgat gatggttcag   1380
ctatgctgac ttttgagtct ctctcagaaa ccgcagaatt tgctagaaag tgggttccct   1440
tttgtaagaa gcacaatatt gaaccaagag ctccagaatt ttactttgct caaaaaatag   1500
attacctgaa ggacaaaatt caaccttcat tgttaagga agacgcgca atgaagaggg   1560
agtatgaaga attcaaagta agaatcaatg cccttgttgc caaagcacag aaagtgcctg   1620
aagagggtg gaccatggct gatggaactg catggcctgg aataatcct agggaccatc   1680
ctggcatgat tcaggttttc ttggggcaca gtggtgggct cgacactgat ggaaatgagt   1740
taccacgtct tgtctatgtc tctcgtgaaa agagaccagg ctttcagcat cacaagaagg   1800
ctggtgcaat gaatgcgctg attcgtgtat ctgctgtgct gacaaatggt gcctatcttc   1860
tcaatgtgga ttgcgaccat tacttcaata gcagcaaagc tcttagagaa gcaatgtgct   1920
tcatgatgga tccggctcta ggaaggaaaa cttgttatgt acaatttcca cagagatttg   1980
atggcattga cttgcacgat cgatatgcta atcggaacat agttttcttt gatatcaaca   2040
tgaaaggtct ggatggcatt cagggtccag tttacgtggg aacaggatgc tgtttcaata   2100
gacaggcttt gtatggatac gatcctgttt tgactgaagc tgatctggag ccaaacattg   2160
ttattaagag ctgctgtggt agaaggaaga aaaagaacaa gagttatatg gatagtcaaa   2220
gccgtattat gaagagaaca gaatcttcag ctcccatctt caatatggaa gacatcgaag   2280
agggtattga aggttacgag gatgaaaggt cagtgcttat gtcccagagg aaattggaga   2340
aacgctttgg tcagtctcct attttcattg catccacctt tatgacacaa ggtggcatac   2400
cacctcaac aaacccagct tctctactaa aggaagctat ccatgtcatc agttgtggat   2460
atgaggacaa aactgaatgg ggaaaagaga ttggctggat ctatggttca gtaacggagg   2520
```

-continued

```
atattctgac tgggtttaaa atgcatgcaa ggggctggca atcaatctac tgcatgccac    2580
cacgaccttg tttcaagggt tctgcaccaa tcaatctttc cgatcgtctt aatcaggtgc    2640
tccgttgggc tcttgggtca gtggaaattc tgcttagtag acattgtcct atctggtatg    2700
gttacaatgg acgattgaag cttttggaga ggctggctta catcaacact attgtatatc    2760
caatcacatc cattccgctt attgccatat tgtgtgcttcc cgctatctgc ctccttacca    2820
ataaatttat cattcctgag attagcaatt atgctgggat gttcttcatt cttcttttcg    2880
cctccatttt tgccactggt atattggagc ttagatggag tggtgttggc attgaagatt    2940
ggtggagaaa tgagcagttt tgggttattg gtggcacctc tgcccatctc ttcgcagtgt    3000
tccagggtct gctgaaagtg ttggctggga ttgataccaa cttcacagtt acctcaaagg    3060
catctgatga ggatggcgac tttgctgagc tatatgtgtt caagtggacc agtttgctca    3120
ttcctccgac cactgttctt gtcattaacc tggtcggaat ggtggcagga atttcttatg    3180
ccattaacag tggctaccaa tcctggggtc cgctctttgg aaagctgttc ttctcgatct    3240
gggtgatcct ccatctctac cccttcctca agggtctcat gggaaggcag aaccgcacac    3300
caacaatcgt cattgtctgg tccatccttc ttgcatctat cttctccttg ctgtgggtga    3360
agatcgatcc tttcatctcc ccgacacaga aagctgctgc cttggggcaa tgtggcgtca    3420
actgctgatc gagacagtga ctcttatttg aagaggctca atcaagatct gcccctcgt    3480 gtaaatacct gaggaggcta gatgggaatt ccttttgttg taggtgagga tggatttgca    3540
tctaagttat gcctctgttc attagcttct tccgtgccgg tgctgctgcg gactaagaat    3600
cacggagcct ttctaccttc catgtagcgc cagccagcag cgtaagatgt gaattttgaa    3660
gttttgttat gcgtgcagtt tattgtttta gagtaaatta tcatttgttt gtgggaactg    3720
ttcacacgag cttataatgg caatgctgtt atttaaaaaa aaaaaaaaaa gggcggccgc    3780
```

<210> SEQ ID NO 20
<211> LENGTH: 1075
<212> TYPE: PRT
<213> ORGANISM: Zea mays

<400> SEQUENCE: 20

```
Met Ala Ala Asn Lys Gly Met Val Ala Gly Ser His Asn Arg Asn Glu
1               5                   10                  15

Phe Val Met Ile Arg His Asp Gly Asp Val Pro Gly Ser Ala Lys Pro
            20                  25                  30

Thr Lys Ser Ala Asn Gly Gln Val Cys Gln Ile Cys Gly Asp Ser Val
        35                  40                  45

Gly Val Ser Ala Thr Gly Asp Val Phe Val Ala Cys Asn Glu Cys Ala
    50                  55                  60

Phe Pro Val Cys Arg Pro Cys Tyr Glu Tyr Glu Arg Lys Glu Gly Asn
65                  70                  75                  80

Gln Cys Cys Pro Gln Cys Lys Thr Arg Tyr Lys Arg Gln Lys Gly Ser
                85                  90                  95

Pro Arg Val His Gly Asp Glu Asp Glu Glu Asp Val Asp Asp Leu Asp
            100                 105                 110

Asn Glu Phe Asn Tyr Lys Gln Gly Ser Gly Lys Gly Pro Glu Trp Gln
        115                 120                 125

Leu Gln Gly Asp Asp Ala Asp Leu Ser Ser Ser Ala Arg His Glu Pro
    130                 135                 140

His His Arg Ile Pro Arg Leu Thr Ser Gly Gln Gln Ile Ser Gly Glu
145                 150                 155                 160
```

-continued

```
Ile Pro Asp Ala Ser Pro Asp Arg His Ser Ile Arg Ser Pro Thr Ser
                165                 170                 175
Ser Tyr Val Asp Pro Ser Val Pro Val Pro Val Arg Ile Val Asp Pro
            180                 185                 190
Ser Lys Asp Leu Asn Ser Tyr Gly Leu Asn Ser Val Asp Trp Lys Glu
        195                 200                 205
Arg Val Glu Ser Trp Arg Val Lys Gln Asp Lys Asn Met Met Gln Val
    210                 215                 220
Thr Asn Lys Tyr Pro Glu Ala Arg Gly Gly Asp Met Glu Gly Thr Gly
225                 230                 235                 240
Ser Asn Gly Glu Asp Met Gln Met Val Asp Asp Ala Arg Leu Pro Leu
                245                 250                 255
Ser Arg Ile Val Pro Ile Ser Ser Asn Gln Leu Asn Leu Tyr Arg Val
            260                 265                 270
Val Ile Ile Leu Arg Leu Ile Ile Leu Cys Phe Phe Phe Gln Tyr Arg
        275                 280                 285
Val Ser His Pro Val Arg Asp Ala Tyr Gly Leu Trp Leu Val Ser Val
    290                 295                 300
Ile Cys Glu Val Trp Phe Ala Leu Ser Trp Leu Leu Asp Gln Phe Pro
305                 310                 315                 320
Lys Trp Tyr Pro Ile Asn Arg Glu Thr Tyr Leu Asp Arg Leu Ala Leu
                325                 330                 335
Arg Tyr Asp Arg Glu Gly Glu Pro Ser Gln Leu Ala Pro Ile Asp Val
            340                 345                 350
Phe Val Ser Thr Val Asp Pro Leu Lys Glu Pro Pro Leu Ile Thr Ala
        355                 360                 365
Asn Thr Val Leu Ser Ile Leu Ser Val Asp Tyr Pro Val Asp Lys Val
    370                 375                 380
Ser Cys Tyr Val Ser Asp Asp Gly Ser Ala Met Leu Thr Phe Glu Ser
385                 390                 395                 400
Leu Ser Glu Thr Ala Glu Phe Ala Arg Lys Trp Val Pro Phe Cys Lys
                405                 410                 415
Lys His Asn Ile Glu Pro Arg Ala Pro Glu Phe Tyr Phe Ala Gln Lys
            420                 425                 430
Ile Asp Tyr Leu Lys Asp Lys Ile Gln Pro Ser Phe Val Lys Glu Arg
        435                 440                 445
Arg Ala Met Lys Arg Glu Tyr Glu Glu Phe Lys Val Arg Ile Asn Ala
    450                 455                 460
Leu Val Ala Lys Ala Gln Lys Val Pro Glu Glu Gly Trp Thr Met Ala
465                 470                 475                 480
Asp Gly Thr Ala Trp Pro Gly Asn Asn Pro Arg Asp His Pro Gly Met
                485                 490                 495
Ile Gln Val Phe Leu Gly His Ser Gly Gly Leu Asp Thr Asp Gly Asn
            500                 505                 510
Glu Leu Pro Arg Leu Val Tyr Val Ser Arg Glu Lys Arg Pro Gly Phe
        515                 520                 525
Gln His His Lys Lys Ala Gly Ala Met Asn Ala Leu Ile Arg Val Ser
    530                 535                 540
Ala Val Leu Thr Asn Gly Ala Tyr Leu Leu Asn Val Asp Cys Asp His
545                 550                 555                 560
Tyr Phe Asn Ser Ser Lys Ala Leu Arg Glu Ala Met Cys Phe Met Met
                565                 570                 575
```

```
Asp Pro Ala Leu Gly Arg Lys Thr Cys Tyr Val Gln Phe Pro Gln Arg
            580                 585                 590

Phe Asp Gly Ile Asp Leu His Asp Arg Tyr Ala Asn Arg Asn Ile Val
            595                 600                 605

Phe Phe Asp Ile Asn Met Lys Gly Leu Asp Gly Ile Gln Gly Pro Val
610                 615                 620

Tyr Val Gly Thr Gly Cys Cys Phe Asn Arg Gln Ala Leu Tyr Gly Tyr
625                 630                 635                 640

Asp Pro Val Leu Thr Glu Ala Asp Leu Glu Pro Asn Ile Val Ile Lys
            645                 650                 655

Ser Cys Cys Gly Arg Arg Lys Lys Asn Lys Ser Tyr Met Asp Ser
            660                 665                 670

Gln Ser Arg Ile Met Lys Arg Thr Glu Ser Ser Ala Pro Ile Phe Asn
            675                 680                 685

Met Glu Asp Ile Glu Glu Gly Ile Glu Gly Tyr Glu Asp Glu Arg Ser
690                 695                 700

Val Leu Met Ser Gln Arg Lys Leu Glu Lys Arg Phe Gly Gln Ser Pro
705                 710                 715                 720

Ile Phe Ile Ala Ser Thr Phe Met Thr Gln Gly Gly Ile Pro Pro Ser
                725                 730                 735

Thr Asn Pro Ala Ser Leu Leu Lys Glu Ala Ile His Val Ile Ser Cys
            740                 745                 750

Gly Tyr Glu Asp Lys Thr Glu Trp Gly Lys Glu Ile Gly Trp Ile Tyr
            755                 760                 765

Gly Ser Val Thr Glu Asp Ile Leu Thr Gly Phe Lys Met His Ala Arg
770                 775                 780

Gly Trp Gln Ser Ile Tyr Cys Met Pro Pro Arg Pro Cys Phe Lys Gly
785                 790                 795                 800

Ser Ala Pro Ile Asn Leu Ser Asp Arg Leu Asn Gln Val Leu Arg Trp
            805                 810                 815

Ala Leu Gly Ser Val Glu Ile Leu Leu Ser Arg His Cys Pro Ile Trp
            820                 825                 830

Tyr Gly Tyr Asn Gly Arg Leu Lys Leu Leu Glu Arg Leu Ala Tyr Ile
            835                 840                 845

Asn Thr Ile Val Tyr Pro Ile Thr Ser Ile Pro Leu Ile Ala Tyr Cys
850                 855                 860

Val Leu Pro Ala Ile Cys Leu Leu Thr Asn Lys Phe Ile Ile Pro Glu
865                 870                 875                 880

Ile Ser Asn Tyr Ala Gly Met Phe Phe Ile Leu Phe Ala Ser Ile
                885                 890                 895

Phe Ala Thr Gly Ile Leu Glu Leu Arg Trp Ser Gly Val Gly Ile Glu
            900                 905                 910

Asp Trp Trp Arg Asn Glu Gln Phe Trp Val Ile Gly Thr Ser Ala
            915                 920                 925

His Leu Phe Ala Val Phe Gln Gly Leu Leu Lys Val Leu Ala Gly Ile
            930                 935                 940

Asp Thr Asn Phe Thr Val Thr Ser Lys Ala Ser Asp Glu Asp Gly Asp
945                 950                 955                 960

Phe Ala Glu Leu Tyr Val Phe Lys Trp Thr Ser Leu Leu Ile Pro Pro
            965                 970                 975

Thr Thr Val Leu Val Ile Asn Leu Val Gly Met Val Ala Gly Ile Ser
            980                 985                 990

Tyr Ala Ile Asn Ser Gly Tyr Gln Ser Trp Gly Pro Leu Phe Gly Lys
```

|  | 995 |  | 1000 |  | 1005 |  |
|---|---|---|---|---|---|---|

Leu Phe Phe Ser Ile Trp Val Ile Leu His Leu Tyr Pro Phe Leu
    1010                      1015                      1020

Lys Gly Leu Met Gly Arg Gln Asn Arg Thr Pro Thr Ile Val Ile
    1025                      1030                      1035

Val Trp Ser Ile Leu Leu Ala Ser Ile Phe Ser Leu Leu Trp Val
    1040                      1045                      1050

Lys Ile Asp Pro Phe Ile Ser Pro Thr Gln Lys Ala Ala Ala Leu
    1055                      1060                      1065

Gly Gln Cys Gly Val Asn Cys
    1070                      1075

```
<210> SEQ ID NO 21
<211> LENGTH: 3725
<212> TYPE: DNA
<213> ORGANISM: Zea mays

<400> SEQUENCE: 21
gcagcagcag caccaccact gcgcggcatt gcagcgagca agcgggaggg atctggggca      60
tggtggcggt cgctgccgct gccgctcgga tctagagggc cgcacgggct gattgccctc     120
cgccggcctc gtcggtgtcg gtggagtgtg aatcggtgtg tgtaggagga gcgcggagat     180
ggcggccaac aaggggatgg tggcaggctc tcacaaccgc aacgagttcg tcatgatccg     240
ccacgacggc gacgcgcctg tcccggctaa gcccacgaag agtgcgaatg ggcaggtctg     300
ccagatttgt ggcgacactg ttggcgtttc agccactggt gatgtctttg ttgcctgcaa     360
tgagtgtgcc ttccctgtct gccgcccttg ctatgagtac agcgcaagg aagggaacca      420 atgctgccct cagtgcaaga ctagatacaa gagacagaaa ggtagccctc gagttcatgg     480
tgatgatgag gaggaagatg ttgatgacct ggacaatgaa ttcaactata gcaaggcaa      540 tgggaagggc ccagagtggc agcttcaagg agatgacgct gatctgtctt catctgctcg     600
ccatgaccca caccatcgga ttccacgcct acaagtggaa caacagatat ctggagagat     660
ccctgatgca tccctgacc gtcattctat ccgcagtcca acatcgagct atgttgatcc      720
aagcgttcca gttcctgtga ggattgtgga ccctcgaag gacttgaatt cctatgggct      780
taatagtgtt gactggaagg aaagagttga gagctggagg gttaaacagg acaaaaatat     840
gttgcaagtg actaataaat atccagaggc tagaggagac atggaggga ctggctcaaa      900 tggagaagat atgcaaatgg ttgatgatgc acgcctacct tgagccgca ttgtgccaat      960 ttcctcaaac cagctcaacc tttaccggat agtaatcatt ctccgtctta tcatcctgtg    1020
cttcttcttc caatatcgta tcagtcatcc agtgcgtaat gcttatggat gtgggctagt    1080
atctgttatc tgtgaggtct ggtttgcctt gtcctggctt ctagatcagt tcccaaaatg    1140
gtatccaatc aaccgtgaga catatctcga caggcttgca ttgaggtatg atagagaggg    1200
agagccatca cagctggctc ccattgatgt ctttgtcagt acagtggatc cattgaagga    1260
acctccactg atcacagcca acactgtttt gtccattctt gctgtggatt accctgttga    1320
caaagtgtca tgctatgttt ctgatgatgg ctcagctatg ctgactttg agtctctctc     1380 tgaaactgcc gaatttgcta aaagtgggt tccctttgt aagaagcaca atattgaacc      1440
aagagctcca gaattttact tgctcaaaa aatagattac ctgaaggaca aaattcaacc     1500
ttcatttgtt aaggaaagac gagcaatgaa gagagagtat gaagaattca aaataagaat    1560 caatgcccctt gttgccaaag cacagaaagt gcctgaagag gggtggacca tggctgatgg    1620
```

```
aactgcttgg cctgggaata accctaggga ccatcctggc atgattcagg tgttcttggg    1680
gcacagtggt gggcttgaca ctgatggaaa tgaattacca cgtcttgtct atgtctctcg    1740
tgaaaagaga ccaggctttc agcatcacaa gaaggctggt gcaatgaatg cactgattcg    1800
tgtatctgct gtgctgacaa atggtgccta tcttctcaat gtggattgtg accattactt    1860
caatagcagc aaagctctta gagaagcaat gtgcttcatg atggatccag ctctaggaag    1920
gaaaacttgt tatgtacaat ttccacaaag atttgatggc attgacttgc acgatcgata    1980
tgctaatagg aacatagtct tctttgatat caacatgaaa ggtctagatg cattcaggg     2040
tccagtctat gtgggaacag gatgctgttt caataggcag gctttgtatg gatatgatcc    2100
tgttttgact gaagctgatc tggaacctaa cattgttgtt aagagctgct gtggtagaag    2160
gaagagaaag aacaagagtt atatggatag tcaaagccgt attatgaaga gaacagaatc    2220
ttcagctccc atctttaaca tggaagacat cgaggagggt attgaaggtt atgaggatga    2280
aaggtcagtg cttatgtccc agaggaaatt ggagaaacgc tttggtcagt ctccaatctt    2340
cattgcatcc acctttatga ctcaaggtgg cataccacct tcaacaaacc cagcttctct    2400
actgaaggaa gctatccatg ttatcagctg tgggtacgag gacaaaactg aatggggaaa    2460
agagattggc tggatctatg gttcagttac agaggatatt ctgactgggt ttaaaatgca    2520
tgcaagaggc tggcaatcaa tctactgcat gccaccacga ccttgtttca agggttctgc    2580
accaatcaat ctttctgatc gtcttaatca ggtgctccgt tgggctcttg ggtcagtgga    2640
aattctgctt agcagacatt gtcctatatg gtatggctac aatgggcgat tgaagctttt    2700
ggagaggctg gcttacatta acaccattgt ttatccaatc acatctgttc cgcttatcgc    2760
ctattgtgtg cttcctgcta tctgtcttct taccaataaa tttatcattc ctgagattag    2820
taattatgct ggaatgttct tcattcttct ttttgcctcc attttcgcaa ctggtatatt    2880
ggagctcaga tggagtggtg ttggcattga agattggtgg agaaatgagc agttttgggt    2940
tattggtggc acctctgccc atctcttcgc ggtgttccag ggtctgctga agtgttggc     3000
tgggattgat accaacttca cagttacctc aaaggcatct gatgaggatg gcgactttgc    3060
tgagctatat gtgttcaagt ggaccagttt gctcatccct ccgaccactg ttcttgtcat    3120
taacctggtc ggaatggtgg caggaatttc gtatgccatt aacagcggct accaatcctg    3180
gggtccgctc tttggaaagc tgttcttctc gatctgggtg atcctccatc tctacccctt    3240
cctcaagggt ctcatgggca ggcagaaccg cacgccaaca atcgtcatcg tttggtccat    3300
cctccttgcg tctatcttct ccttgctgtg ggtgaagatc gatccttttca tctccccgac    3360
acagaaagct gccgccttgg ggcaatgtgg tgtgaactgc tgatccagat tgtgactctt    3420
atctgaagag gctcagccaa agatctgccc cctcgtgtaa atacctgagg gggctagatg    3480
ggaattttt gttgtagatg aggatggatc tgcatccaag ttatgcctct gtttattagc    3540
ttcttcggtg ccggtgctgc tgcagacaat catggagcct ttctaccttg cttgtagtgc    3600
tggccagcag cgtaaattgt gaattctgca ttttttttata cgtggtgttt attgttttag    3660
agtaaattat catttgtttg aggtaactat tcacacgaac tatatggcaa tgctgttatt    3720
taaaa                                                                3725
```

<210> SEQ ID NO 22
<211> LENGTH: 1074
<212> TYPE: PRT
<213> ORGANISM: Zea mays

<400> SEQUENCE: 22

-continued

```
Met Ala Ala Asn Lys Gly Met Val Ala Gly Ser His Asn Arg Asn Glu
1               5                   10                  15

Phe Val Met Ile Arg His Asp Gly Asp Ala Pro Val Pro Ala Lys Pro
                20                  25                  30

Thr Lys Ser Ala Asn Gly Gln Val Cys Gln Ile Cys Gly Asp Thr Val
            35                  40                  45

Gly Val Ser Ala Thr Gly Asp Val Phe Val Ala Cys Asn Glu Cys Ala
    50                  55                  60

Phe Pro Val Cys Arg Pro Cys Tyr Glu Tyr Glu Arg Lys Gly Asn
65              70                  75                  80

Gln Cys Cys Pro Gln Cys Lys Thr Arg Tyr Lys Arg Gln Lys Gly Ser
                85                  90                  95

Pro Arg Val His Gly Asp Asp Glu Glu Asp Val Asp Asp Leu Asp
                100                 105                 110

Asn Glu Phe Asn Tyr Lys Gln Gly Asn Gly Lys Gly Pro Glu Trp Gln
            115                 120                 125

Leu Gln Gly Asp Asp Ala Asp Leu Ser Ser Ser Ala Arg His Asp Pro
    130                 135                 140

His His Arg Ile Pro Arg Leu Thr Ser Gly Gln Gln Ile Ser Gly Glu
145                 150                 155                 160

Ile Pro Asp Ala Ser Pro Asp Arg His Ser Ile Arg Ser Pro Thr Ser
                165                 170                 175

Ser Tyr Val Asp Pro Ser Val Pro Val Pro Val Arg Ile Val Asp Pro
            180                 185                 190

Ser Lys Asp Leu Asn Ser Tyr Gly Leu Asn Ser Val Asp Trp Lys Glu
    195                 200                 205

Arg Val Glu Ser Trp Arg Val Lys Gln Asp Lys Asn Met Leu Gln Val
    210                 215                 220

Thr Asn Lys Tyr Pro Glu Ala Arg Gly Asp Met Glu Gly Thr Gly Ser
225                 230                 235                 240

Asn Gly Glu Asp Met Gln Met Val Asp Asp Ala Arg Leu Pro Leu Ser
                245                 250                 255

Arg Ile Val Pro Ile Ser Ser Asn Gln Leu Asn Leu Tyr Arg Ile Val
                260                 265                 270

Ile Ile Leu Arg Leu Ile Ile Leu Cys Phe Phe Gln Tyr Arg Ile
    275                 280                 285

Ser His Pro Val Arg Asn Ala Tyr Gly Leu Trp Leu Ser Val Ile
    290                 295                 300

Cys Glu Val Trp Phe Ala Leu Ser Trp Leu Leu Asp Gln Phe Pro Lys
305                 310                 315                 320

Trp Tyr Pro Ile Asn Arg Glu Thr Tyr Leu Asp Arg Leu Ala Leu Arg
                325                 330                 335

Tyr Asp Arg Glu Gly Glu Pro Ser Gln Leu Ala Pro Ile Asp Val Phe
            340                 345                 350

Val Ser Thr Val Asp Pro Leu Lys Glu Pro Pro Leu Ile Thr Ala Asn
    355                 360                 365

Thr Val Leu Ser Ile Leu Ala Val Asp Tyr Pro Val Asp Lys Val Ser
    370                 375                 380

Cys Tyr Val Ser Asp Asp Gly Ser Ala Met Leu Thr Phe Glu Ser Leu
385                 390                 395                 400

Ser Glu Thr Ala Glu Phe Ala Arg Lys Trp Val Pro Phe Cys Lys Lys
                405                 410                 415
```

```
His Asn Ile Glu Pro Arg Ala Pro Glu Phe Tyr Phe Ala Gln Lys Ile
            420                 425                 430

Asp Tyr Leu Lys Asp Lys Ile Gln Pro Ser Phe Val Lys Glu Arg Arg
        435                 440                 445

Ala Met Lys Arg Glu Tyr Glu Glu Phe Lys Ile Arg Ile Asn Ala Leu
    450                 455                 460

Val Ala Lys Ala Gln Lys Val Pro Glu Gly Trp Thr Met Ala Asp
465                 470                 475                 480

Gly Thr Ala Trp Pro Gly Asn Asn Pro Arg Asp His Pro Gly Met Ile
                485                 490                 495

Gln Val Phe Leu Gly His Ser Gly Gly Leu Asp Thr Asp Gly Asn Glu
            500                 505                 510

Leu Pro Arg Leu Val Tyr Val Ser Arg Glu Lys Arg Pro Gly Phe Gln
        515                 520                 525

His His Lys Lys Ala Gly Ala Met Asn Ala Leu Ile Arg Val Ser Ala
    530                 535                 540

Val Leu Thr Asn Gly Ala Tyr Leu Leu Asn Val Asp Cys Asp His Tyr
545                 550                 555                 560

Phe Asn Ser Ser Lys Ala Leu Arg Glu Ala Met Cys Phe Met Met Asp
                565                 570                 575

Pro Ala Leu Gly Arg Lys Thr Cys Tyr Val Gln Phe Pro Gln Arg Phe
            580                 585                 590

Asp Gly Ile Asp Leu His Asp Arg Tyr Ala Asn Arg Asn Ile Val Phe
        595                 600                 605

Phe Asp Ile Asn Met Lys Gly Leu Asp Gly Ile Gln Gly Pro Val Tyr
    610                 615                 620

Val Gly Thr Gly Cys Cys Phe Asn Arg Gln Ala Leu Tyr Gly Tyr Asp
625                 630                 635                 640

Pro Val Leu Thr Glu Ala Asp Leu Glu Pro Asn Ile Val Val Lys Ser
                645                 650                 655

Cys Cys Gly Arg Arg Lys Arg Lys Asn Lys Ser Tyr Met Asp Ser Gln
            660                 665                 670

Ser Arg Ile Met Lys Arg Thr Glu Ser Ser Ala Pro Ile Phe Asn Met
        675                 680                 685

Glu Asp Ile Glu Glu Gly Ile Glu Gly Tyr Glu Asp Glu Arg Ser Val
    690                 695                 700

Leu Met Ser Gln Arg Lys Leu Glu Lys Arg Phe Gly Gln Ser Pro Ile
705                 710                 715                 720

Phe Ile Ala Ser Thr Phe Met Thr Gln Gly Gly Ile Pro Pro Ser Thr
                725                 730                 735

Asn Pro Ala Ser Leu Leu Lys Glu Ala Ile His Val Ile Ser Cys Gly
            740                 745                 750

Tyr Glu Asp Lys Thr Glu Trp Gly Lys Glu Ile Gly Trp Ile Tyr Gly
        755                 760                 765

Ser Val Thr Glu Asp Ile Leu Thr Gly Phe Lys Met His Ala Arg Gly
    770                 775                 780

Trp Gln Ser Ile Tyr Cys Met Pro Pro Arg Pro Cys Phe Lys Gly Ser
785                 790                 795                 800

Ala Pro Ile Asn Leu Ser Asp Arg Leu Asn Gln Val Leu Arg Trp Ala
                805                 810                 815

Leu Gly Ser Val Glu Ile Leu Leu Ser Arg His Cys Pro Ile Trp Tyr
            820                 825                 830

Gly Tyr Asn Gly Arg Leu Lys Leu Leu Glu Arg Leu Ala Tyr Ile Asn
```

Thr Ile Val Tyr Pro Ile Thr Ser Val Pro Leu Ile Ala Tyr Cys Val
835                 840                 845
                                                             850

Leu Pro Ala Ile Cys Leu Leu Thr Asn Lys Phe Ile Ile Pro Glu Ile
865                 870                 875                 880

Ser Asn Tyr Ala Gly Met Phe Phe Ile Leu Leu Phe Ala Ser Ile Phe
                885                 890                 895

Ala Thr Gly Ile Leu Glu Leu Arg Trp Ser Gly Val Gly Ile Glu Asp
                900                 905                 910

Trp Trp Arg Asn Glu Gln Phe Trp Val Ile Gly Gly Thr Ser Ala His
            915                 920                 925

Leu Phe Ala Val Phe Gln Gly Leu Leu Lys Val Leu Ala Gly Ile Asp
930                 935                 940

Thr Asn Phe Thr Val Thr Ser Lys Ala Ser Asp Glu Asp Gly Asp Phe
945                 950                 955                 960

Ala Glu Leu Tyr Val Phe Lys Trp Thr Ser Leu Leu Ile Pro Pro Thr
                965                 970                 975

Thr Val Leu Val Ile Asn Leu Val Gly Met Val Ala Gly Ile Ser Tyr
                980                 985                 990

Ala Ile Asn Ser Gly Tyr Gln Ser Trp Gly Pro Leu Phe Gly Lys Leu
                995                 1000                1005

Phe Phe Ser Ile Trp Val Ile Leu His Leu Tyr Pro Phe Leu Lys
1010                1015                1020

Gly Leu Met Gly Arg Gln Asn Arg Thr Pro Thr Ile Val Ile Val
1025                1030                1035

Trp Ser Ile Leu Leu Ala Ser Ile Phe Ser Leu Leu Trp Val Lys
1040                1045                1050

Ile Asp Pro Phe Ile Ser Pro Thr Gln Lys Ala Ala Leu Gly
1055                1060                1065

Gln Cys Gly Val Asn Cys
    1070

<210> SEQ ID NO 23
<211> LENGTH: 2830
<212> TYPE: DNA
<213> ORGANISM: Zea mays
<220> FEATURE:
<221> NAME/KEY: misc_feature
<222> LOCATION: (2809)..(2809)
<223> OTHER INFORMATION: n is a, c, g, or t
<220> FEATURE:
<221> NAME/KEY: misc_feature
<222> LOCATION: (2818)..(2818)
<223> OTHER INFORMATION: n is a, c, g, or t
<220> FEATURE:
<221> NAME/KEY: misc_feature
<222> LOCATION: (2824)..(2824)
<223> OTHER INFORMATION: n is a, c, g, or t
<220> FEATURE:
<221> NAME/KEY: misc_feature
<222> LOCATION: (2826)..(2826)
<223> OTHER INFORMATION: n is a, c, g, or t
<220> FEATURE:
<221> NAME/KEY: misc_feature
<222> LOCATION: (2829)..(2829)
<223> OTHER INFORMATION: n is a, c, g, or t

<400> SEQUENCE: 23
tacctctaag tcgcatagtt ccgatatctc caaacgagct taaccttat cggatcgtga      60 ttgttctccg gcttatcatc ctatgttcct tctttcaata tcgtataact catccagtgg    120

```
aagatgctta tgggttgtgg cttgtatctg ttatttgtga agtttggttt gccttgtctt    180
ggcttctaga tcagttccca aagtggtatc ctatcaaccg tgaaacttac ctcgatagac    240
ttgcattgag atatgatagg gagggtgagc catcccagtt ggctccaatc gatgtctttg    300
ttagtacagt ggatccactt aaggaacctc ctctaattac tggcaacact gtcctgtcca    360
ttcttgctgt ggattaccct gttgacaaag tatcatgtta tgtttctgat gacggttcag    420
ctatgttgac ttttgaagcg ctatctgaaa ccgcagagtt tgcaaggaaa tgggttccct    480
tttgcaagaa acacaatatt gaacctaggg ctccagagtt ttactttgct cgaaagatag    540
attacctaaa ggacaaaata caaccttctt ttgtgaaaga aaggcgggct atgaagaggg    600
agtgtgaaga gttcaaagta cggatcgatg cccttgttgc aaaagcgcaa aaaatacctg    660
aggagggctg gaccatggct gatggcactc cttggcctgg gaataaccct agagatcatc    720
caggaatgat ccaagtattc ttgggccaca gtggtgggct tgacacggat gggaatgagt    780
tgccacggct tgtttatgtt tctcgtgaaa agaggccagg cttccagcac acaagaagg    840
ctggtgccat gaatgctttg attcgcgtat cagctgtcct gacgaatggt gcttatcttc    900
ttaatgtgga ttgtgatcac tacttcaata gcagcaaagc tcttagagag gctatgtgtt    960
tcatgatgga tccagcacta ggaaggaaaa cttgctatgt tcagtttcca caaagatttg   1020
atggtataga cttgcatgat cgatatgcaa accggaacat tgtcttcttt gatattaata   1080
tgaagggtct agatggcatt caaggacctg tttatgtggg aacaggatgc tgtttcaata   1140
ggcaggcctt gtatgctat gatcctgtat tgacagaagc tgatttggag cctaacatta   1200
tcattaaaag ttgctgtggc ggaagaaaaa agaaggacaa gagctatatt gattccaaaa   1260
accgtgatat gaagagaaca gaatcttcgg ctcccatctt caacatggaa gatatagaag   1320
agggatttga aggttacgag gatgaaaggt cactgcttat gtctcagaag agcttggaga   1380
aacgctttgg ccagtctcca atttttattg catccacctt tatgactcaa ggtggcatac   1440
cccttcaac aaacccaggt tccctgctaa aggaagctat acatgtcatt agttgtggat   1500
atgaggataa aacagaatgg gggaaagaga tcggatggat atatggctct gttactgaag   1560
atattttaac tggtttcaag atgcatgcaa gaggttggat atccatctac tgcatgccac   1620
ttcggccttg cttcaagggt tctgctccaa ttaatctttc tgatcgtctc aaccaagtgt   1680
tacgctgggc tcttggttca gttgaaattc tacttagcag acactgtcct atctggtatg   1740
gttacaatgg aaggctaaag cttctggaga gactggcata catcaacacc attgtttatc   1800
caattacatc tatcccacta gtagcatact gcgtccttcc tgctatctgt ttactcacca   1860
acaaatttat tattcctgcg attagcaatt atgctgggc gttcttcatc ctgcttttg    1920
cttccatctt cgccactggt attttggagc ttcgatggag tggtgttggc attgaggatt   1980
ggtggagaaa tgagcagttt tgggtcattg gtggcacctc tgcacatctc tttgctgtgt   2040
tccaaggtct cttaaaagtg ctagcaggga tcgacacaaa cttcacggtc acatcaaagg   2100
caaccgatga tgatggtgat tttgctgagc tgtatgtgtt caagtggaca actcttctga   2160
tcccccccac cactgtgctt gtgattaacc tggttggtat agtggctgga gtgtcgtatg   2220
ctatcaacag tggctaccaa tcatggggtc cactattcgg gaagctgttc tttgcaatct   2280
gggtgatcct ccacctctac cctttcctga agggtctcat ggggaagcag aaccgcacac   2340
cgaccatcgt catcgtttgg tccgtccttc ttgcttccat attctcgctg ctgtgggtga   2400
agatcgaccc cttcatatcc cctacccaga aggctctttc ccgtgggcag tgtggtgtaa   2460
actgctgaaa tgatccgaac tgcctgctga ataacattgc tccggcacaa tcatgatcta   2520
```

-continued

```
cccctctcgtg taaataccag aggttaggca agactttcct tggtaggtgg cgaagatgtg   2580
tcgtttaagt tcactctact gcatttgggg tgggcagcat gaaactttgt caacttatgt   2640
cgtgctactt atttgtagct aagtagcagt aagtagtgcc tgtttcatgt tgactgtcgt   2700
gactacctgt tcaccgtggg ctctggactg tcgtgatgta acctgtatgt tggaacttca   2760
agtactgatt gagctgtttg gtcaatgaca ttgagggatt ctctctctng aaattaaaac   2820 aaantnggnt                                                           2830
```

<210> SEQ ID NO 24
<211> LENGTH: 821
<212> TYPE: PRT
<213> ORGANISM: Zea mays

<400> SEQUENCE: 24

| Pro | Leu | Ser | Arg | Ile | Val | Pro | Ile | Ser | Pro | Asn | Glu | Leu | Asn | Leu | Tyr |
|1|||||5|||||10|||||15||

| Arg | Ile | Val | Ile | Val | Leu | Arg | Leu | Ile | Ile | Leu | Cys | Phe | Phe | Phe | Gln |
|||||20|||||25|||||30|||

| Tyr | Arg | Ile | Thr | His | Pro | Val | Glu | Asp | Ala | Tyr | Gly | Leu | Trp | Leu | Val |
||||35|||||40|||||45||||

| Ser | Val | Ile | Cys | Glu | Val | Trp | Phe | Ala | Leu | Ser | Trp | Leu | Leu | Asp | Gln |
|50|||||55|||||60|||||||

| Phe | Pro | Lys | Trp | Tyr | Pro | Ile | Asn | Arg | Glu | Thr | Tyr | Leu | Asp | Arg | Leu |
|65|||||70|||||75|||||80||

| Ala | Leu | Arg | Tyr | Asp | Arg | Glu | Gly | Glu | Pro | Ser | Gln | Leu | Ala | Pro | Ile |
|||||85|||||90|||||95|||

| Asp | Val | Phe | Val | Ser | Thr | Val | Asp | Pro | Leu | Lys | Glu | Pro | Pro | Leu | Ile |
||||100|||||105|||||110||||

| Thr | Gly | Asn | Thr | Val | Leu | Ser | Ile | Leu | Ala | Val | Asp | Tyr | Pro | Val | Asp |
||||115|||||120|||||125||||

| Lys | Val | Ser | Cys | Tyr | Val | Ser | Asp | Asp | Gly | Ser | Ala | Met | Leu | Thr | Phe |
|130|||||135|||||140|||||||

| Glu | Ala | Leu | Ser | Glu | Thr | Ala | Glu | Phe | Ala | Arg | Lys | Trp | Val | Pro | Phe |
|145|||||150|||||155|||||160||

| Cys | Lys | Lys | His | Asn | Ile | Glu | Pro | Arg | Ala | Pro | Glu | Phe | Tyr | Phe | Ala |
|||||165|||||170|||||175|||

| Arg | Lys | Ile | Asp | Tyr | Leu | Lys | Asp | Lys | Ile | Gln | Pro | Ser | Phe | Val | Lys |
||||180|||||185|||||190||||

| Glu | Arg | Arg | Ala | Met | Lys | Arg | Glu | Cys | Glu | Glu | Phe | Lys | Val | Arg | Ile |
||||195|||||200|||||205||||

| Asp | Ala | Leu | Val | Ala | Lys | Ala | Gln | Lys | Ile | Pro | Glu | Glu | Gly | Trp | Thr |
|210|||||215|||||220|||||||

| Met | Ala | Asp | Gly | Thr | Pro | Trp | Pro | Gly | Asn | Asn | Pro | Arg | Asp | His | Pro |
|225|||||230|||||235|||||240||

| Gly | Met | Ile | Gln | Val | Phe | Leu | Gly | His | Ser | Gly | Gly | Leu | Asp | Thr | Asp |
|||||245|||||250|||||255|||

| Gly | Asn | Glu | Leu | Pro | Arg | Leu | Val | Tyr | Val | Ser | Arg | Glu | Lys | Arg | Pro |
||||260|||||265|||||270||||

| Gly | Phe | Gln | His | His | Lys | Lys | Ala | Gly | Ala | Met | Asn | Ala | Leu | Ile | Arg |
||||275|||||280|||||285||||

| Val | Ser | Ala | Val | Leu | Thr | Asn | Gly | Ala | Tyr | Leu | Leu | Asn | Val | Asp | Cys |
|290|||||295|||||300|||||||

| Asp | His | Tyr | Phe | Asn | Ser | Ser | Lys | Ala | Leu | Arg | Glu | Ala | Met | Cys | Phe |

-continued

```
            305                 310                 315                 320
    Met Met Asp Pro Ala Leu Gly Arg Lys Thr Cys Tyr Val Gln Phe Pro
                    325                 330                 335

Gln Arg Phe Asp Gly Ile Asp Leu His Asp Arg Tyr Ala Asn Arg Asn
                    340                 345                 350

Ile Val Phe Phe Asp Ile Asn Met Lys Gly Leu Asp Gly Ile Gln Gly
                    355                 360                 365

Pro Val Tyr Val Gly Thr Gly Cys Cys Phe Asn Arg Gln Ala Leu Tyr
                    370                 375                 380

Gly Tyr Asp Pro Val Leu Thr Glu Ala Asp Leu Glu Pro Asn Ile Ile
    385                 390                 395                 400

Ile Lys Ser Cys Cys Gly Gly Arg Lys Lys Lys Asp Lys Ser Tyr Ile
                    405                 410                 415

Asp Ser Lys Asn Arg Asp Met Lys Arg Thr Glu Ser Ser Ala Pro Ile
                    420                 425                 430

Phe Asn Met Glu Asp Ile Glu Glu Gly Phe Glu Gly Tyr Glu Asp Glu
                    435                 440                 445

Arg Ser Leu Leu Met Ser Gln Lys Ser Leu Glu Lys Arg Phe Gly Gln
                    450                 455                 460

Ser Pro Ile Phe Ile Ala Ser Thr Phe Met Thr Gln Gly Gly Ile Pro
    465                 470                 475                 480

Pro Ser Thr Asn Pro Gly Ser Leu Leu Lys Glu Ala Ile His Val Ile
                    485                 490                 495

Ser Cys Gly Tyr Glu Asp Lys Thr Glu Trp Gly Lys Glu Ile Gly Trp
                    500                 505                 510

Ile Tyr Gly Ser Val Thr Glu Asp Ile Leu Thr Gly Phe Lys Met His
                    515                 520                 525

Ala Arg Gly Trp Ile Ser Ile Tyr Cys Met Pro Leu Arg Pro Cys Phe
                    530                 535                 540

Lys Gly Ser Ala Pro Ile Asn Leu Ser Asp Arg Leu Asn Gln Val Leu
    545                 550                 555                 560

Arg Trp Ala Leu Gly Ser Val Glu Ile Leu Leu Ser Arg His Cys Pro
                    565                 570                 575

Ile Trp Tyr Gly Tyr Asn Gly Arg Leu Lys Leu Leu Glu Arg Leu Ala
                    580                 585                 590

Tyr Ile Asn Thr Ile Val Tyr Pro Ile Thr Ser Ile Pro Leu Val Ala
                    595                 600                 605

Tyr Cys Val Leu Pro Ala Ile Cys Leu Leu Thr Asn Lys Phe Ile Ile
                    610                 615                 620

Pro Ala Ile Ser Asn Tyr Ala Gly Ala Phe Phe Ile Leu Leu Phe Ala
    625                 630                 635                 640

Ser Ile Phe Ala Thr Gly Ile Leu Glu Leu Arg Trp Ser Gly Val Gly
                    645                 650                 655

Ile Glu Asp Trp Trp Arg Asn Glu Gln Phe Trp Val Ile Gly Gly Thr
                    660                 665                 670

Ser Ala His Leu Phe Ala Val Phe Gln Gly Leu Leu Lys Val Leu Ala
                    675                 680                 685

Gly Ile Asp Thr Asn Phe Thr Val Thr Ser Lys Ala Thr Asp Asp Asp
                    690                 695                 700

Gly Asp Phe Ala Glu Leu Tyr Val Phe Lys Trp Thr Thr Leu Leu Ile
    705                 710                 715                 720

Pro Pro Thr Thr Val Leu Val Ile Asn Leu Val Gly Ile Val Ala Gly
                    725                 730                 735
```

```
Val Ser Tyr Ala Ile Asn Ser Gly Tyr Gln Ser Trp Gly Pro Leu Phe
            740                 745                 750

Gly Lys Leu Phe Phe Ala Ile Trp Val Ile Leu His Leu Tyr Pro Phe
            755                 760                 765

Leu Lys Gly Leu Met Gly Lys Gln Asn Arg Thr Pro Thr Ile Val Ile
        770                 775                 780

Val Trp Ser Val Leu Leu Ala Ser Ile Phe Ser Leu Leu Trp Val Lys
785                 790                 795                 800

Ile Asp Pro Phe Ile Ser Pro Thr Gln Lys Ala Leu Ser Arg Gly Gln
                805                 810                 815

Cys Gly Val Asn Cys
            820

<210> SEQ ID NO 25
<211> LENGTH: 3773
<212> TYPE: DNA
<213> ORGANISM: Zea mays

<400> SEQUENCE: 25
gtcgacccac gcgtccgcta ggatcaaaac cgtctcgccg ctgcaataat cttttgtcaa      60
ttcttaatcc ctcgcgtcga cagcgacagc ggaaccaact cacgttgccg cggcttcctc     120
catcggtgcg gtgccctgtc cttttctctc gtccctcctc cccccgtata gttaagcccc     180
gccccgctac tactactact agcagcagca gcgctctcgc agcgggagat gcggtgttga     240
tccgtgcccc gctcggatct cgggactggt gccggctctg cccaggcccc aggctccagg     300
ccagctccct cgacgtttct cggcgagctc gcttgccatg gagggcgacg cggacggcgt     360
gaagtcgggg aggcgcggtg gcggacaggt gtgccagatc tgcggcgacg gcgtgggcac     420
cacggcggag ggggacgtct tcgccgcctg cgacgtctgc gggtttccgg tgtgccgccc     480
ctgctacgag tacgagcgca aggacggcac gcaggcgtgc ccccagtgca agaccaagta     540
caagcgccac aaggggagcc cggcgatccg tggggaggaa ggagacgaca ctgatgccga     600
tagcgacttc aattaccttg catctggcaa tgaggaccag aagcagaaga ttgccgacag     660
aatgcgcagc tggcgcatga cgttgggggg cagcggggat gttggtcgcc caagtatga      720
cagtggcgag atcgggctta ccaagtatga cagtggcgag attcctcggg atacatccc      780
atcagtcact aacagccaga tctcaggaga aatccctggt gcttcccctg accatcatat     840
gatgtcccca actgggaaca ttggcaagcg tgctccattt ccctatgtga accattcgcc     900
aaatccgtca agggagttct ctggtagcat tgggaatgtt gcctggaaag agagggttga     960
tggctggaaa atgaagcagg acaagggggac gattcccatg acgaatggca caagcattgc    1020
tccctctgag ggtcggggtg ttggtgatat tgatgcatca actgattaca acatggaaga    1080
tgccttattg aacgacgaaa ctcgacagcc tctatctagg aaagttccac ttccttcctc    1140
caggataaat ccatacagga tggtcattgt gctgcgattg attgttctaa gcatcttctt    1200
gcactaccgt atcacaaatc ctgtgcgcaa tgcatacca ttatggcttc tatctgttat     1260
atgtgagatc tggtttgctc tttcgtggat attggatcag ttccctaagt ggtttccaat    1320
caaccgggag acgtaccttg ataggctggc attaaggtat gaccgggaag gtgagccatc    1380
tcagttggct gctgttgaca ttttcgtcag tacagtcgac ccaatgaagg agcctcctct    1440
tgtcactgcc ataccgtgc tatccattct tgctgtggat taccctgtgg ataaggtctc     1500
ttgctatgta tctgatgatg gagctgcgat gctgacattt gatgcactag ctgagacttc     1560
```

```
agagtttgct agaaaatggg taccatttgt taagaagtac aacattgaac ctagagctcc   1620
tgaatggtac ttctcccaga aaattgatta cttgaaggac aaagtgcacc cttcatttgt   1680
taaagaccgc cgggccatga agagagaata tgaagaattc aaagttaggg taaatggcct   1740
tgttgctaag gcacagaaag ttcctgagga aggatggatc atgcaagatg gcacaccatg   1800
gccaggaaac aataccaggg accatcctgg aatgattcag gttttccttg gtcacagtgg   1860
tggccttgat actgagggca atgagctacc ccgtttggtc tatgtttctc gtgaaaagcg   1920
tcctggattc cagcatcaca agaaagctgg tgccatgaat gctcttgttc gtgtctcagc   1980
tgtgcttacc aatggacaat acatgttgaa tcttgattgt gatcactaca ttaacaacag   2040
taaggctctc agggaagcta tgtgcttcct tatggaccct aacctaggaa ggagtgtctg   2100
ctacgtccag tttccccaga gattcgatgg cattgacagg aatgatcgat atgccaacag   2160
gaacaccgtg tttttcgata ttaacttgag aggtcttgat ggcatccaag gaccagttta   2220
tgtcggaact ggctgtgttt tcaaccgaac agctctatat ggttatgagc ccccaattaa   2280
gcagaagaag ggtggtttct tgtcatcact atgtggcggt aggaagaagg caagcaaatc   2340
aaagaagggc tcggacaaga agaagtcgca gaagcatgtg gacagttctg tgccagtatt   2400
caaccttgaa gatatagagg agggagttga aggcgctgga tttgacgacg agaaatcact   2460
tcttatgtct caaatgagcc tggagaagag atttggccag tccgcagcgt tgttgcctc    2520
cactctgatg gagtatggtg gtgttcctca gtccgcaact ccggagtctc ttctgaaaga   2580
agctatccat gttataagct gtggctatga ggacaagact gaatgggaa ctgagatcgg    2640
gtggatctac ggttctgtga cagaagacat tctcaccgga ttcaagatgc acgcgcgagg   2700
ctggcggtcg atctactgca tgcccaagcg gccagctttc aagggggtctg cccccatcaa   2760
tctttcggac cgtctgaacc aggtgctccg gtgggctctt gggtccgtgg agatcctctt   2820
cagccggcac tgcccccctgt ggtacggcta cggagggcgg ctcaagttcc tggagagatt   2880
cgcgtacatc aacaccacca tctacccgct cacgtccatc ccgcttctca tctactgcat   2940
cctgcccgcc atctgtctgc tcaccggaaa gttcatcatt ccagagatca gcaacttcgc   3000
cagcatctgg ttcatctccc tcttcatctc gatcttcgcc acgggcatcc tggagatgag   3060
gtggagcggg gtgggcatcg acgagtggtg gaggaacgag cagttctggg tgatcggggg   3120
catctccgcg cacctcttcg ccgtgttcca gggcctgctc aaggtgctgg ccggcatcga   3180
caccaacttc accgtcacct ccaaggcctg ggacgaggac ggcgacttcg cggagctgta   3240
catgttcaag tggacgacgc tcctgatccc gcccaccacc atcctgatca tcaacctggt   3300
cggcgtcgtc gccggcatct cctacgccat caacagcgga taccagtcgt ggggcccgct   3360
cttcggcaag ctcttcttcg ccttctgggt catcgtccac ctgtacccgt tcctcaaggg   3420
cctcatgggc aggcagaacc gcacccccgac catcgtcgtc gtctgggcca tcctgctggc   3480
gtccatcttc tccttgctgt gggttcgcat cgacccttc accacccgcg tcactggccc    3540
ggatacccag acgtgtggca tcaactgcta gggaagtgga aggtttgtac tttgtagaaa   3600
cggaggaata ccacgtgcca tctgttgtct gttaagttat atatatataa gcagcaagtg   3660
gcgttattta cagctacgta cagaccagtg gatattgttt accacaaagt tttacttgtg   3720
ttaatatgca ttctttttgtt gatataaaaa aaaaaaaaa aaagggcggc cgc          3773
```

<210> SEQ ID NO 26
<211> LENGTH: 1077
<212> TYPE: PRT
<213> ORGANISM: Zea mays

<400> SEQUENCE: 26

```
Met Glu Gly Asp Ala Asp Gly Val Lys Ser Gly Arg Arg Gly Gly Gly
1               5                   10                  15
Gln Val Cys Gln Ile Cys Gly Asp Gly Val Gly Thr Thr Ala Glu Gly
            20                  25                  30
Asp Val Phe Ala Ala Cys Asp Val Cys Gly Phe Pro Val Cys Arg Pro
        35                  40                  45
Cys Tyr Glu Tyr Glu Arg Lys Asp Gly Thr Gln Ala Cys Pro Gln Cys
    50                  55                  60
Lys Thr Lys Tyr Lys Arg His Lys Gly Ser Pro Ala Ile Arg Gly Glu
65                  70                  75                  80
Glu Gly Asp Asp Thr Asp Ala Asp Ser Asp Phe Asn Tyr Leu Ala Ser
                85                  90                  95
Gly Asn Glu Asp Gln Lys Gln Lys Ile Ala Asp Arg Met Arg Ser Trp
            100                 105                 110
Arg Met Asn Val Gly Gly Ser Gly Asp Val Gly Arg Pro Lys Tyr Asp
        115                 120                 125
Ser Gly Glu Ile Gly Leu Thr Lys Tyr Asp Ser Gly Glu Ile Pro Arg
    130                 135                 140
Gly Tyr Ile Pro Ser Val Thr Asn Ser Gln Ile Ser Gly Glu Ile Pro
145                 150                 155                 160
Gly Ala Ser Pro Asp His His Met Met Ser Pro Thr Gly Asn Ile Gly
                165                 170                 175
Lys Arg Ala Pro Phe Pro Tyr Val Asn His Ser Pro Asn Pro Ser Arg
            180                 185                 190
Glu Phe Ser Gly Ser Ile Gly Asn Val Ala Trp Lys Glu Arg Val Asp
        195                 200                 205
Gly Trp Lys Met Lys Gln Asp Lys Gly Thr Ile Pro Met Thr Asn Gly
    210                 215                 220
Thr Ser Ile Ala Pro Ser Glu Gly Arg Gly Val Gly Asp Ile Asp Ala
225                 230                 235                 240
Ser Thr Asp Tyr Asn Met Glu Asp Ala Leu Leu Asn Asp Glu Thr Arg
                245                 250                 255
Gln Pro Leu Ser Arg Lys Val Pro Leu Pro Ser Ser Arg Ile Asn Pro
            260                 265                 270
Tyr Arg Met Val Ile Val Leu Arg Leu Ile Val Leu Ser Ile Phe Leu
        275                 280                 285
His Tyr Arg Ile Thr Asn Pro Val Arg Asn Ala Tyr Pro Leu Trp Leu
    290                 295                 300
Leu Ser Val Ile Cys Glu Ile Trp Phe Ala Leu Ser Trp Ile Leu Asp
305                 310                 315                 320
Gln Phe Pro Lys Trp Phe Pro Ile Asn Arg Glu Thr Tyr Leu Asp Arg
                325                 330                 335
Leu Ala Leu Arg Tyr Asp Arg Glu Gly Glu Pro Ser Gln Leu Ala Ala
            340                 345                 350
Val Asp Ile Phe Val Ser Thr Val Asp Pro Met Lys Glu Pro Pro Leu
        355                 360                 365
Val Thr Ala Asn Thr Val Leu Ser Ile Leu Ala Val Asp Tyr Pro Val
    370                 375                 380
Asp Lys Val Ser Cys Tyr Val Ser Asp Asp Gly Ala Ala Met Leu Thr
385                 390                 395                 400
Phe Asp Ala Leu Ala Glu Thr Ser Glu Phe Ala Arg Lys Trp Val Pro
```

-continued

```
                405                 410                 415
Phe Val Lys Lys Tyr Asn Ile Glu Pro Arg Ala Pro Glu Trp Tyr Phe
            420                 425                 430
Ser Gln Lys Ile Asp Tyr Leu Lys Asp Lys Val His Pro Ser Phe Val
            435                 440                 445
Lys Asp Arg Arg Ala Met Lys Arg Glu Tyr Glu Glu Phe Lys Val Arg
            450                 455                 460
Val Asn Gly Leu Val Ala Lys Ala Gln Lys Val Pro Glu Glu Gly Trp
465                 470                 475                 480
Ile Met Gln Asp Gly Thr Pro Trp Pro Gly Asn Asn Thr Arg Asp His
                485                 490                 495
Pro Gly Met Ile Gln Val Phe Leu Gly His Ser Gly Gly Leu Asp Thr
                500                 505                 510
Glu Gly Asn Glu Leu Pro Arg Leu Val Tyr Val Ser Arg Glu Lys Arg
            515                 520                 525
Pro Gly Phe Gln His His Lys Lys Ala Gly Ala Met Asn Ala Leu Val
            530                 535                 540
Arg Val Ser Ala Val Leu Thr Asn Gly Gln Tyr Met Leu Asn Leu Asp
545                 550                 555                 560
Cys Asp His Tyr Ile Asn Asn Ser Lys Ala Leu Arg Glu Ala Met Cys
                565                 570                 575
Phe Leu Met Asp Pro Asn Leu Gly Arg Ser Val Cys Tyr Val Gln Phe
                580                 585                 590
Pro Gln Arg Phe Asp Gly Ile Asp Arg Asn Asp Arg Tyr Ala Asn Arg
            595                 600                 605
Asn Thr Val Phe Phe Asp Ile Asn Leu Arg Gly Leu Asp Gly Ile Gln
            610                 615                 620
Gly Pro Val Tyr Val Gly Thr Gly Cys Val Phe Asn Arg Thr Ala Leu
625                 630                 635                 640
Tyr Gly Tyr Glu Pro Pro Ile Lys Gln Lys Lys Gly Gly Phe Leu Ser
                645                 650                 655
Ser Leu Cys Gly Gly Arg Lys Lys Ala Ser Lys Ser Lys Lys Gly Ser
                660                 665                 670
Asp Lys Lys Lys Ser Gln Lys His Val Asp Ser Ser Val Pro Val Phe
            675                 680                 685
Asn Leu Glu Asp Ile Glu Glu Gly Val Glu Gly Ala Gly Phe Asp Asp
            690                 695                 700
Glu Lys Ser Leu Leu Met Ser Gln Met Ser Leu Glu Lys Arg Phe Gly
705                 710                 715                 720
Gln Ser Ala Ala Phe Val Ala Ser Thr Leu Met Glu Tyr Gly Gly Val
                725                 730                 735
Pro Gln Ser Ala Thr Pro Glu Ser Leu Leu Lys Glu Ala Ile His Val
            740                 745                 750
Ile Ser Cys Gly Tyr Glu Asp Lys Thr Glu Trp Gly Thr Glu Ile Gly
                755                 760                 765
Trp Ile Tyr Gly Ser Val Thr Glu Asp Ile Leu Thr Gly Phe Lys Met
            770                 775                 780
His Ala Arg Gly Trp Arg Ser Ile Tyr Cys Met Pro Lys Arg Pro Ala
785                 790                 795                 800
Phe Lys Gly Ser Ala Pro Ile Asn Leu Ser Asp Arg Leu Asn Gln Val
                805                 810                 815
Leu Arg Trp Ala Leu Gly Ser Val Glu Ile Leu Phe Ser Arg His Cys
            820                 825                 830
```

```
Pro Leu Trp Tyr Gly Tyr Gly Gly Arg Leu Lys Phe Leu Glu Arg Phe
        835                 840                 845

Ala Tyr Ile Asn Thr Thr Ile Tyr Pro Leu Thr Ser Ile Pro Leu Leu
    850                 855                 860

Ile Tyr Cys Ile Leu Pro Ala Ile Cys Leu Leu Thr Gly Lys Phe Ile
865                 870                 875                 880

Ile Pro Glu Ile Ser Asn Phe Ala Ser Ile Trp Phe Ile Ser Leu Phe
                885                 890                 895

Ile Ser Ile Phe Ala Thr Gly Ile Leu Glu Met Arg Trp Ser Gly Val
            900                 905                 910

Gly Ile Asp Glu Trp Trp Arg Asn Glu Gln Phe Trp Val Ile Gly Gly
        915                 920                 925

Ile Ser Ala His Leu Phe Ala Val Phe Gln Gly Leu Leu Lys Val Leu
    930                 935                 940

Ala Gly Ile Asp Thr Asn Phe Thr Val Thr Ser Lys Ala Ser Asp Glu
945                 950                 955                 960

Asp Gly Asp Phe Ala Glu Leu Tyr Met Phe Lys Trp Thr Thr Leu Leu
                965                 970                 975

Ile Pro Pro Thr Thr Ile Leu Ile Ile Asn Leu Val Gly Val Val Ala
            980                 985                 990

Gly Ile Ser Tyr Ala Ile Asn Ser  Gly Tyr Gln Ser Trp  Gly Pro Leu
        995                 1000                 1005

Phe Gly  Lys Leu Phe Phe Ala  Phe Trp Val Ile  His Leu Tyr
    1010                 1015                 1020

Pro Phe  Leu Lys Gly Leu Met  Gly Arg Gln Asn Arg  Thr Pro Thr
    1025                 1030                 1035

Ile Val  Val Val Trp Ala Ile  Leu Leu Ala Ser Ile  Phe Ser Leu
    1040                 1045                 1050

Leu Trp  Val Arg Ile Asp Pro  Phe Thr Thr Arg Val  Thr Gly Pro
    1055                 1060                 1065

Asp Thr  Gln Thr Cys Gly Ile  Asn Cys
    1070                 1075

<210> SEQ ID NO 27
<211> LENGTH: 3704
<212> TYPE: DNA
<213> ORGANISM: Zea mays

<400> SEQUENCE: 27
gtcgacccac gcttccggtc ggttccgcgt ccctttcccc ctccccctc cgtcgccgcc      60 tcgagcgagc tccaccactt gctcctgcgc gaggtgaaca ctgggttagg gccactgcca     120
ccgctgggct gcctctgctt ctgcctctcc cgccagcgcg cgagcccggg ggcgattcgg     180
cgccggcacg cgggagggga agccgaggaa tgcggtgagt cggcggggt ccggcgtttg     240 tgaactcgtg gagggctcgg attggtgcgc catggacggc ggcgacgcca cgaattcggg     300
gaagcatgtg gccgggcagg tgtgccagat ctgcggcgac ggcgtgggca ccgcggcgga     360 cggcgaccte ttcaccgcct gcgacgtctg cggcttcccc gtgtgccgcc catgctacga     420
gtacgagcgc aaggacggca cccaggcgtg cccgcagtgc aagactaagt acaagcgcca     480
caaagggagc ccaccagtac acggtgagga aaatgaggat gtggatgctg acgatgtgag     540
tgactacaac taccaagcat ctggcaacca ggatcagaag caaaagattg ctgagagaat     600
gctcacttgg cggacaaact cacgtggcag tgatattggc ctggctaagt atgacagcgg     660
```

```
tgaaattggg catgggaagt atgacagtgg tgagatccct cgtggatata tcccgtcact    720
aactcatagc cagatctcag gagagattcc tggagcttcc cctgatcata tgatgtctcc    780
tgttgggaac attggcaggc gtggacatca atttccttat gtaaatcatt ctccaaaccc    840
atcgagggag ttctccggta gccttggcaa tgttgcatgg aaagagaggg tggatggatg    900
gaaaatgaag gataaaggtg caattcctat gaccaatgga acaagcattg ctccatcaga    960
agggcgtgga gttgctgata ttgatgcttc tactgattat aacatggaag atgccttact   1020
gaatgatgaa actcggcaac ctctatctag aaaagtgcca attccttcat ccagaataaa   1080
tccgtacaga atggtcattg tgctacgttt ggctgttcta tgcatattct tgcgctaccg   1140
tatcacacat cctgtgaaca atgcatatcc actgtggctt ttatccgtca tatgtgagat   1200
ctggtttgct ttgtcctgga ttttggatca gttcccaaag tggtcccaa tcaaccgtga    1260 aacatacctt gatagactgg ctttaaggta tgaccgagaa ggtgaaccat ctcaattagc   1320
tcctgttgat atttttgtca gtactgtgga tccaatgaag gagcctcctc ttgtcactgc   1380
aaatactgtg ctttccatcc ttgctgtcga ttatccggtt gacaaggtat cttgctatgt   1440
ttcggatgat ggagctgcta tgctgacttt tgatgctctc tctgaaactt cagagtttgc   1500
tagaaaatgg gttccgttct gtaagaagta caacatagag cctagggccc cggaatggta   1560
ctttgctcag aaaattgatt acttgaaaga caaagttcaa acctcatttg tgaaagaacg   1620
ccgggccatg aagagagaat atgaagaatt caaagttcgt atcaatggtc ttgtagccaa   1680
ggcacaaaaa gttcccgagg agggatggat catgcaagat ggtacacctt ggcctgggaa   1740
caatactagg gaccatcctg gaatgattca ggttttcctg gtcacagtg gagggcttga    1800 cgttgaaggc aatgaacttc ctcgtttggt ttatgtgtct cgtgaaaaac gtcctggatt   1860
ccaacatcac aagaaggctg gtgccatgaa tgcacttgtt cgtgtatcag ctgtccttac   1920
taatgggcaa tacatgttga atcttgattg tgaccactac atcaataata gcaaggctct   1980
tcgagaagct atgtgcttcc ttatggaccc aaacctagga aggaatgtct gttatgtcca   2040
atttcctcag aggtttgatg gtattgatag gaatgaccga tatgcaaaca ggaacactgt   2100 gttttcgat attaacttga gaggtcttga cggcattcaa gggccagttt atgtgggaac    2160
tggttgtgtg tttaacagaa cggccttata tggttatgag cctccagtca agaaaaaaaa   2220
gccaggcttc ttctcttcgc tttgtggggg aaggaaaaag acgtcaaaat ctaagaagag   2280
ctcggaaaag aagaagtcac atagacacgc agacagttct gtaccagtat ttaatctcga   2340
agatatagag gaagggattg aaggttctca gtttgatgat gagaaatcgc tgattatgtc   2400
tcaaatgagc ttggagaaga gatttggcca gtccagtgtt tttgtagcct ctactctgat   2460
ggaatatggt ggtgttccac aatctgcaac tccagagtct cttctgaaag aagctattca   2520
tgtcatcagc tgtggctatg aggacaaaac tgactgggga actgagattg ggtggatcta   2580
tggttctgtt acagaagaca ttctcaccgg attcaagatg catgctcgag ctggcgatc    2640 aatctactgc atgcctaagc gaccagcttt caagggatct gctcctatca accttccgga   2700
tcgtttgaat caagtgcttc ggtgggctct tggttccatt gaaattcttt tcagcaggca   2760
ttgtcccata tggtatggct atggaggccg gcttaaattc ctggagagat tgcttatat    2820 caacacaaca atttatccac tcacatcaat cccgctcctc ctgtactgca tattgccagc   2880
agtttgtctt ctcactggga agttcatcat cccaaagatt agtaacctag agagtgtttg   2940
gtttatatcg ctcttatct caatctttgc cactggtatc cttgagatga ggtggagtgg   3000
tgttggcatt gatgaatggt ggaggaacga gcagttctgg gtcattggtg gtatttctgc   3060
```

-continued

```
gcatttattt gccgtcttcc agggtctcct gaaggtgctt gctggtatcg acacgagctt    3120
cactgtcacc tctaaggcca ctgacgaaga aggtgatttt gccgagctct acatgttcaa    3180
gtggacaacg cttctgatcc caccaaccac tattttgatc atcaacctgg tcggcgtggt    3240
cgctggcatt tcctacgcaa tcaatagcgg ttaccagtca tggggacctc ttttcgggaa    3300
gctcttcttt gcgttctggg tgattgtcca cctgtacccc ttcctcaagg gcctcatggg    3360
gaagcagaac cgcacgccga ccattgtcgt tgtctgggct atcctccttg cgtcgatctt    3420
ttccctgatg tgggttcgta tcgatccatt caccacccgg gtcactggcc ctgatatcgc    3480
gaaatgtggc atcaactgct aggatgagct gaagatagtt aaagagtgga actagacgca    3540
ttgtgcatcg taagttatca gtgggtggct cttttatag tatggtagga acttggtcgg    3600
gagacgttaa ttacatatgc tatatgtacc tccgctggtc tttatccgta agttaatata    3660
tatactgctt tgagaattaa aaaaaaaaaa aaaagggcgg ccgc                     3704
```

<210> SEQ ID NO 28
<211> LENGTH: 1076
<212> TYPE: PRT
<213> ORGANISM: Zea mays

<400> SEQUENCE: 28

```
Met Asp Gly Gly Asp Ala Thr Asn Ser Gly Lys His Val Ala Gly Gln
1               5                   10                  15

Val Cys Gln Ile Cys Gly Asp Gly Val Gly Thr Ala Ala Asp Gly Asp
            20                  25                  30

Leu Phe Thr Ala Cys Asp Val Cys Gly Phe Pro Val Cys Arg Pro Cys
        35                  40                  45

Tyr Glu Tyr Glu Arg Lys Asp Gly Thr Gln Ala Cys Pro Gln Cys Lys
    50                  55                  60

Thr Lys Tyr Lys Arg His Lys Gly Ser Pro Pro Val His Gly Glu Glu
65                  70                  75                  80

Asn Glu Asp Val Asp Ala Asp Asp Val Ser Asp Tyr Asn Tyr Gln Ala
                85                  90                  95

Ser Gly Asn Gln Asp Gln Lys Gln Lys Ile Ala Glu Arg Met Leu Thr
            100                 105                 110

Trp Arg Thr Asn Ser Arg Gly Ser Asp Ile Gly Leu Ala Lys Tyr Asp
        115                 120                 125

Ser Gly Glu Ile Gly His Gly Lys Tyr Asp Ser Gly Glu Ile Pro Arg
    130                 135                 140

Gly Tyr Ile Pro Ser Leu Thr His Ser Gln Ile Ser Gly Glu Ile Pro
145                 150                 155                 160

Gly Ala Ser Pro Asp His Met Met Ser Pro Val Gly Asn Ile Gly Arg
                165                 170                 175

Arg Gly His Gln Phe Pro Tyr Val Asn His Ser Pro Asn Pro Ser Arg
            180                 185                 190

Glu Phe Ser Gly Ser Leu Gly Asn Val Ala Trp Lys Glu Arg Val Asp
        195                 200                 205

Gly Trp Lys Met Lys Asp Lys Gly Ala Ile Pro Met Thr Asn Gly Thr
    210                 215                 220

Ser Ile Ala Pro Ser Glu Gly Arg Gly Val Ala Asp Ile Asp Ala Ser
225                 230                 235                 240

Thr Asp Tyr Asn Met Glu Asp Ala Leu Leu Asn Asp Glu Thr Arg Gln
                245                 250                 255
```

-continued

```
Pro Leu Ser Arg Lys Val Pro Ile Pro Ser Ser Arg Ile Asn Pro Tyr
            260                 265                 270

Arg Met Val Ile Val Leu Arg Leu Ala Val Leu Cys Ile Phe Leu Arg
        275                 280                 285

Tyr Arg Ile Thr His Pro Val Asn Asn Ala Tyr Pro Leu Trp Leu Leu
    290                 295                 300

Ser Val Ile Cys Glu Ile Trp Phe Ala Leu Ser Trp Ile Leu Asp Gln
305                 310                 315                 320

Phe Pro Lys Trp Ser Pro Ile Asn Arg Glu Thr Tyr Leu Asp Arg Leu
                325                 330                 335

Ala Leu Arg Tyr Asp Arg Glu Gly Glu Pro Ser Gln Leu Ala Pro Val
            340                 345                 350

Asp Ile Phe Val Ser Thr Val Asp Pro Met Lys Glu Pro Pro Leu Val
        355                 360                 365

Thr Ala Asn Thr Val Leu Ser Ile Leu Ala Val Asp Tyr Pro Val Asp
    370                 375                 380

Lys Val Ser Cys Tyr Val Ser Asp Asp Gly Ala Ala Met Leu Thr Phe
385                 390                 395                 400

Asp Ala Leu Ser Glu Thr Ser Glu Phe Ala Arg Lys Trp Val Pro Phe
                405                 410                 415

Cys Lys Lys Tyr Asn Ile Glu Pro Arg Ala Pro Glu Trp Tyr Phe Ala
            420                 425                 430

Gln Lys Ile Asp Tyr Leu Lys Asp Lys Val Gln Thr Ser Phe Val Lys
        435                 440                 445

Glu Arg Arg Ala Met Lys Arg Glu Tyr Glu Glu Phe Lys Val Arg Ile
    450                 455                 460

Asn Gly Leu Val Ala Lys Ala Gln Lys Val Pro Glu Glu Gly Trp Ile
465                 470                 475                 480

Met Gln Asp Gly Thr Pro Trp Pro Gly Asn Asn Thr Arg Asp His Pro
                485                 490                 495

Gly Met Ile Gln Val Phe Leu Gly His Ser Gly Gly Leu Asp Val Glu
            500                 505                 510

Gly Asn Glu Leu Pro Arg Leu Val Tyr Val Ser Arg Glu Lys Arg Pro
        515                 520                 525

Gly Phe Gln His His Lys Lys Ala Gly Ala Met Asn Ala Leu Val Arg
    530                 535                 540

Val Ser Ala Val Leu Thr Asn Gly Gln Tyr Met Leu Asn Leu Asp Cys
545                 550                 555                 560

Asp His Tyr Ile Asn Asn Ser Lys Ala Leu Arg Glu Ala Met Cys Phe
                565                 570                 575

Leu Met Asp Pro Asn Leu Gly Arg Asn Val Cys Tyr Val Gln Phe Pro
            580                 585                 590

Gln Arg Phe Asp Gly Ile Asp Arg Asn Asp Arg Tyr Ala Asn Arg Asn
        595                 600                 605

Thr Val Phe Phe Asp Ile Asn Leu Arg Gly Leu Asp Gly Ile Gln Gly
    610                 615                 620

Pro Val Tyr Val Gly Thr Gly Cys Val Phe Asn Arg Thr Ala Leu Tyr
625                 630                 635                 640

Gly Tyr Glu Pro Pro Val Lys Lys Lys Pro Gly Phe Phe Ser Ser
                645                 650                 655

Leu Cys Gly Gly Arg Lys Lys Thr Ser Lys Ser Lys Lys Ser Ser Glu
            660                 665                 670

Lys Lys Lys Ser His Arg His Ala Asp Ser Ser Val Pro Val Phe Asn
```

```
                675                 680                 685
Leu Glu Asp Ile Glu Glu Gly Ile Glu Gly Ser Gln Phe Asp Asp Glu
        690                 695                 700

Lys Ser Leu Ile Met Ser Gln Met Ser Leu Glu Lys Arg Phe Gly Gln
705                 710                 715                 720

Ser Ser Val Phe Val Ala Ser Thr Leu Met Glu Tyr Gly Gly Val Pro
                725                 730                 735

Gln Ser Ala Thr Pro Glu Ser Leu Leu Lys Glu Ala Ile His Val Ile
                740                 745                 750

Ser Cys Gly Tyr Glu Asp Lys Thr Asp Trp Gly Thr Glu Ile Gly Trp
                755                 760                 765

Ile Tyr Gly Ser Val Thr Glu Asp Ile Leu Thr Gly Phe Lys Met His
        770                 775                 780

Ala Arg Gly Trp Arg Ser Ile Tyr Cys Met Pro Lys Arg Pro Ala Phe
785                 790                 795                 800

Lys Gly Ser Ala Pro Ile Asn Leu Ser Asp Arg Leu Asn Gln Val Leu
                805                 810                 815

Arg Trp Ala Leu Gly Ser Ile Glu Ile Leu Phe Ser Arg His Cys Pro
            820                 825                 830

Ile Trp Tyr Gly Tyr Gly Gly Arg Leu Lys Phe Leu Glu Arg Phe Ala
        835                 840                 845

Tyr Ile Asn Thr Thr Ile Tyr Pro Leu Thr Ser Ile Pro Leu Leu Leu
850                 855                 860

Tyr Cys Ile Leu Pro Ala Val Cys Leu Leu Thr Gly Lys Phe Ile Ile
865                 870                 875                 880

Pro Lys Ile Ser Asn Leu Glu Ser Val Trp Phe Ile Ser Leu Phe Ile
                885                 890                 895

Ser Ile Phe Ala Thr Gly Ile Leu Glu Met Arg Trp Ser Gly Val Gly
            900                 905                 910

Ile Asp Glu Trp Trp Arg Asn Glu Gln Phe Trp Val Ile Gly Gly Ile
        915                 920                 925

Ser Ala His Leu Phe Ala Val Phe Gln Gly Leu Leu Lys Val Leu Ala
        930                 935                 940

Gly Ile Asp Thr Ser Phe Thr Val Thr Ser Lys Ala Thr Asp Glu Glu
945                 950                 955                 960

Gly Asp Phe Ala Glu Leu Tyr Met Phe Lys Trp Thr Thr Leu Leu Ile
                965                 970                 975

Pro Pro Thr Thr Ile Leu Ile Ile Asn Leu Val Gly Val Val Ala Gly
                980                 985                 990

Ile Ser Tyr Ala Ile Asn Ser Gly Tyr Gln Ser Trp Gly Pro Leu Phe
        995                 1000                1005

Gly Lys Leu Phe Phe Ala Phe Trp Val Ile Val His Leu Tyr Pro
    1010                1015                1020

Phe Leu Lys Gly Leu Met Gly Lys Gln Asn Arg Thr Pro Thr Ile
    1025                1030                1035

Val Val Val Trp Ala Ile Leu Leu Ala Ser Ile Phe Ser Leu Met
    1040                1045                1050

Trp Val Arg Ile Asp Pro Phe Thr Thr Arg Val Thr Gly Pro Asp
    1055                1060                1065

Ile Ala Lys Cys Gly Ile Asn Cys
    1070                1075

<210> SEQ ID NO 29
```

```
<211> LENGTH: 3568
<212> TYPE: DNA
<213> ORGANISM: Zea mays
<220> FEATURE:
<221> NAME/KEY: misc_feature
<222> LOCATION: (3487)..(3487)
<223> OTHER INFORMATION: n is a, c, g, or t

<400> SEQUENCE: 29
gtcgacccac gcgtccggag ctcgtcgtca tccgccgcga tggcgagcca gggccgaagc      60
ccatggacca gcggaacggc caggtgtgcc agatttgcgg cgacgacgtg gggcgcaacc     120
ccgacgggga gcctttcgtg gcctgcaacg agtgcgcctt ccccatctgc cgggactgct     180
acgagtacga gcgccgcgag ggcacgcaga actgcccccca gtgcaagacc cgcttcaagc    240
gcttcaaggg gtgcgcgcgc gtgcccgggg acgaggagga ggacgcgtc gacgacctgg      300 agaacgagtt caactggagc gacaagcacg actcccagta cctcgccgag tccatgctcc     360
acgcccacat gagctacggc cgcggcgccc acctcgacgg cgtgccgcag ccattccacc     420
ccatccccaa tgttcccctc ctcaccaacg gacagatggt cgatgacatc ccgccggacc     480
agcacgccct tgtgccctcg ttcgtgggtg cgggggggaa gaggattcac cctctcccgt     540
acgcggatcc caaccttcct gtgcaaccga ggtctatgga cccttccaag gatctcgccg     600
catatggcta cgggagcgta gcatggaagg agaggatgga gagctggaag cagaagcagg     660
agaggatgca ccagacgagg aacgatggcg gcggcgatga tggtgatgat gcagatctac     720
cactaatgga tgaagctaga cagccattgt ccagaaagat cccgcttcct tcaagccaaa     780
tcaaccccta taggatgatt ataataattc ggctagtggt tttgtgtttc ttcttccact     840
accgagtgat gcatccggtg cctgatgcat ttgctttatg gctcatatct gtgatctgtg     900
aaatttggtt tgccatgtct tggattcttg accagtttcc aaagtggttt cctatcgaga     960
gggaaaccta tcttgaccgg ctgagtttaa ggtttgacaa ggaagggcat ccttctcaac    1020
tcgcccctgt tgatttcttt gtcagtacgg ttgatcccctt gaaggaacct ccattggtca    1080
ctgctaatac tgttctatct atccttttcgg tggattatcc agttgataag gtttcatgct    1140
acgtttctga tgatggtgct gccatgctga catttgaagc attgtctgaa acatctgaat    1200
ttgcaaagaa atgggttcct ttctgcaaaa gatatagcct tgagcctcgt gctccagagt    1260
ggtacttcca acagaagata gactacctga agacaaggt ggcgccaaac tttgttagag      1320
aacggagagc aatgaagaga gagtatgagg aattcaaggt cagaatcaat gccttggttg    1380
ctaaagccca aaaggttcct gaggaaggat ggacaatgca ggatggaact ccatggcccg    1440
gaaataatgt ccgtgatcat cctggaatga ttcaggtttt ccttggtcaa agtggtggcc    1500
atgatgtgga aggaaatgag ctgcctcgat tggtttatgt ttcaagagaa aaacggccag    1560
gctacaacca tcacaagaag gctggtgcta tgaatgcatt ggtccgagtc tctgctgtac    1620
taactaatgc tccttatttg ctgaacttgg attgtgatca ctatatcaat aatagtaagg    1680
ctataaagga agcaatgtgt tttatgatgg atccttttgct tggaaagaaa gtttgctatg    1740
tgcagtttcc tcaaagattt gatgggattg atcgccatga tcgatatgct aacagaaatg    1800
ttgtcttttt cgatatcaac atgaaaggtt tggatggtat ccagggccca atttatgtgg    1860
gtactggatg tgtcttcaga aggcaggcat tatatgcta cgatgctccc aaaacaaaga    1920
agccaccatc aagaacttgc aactgctggc caaagtggtg catttgctgt tgctgttttg    1980
gtaacaggaa gaccaagaag aagaccaaga cctctaaacc taaatttgag aagataaaga    2040 aacttttttaa gaaaaaggaa aatcaagccc ctgcatatgc tcttggtgaa attgatgaag    2100
```

```
ccgctccagg agctgaaaat gaaaaggcta gtattgtaaa tcaacagaag ttggaaaaga   2160
aatttggcca gtcttcagtt tttgttgcat ccacacttct tgagaatggt ggaaccctga   2220
agagtgccag tccagcttct cttctgaagg aagctataca tgtcatcagt tgtggatatg   2280
aagacaaaac aggctgggga aagatattg gttggattta tggatcagtc acagaagata    2340
ttcttactgg gtttaagatg cactgccatg gttggcggtc aatttactgc atacctaaac   2400
gggccgcctt caaaggttcc gcacctctca atctttccga tcgttttcac caggttcttc   2460
ggtgggctct tggttcaatt gaaattttgt tcagcaacca ctgccctctc tggtatgggt   2520
atggtggtgg actaaagttc ctggaaaggt tttcgtacat taactccatc gtatacccct   2580
ggacatctat cccgctcttg gcctattgca cattgcctgc catctgcttg ctgacaggga   2640
aatttatcac gccagagctt aacaatgttg ccagcctctg gttcatgtca cttttcatct   2700 gcattttttgc tacgagcatc ctggaaatga gatggagtgg tgtaggcatc gatgactggt   2760
ggagaaacga gcagttttgg gtcattggag gcgtgtcttc acatctcttt gctgtgttcc   2820
agggactcct caaggtcata gctggtgtag acacgagctt cactgtgaca tccaagggcg   2880
gagacgacga ggagttctca gagctgtaca cattcaaatg gacgacccct ctgataccctc   2940 cgacaaccct gctcctactg aacttcattg gagtggtagc tggcatctcc aatgcgatca   3000
acaacggata tgaatcatgg ggccccctgt tcgggaagct cttctttgca ttttgggtga   3060
tcgtccatct ttacccgttc ctcaagggtc tggttgggag cagaacagg acgccaacga    3120 ttgtcattgt ctggtccatc ctcctggctt cgatcttctc gctgctttgg gtccggatcg   3180
acccgttcct tgcgaaggat gatggtcccc tgttggagga gtgtggtctg gattgcaact   3240
aggaggtcag cacgtggact tccccgtcag tgtgtggtcg aagaagtatt tttgcagatg   3300
ttttgtgccc atatttcttt actcaatttt tgtccctctg tagattgaaa caaggggtga   3360
aggggaaaaa aagtacttgt atttcttttg ttccatggtg gtggtggtgg tgggcggctc   3420
agcctcgtga gtgcaatatt gggcaaaccg gaggttgcgg caaccttgtg cagttcgtcc   3480
acgaatntac tagggatgat cgcgaccaat caatcaatcg atgaccgagt tcaattgttc   3540
aaaaaaaaaa aaaaaaaagg gcggccgc                                     3568
```

<210> SEQ ID NO 30
<211> LENGTH: 1059
<212> TYPE: PRT
<213> ORGANISM: Zea mays

<400> SEQUENCE: 30

```
Met Asp Gln Arg Asn Gly Gln Val Cys Gln Ile Cys Gly Asp Val
1               5                   10                  15

Gly Arg Asn Pro Asp Gly Glu Pro Phe Val Ala Cys Asn Glu Cys Ala
            20                  25                  30

Phe Pro Ile Cys Arg Asp Cys Tyr Glu Tyr Glu Arg Glu Gly Thr
                35                  40                  45

Gln Asn Cys Pro Gln Cys Lys Thr Arg Phe Lys Arg Phe Lys Gly Cys
        50                  55                  60

Ala Arg Val Pro Gly Asp Glu Glu Asp Gly Val Asp Asp Leu Glu
65                  70                  75                  80

Asn Glu Phe Asn Trp Ser Asp Lys His Asp Ser Gln Tyr Leu Ala Glu
                85                  90                  95

Ser Met Leu His Ala His Met Ser Tyr Gly Arg Gly Ala Asp Leu Asp
            100                 105                 110
```

```
Gly Val Pro Gln Pro Phe His Pro Ile Pro Asn Val Pro Leu Leu Thr
            115                 120                 125
Asn Gly Gln Met Val Asp Asp Ile Pro Pro Asp Gln His Ala Leu Val
130                 135                 140
Pro Ser Phe Val Gly Gly Gly Lys Arg Ile His Pro Leu Pro Tyr
145                 150                 155                 160
Ala Asp Pro Asn Leu Pro Val Gln Pro Arg Ser Met Asp Pro Ser Lys
                165                 170                 175
Asp Leu Ala Ala Tyr Gly Tyr Gly Ser Val Ala Trp Lys Glu Arg Met
                180                 185                 190
Glu Ser Trp Lys Gln Lys Gln Glu Arg Met His Gln Thr Arg Asn Asp
            195                 200                 205
Gly Gly Gly Asp Asp Gly Asp Asp Ala Asp Leu Pro Leu Met Asp Glu
            210                 215                 220
Ala Arg Gln Pro Leu Ser Arg Lys Ile Pro Leu Pro Ser Ser Gln Ile
225                 230                 235                 240
Asn Pro Tyr Arg Met Ile Ile Ile Arg Leu Val Val Leu Cys Phe
                245                 250                 255
Phe Phe His Tyr Arg Val Met His Pro Val Pro Asp Ala Phe Ala Leu
            260                 265                 270
Trp Leu Ile Ser Val Ile Cys Glu Ile Trp Phe Ala Met Ser Trp Ile
            275                 280                 285
Leu Asp Gln Phe Pro Lys Trp Phe Pro Ile Glu Arg Glu Thr Tyr Leu
            290                 295                 300
Asp Arg Leu Ser Leu Arg Phe Asp Lys Glu Gly His Pro Ser Gln Leu
305                 310                 315                 320
Ala Pro Val Asp Phe Phe Val Ser Thr Val Asp Pro Leu Lys Glu Pro
                325                 330                 335
Pro Leu Val Thr Ala Asn Thr Val Leu Ser Ile Leu Ser Val Asp Tyr
            340                 345                 350
Pro Val Asp Lys Val Ser Cys Tyr Val Ser Asp Asp Gly Ala Ala Met
            355                 360                 365
Leu Thr Phe Glu Ala Leu Ser Glu Thr Ser Glu Phe Ala Lys Lys Trp
            370                 375                 380
Val Pro Phe Cys Lys Arg Tyr Ser Leu Glu Pro Arg Ala Pro Glu Trp
385                 390                 395                 400
Tyr Phe Gln Gln Lys Ile Asp Tyr Leu Lys Asp Lys Val Ala Pro Asn
                405                 410                 415
Phe Val Arg Glu Arg Arg Ala Met Lys Arg Glu Tyr Glu Glu Phe Lys
                420                 425                 430
Val Arg Ile Asn Ala Leu Val Ala Lys Ala Gln Lys Val Pro Glu Glu
            435                 440                 445
Gly Trp Thr Met Gln Asp Gly Thr Pro Trp Pro Gly Asn Asn Val Arg
            450                 455                 460
Asp His Pro Gly Met Ile Gln Val Phe Leu Gly Gln Ser Gly Gly His
465                 470                 475                 480
Asp Val Glu Gly Asn Glu Leu Pro Arg Leu Val Tyr Val Ser Arg Glu
                485                 490                 495
Lys Arg Pro Gly Tyr Asn His His Lys Lys Ala Gly Ala Met Asn Ala
                500                 505                 510
Leu Val Arg Val Ser Ala Val Leu Thr Asn Ala Pro Tyr Leu Leu Asn
            515                 520                 525
```

-continued

```
Leu Asp Cys Asp His Tyr Ile Asn Asn Ser Lys Ala Ile Lys Glu Ala
    530                 535                 540

Met Cys Phe Met Met Asp Pro Leu Leu Gly Lys Lys Val Cys Tyr Val
545                 550                 555                 560

Gln Phe Pro Gln Arg Phe Asp Gly Ile Asp Arg His Asp Arg Tyr Ala
            565                 570                 575

Asn Arg Asn Val Val Phe Phe Asp Ile Asn Met Lys Gly Leu Asp Gly
                580                 585                 590

Ile Gln Gly Pro Ile Tyr Val Gly Thr Gly Cys Val Phe Arg Arg Gln
            595                 600                 605

Ala Leu Tyr Gly Tyr Asp Ala Pro Lys Thr Lys Lys Pro Pro Ser Arg
    610                 615                 620

Thr Cys Asn Cys Trp Pro Lys Trp Cys Ile Cys Cys Cys Cys Phe Gly
625                 630                 635                 640

Asn Arg Lys Thr Lys Lys Thr Lys Thr Ser Lys Pro Lys Phe Glu
            645                 650                 655

Lys Ile Lys Lys Leu Phe Lys Lys Glu Asn Gln Ala Pro Ala Tyr
    660                 665                 670

Ala Leu Gly Glu Ile Asp Glu Ala Ala Pro Gly Ala Glu Asn Glu Lys
    675                 680                 685

Ala Ser Ile Val Asn Gln Gln Lys Leu Glu Lys Lys Phe Gly Gln Ser
    690                 695                 700

Ser Val Phe Val Ala Ser Thr Leu Leu Glu Asn Gly Gly Thr Leu Lys
705                 710                 715                 720

Ser Ala Ser Pro Ala Ser Leu Leu Lys Glu Ala Ile His Val Ile Ser
            725                 730                 735

Cys Gly Tyr Glu Asp Lys Thr Gly Trp Gly Lys Asp Ile Gly Trp Ile
            740                 745                 750

Tyr Gly Ser Val Thr Glu Asp Ile Leu Thr Gly Phe Lys Met His Cys
            755                 760                 765

His Gly Trp Arg Ser Ile Tyr Cys Ile Pro Lys Arg Ala Ala Phe Lys
    770                 775                 780

Gly Ser Ala Pro Leu Asn Leu Ser Asp Arg Phe His Gln Val Leu Arg
785                 790                 795                 800

Trp Ala Leu Gly Ser Ile Glu Ile Leu Phe Ser Asn His Cys Pro Leu
            805                 810                 815

Trp Tyr Gly Tyr Gly Gly Gly Leu Lys Phe Leu Glu Arg Phe Ser Tyr
            820                 825                 830

Ile Asn Ser Ile Val Tyr Pro Trp Thr Ser Ile Pro Leu Leu Ala Tyr
    835                 840                 845

Cys Thr Leu Pro Ala Ile Cys Leu Leu Thr Gly Lys Phe Ile Thr Pro
850                 855                 860

Glu Leu Asn Asn Val Ala Ser Leu Trp Phe Met Ser Leu Phe Ile Cys
865                 870                 875                 880

Ile Phe Ala Thr Ser Ile Leu Glu Met Arg Trp Ser Gly Val Gly Ile
            885                 890                 895

Asp Asp Trp Trp Arg Asn Glu Gln Phe Trp Val Ile Gly Gly Val Ser
            900                 905                 910

Ser His Leu Phe Ala Val Phe Gln Gly Leu Leu Lys Val Ile Ala Gly
    915                 920                 925

Val Asp Thr Ser Phe Thr Val Thr Ser Lys Gly Gly Asp Asp Glu Glu
    930                 935                 940

Phe Ser Glu Leu Tyr Thr Phe Lys Trp Thr Thr Leu Leu Ile Pro Pro
```

```
                 945                 950                 955                 960

Thr Thr Leu Leu Leu Leu Asn Phe Ile Gly Val Val Ala Gly Ile Ser
                965                 970                 975

Asn Ala Ile Asn Asn Gly Tyr Glu Ser Trp Gly Pro Leu Phe Gly Lys
            980                 985                 990

Leu Phe Phe Ala Phe Trp Val Ile Val His Leu Tyr Pro Phe Leu Lys
        995                 1000                1005

Gly Leu Val Gly Arg Gln Asn Arg Thr Pro Thr Ile Val Ile Val
        1010                1015                1020

Trp Ser Ile Leu Leu Ala Ser Ile Phe Ser Leu Leu Trp Val Arg
    1025                1030                1035

Ile Asp Pro Phe Leu Ala Lys Asp Asp Gly Pro Leu Leu Glu Glu
    1040                1045                1050

Cys Gly Leu Asp Cys Asn
    1055

<210> SEQ ID NO 31
<211> LENGTH: 3969
<212> TYPE: DNA
<213> ORGANISM: Zea mays

<400> SEQUENCE: 31
cttctccctc gtcggtgcgg cgtggcgcgg ctcggcgttc ggtgagaaac cactcggggg      60
atgaggatct gctgctagag tgagaggagc tacggtcagt atcctctgcc ttcgtcggcg     120
gcggaagtgg aggggaggaa gcgatggagg cgagcgccgg gctggtggcc ggctcccaca     180
accgcaacga gctcgtcgtc atccgccgcg acggcgatcc cgggccgaag ccgccgcggg     240
agcagaacga gcaggtgtgc cagatttgcg gcgacgacgt cggccttgcc cccggcgggg     300
accccttcgt ggcgtgcaac gagtgcgcct tccccgtctg ccgggactgc tacgaatacg     360
agcgccggga gggcacgcag aactgccccc agtgcaagac tcgatacaag cgcctcaagg     420
gctgccaacg tgtgaccggt gacgaggagg aggacggcgt cgatgacctg gacaacgagt     480
tcaactggga cggccatgac tcgcagtctg tggccgagtc catgctctac ggccacatga     540
gctacggccg tggaggtgac cctaatggcg cgccacaagc tttccagctc aaccccaatg     600
ttccactcct caccaacggg caaatggtgg atgacatccc accggagcag cacgcgctgg     660
tgccttcttt catgggtggt gggggaaaga ggatacatcc ccttccttat gcggatccca     720
gcttacctgt gcaacccagg tctatggacc catccaagga tcttgctgca tatgggtatg     780
gtagtgttgc ttggaaggaa cggatggaga attggaagca gagacaagag aggatgcacc     840
agacggggaa tgatggtggt ggtgatgatg gtgacgatgc tgatctacca ctaatggatg     900
aagcaagaca caactgtcc aggaaaattc cacttccatc aagccagatt aatccatata     960
ggatgattat cattattcgg cttgtggttt tggggttctt cttccactac cgagtgatgc    1020
atccggtgaa tgatgcattt gctttgtggc tcatatctgt tatctgtgaa atctggtttg    1080
ccatgtcttg gattcttgat caattcccaa agtggttccc tattgagaga gagacttacc    1140
tagaccggct gtcactgagg ttcgacaagg aaggccagcc atctcaactt gctccaattg    1200
atttctttgt cagtacggtt gatcccttaa aggaacctcc tttggtcaca acaaatactg    1260
ttctatctat cctttcggtg gattatcctg ttgataaggt ttcttgctat gtttctgatg    1320
atggtgctgc aatgctaacg tttgaagcat atctgaaaac atctgaattt gcaaagaaat    1380
gggttccttt ctgcaaacgg tacaatattg aacctcgcgc tccagagtgg tacttccaac    1440
```

```
agaagataga ctacttgaaa gacaaggtgg cagcaaactt tgttagggag aggagagcaa    1500
tgaagagaga gtatgaggaa ttcaaggtga gaatcaatgc cttagttgcc aaagcccaga    1560
aagttcctga agaaggatgg acaatgcaag atggaacccc ctggcctgga acaatgttc     1620 gtgatcatcc tggaatgatt caggtcttcc ttggccaaag cggaggcctt gactgtgagg    1680
gaaatgaact gccacgattg gtttatgttt ctagagagaa acgaccaggc tataaccatc    1740
ataagaaagc tggtgctatg aatgcattgg tccgagtctc tgctgtacta acaaatgctc    1800
catatttgtt aaacttggat tgtgatcact acatcaacaa cagcaaggct ataaaggaag    1860
caatgtgttt tatgatggac cctttactag gaaagaaggt ttgctatgta cagttccctc    1920
aaagatttga tgggattgat cgccatgacc gatatgctaa ccggaatgtt gtcttttttg    1980
atatcaacat gaaaggtttg gatggtattc agggtccaat ttatgttggt actggatgtg    2040
tatttagaag gcaggcatta tatggttatg atgcccccaa aacaaagaag ccaccatcaa    2100
ggacttgcaa ctgctggccc aagtggtgct tttgctgttg ctgctttggc aataggaagc    2160
aaaagaagac taccaaaccc aaaacagaga agaaaaagtt attattttc aagaaagaag     2220 agaaccaatc ccctgcatat gctcttggtg aaattgacga agctgctcca ggagctgaga    2280
atgaaaaggc cggtattgta aatcaacaaa aattagaaaa gaaatttggc caatcttctg    2340 ttttgttac atccacactt ctcgagaatg gtggaacctt gaagagtgca agtcctgctt      2400
ctcttttgaa agaagctata catgtcatta gttgtggtta tgaagacaag acagactggg    2460
gaaaagagat tggctggatc tatggatcag ttacagaaga tattctaact ggtttcaaga    2520
tgcattgtca tggttggcgg tcaatttact gcatacctaa acgggttgca ttcaaaggtt    2580
ctgcacctct gaatctttca gatcgtcttc accaggtgct tcggtgggct cttgggtcta    2640
ttgagatctt cttcagcaat cattgccctc tttggtatgg gtatggtggc ggtctgaaat    2700
ttttggaaag attttcctac atcaactcca tcgtgtatcc ttggacatct attccctct     2760 tggcttactg tacattgcct gccatctgtt tattgacagg gaaatttatc actccagagc    2820
tgaataatgt tgccagcctg tggttcatgt cactttttat ctgcattttt gctacgagca    2880
tcctagaaat gagatggagt ggtgttggaa ttgatgactg gtggaggaat gagcagttct    2940
gggtcattgg aagtgtgtcc tcacacctct ttgctgtgtt ccagggactt ctcaaggtca    3000
tagctggtgt tgatacaagc ttcaccgtga catcaaaggg tggagatgat gaggagttct    3060
cagagctata tacattcaaa tggactacct tattgatacc tcctaccacc ttgcttctat    3120
tgaacttcat tggtgtggtc gctggcgttt caaatgcgat caataacgga tatgagtcat    3180
ggggccccct ctttgggaag ctattctttg cattttgggt gattgtccat ctttatccct    3240
ttctcaaagg ttttggttga aggcaaaaca ggacaccaac gattgtcatc gtctggtcca    3300
ttctgctggc ttcaatcttc tcgctccttt gggttcggat tgatcctttc cttgcgaagg    3360
atgatggtcc gcttcttgag gagtgtggtt tggattgcaa ctaggatgtc agtgcatcag    3420
ctcccccaat ctgcatatgc ttgaagtata ttttctggtg tttgtcccca tattcagtgt    3480
ctgtagataa gagacatgaa atgtcccaag tttcttttga tccatggtga acctacttaa    3540
tatctgagag atatactggg ggaaaatgga ggctgcggca atccttgtgc agttgggccg    3600
tggaatacag catatgcaag tgtttgattg tgcagcattc tttattactt ggtcgcaata    3660
tagatgggct gagccgaaca gcaaggtatt ttgattctgc actgctcccg tgtacaaact    3720
tggttctcaa taaggcaggc aggaatgcat ctgccagtgg aacagagcaa cctgcacatt    3780
atttatgtat gcctgttcat tggagggctt gttcattaca tgttcgtcta tactagaaaa    3840
```

-continued

```
aacagaatat tagcattaat ctatagttaa ttaaagtatg taaatgcgcc tgtttttgt     3900 tgtgtactgt aatcatctga gttggttttg tgaaaaaaaa aaaaaaaaaa aaaaaaaaaa    3960
aaaaaaaaa                                                            3969
```

<210> SEQ ID NO 32
<211> LENGTH: 1086
<212> TYPE: PRT
<213> ORGANISM: Zea mays

<400> SEQUENCE: 32

```
Met Glu Ala Ser Ala Gly Leu Val Ala Gly Ser His Asn Arg Asn Glu
1               5                   10                  15

Leu Val Val Ile Arg Arg Asp Gly Asp Pro Gly Pro Lys Pro Pro Arg
            20                  25                  30

Glu Gln Asn Gly Gln Val Cys Gln Ile Cys Gly Asp Asp Val Gly Leu
        35                  40                  45

Ala Pro Gly Gly Asp Pro Phe Val Ala Cys Asn Glu Cys Ala Phe Pro
    50                  55                  60

Val Cys Arg Asp Cys Tyr Glu Tyr Glu Arg Arg Glu Gly Thr Gln Asn
65                  70                  75                  80

Cys Pro Gln Cys Lys Thr Arg Tyr Lys Arg Leu Lys Gly Cys Gln Arg
                85                  90                  95

Val Thr Gly Asp Glu Glu Glu Asp Gly Val Asp Asp Leu Asp Asn Glu
            100                 105                 110

Phe Asn Trp Asp Gly His Asp Ser Gln Ser Val Ala Glu Ser Met Leu
        115                 120                 125

Tyr Gly His Met Ser Tyr Gly Arg Gly Asp Pro Asn Gly Ala Pro
    130                 135                 140

Gln Ala Phe Gln Leu Asn Pro Asn Val Pro Leu Leu Thr Asn Gly Gln
145                 150                 155                 160

Met Val Asp Asp Ile Pro Pro Glu Gln His Ala Leu Val Pro Ser Phe
                165                 170                 175

Met Gly Gly Gly Lys Arg Ile His Pro Leu Pro Tyr Ala Asp Pro
            180                 185                 190

Ser Leu Pro Val Gln Pro Arg Ser Met Asp Pro Ser Lys Asp Leu Ala
        195                 200                 205

Ala Tyr Gly Tyr Gly Ser Val Ala Trp Lys Glu Arg Met Glu Asn Trp
    210                 215                 220

Lys Gln Arg Gln Glu Arg Met His Gln Thr Gly Asn Asp Gly Gly Gly
225                 230                 235                 240

Asp Asp Gly Asp Asp Ala Asp Leu Pro Leu Met Asp Glu Ala Arg Gln
                245                 250                 255

Gln Leu Ser Arg Lys Ile Pro Leu Pro Ser Ser Gln Ile Asn Pro Tyr
            260                 265                 270

Arg Met Ile Ile Ile Ile Arg Leu Val Val Leu Gly Phe Phe His
        275                 280                 285

Tyr Arg Val Met His Pro Val Asn Asp Ala Phe Ala Leu Trp Leu Ile
    290                 295                 300

Ser Val Ile Cys Glu Ile Trp Phe Ala Met Ser Trp Ile Leu Asp Gln
305                 310                 315                 320

Phe Pro Lys Trp Phe Pro Ile Glu Arg Glu Thr Tyr Leu Asp Arg Leu
                325                 330                 335

Ser Leu Arg Phe Asp Lys Glu Gly Gln Pro Ser Gln Leu Ala Pro Ile
```

-continued

```
                340             345             350
Asp Phe Phe Val Ser Thr Val Asp Pro Leu Lys Glu Pro Pro Leu Val
            355                 360                 365
Thr Thr Asn Thr Val Leu Ser Ile Leu Ser Val Asp Tyr Pro Val Asp
370                 375                 380
Lys Val Ser Cys Tyr Val Ser Asp Asp Gly Ala Ala Met Leu Thr Phe
385                 390                 395                 400
Glu Ala Leu Ser Glu Thr Ser Glu Phe Ala Lys Lys Trp Val Pro Phe
                405                 410                 415
Cys Lys Arg Tyr Asn Ile Glu Pro Arg Ala Pro Glu Trp Tyr Phe Gln
            420                 425                 430
Gln Lys Ile Asp Tyr Leu Lys Asp Lys Val Ala Ala Asn Phe Val Arg
            435                 440                 445
Glu Arg Arg Ala Met Lys Arg Glu Tyr Glu Glu Phe Lys Val Arg Ile
            450                 455                 460
Asn Ala Leu Val Ala Lys Ala Gln Lys Val Pro Glu Glu Gly Trp Thr
465                 470                 475                 480
Met Gln Asp Gly Thr Pro Trp Pro Gly Asn Asn Val Arg Asp His Pro
                485                 490                 495
Gly Met Ile Gln Val Phe Leu Gly Gln Ser Gly Gly Leu Asp Cys Glu
                500                 505                 510
Gly Asn Glu Leu Pro Arg Leu Val Tyr Val Ser Arg Glu Lys Arg Pro
            515                 520                 525
Gly Tyr Asn His His Lys Lys Ala Gly Ala Met Asn Ala Leu Val Arg
            530                 535                 540
Val Ser Ala Val Leu Thr Asn Ala Pro Tyr Leu Leu Asn Leu Asp Cys
545                 550                 555                 560
Asp His Tyr Ile Asn Asn Ser Lys Ala Ile Lys Glu Ala Met Cys Phe
                565                 570                 575
Met Met Asp Pro Leu Leu Gly Lys Lys Val Cys Tyr Val Gln Phe Pro
                580                 585                 590
Gln Arg Phe Asp Gly Ile Asp Arg His Asp Arg Tyr Ala Asn Arg Asn
            595                 600                 605
Val Val Phe Phe Asp Ile Asn Met Lys Gly Leu Asp Gly Ile Gln Gly
            610                 615                 620
Pro Ile Tyr Val Gly Thr Gly Cys Val Phe Arg Arg Gln Ala Leu Tyr
625                 630                 635                 640
Gly Tyr Asp Ala Pro Lys Thr Lys Lys Pro Pro Ser Arg Thr Cys Asn
                645                 650                 655
Cys Trp Pro Lys Trp Cys Phe Cys Cys Cys Phe Gly Asn Arg Lys
                660                 665                 670
Gln Lys Lys Thr Thr Lys Pro Lys Thr Glu Lys Lys Lys Leu Leu Phe
            675                 680                 685
Phe Lys Lys Glu Glu Asn Gln Ser Pro Ala Tyr Ala Leu Gly Glu Ile
            690                 695                 700
Asp Glu Ala Ala Pro Gly Ala Glu Asn Glu Lys Ala Gly Ile Val Asn
705                 710                 715                 720
Gln Gln Lys Leu Glu Lys Lys Phe Gly Gln Ser Ser Val Phe Val Thr
                725                 730                 735
Ser Thr Leu Leu Glu Asn Gly Gly Thr Leu Lys Ser Ala Ser Pro Ala
                740                 745                 750
Ser Leu Leu Lys Glu Ala Ile His Val Ile Ser Cys Gly Tyr Glu Asp
            755                 760                 765
```

Lys Thr Asp Trp Gly Lys Glu Ile Gly Trp Ile Tyr Gly Ser Val Thr
770                 775                 780

Glu Asp Ile Leu Thr Gly Phe Lys Met His Cys His Gly Trp Arg Ser
785                 790                 795                 800

Ile Tyr Cys Ile Pro Lys Arg Val Ala Phe Lys Gly Ser Ala Pro Leu
                805                 810                 815

Asn Leu Ser Asp Arg Leu His Gln Val Leu Arg Trp Ala Leu Gly Ser
                820                 825                 830

Ile Glu Ile Phe Phe Ser Asn His Cys Pro Leu Trp Tyr Gly Tyr Gly
            835                 840                 845

Gly Gly Leu Lys Phe Leu Glu Arg Phe Ser Tyr Ile Asn Ser Ile Val
        850                 855                 860

Tyr Pro Trp Thr Ser Ile Pro Leu Leu Ala Tyr Cys Thr Leu Pro Ala
865                 870                 875                 880

Ile Cys Leu Leu Thr Gly Lys Phe Ile Thr Pro Glu Leu Asn Asn Val
                885                 890                 895

Ala Ser Leu Trp Phe Met Ser Leu Phe Ile Cys Ile Phe Ala Thr Ser
                900                 905                 910

Ile Leu Glu Met Arg Trp Ser Gly Val Gly Ile Asp Asp Trp Trp Arg
            915                 920                 925

Asn Glu Gln Phe Trp Val Ile Gly Gly Val Ser His Leu Phe Ala
        930                 935                 940

Val Phe Gln Gly Leu Leu Lys Val Ile Ala Gly Val Asp Thr Ser Phe
945                 950                 955                 960

Thr Val Thr Ser Lys Gly Gly Asp Asp Glu Glu Phe Ser Glu Leu Tyr
                965                 970                 975

Thr Phe Lys Trp Thr Thr Leu Leu Ile Pro Pro Thr Thr Leu Leu Leu
            980                 985                 990

Leu Asn Phe Ile Gly Val Val Ala Gly Val Ser Asn Ala Ile Asn Asn
        995                 1000                1005

Gly Tyr Glu Ser Trp Gly Pro Leu Phe Gly Lys Leu Phe Phe Ala
    1010                1015                1020

Phe Trp Val Ile Val His Leu Tyr Pro Phe Leu Lys Gly Leu Val
    1025                1030                1035

Gly Arg Gln Asn Arg Thr Pro Thr Ile Val Ile Val Trp Ser Ile
    1040                1045                1050

Leu Leu Ala Ser Ile Phe Ser Leu Leu Trp Val Arg Ile Asp Pro
    1055                1060                1065

Phe Leu Ala Lys Asp Asp Gly Pro Leu Leu Glu Glu Cys Gly Leu
    1070                1075                1080

Asp Cys Asn
    1085

<210> SEQ ID NO 33
<211> LENGTH: 3813
<212> TYPE: DNA
<213> ORGANISM: Zea mays

<400> SEQUENCE: 33
ccacagctca tataccaaga gccggagcag cttagcgcag cccagagcgg cgccgcgcca      60
agcacaaccc ccacccgcca cagccgcgtg cgcatgtgag cggtcgccgc ggccgggaga     120
ccagaggagg ggaggactac gtgcatttcg ctgtgccgcc gccgcggggt tcgtgcgcga     180
gcgagatccg gcggggcggg gcggggggcc tgagatggag gctagcgcgg ggctggtggc     240

-continued

```
cggctcgcat aaccggaacg agctggtggt gatccgccgc gaccgcgagt cgggagccgc    300
gggcggcggc gcggcgcgcc gggcggaggc gccgtgccag atatgcggcg acgaggtcgg    360
ggtgggcttc gacggggagc ccttcgtggc gtgcaacgag tgcgccttcc ccgtctgccg    420
cgcctgctac gagtacgagc gccgcgaggg ctcgcaagcg tgcccgcagt gcaggacccg    480
ctacaagcgc ctcaagggct gcccgcgggt ggccggcgac gaggaggagg acggcgtcga    540
cgacctggag ggcgagttcg gcctgcagga cggcgccgcc cacgaggacg acccgcagta    600
cgtcgccgag tccatgctca gggcgcagat gagctacggc cgcggcggcg acgcgcaccc    660
cggcttcagc cccgtcccca acgtgccgct cctcaccaac ggccagatgg ttgatgacat    720
cccgccggag cagcacgcgc tcgtgccgtc ctacatgagc ggcggcggcg cgggggcaa     780
gaggatccac ccgctcccct tcgcagatcc caaccttcca gtgcaaccga gatccatgga    840
cccgtccaag gatctggccg cctacggata tggcagcgtg gcctggaagg agagaatgga    900
gggctggaag cagaagcagg agcgcctgca gcatgtcagg agcgagggtg cggtgattg     960
ggatggcgac gatgcagatc tgccactaat ggatgaagct aggcagccat tgtccagaaa   1020
agtccctata tcatcaagcc gaattaatcc ctacaggatg attatcgtta tccggttggt   1080
ggttttgggt ttcttcttcc actaccgagt gatgcatccg gcgaaagatg catttgcatt   1140
gtggctcata tctgtaatct gtgaaatctg gtttgcgatg tcctggattc ttgatcagtt   1200
cccaaagtgg cttccaatcg agagagagac ttacctggac cgtttgtcac taaggtttga   1260
caaggaaggt caaccctctc agcttgctcc aatcgacttc tttgtcagta cggttgatcc   1320
cacaaaggaa cctcccttgg tcacagcgaa cactgtcctt tccatccttt ctgtggatta   1380
tccggttgag aaggtctcct gctatgtttc tgatgatggt gctgcaatgc ttacgtttga   1440
agcattgtct gaaacatctg aatttgcaaa gaaatgggtt cctttcagca aaaagtttaa   1500
tatcgagcct cgtgctcctg agtggtactt ccaacagaag atagactacc tgaaagacaa   1560
ggttgctgct tcatttgtta gggagaggag ggcgatgaag agagaatacg aggaattcaa   1620
ggtaaggatc aatgccttgg ttgcaaaagc ccaaaaggtt cctgaggaag atggacaat    1680
gcaagatgga agcccctggc ctggaaacaa cgtacgcgat catcctggaa tgattcaggt   1740
attccttggc caaagtggcg gtcgtgatgt ggaaggaaat gagttgcctc gcctggttta   1800
tgtctcgaga gaaaagaggc caggttataa ccatcacaag aaggctggtg ccatgaatgc   1860
actggtccgt gtctctgctg tcttatcaaa tgctgcatac ctattgaact tggactgtga   1920
tcactacatc aacaatagca aggccataaa agaggctatg tgtttcatga tggatccttt   1980
ggtgggaag aaagtgtgct atgtacagtt ccctcagagg tttgatggta ttgacaaaaa    2040
tgatcgatac gctaacagga acgttgtctt ttttgacatc aacatgaaag gtttggacgg   2100
tattcaagga cccatttatg tgggtactgg atgtgttttc agacggcagg cactgtatgg   2160
ttatgatgct cctaaaacga agaagccacc atcaagaact tgcaactgct ggcccaagtg   2220
gtgcctctct tgctgctgca gcaggaacaa gaataaaaag aagactacaa aaccaaagac   2280
ggagaagaag aaaagattat tttttcaagaa agcagaaaac ccatctcctg catatgcttt   2340
gggtgaaatt gatgaaggtg ctccaggtgc tgatatcgag aaggccggaa tcgtaaatca   2400
acagaaacta gagaagaaat ttgggcagtc ttctgttttt gtcgcatcaa cacttcttga   2460
gaacggaggg accctgaaga gcgcaagtcc agcttctctt ctgaaggaag ctatacatgt   2520
tatcagctgc ggctacgaag acaagaccga ctggggaaaa gagattggct ggatttacgg   2580
```

-continued

```
atcgatcaca gaggatatct tgactggatt taagatgcac tgccatggct ggcggtctat    2640
ttactgcatc ccgaagcggc ctgcattcaa aggttctgcg cctctgaacc tttccgaccg    2700
tcttcaccag gtccttcgct gggcccttgg gtccgtcgaa attttcttca gcaagcactg    2760
cccactttgg tacggatacg gcggcgggct aaaattcctg gaaaggtttt cttatatcaa    2820
ctccatcgtt tatccctgga cgtccattcc tctcctggct tactgtacct tgcctgccat    2880
ctgcctgctc acggggaagt ttatcacacc agagcttacc aatgtcgcca gtatctggtt    2940
catggcactt ttcatctgca tctccgtgac cggcatcctg gaaatgaggt ggagtggcgt    3000
ggccatcgac gactggtgga ggaacgagca gttctgggtc atcggaggcg tttcggcgca    3060
tctgttcgcg gtgttccagg cctgctgaa ggtgttcgcc ggcatcgaca cgagcttcac    3120
cgtgacgtcg aaggccgggg acgacgagga gttctcggag ctgtacacgt tcaagtggac    3180
caccctgctg ataccccga ccacgctcct cctgctgaac ttcatcgggg tggtggccgg    3240
gatctcgaac gcgatcaaca cgggtacga gtcgtgggc cccctgttcg ggaagctctt    3300
cttcgccttc tgggtgatcg tccacctgta cccgttcctc aagggtctgg tggggaggca    3360
gaacaggacg ccgacgatcg tcatcgtctg gtccatcctg ctggcctcga tcttctcgct    3420
cctgtgggtc cgcgtcgacc cgttcctcgc caagagcaac ggcccgctcc tggaggagtg    3480
tggcctggac tgcaactgaa gtgggggccc cctgtcactc gaagttctgt cacgggcgaa    3540
ttacgcctga ttttttgttg ttgttgttgt tggaattctt tgctgtagat agaaaccaca    3600
tgtccacggc atctctgctg tgtccattgg agcaggagag aggtgcctgc tgctgtttgt    3660
tgagtaaatt aaaagtttta aagttataca gtgatgcaca ttccagtgcc cagtgtattc    3720 ccttttaca gtctgtatat tagcgacaaa ggacatattg gttaggagtt tgattctttt    3780
gtaaaaaaaa aaaaaaaaaa aaaaaaaaaa aaa    3813
```

<210> SEQ ID NO 34
<211> LENGTH: 1094
<212> TYPE: PRT
<213> ORGANISM: Zea mays

<400> SEQUENCE: 34

```
Met Glu Ala Ser Ala Gly Leu Val Ala Gly Ser His Asn Arg Asn Glu
1               5                   10                  15

Leu Val Val Ile Arg Arg Asp Arg Glu Ser Gly Ala Ala Gly Gly Gly
            20                  25                  30

Ala Ala Arg Arg Ala Glu Ala Pro Cys Gln Ile Cys Gly Asp Glu Val
        35                  40                  45

Gly Val Gly Phe Asp Gly Glu Pro Phe Val Ala Cys Asn Glu Cys Ala
    50                  55                  60

Phe Pro Val Cys Arg Ala Cys Tyr Glu Tyr Glu Arg Arg Glu Gly Ser
65                  70                  75                  80

Gln Ala Cys Pro Gln Cys Arg Thr Arg Tyr Lys Arg Leu Lys Gly Cys
                85                  90                  95

Pro Arg Val Ala Gly Asp Glu Glu Asp Gly Val Asp Asp Leu Glu
            100                 105                 110

Gly Glu Phe Gly Leu Gln Asp Gly Ala Ala His Glu Asp Asp Pro Gln
        115                 120                 125

Tyr Val Ala Glu Ser Met Leu Arg Ala Gln Met Ser Tyr Gly Arg Gly
    130                 135                 140

Gly Asp Ala His Pro Gly Phe Ser Pro Val Pro Asn Val Pro Leu Leu
145                 150                 155                 160
```

-continued

```
Thr Asn Gly Gln Met Val Asp Asp Ile Pro Pro Glu Gln His Ala Leu
                165                 170                 175
Val Pro Ser Tyr Met Ser Gly Gly Gly Gly Lys Arg Ile His
        180                 185                 190
Pro Leu Pro Phe Ala Asp Pro Asn Leu Pro Val Gln Pro Arg Ser Met
        195                 200                 205
Asp Pro Ser Lys Asp Leu Ala Ala Tyr Gly Tyr Gly Ser Val Ala Trp
    210                 215                 220
Lys Glu Arg Met Glu Gly Trp Lys Gln Lys Gln Glu Arg Leu Gln His
225                 230                 235                 240
Val Arg Ser Glu Gly Gly Asp Trp Asp Gly Asp Ala Asp Leu
                245                 250                 255
Pro Leu Met Asp Glu Ala Arg Gln Pro Leu Ser Arg Lys Val Pro Ile
                260                 265                 270
Ser Ser Ser Arg Ile Asn Pro Tyr Arg Met Ile Ile Val Ile Arg Leu
            275                 280                 285
Val Val Leu Gly Phe Phe Phe His Tyr Arg Val Met His Pro Ala Lys
        290                 295                 300
Asp Ala Phe Ala Leu Trp Leu Ile Ser Val Ile Cys Glu Ile Trp Phe
305                 310                 315                 320
Ala Met Ser Trp Ile Leu Asp Gln Phe Pro Lys Trp Leu Pro Ile Glu
                325                 330                 335
Arg Glu Thr Tyr Leu Asp Arg Leu Ser Leu Arg Phe Asp Lys Glu Gly
                340                 345                 350
Gln Pro Ser Gln Leu Ala Pro Ile Asp Phe Phe Val Ser Thr Val Asp
            355                 360                 365
Pro Thr Lys Glu Pro Pro Leu Val Thr Ala Asn Thr Val Leu Ser Ile
        370                 375                 380
Leu Ser Val Asp Tyr Pro Val Glu Lys Val Ser Cys Tyr Val Ser Asp
385                 390                 395                 400
Asp Gly Ala Ala Met Leu Thr Phe Glu Ala Leu Ser Glu Thr Ser Glu
                405                 410                 415
Phe Ala Lys Lys Trp Val Pro Phe Ser Lys Lys Phe Asn Ile Glu Pro
            420                 425                 430
Arg Ala Pro Glu Trp Tyr Phe Gln Gln Lys Ile Asp Tyr Leu Lys Asp
        435                 440                 445
Lys Val Ala Ala Ser Phe Val Arg Glu Arg Ala Met Lys Arg Glu
450                 455                 460
Tyr Glu Glu Phe Lys Val Arg Ile Asn Ala Leu Val Ala Lys Ala Gln
465                 470                 475                 480
Lys Val Pro Glu Glu Gly Trp Thr Met Gln Asp Gly Ser Pro Trp Pro
            485                 490                 495
Gly Asn Asn Val Arg Asp His Pro Gly Met Ile Gln Val Phe Leu Gly
                500                 505                 510
Gln Ser Gly Gly Arg Asp Val Glu Gly Asn Glu Leu Pro Arg Leu Val
            515                 520                 525
Tyr Val Ser Arg Glu Lys Arg Pro Gly Tyr Asn His His Lys Lys Ala
        530                 535                 540
Gly Ala Met Asn Ala Leu Val Arg Val Ser Ala Val Leu Ser Asn Ala
545                 550                 555                 560
Ala Tyr Leu Leu Asn Leu Asp Cys Asp His Tyr Ile Asn Asn Ser Lys
                565                 570                 575
```

```
Ala Ile Lys Glu Ala Met Cys Phe Met Met Asp Pro Leu Val Gly Lys
            580                 585                 590

Lys Val Cys Tyr Val Gln Phe Pro Gln Arg Phe Asp Gly Ile Asp Lys
        595                 600                 605

Asn Asp Arg Tyr Ala Asn Arg Asn Val Val Phe Phe Asp Ile Asn Met
    610                 615                 620

Lys Gly Leu Asp Gly Ile Gln Gly Pro Ile Tyr Val Gly Thr Gly Cys
625                 630                 635                 640

Val Phe Arg Arg Gln Ala Leu Tyr Gly Tyr Asp Ala Pro Lys Thr Lys
                645                 650                 655

Lys Pro Pro Ser Arg Thr Cys Asn Cys Trp Pro Lys Trp Cys Leu Ser
            660                 665                 670

Cys Cys Cys Ser Arg Asn Lys Asn Lys Lys Thr Thr Lys Pro Lys
        675                 680                 685

Thr Glu Lys Lys Lys Arg Leu Phe Phe Lys Lys Ala Glu Asn Pro Ser
    690                 695                 700

Pro Ala Tyr Ala Leu Gly Glu Ile Asp Glu Gly Ala Pro Gly Ala Asp
705                 710                 715                 720

Ile Glu Lys Ala Gly Ile Val Asn Gln Gln Lys Leu Glu Lys Lys Phe
                725                 730                 735

Gly Gln Ser Ser Val Phe Val Ala Ser Thr Leu Leu Glu Asn Gly Gly
            740                 745                 750

Thr Leu Lys Ser Ala Ser Pro Ala Ser Leu Leu Lys Glu Ala Ile His
        755                 760                 765

Val Ile Ser Cys Gly Tyr Glu Asp Lys Thr Asp Trp Gly Lys Glu Ile
    770                 775                 780

Gly Trp Ile Tyr Gly Ser Ile Thr Glu Asp Ile Leu Thr Gly Phe Lys
785                 790                 795                 800

Met His Cys His Gly Trp Arg Ser Ile Tyr Cys Ile Pro Lys Arg Pro
                805                 810                 815

Ala Phe Lys Gly Ser Ala Pro Leu Asn Leu Ser Asp Arg Leu His Gln
            820                 825                 830

Val Leu Arg Trp Ala Leu Gly Ser Val Glu Ile Phe Phe Ser Lys His
        835                 840                 845

Cys Pro Leu Trp Tyr Gly Tyr Gly Gly Gly Leu Lys Phe Leu Glu Arg
    850                 855                 860

Phe Ser Tyr Ile Asn Ser Ile Val Tyr Pro Trp Thr Ser Ile Pro Leu
865                 870                 875                 880

Leu Ala Tyr Cys Thr Leu Pro Ala Ile Cys Leu Leu Thr Gly Lys Phe
                885                 890                 895

Ile Thr Pro Glu Leu Thr Asn Val Ala Ser Ile Trp Phe Met Ala Leu
            900                 905                 910

Phe Ile Cys Ile Ser Val Thr Gly Ile Leu Glu Met Arg Trp Ser Gly
        915                 920                 925

Val Ala Ile Asp Asp Trp Trp Arg Asn Glu Gln Phe Trp Val Ile Gly
    930                 935                 940

Gly Val Ser Ala His Leu Phe Ala Val Phe Gln Gly Leu Leu Lys Val
945                 950                 955                 960

Phe Ala Gly Ile Asp Thr Ser Phe Thr Val Thr Ser Lys Ala Gly Asp
                965                 970                 975

Asp Glu Glu Phe Ser Glu Leu Tyr Thr Phe Lys Trp Thr Thr Leu Leu
            980                 985                 990

Ile Pro Pro Thr Thr Leu Leu Leu  Leu Asn Phe Ile Gly  Val Val Ala
```

-continued

```
            995                1000               1005
Gly Ile Ser Asn Ala Ile Asn  Asn Gly Tyr Glu Ser  Trp Gly Pro
    1010                1015                1020

Leu Phe Gly Lys Leu Phe Phe  Ala Phe Trp Val Ile  Val His Leu
    1025                1030                1035

Tyr Pro Phe Leu Lys Gly Leu  Val Gly Arg Gln Asn  Arg Thr Pro
    1040                1045                1050

Thr Ile Val Ile Val Trp Ser  Ile Leu Leu Ala Ser  Ile Phe Ser
    1055                1060                1065

Leu Leu Trp Val Arg Val Asp  Pro Phe Leu Ala Lys  Ser Asn Gly
    1070                1075                1080

Pro Leu Leu Glu Glu Cys Gly  Leu Asp Cys Asn
    1085                1090
```

<210> SEQ ID NO 35
<211> LENGTH: 3799
<212> TYPE: DNA
<213> ORGANISM: Zea mays
<220> FEATURE:
<221> NAME/KEY: misc_feature
<222> LOCATION: (3757)..(3757)
<223> OTHER INFORMATION: n is a, c, g, or t
<220> FEATURE:
<221> NAME/KEY: misc_feature
<222> LOCATION: (3775)..(3775)
<223> OTHER INFORMATION: n is a, c, g, or t
<220> FEATURE:
<221> NAME/KEY: misc_feature
<222> LOCATION: (3777)..(3777)
<223> OTHER INFORMATION: n is a, c, g, or t
<220> FEATURE:
<221> NAME/KEY: misc_feature
<222> LOCATION: (3782)..(3782)
<223> OTHER INFORMATION: n is a, c, g, or t

<400> SEQUENCE: 35

```
caactcacgt tgccgcggct tcctccatcg gtgcggtgcc ctgtcctttt ctctcctcca      60
cctccctagt ccctcctccc cccgcatac atagctacta ctagtagcac cacgctcgca     120
gcgggagatg cggtgctgat ccgtgcccct gctcggatct cgggagtggt gccgacttgt     180
gtcgcttcgg ctctgcctag gccagctcct tgtcggttct gggcgagctc gcctgccatg     240
gagggcgacg cggacggcgt gaagtcgggg aggcgcgggg gagggcaggt gtgccagatc     300
tgcggcgatg gcgtgggcac tacgcggag ggagacgtct tcaccgcctg cgacgtctgc     360
gggttcccgg tgtgccgccc ctgctacgag tacgagcgca aggacggcac acaagcgtgc     420
ccccagtgca aaacaagta caagcgccac aagggagtc cagcgatccg aggggaggaa     480
ggagacgata ctgatgccga tgatgctagc gacttcaact accctgcatc tggcaatgac     540
gaccagaagc agaagattgc tgacaggatg cgcagctggc gcatgaatgc tggggggcagc     600
gggggatgttg gccgcccaa gtatgacagt ggtgagatcg gcttaccaa gtacgacagt     660
ggtgagatcc ctcggggata catcccgtca gtcactaaca gccagatttc gggagaaatc     720
cctggtgctt ccctgacca tcatatgatg tctcctactg gaacattgg caggcgcgcc     780
ccattccct atatgaatca ttcatcaaat ccgtcgaggg aattctctgg tagcgttggg     840
aatgttgcct ggaaagagag ggttgatggc tggaaaatga agcaggacaa gggaacaatt     900
cccatgacga atggcacaag cattgctccc tctgagggcc gggtgttgg tgatattgat     960
gcatcaactg attacaacat ggaagatgcc ttattaaacg atgaaactcg ccagcctcta    1020
tctaggaaag ttccacttcc ttcctccagg ataaatccat acaggatggt cattgtgcta    1080
```

```
cgattgattg ttctaagcat cttcttgcac taccggatca caaatcctgt gcgtaatgca   1140
tacccactgt ggcttctatc tgttatatgt gagatctggt ttgctctttc ctggatattg   1200
gatcagtttc caaagtggtt tccaatcaac cgcgagactt accttgatag actcgcatta   1260
aggtatgacc gggaaggtga gccatctcag ttggctgctg ttgacatttt tgtcagtact   1320
gtcgacccaa tgaaggagcc tcctcttgtc actgccaata ccgtgctatc cattctcgct   1380
gtggactatc ctgtggataa ggtctcttgc tatgtatctg atgatggagc tgctatgctg   1440
acatttgatg cactagctga gacttcagag tttgctagaa atgggtgcc atttgttaag    1500 aagtacaaca ttgaacctag agctcctgaa tggtacttct cccagaaaat tgattacttg   1560
aaggacaaag tgcacccttc atttgttaaa gaccgccggg ccatgaagag agaatatgaa   1620
gaattcaaaa ttagggtaaa tggccttgtt gctaaggcac aaaaagtccc tgaggaagga   1680
tggatcatgc aagatggcac accatggcca ggaaacaata ccaggaccca tcctggaatg   1740
attcaggttt tccttggtca cagtggtggt cttgatactg agggtaatga gctacccgt    1800 ttggtctatg tttctcgtga aaaacgtcct ggattccagc atcacaagaa agctggtgcc   1860
atgaatgctc ttgtccgcgt ctcagctgtg cttaccaatg acaatacat gttgaatctt    1920 gattgtgatc actacatcaa caacagtaag gctctcaggg aagctatgtg cttccttatg   1980
gatcctaacc taggaaggag tgtctgctat gttcagtttc cccagaggtt cgatggtatt   2040
gataggaatg atcgatatgc caacaggaac accgtgtttt tcgatattaa cttgagaggt   2100
cttgatggca tccaaggacc agtttatgtg ggcactggct gtgttttcaa cagaacagct   2160
ctatatggtt atgagccccc aattaagcaa aagaagggtg gtttcttgtc atcactatgt   2220
ggtggcagga agaagggaag caaatcaaag aagggctcag acaagaaaaa gtcacagaag   2280
catgtggaca gttctgtgcc agtattcaat cttgaagata tagaggaggg agttgaaggc   2340
gctggatttg atgatgagaa atcacttctt atgtctcaaa tgagcttgga agagagattt   2400
ggccaatctg cagcttttgt tgcgtccact ctgatggaat atggtggtgt tcctcagtct   2460
gcgactccag aatctcttct gaaagaagct atccatgtca aagttgtgg ctacgaggac    2520 aagattgaat ggggaactga gattgggtgg atctatggtt ctgtgacgga agatattctc   2580
actgggttca agatgcacgc acgaggctgg cggtcgatct actgcatgcc taagcggccg   2640
gccttcaagg gatcggctcc catcaatctc tcagaccgtc tgaaccaggt gctccggtgg   2700
gctctcggtt cagtggaaat ccttttcagc cggcattgcc ccctatggta cgggtacgga   2760
ggacgcctga agttcttgga gagattcgcc tacatcaaca ccaccatcta cccgctcacg   2820
tccctcccgc tcctcattta ctgtatcctg cctgccatct gcctgctcac ggggaagttc   2880
atcatcccag agatcagcaa cttcgctagt atctggttca tctctctctt catctcgatc   2940
ttcgccacgg gtatcctgga gatgaggtgg agcggcgtgg gcatcgacga gtggtggagg   3000
aacgagcagt tctgggtcat cggaggcatc tccgcccacc tcttcgccgt cttccagggc   3060
ctcctcaagg tgcttgccgg catcgacacc aacttcaccg tcacctccaa ggcctcggat   3120
gaagacggcg acttcgcgga gctgtacatg ttcaagtgga cgacacttct gatcccgccc   3180
accaccatcc tgatcatcaa cctggtcggc gttgttgccg gcatctccta cgccatcaac   3240
agcgggtacc agtcgtgggg tccgctcttc ggcaagctct tcttcgcctt ctgggtgatc   3300
gttcacctgt acccgttcct caagggtctc atgggtcggc agaaccgcac cccgaccatc   3360
gtggttgtct gggcgatcct gctggcgtcg atcttctcct tgctgtgggt tcgcatcgat   3420
```

```
ccgttcacca accgcgtcac tggcccggat actcgaacgt gtggcatcaa ctgctaggga   3480
ggtggaaggt ttgtagaaac agagagatac cacgaatgtg ccgctgccac aaattgtctg   3540
ttagtaagtt atataggcag gtggcgttat ttacagctac gtacacacaa ggggatactc   3600
cgtttatcac tggtgtgcat tcttttgttg atataagtta ctatatatac gtattgcttc   3660
tactttgtgg agagtggctg acaggaccag ttttgtaatg ttatgaacag caaagaaata   3720
agttagtttc caaaaaaaaa aaaaaaaaaa aaaaanaaa aaaaaaaaaa aaaananaaa   3780
anaaaaaaaa aaaaacccc                                                3799
```

<210> SEQ ID NO 36
<211> LENGTH: 1079
<212> TYPE: PRT
<213> ORGANISM: Zea mays

<400> SEQUENCE: 36

```
Met Glu Gly Asp Ala Asp Gly Val Lys Ser Gly Arg Arg Gly Gly
1               5                   10                  15

Gln Val Cys Gln Ile Cys Gly Asp Gly Val Gly Thr Thr Ala Glu Gly
                20                  25                  30

Asp Val Phe Thr Ala Cys Asp Val Cys Gly Phe Pro Val Cys Arg Pro
            35                  40                  45

Cys Tyr Glu Tyr Glu Arg Lys Asp Gly Thr Gln Ala Cys Pro Gln Cys
        50                  55                  60

Lys Asn Lys Tyr Lys Arg His Lys Gly Ser Pro Ala Ile Arg Gly Glu
65                  70                  75                  80

Glu Gly Asp Asp Thr Asp Ala Asp Asp Ala Ser Asp Phe Asn Tyr Pro
                85                  90                  95

Ala Ser Gly Asn Asp Asp Gln Lys Gln Lys Ile Ala Asp Arg Met Arg
            100                 105                 110

Ser Trp Arg Met Asn Ala Gly Gly Ser Gly Asp Val Gly Arg Pro Lys
        115                 120                 125

Tyr Asp Ser Gly Glu Ile Gly Leu Thr Lys Tyr Asp Ser Gly Glu Ile
    130                 135                 140

Pro Arg Gly Tyr Ile Pro Ser Val Thr Asn Ser Gln Ile Ser Gly Glu
145                 150                 155                 160

Ile Pro Gly Ala Ser Pro Asp His His Met Met Ser Pro Thr Gly Asn
                165                 170                 175

Ile Gly Arg Arg Ala Pro Phe Pro Tyr Met Asn His Ser Ser Asn Pro
            180                 185                 190

Ser Arg Glu Phe Ser Gly Ser Val Gly Asn Val Ala Trp Lys Glu Arg
        195                 200                 205

Val Asp Gly Trp Lys Met Lys Gln Asp Lys Gly Thr Ile Pro Met Thr
    210                 215                 220

Asn Gly Thr Ser Ile Ala Pro Ser Glu Gly Arg Gly Val Gly Asp Ile
225                 230                 235                 240

Asp Ala Ser Thr Asp Tyr Asn Met Glu Asp Ala Leu Leu Asn Asp Glu
                245                 250                 255

Thr Arg Gln Pro Leu Ser Arg Lys Val Pro Leu Pro Ser Ser Arg Ile
            260                 265                 270

Asn Pro Tyr Arg Met Val Ile Val Leu Arg Leu Ile Val Leu Ser Ile
        275                 280                 285

Phe Leu His Tyr Arg Ile Thr Asn Pro Val Arg Asn Ala Tyr Pro Leu
    290                 295                 300
```

-continued

```
Trp Leu Leu Ser Val Ile Cys Glu Ile Trp Phe Ala Leu Ser Trp Ile
305                 310                 315                 320

Leu Asp Gln Phe Pro Lys Trp Phe Pro Ile Asn Arg Glu Thr Tyr Leu
            325                 330                 335

Asp Arg Leu Ala Leu Arg Tyr Asp Arg Glu Gly Glu Pro Ser Gln Leu
            340                 345                 350

Ala Ala Val Asp Ile Phe Val Ser Thr Val Asp Pro Met Lys Glu Pro
            355                 360                 365

Pro Leu Val Thr Ala Asn Thr Val Leu Ser Ile Leu Ala Val Asp Tyr
            370                 375                 380

Pro Val Asp Lys Val Ser Cys Tyr Val Ser Asp Asp Gly Ala Ala Met
385                 390                 395                 400

Leu Thr Phe Asp Ala Leu Ala Glu Thr Ser Glu Phe Ala Arg Lys Trp
            405                 410                 415

Val Pro Phe Val Lys Lys Tyr Asn Ile Glu Pro Arg Ala Pro Glu Trp
            420                 425                 430

Tyr Phe Ser Gln Lys Ile Asp Tyr Leu Lys Asp Lys Val His Pro Ser
            435                 440                 445

Phe Val Lys Asp Arg Arg Ala Met Lys Arg Glu Tyr Glu Glu Phe Lys
            450                 455                 460

Ile Arg Val Asn Gly Leu Val Ala Lys Ala Gln Lys Val Pro Glu Glu
465                 470                 475                 480

Gly Trp Ile Met Gln Asp Gly Thr Pro Trp Pro Gly Asn Asn Thr Arg
            485                 490                 495

Asp His Pro Gly Met Ile Gln Val Phe Leu Gly His Ser Gly Gly Leu
            500                 505                 510

Asp Thr Glu Gly Asn Glu Leu Pro Arg Leu Val Tyr Val Ser Arg Glu
            515                 520                 525

Lys Arg Pro Gly Phe Gln His His Lys Lys Ala Gly Ala Met Asn Ala
            530                 535                 540

Leu Val Arg Val Ser Ala Val Leu Thr Asn Gly Gln Tyr Met Leu Asn
545                 550                 555                 560

Leu Asp Cys Asp His Tyr Ile Asn Asn Ser Lys Ala Leu Arg Glu Ala
            565                 570                 575

Met Cys Phe Leu Met Asp Pro Asn Leu Gly Arg Ser Val Cys Tyr Val
            580                 585                 590

Gln Phe Pro Gln Arg Phe Asp Gly Ile Asp Arg Asn Asp Arg Tyr Ala
            595                 600                 605

Asn Arg Asn Thr Val Phe Phe Asp Ile Asn Leu Arg Gly Leu Asp Gly
            610                 615                 620

Ile Gln Gly Pro Val Tyr Val Gly Thr Gly Cys Val Phe Asn Arg Thr
625                 630                 635                 640

Ala Leu Tyr Gly Tyr Glu Pro Pro Ile Lys Gln Lys Lys Gly Gly Phe
            645                 650                 655

Leu Ser Ser Leu Cys Gly Gly Arg Lys Lys Gly Ser Lys Ser Lys Lys
            660                 665                 670

Gly Ser Asp Lys Lys Ser Gln Lys His Val Asp Ser Ser Val Pro
            675                 680                 685

Val Phe Asn Leu Glu Asp Ile Glu Glu Gly Val Glu Gly Ala Gly Phe
            690                 695                 700

Asp Asp Glu Lys Ser Leu Leu Met Ser Gln Met Ser Leu Glu Lys Arg
705                 710                 715                 720

Phe Gly Gln Ser Ala Ala Phe Val Ala Ser Thr Leu Met Glu Tyr Gly
```

```
                    725                 730                 735
Gly Val Pro Gln Ser Ala Thr Pro Glu Ser Leu Leu Lys Glu Ala Ile
                740                 745                 750
His Val Ile Ser Cys Gly Tyr Glu Asp Lys Ile Glu Trp Gly Thr Glu
                755                 760                 765
Ile Gly Trp Ile Tyr Gly Ser Val Thr Glu Asp Ile Leu Thr Gly Phe
                770                 775                 780
Lys Met His Ala Arg Gly Trp Arg Ser Ile Tyr Cys Met Pro Lys Arg
785                 790                 795                 800
Pro Ala Phe Lys Gly Ser Ala Pro Ile Asn Leu Ser Asp Arg Leu Asn
                805                 810                 815
Gln Val Leu Arg Trp Ala Leu Gly Ser Val Glu Ile Leu Phe Ser Arg
                820                 825                 830
His Cys Pro Leu Trp Tyr Gly Tyr Gly Gly Arg Leu Lys Phe Leu Glu
                835                 840                 845
Arg Phe Ala Tyr Ile Asn Thr Thr Ile Tyr Pro Leu Thr Ser Leu Pro
                850                 855                 860
Leu Leu Ile Tyr Cys Ile Leu Pro Ala Ile Cys Leu Leu Thr Gly Lys
865                 870                 875                 880
Phe Ile Ile Pro Glu Ile Ser Asn Phe Ala Ser Ile Trp Phe Ile Ser
                885                 890                 895
Leu Phe Ile Ser Ile Phe Ala Thr Gly Ile Leu Glu Met Arg Trp Ser
                900                 905                 910
Gly Val Gly Ile Asp Glu Trp Trp Arg Asn Glu Gln Phe Trp Val Ile
                915                 920                 925
Gly Gly Ile Ser Ala His Leu Phe Ala Val Phe Gln Gly Leu Leu Lys
                930                 935                 940
Val Leu Ala Gly Ile Asp Thr Asn Phe Thr Val Thr Ser Lys Ala Ser
945                 950                 955                 960
Asp Glu Asp Gly Asp Phe Ala Glu Leu Tyr Met Phe Lys Trp Thr Thr
                965                 970                 975
Leu Leu Ile Pro Pro Thr Thr Ile Leu Ile Ile Asn Leu Val Gly Val
                980                 985                 990
Val Ala Gly Ile Ser Tyr Ala Ile Asn Ser Gly Tyr Gln Ser Trp Gly
                995                 1000                1005
Pro Leu Phe Gly Lys Leu Phe Phe Ala Phe Trp Val Ile Val His
                1010                1015                1020
Leu Tyr Pro Phe Leu Lys Gly Leu Met Gly Arg Gln Asn Arg Thr
                1025                1030                1035
Pro Thr Ile Val Val Val Trp Ala Ile Leu Leu Ala Ser Ile Phe
                1040                1045                1050
Ser Leu Leu Trp Val Arg Ile Asp Pro Phe Thr Asn Arg Val Thr
                1055                1060                1065
Gly Pro Asp Thr Arg Thr Cys Gly Ile Asn Cys
                1070                1075

<210> SEQ ID NO 37
<211> LENGTH: 3470
<212> TYPE: DNA
<213> ORGANISM: Zea mays

<400> SEQUENCE: 37
gcccccggtc gatcgctcgg caatcggcat ggacgccggc tcggtcaccg gtggcctcgc      60
cgcgggctcg cacatgcggg acgagctgca tgtcatgcgc gcccgcgagg agccgaacgc     120
```

```
caaggtccgg agcgccgacg tgaagacgtg ccgcgtgtgc gccgacgagg tcgggacgcg    180
ggaggacggg cagcccttcg tggcgtgcgc cgagtgcggc ttccccgtct gccggccctg    240
ctacgagtac gagcgcagcg agggcacgca gtgctgcccg cagtgcaaca cccgctacaa    300
gcgccagaaa gggtgcccga gggtggaagg ggacgaggag gagggcccgg agatggacga    360
cttcgaggac gagttccccg ccaagagccc caagaagcct cacgagcctg tcgcgttcga    420
cgtctactcg gagaacggcg agcacccggc gcagaaatgg cggacgggtg ccagacgct    480
gtcgtccttc accggaagcg tcgccggaa ggacctggag gcggagaggg agatggaggg    540
gagcatggag tggaaggacc ggatcgacaa gtggaagacc aagcaggaga agaggggcaa    600
gctcaaccac gacgacagcg acgacgacga cgacaagaac gaagacgagt acatgctgct    660
tgccgaggcc cgacagccgc tgtggcgcaa ggttccgatc ccgtcgagca tgatcaaccc    720
gtaccgcatc gtcatcgtgc tccgcctggt ggtgctctgc ttcttcctca agttccggat    780
cacgacgccc gccacggacg ccgtgcctct gtggctggcg tccgtcatct gcgagctctg    840
gttcgccttc tcctggatcc tggaccagct gccaaagtgg gcgccggtga cgcgggagac    900
gtacctggac cgcctggcgc tgcggtacga ccgtgagggc gaggcgtgcc ggctgtcccc    960
catcgacttc ttcgtcagca cggtggaccc gctcaaggag ccgcccatca tcaccgccaa   1020
caccgtgctg tccatcctcg ccgtcgacta ccccgtggac cgcgtcagct gctacgtctc   1080
cgacgacggc gcgtccatgc tgctcttcga cgcgctgtcc gagaccgccg agttcgcgcg   1140
ccgctgggtg cccttctgca agaagttcgc cgtggagccg cgcgccccgg agttctactt   1200
ctcgcagaag atcgactacc tcaaggacaa ggtgcagccg acgttcgtca aggagcgccg   1260
cgccatgaag agggagtacg aggagttcaa ggtgcgcatc aacgcgctgg tggccaaggc   1320
gcagaagaag cccgaggagg ggtgggtcat gcaggacggc acgccgtggc ccgggaacaa   1380
cacgcgcgac cacccgggta tgatccaggt ctacctcggc aaccagggcg cgctggacgt   1440
ggagggccac gagctgccgc gcctcgtcta cgtgtcccgt gagaagcgcc ccgggtacaa   1500
ccaccacaag aaggcgggcg ccatgaacgc gctggtgcgc gtctccgccg tgctcaccaa   1560
cgcgcccttc atcctcaacc tcgactgcga ccactacgtc aacaacagca aggccgtgcg   1620
cgaggccatg tgcttcctca tggacccgca gctggggaag aagctctgct acgtccagtt   1680
cccgcagcgc ttcgatggca tcgatcgcca cgaccgatac gccaaccgca acgtcgtctt   1740
cttcgacatc aacatgaagg ggctggacgg catccagggc ccggtgtacg tcggcacggg   1800
gtgcgtgttc aaccgccagg cgctgtacgg ctacgacccg ccgcggcccg agaagcggcc   1860
caagatgacg tgcgactgct ggccgtcgtg gtgctgctgc tgctgctgct cggcggcgg    1920
caagcgcggc aaggcgcgca aggacaagaa gggcgacggc ggcgaggagc cgcgccgggg   1980
cctgctcggc ttctacagga agcggagcaa gaaggacaag ctcggcggcg gtcggtggc    2040
cggcagcaag aagggcggcg ggctgtacaa gaagcaccag cgcgcgttcg agctggagga   2100
gatcgaggag gggctggagg ggtacgacga gctggagcgc tcctcgctca tgtcgcagaa   2160
gagcttcgag aagcggttcg ccagtcgcc cgtgttcatc gcctccacgc tcgtcgagga   2220
cggcggcctg ccgcagggcg ccgccgccga ccccgccgcg ctcatcaagg aggccatcca   2280
cgtcatcagc tgcggatacg aggagaagac cgagtggggc aaggagattg gtggatcta   2340
tgggtcggtg acagaggata tcctgacggg gttcaagatg cactgccggg ggtggaagtc   2400
cgtgtactgc acgccgacac ggccggcgtt caaggggtcg gcgcccatca acttgtctga   2460
```

-continued

```
tcgtctccac caggtgctgc gctgggcgct ggggtccgtg agatcttca tgagccgcca    2520 ctgcccgctc cggtacgcct acggcggccg gctcaagtgg ctggagcgct cgcctacac    2580 caacaccatc gtgtacccct tcacctccat cccgctcctc gcctactgca ccatccccgc    2640
cgtctgcctg ctcaccggca agttcatcat tcccacgctg aacaacctcg ccagcatctg    2700
gttcatcgcg ctcttcctgt ccatcatcgc gacgagcgtc ctggagctgc ggtggagcgg    2760
ggtgagcatc gaggactggt ggcgcaacga gcagttctgg gtcatcggcg cgtgtccgc    2820 gcatctcttc gccgtgttcc agggcttcct caaggttctg gcggcgtgg acaccagctt    2880 caccgtcacc tccaaggcgg ccggcgacga ggccgacgcc ttcggggacc tctacctctt    2940
caagtggacc accctgctgg tgcccccac acgctcatc atcatcaaca tggtgggcat     3000
cgtggccggc gtgtccgacg ccgtcaacaa cggctacggc tcctgggcc cgctcttcgg    3060 caagctcttc ttctccttct gggtcatcgt ccacctctac ccgttcctca aggggctcat    3120
ggggaggcag aaccggacgc ccaccatcgt cgtgctctgg tccatcctcc tcgcctccat    3180
cttctcgctc gtctgggtca ggatcgaccc gtttatcccg aaggccaagg ccccatcct    3240 caagccatgc ggagtcgagt gctgagctca cctagctacc ttcttgttgc atgtacggac    3300
gccgccgtgc gtttggacat acaggcactt ttgggccagg ctactcatgt tcgacttttt    3360 ttttaattt gtacaagatt tgtgatcgag tgactgagtg agacagagtg ttgggtgtaa    3420
gaactgtgat ggaattcact caaattaatg gacatttttt ttcttcaaaa              3470
```

```
<210> SEQ ID NO 38
<211> LENGTH: 1078
<212> TYPE: PRT
<213> ORGANISM: Zea mays

<400> SEQUENCE: 38
```

```
Met Asp Ala Gly Ser Val Thr Gly Gly Leu Ala Ala Gly Ser His Met
1               5                   10                  15

Arg Asp Glu Leu His Val Met Arg Ala Arg Glu Glu Pro Asn Ala Lys
            20                  25                  30

Val Arg Ser Ala Asp Val Lys Thr Cys Arg Val Cys Ala Asp Glu Val
        35                  40                  45

Gly Thr Arg Glu Asp Gly Gln Pro Phe Val Ala Cys Ala Glu Cys Gly
    50                  55                  60

Phe Pro Val Cys Arg Pro Cys Tyr Glu Tyr Glu Arg Ser Glu Gly Thr
65                  70                  75                  80

Gln Cys Cys Pro Gln Cys Asn Thr Arg Tyr Lys Arg Gln Lys Gly Cys
                85                  90                  95

Pro Arg Val Glu Gly Asp Glu Glu Gly Pro Glu Met Asp Asp Phe
            100                 105                 110

Glu Asp Glu Phe Pro Ala Lys Ser Pro Lys Lys Pro His Glu Pro Val
        115                 120                 125

Ala Phe Asp Val Tyr Ser Glu Asn Gly Glu His Pro Ala Gln Lys Trp
    130                 135                 140

Arg Thr Gly Gly Gln Thr Leu Ser Ser Phe Thr Gly Ser Val Ala Gly
145                 150                 155                 160

Lys Asp Leu Glu Ala Glu Arg Glu Met Glu Gly Ser Met Glu Trp Lys
                165                 170                 175

Asp Arg Ile Asp Lys Trp Lys Thr Lys Gln Glu Lys Arg Gly Lys Leu
            180                 185                 190

Asn His Asp Asp Ser Asp Asp Asp Asp Lys Asn Glu Asp Glu Tyr
```

-continued

```
            195                 200                 205
Met Leu Leu Ala Glu Ala Arg Gln Pro Leu Trp Arg Lys Val Pro Ile
    210                 215                 220

Pro Ser Ser Met Ile Asn Pro Tyr Arg Ile Val Ile Val Leu Arg Leu
225                 230                 235                 240

Val Val Leu Cys Phe Phe Leu Lys Phe Arg Ile Thr Thr Pro Ala Thr
                245                 250                 255

Asp Ala Val Pro Leu Trp Leu Ala Ser Val Ile Cys Glu Leu Trp Phe
                260                 265                 270

Ala Phe Ser Trp Ile Leu Asp Gln Leu Pro Lys Trp Ala Pro Val Thr
                275                 280                 285

Arg Glu Thr Tyr Leu Asp Arg Leu Ala Leu Arg Tyr Asp Arg Glu Gly
    290                 295                 300

Glu Ala Cys Arg Leu Ser Pro Ile Asp Phe Phe Val Ser Thr Val Asp
305                 310                 315                 320

Pro Leu Lys Glu Pro Pro Ile Ile Thr Ala Asn Thr Val Leu Ser Ile
                325                 330                 335

Leu Ala Val Asp Tyr Pro Val Asp Arg Val Ser Cys Tyr Val Ser Asp
                340                 345                 350

Asp Gly Ala Ser Met Leu Leu Phe Asp Ala Leu Ser Glu Thr Ala Glu
                355                 360                 365

Phe Ala Arg Arg Trp Val Pro Phe Cys Lys Lys Phe Ala Val Glu Pro
    370                 375                 380

Arg Ala Pro Glu Phe Tyr Phe Ser Gln Lys Ile Asp Tyr Leu Lys Asp
385                 390                 395                 400

Lys Val Gln Pro Thr Phe Val Lys Glu Arg Arg Ala Met Lys Arg Glu
                405                 410                 415

Tyr Glu Glu Phe Lys Val Arg Ile Asn Ala Leu Val Ala Lys Ala Gln
                420                 425                 430

Lys Lys Pro Glu Glu Gly Trp Val Met Gln Asp Gly Thr Pro Trp Pro
                435                 440                 445

Gly Asn Asn Thr Arg Asp His Pro Gly Met Ile Gln Val Tyr Leu Gly
450                 455                 460

Asn Gln Gly Ala Leu Asp Val Glu Gly His Glu Leu Pro Arg Leu Val
465                 470                 475                 480

Tyr Val Ser Arg Glu Lys Arg Pro Gly Tyr Asn His His Lys Lys Ala
                485                 490                 495

Gly Ala Met Asn Ala Leu Val Arg Val Ser Ala Val Leu Thr Asn Ala
                500                 505                 510

Pro Phe Ile Leu Asn Leu Asp Cys Asp His Tyr Val Asn Asn Ser Lys
                515                 520                 525

Ala Val Arg Glu Ala Met Cys Phe Leu Met Asp Pro Gln Leu Gly Lys
                530                 535                 540

Lys Leu Cys Tyr Val Gln Phe Pro Gln Arg Phe Asp Gly Ile Asp Arg
545                 550                 555                 560

His Asp Arg Tyr Ala Asn Arg Asn Val Val Phe Phe Asp Ile Asn Met
                565                 570                 575

Lys Gly Leu Asp Gly Ile Gln Gly Pro Val Tyr Val Gly Thr Gly Cys
                580                 585                 590

Val Phe Asn Arg Gln Ala Leu Tyr Gly Tyr Asp Pro Pro Arg Pro Glu
                595                 600                 605

Lys Arg Pro Lys Met Thr Cys Asp Cys Trp Pro Ser Trp Cys Cys Cys
                610                 615                 620
```

-continued

```
Cys Cys Cys Phe Gly Gly Gly Lys Arg Gly Lys Ala Arg Lys Asp Lys
625                 630                 635                 640

Lys Gly Asp Gly Gly Glu Glu Pro Arg Gly Leu Leu Gly Phe Tyr
            645                 650                 655

Arg Lys Arg Ser Lys Lys Asp Lys Leu Gly Gly Ser Val Ala Gly
            660                 665                 670

Ser Lys Lys Gly Gly Gly Leu Tyr Lys His Gln Arg Ala Phe Glu
            675                 680                 685

Leu Glu Glu Ile Glu Glu Gly Leu Gly Tyr Asp Glu Leu Glu Arg
    690                 695                 700

Ser Ser Leu Met Ser Gln Lys Ser Phe Glu Lys Arg Phe Gly Gln Ser
705                 710                 715                 720

Pro Val Phe Ile Ala Ser Thr Leu Val Glu Asp Gly Gly Leu Pro Gln
                725                 730                 735

Gly Ala Ala Ala Asp Pro Ala Ala Leu Ile Lys Glu Ala Ile His Val
                740                 745                 750

Ile Ser Cys Gly Tyr Glu Glu Lys Thr Glu Trp Gly Lys Glu Ile Gly
                755                 760                 765

Trp Ile Tyr Gly Ser Val Thr Glu Asp Ile Leu Thr Gly Phe Lys Met
770                 775                 780

His Cys Arg Gly Trp Lys Ser Val Tyr Cys Thr Pro Thr Arg Pro Ala
785                 790                 795                 800

Phe Lys Gly Ser Ala Pro Ile Asn Leu Ser Asp Arg Leu His Gln Val
                805                 810                 815

Leu Arg Trp Ala Leu Gly Ser Val Glu Ile Phe Met Ser Arg His Cys
            820                 825                 830

Pro Leu Arg Tyr Ala Tyr Gly Gly Arg Leu Lys Trp Leu Glu Arg Phe
            835                 840                 845

Ala Tyr Thr Asn Thr Ile Val Tyr Pro Phe Thr Ser Ile Pro Leu Leu
850                 855                 860

Ala Tyr Cys Thr Ile Pro Ala Val Cys Leu Leu Thr Gly Lys Phe Ile
865                 870                 875                 880

Ile Pro Thr Leu Asn Asn Leu Ala Ser Ile Trp Phe Ile Ala Leu Phe
                885                 890                 895

Leu Ser Ile Ile Ala Thr Ser Val Leu Glu Leu Arg Trp Ser Gly Val
            900                 905                 910

Ser Ile Glu Asp Trp Trp Arg Asn Glu Gln Phe Trp Val Ile Gly Gly
    915                 920                 925

Val Ser Ala His Leu Phe Ala Val Phe Gln Gly Phe Leu Lys Val Leu
930                 935                 940

Gly Gly Val Asp Thr Ser Phe Thr Val Thr Ser Lys Ala Ala Gly Asp
945                 950                 955                 960

Glu Ala Asp Ala Phe Gly Asp Leu Tyr Leu Phe Lys Trp Thr Thr Leu
            965                 970                 975

Leu Val Pro Pro Thr Thr Leu Ile Ile Ile Asn Met Val Gly Ile Val
            980                 985                 990

Ala Gly Val Ser Asp Ala Val Asn Asn Gly Tyr Gly Ser Trp Gly Pro
            995                 1000                1005

Leu Phe Gly Lys Leu Phe Phe Ser Phe Trp Val Ile Val His Leu
    1010                1015                1020

Tyr Pro Phe Leu Lys Gly Leu Met Gly Arg Gln Asn Arg Thr Pro
    1025                1030                1035
```

```
        Thr Ile Val Val Leu Trp Ser  Ile Leu Leu Ala Ser  Ile Phe Ser
            1040                1045                1050

Leu Val Trp Val Arg Ile Asp  Pro Phe Ile Pro Lys  Ala Lys Gly
            1055                1060                1065

Pro Ile Leu Lys Pro Cys Gly  Val Glu Cys
            1070                1075

<210> SEQ ID NO 39
<211> LENGTH: 3231
<212> TYPE: DNA
<213> ORGANISM: Zea mays

<400> SEQUENCE: 39
ccacgcgtcc gggaggggcc atgatggagt cggcggcggc ccagtcctgc gcggcgtgcg      60
gggacgacgc gcgcgctgcc tgccgcgcgt gcagctacgc gctctgcagg gcgtgcctcg     120
acgaggacgc cgccgagggc cgcaccacat gcgcgcgctg cggaggggac tacgccgcta     180
tcaacccagc gcgcgccagc gagggaaccg aggcggagga ggaggtggtg gagaaccacc     240
acaccgccgg tggcctgcgt gagagggtca ccatgggcag ccacctcaat gatcgccagg     300
atgaagtaag ccacgccagg accatgagca gcttgtcggg aattggtagt gaattgaatg     360
atgaatctgg taagcccatc tggaagaaca gggtggagag ttggaaggaa aagaagaatg     420
agaagaaagc ctcggccaaa aagactgcag ctaaagcaca gcctccgcct gtcgaagaac     480
agatcatgga tgaaaaagac ttgacagatg catatgagcc actctcccgg gtcatcccaa     540
tatcaaagaa caagctcaca ccttacagag cagtgatcat tatgcggtta attgttcttg     600
ggctcttctt tcactaccgt atcaccaatc ctgttaacag tgcctttggt ctctggatga     660
catcagttat atgtgagatc tggtttggtt tctcctggat attggatcaa ttcccgaagt     720
ggtatcctat caatcgtgag acttatgttg ataggctgat tgcacgatat ggagatggtg     780
aagaatctgg gttagcacct gtagatttct ttgtcagtac agtggatcca ttgaaagagc     840
ctccactaat cactgcaaac actgtgctgt ctattcttgc tgtggactat cccgttgaga     900
agatctcatg ctatgtatct gatgatggtt ctgctatgct cacatttgaa tcgctcgcag     960
agactgcaga atatgctaga agtgggtgc cgttttgcaa gaagtacgcc attgagccac    1020
gagctcctga gttctacttc tcacagaaaa ttgactactt gaaggacaag atacacccat    1080
cttttgtcaa ggagcgtagg gctatgaaga gagactatga agagtacaag gtgaggataa    1140
atgctttggt tgccaaggct caaaagacac ctgatgaagg ctggatcatg caagacggta    1200
caccatggcc tgggaacaat cctcgtgacc accctggcat gatccaggtt tcctgggtg     1260 agactggtgc acgggacttt gatggaaatg aacttcctcg gttagtgtat gtgtcaagag    1320
agaaaagacc aggctaccaa caccacaaga aggcagggc tatgaatgct ctggtccgag    1380
tgtctgctgt tctgacaaat gccccttaca ttcttaatct tgattgtgat cactatgtta    1440
acaacagcaa agctgttcgt gaagcaatgt gcttcatgat ggaccctact gttggcagag    1500
atgtctgcta tgtacaattc ccccagaggt tcgatggcat tgatcgcagt gatcgatatg    1560
ccaataggaa cgttgtgttc tttgatgtta atatgaaagg acttgatggc ctccaaggcc    1620
cagtttatgt gggaactggt tgttgtttca taggcaagc actttatggt tatgggcctc    1680
catctctgcc cgcacttcca aagtcttcga tttgttcctg gtgttgctgc tgctgtccca    1740
agaaaaaggt tgaaagaagt gagagggaaa tcaacagaga ctctcggcga gaagacctcg    1800
agtctgccat tttttaacctt cgcgaaattg acaactacga tgagtacgag aggtccatgc    1860
```

-continued

```
tcatctctca gatgagcttc gagaagtctt ttgggctgtc ctcggtcttt attgaatcga    1920
cccttatgga gaatgggggc gtccctgaat ctgcaaaccc atctacccta attaaagaag    1980
ccattcatgt cattagctgt ggatatgaag agaaaactga atggggaaaa gagattggct    2040
ggatctatgg ttcagttaca gaggatattc tgactgggtt aagatgcac tgccgtggct     2100
ggagatccat ctactgcatg ccggtgagac ctgcattcaa gggatcagcc ccaatcaatc    2160
tttccgatcg tcttcaccaa gttctccggt gggctcttgt ttctgtcgag atcttcttca    2220
gtcggcactg cccgctgtgg tacggttacg gtggcggccg tctgaaatgg ctccagaggc    2280
tctcctacat caacaccatc gtgtacccgt tcacttctct tcctctcgtt gcctactgtt    2340
gcctgcctgc catttgcctg ctcacaggaa agttcattat acctacgctg tccaacgctg    2400
caacgatatg gtttcttggc ctcttcatgt ccatcatcgt gacgagcgtg ttggagctgc    2460
ggtggagtgg catcgggatc gaggactggt ggcgcaacga gcagttctgg gtcatcggag    2520
gcgtgtccgc gcacctgttc gccgtgttcc agggtatcct caagatgatt gccgggctgg    2580
acaccaactt cacggtcacg gcaaaggcca cggacgacac tgagttcggg gagctgtacc    2640
tgttcaagtg gacgacggtg ctgatcccgc ccacaagcat cctggtgctg aacctggtgg    2700
gcgtggtggc tgggttctcg gccgcgctca acagcggcta cgagtcctgg ggcccgctct    2760
tcggtaaggt gttcttcgcc atgtgggtga tcatgcacct gtaccgttc ctcaagggtc     2820
tcatgggccg ccagaaccgc acgccgacca tcgtggtgct ctggtccgtc ctcctcgcct    2880
ccgtcttctc cctcctgtgg gtcaagatcg acccattcgt tggaggaacc gagaccgtca    2940
acaccaacaa ctgcaacaca catctgctga ttcaccatcg gtcagctgct gtcgtgccgc    3000
ggcggacgtg tttctggtgt tgcaaacgtg ggttgcctgc ctgatgcggg tctcctctgt    3060
ctatctcgca tctgggcttt tgccccagga tctgaagcgg gtggtgtagg ttagctttat    3120
tttgcgtcca agtgttgatt gatgttgtct gtgttatgaa aagttttggt ggtgaaacct    3180
gaaatgttaa aattcggctc aattgtgaga aaaaaaaaaa aaaaaaaaa a              3231
```

<210> SEQ ID NO 40
<211> LENGTH: 1007
<212> TYPE: PRT
<213> ORGANISM: Zea mays

<400> SEQUENCE: 40

```
Met Met Glu Ser Ala Ala Gln Ser Cys Ala Ala Cys Gly Asp Asp
1               5                   10                  15

Ala Arg Ala Ala Cys Arg Ala Cys Ser Tyr Ala Leu Cys Arg Ala Cys
                20                  25                  30

Leu Asp Glu Asp Ala Ala Glu Gly Arg Thr Thr Cys Ala Arg Cys Gly
            35                  40                  45

Gly Asp Tyr Ala Ala Ile Asn Pro Ala Arg Ala Ser Glu Gly Thr Glu
        50                  55                  60

Ala Glu Glu Glu Val Val Glu Asn His His Thr Ala Gly Gly Leu Arg
    65                  70                  75                  80

Glu Arg Val Thr Met Gly Ser His Leu Asn Asp Arg Gln Asp Glu Val
                85                  90                  95

Ser His Ala Arg Thr Met Ser Ser Leu Ser Gly Ile Gly Ser Glu Leu
                100                 105                 110

Asn Asp Glu Ser Gly Lys Pro Ile Trp Lys Asn Arg Val Glu Ser Trp
            115                 120                 125

Lys Glu Lys Lys Asn Glu Lys Lys Ala Ser Ala Lys Lys Thr Ala Ala
```

-continued

```
            130                 135                 140
Lys Ala Gln Pro Pro Val Glu Glu Gln Ile Met Asp Glu Lys Asp
145                 150                 155                 160

Leu Thr Asp Ala Tyr Glu Pro Leu Ser Arg Val Ile Pro Ile Ser Lys
                165                 170                 175

Asn Lys Leu Thr Pro Tyr Arg Ala Val Ile Ile Met Arg Leu Ile Val
                180                 185                 190

Leu Gly Leu Phe Phe His Tyr Arg Ile Thr Asn Pro Val Asn Ser Ala
                195                 200                 205

Phe Gly Leu Trp Met Thr Ser Val Ile Cys Glu Ile Trp Phe Gly Phe
210                 215                 220

Ser Trp Ile Leu Asp Gln Phe Pro Lys Trp Tyr Pro Ile Asn Arg Glu
225                 230                 235                 240

Thr Tyr Val Asp Arg Leu Ile Ala Arg Tyr Gly Asp Gly Glu Glu Ser
                245                 250                 255

Gly Leu Ala Pro Val Asp Phe Phe Val Ser Thr Val Asp Pro Leu Lys
                260                 265                 270

Glu Pro Pro Leu Ile Thr Ala Asn Thr Val Leu Ser Ile Leu Ala Val
                275                 280                 285

Asp Tyr Pro Val Glu Lys Ile Ser Cys Tyr Val Ser Asp Asp Gly Ser
290                 295                 300

Ala Met Leu Thr Phe Glu Ser Leu Ala Glu Thr Ala Glu Tyr Ala Arg
305                 310                 315                 320

Lys Trp Val Pro Phe Cys Lys Lys Tyr Ala Ile Glu Pro Arg Ala Pro
                325                 330                 335

Glu Phe Tyr Phe Ser Gln Lys Ile Asp Tyr Leu Lys Asp Lys Ile His
                340                 345                 350

Pro Ser Phe Val Lys Glu Arg Arg Ala Met Lys Arg Asp Tyr Glu Glu
                355                 360                 365

Tyr Lys Val Arg Ile Asn Ala Leu Val Ala Lys Ala Gln Lys Thr Pro
                370                 375                 380

Asp Glu Gly Trp Ile Met Gln Asp Gly Thr Pro Trp Pro Gly Asn Asn
385                 390                 395                 400

Pro Arg Asp His Pro Gly Met Ile Gln Val Phe Leu Gly Glu Thr Gly
                405                 410                 415

Ala Arg Asp Phe Asp Gly Asn Glu Leu Pro Arg Leu Val Tyr Val Ser
                420                 425                 430

Arg Glu Lys Arg Pro Gly Tyr Gln His His Lys Lys Ala Gly Ala Met
                435                 440                 445

Asn Ala Leu Val Arg Val Ser Ala Val Leu Thr Asn Ala Pro Tyr Ile
450                 455                 460

Leu Asn Leu Asp Cys Asp His Tyr Val Asn Asn Ser Lys Ala Val Arg
465                 470                 475                 480

Glu Ala Met Cys Phe Met Met Asp Pro Thr Val Gly Arg Asp Val Cys
                485                 490                 495

Tyr Val Gln Phe Pro Gln Arg Phe Asp Gly Ile Asp Arg Ser Asp Arg
                500                 505                 510

Tyr Ala Asn Arg Asn Val Val Phe Phe Asp Val Asn Met Lys Gly Leu
                515                 520                 525

Asp Gly Leu Gln Gly Pro Val Tyr Val Gly Thr Gly Cys Cys Phe Asn
                530                 535                 540

Arg Gln Ala Leu Tyr Gly Tyr Gly Pro Pro Ser Leu Pro Ala Leu Pro
545                 550                 555                 560
```

-continued

```
Lys Ser Ser Ile Cys Ser Trp Cys Cys Cys Cys Pro Lys Lys Lys
            565                 570                 575

Val Glu Arg Ser Glu Arg Glu Ile Asn Arg Asp Ser Arg Arg Glu Asp
            580                 585                 590

Leu Glu Ser Ala Ile Phe Asn Leu Arg Glu Ile Asp Asn Tyr Asp Glu
            595                 600                 605

Tyr Glu Arg Ser Met Leu Ile Ser Gln Met Ser Phe Glu Lys Ser Phe
        610                 615                 620

Gly Leu Ser Ser Val Phe Ile Glu Ser Thr Leu Met Glu Asn Gly Gly
625                 630                 635                 640

Val Pro Glu Ser Ala Asn Pro Ser Thr Leu Ile Lys Glu Ala Ile His
                645                 650                 655

Val Ile Ser Cys Gly Tyr Glu Glu Lys Thr Glu Trp Gly Lys Glu Ile
                660                 665                 670

Gly Trp Ile Tyr Gly Ser Val Thr Glu Asp Ile Leu Thr Gly Phe Lys
            675                 680                 685

Met His Cys Arg Gly Trp Arg Ser Ile Tyr Cys Met Pro Val Arg Pro
        690                 695                 700

Ala Phe Lys Gly Ser Ala Pro Ile Asn Leu Ser Asp Arg Leu His Gln
705                 710                 715                 720

Val Leu Arg Trp Ala Leu Val Ser Val Glu Ile Phe Phe Ser Arg His
                725                 730                 735

Cys Pro Leu Trp Tyr Gly Tyr Gly Gly Gly Arg Leu Lys Trp Leu Gln
                740                 745                 750

Arg Leu Ser Tyr Ile Asn Thr Ile Val Tyr Pro Phe Thr Ser Leu Pro
            755                 760                 765

Leu Val Ala Tyr Cys Cys Leu Pro Ala Ile Cys Leu Leu Thr Gly Lys
        770                 775                 780

Phe Ile Ile Pro Thr Leu Ser Asn Ala Ala Thr Ile Trp Phe Leu Gly
785                 790                 795                 800

Leu Phe Met Ser Ile Ile Val Thr Ser Val Leu Glu Leu Arg Trp Ser
                805                 810                 815

Gly Ile Gly Ile Glu Asp Trp Trp Arg Asn Glu Gln Phe Trp Val Ile
            820                 825                 830

Gly Gly Val Ser Ala His Leu Phe Ala Val Phe Gln Gly Ile Leu Lys
        835                 840                 845

Met Ile Ala Gly Leu Asp Thr Asn Phe Thr Val Thr Ala Lys Ala Thr
850                 855                 860

Asp Asp Thr Glu Phe Gly Glu Leu Tyr Leu Phe Lys Trp Thr Thr Val
865                 870                 875                 880

Leu Ile Pro Pro Thr Ser Ile Leu Val Leu Asn Leu Val Gly Val Val
                885                 890                 895

Ala Gly Phe Ser Ala Ala Leu Asn Ser Gly Tyr Glu Ser Trp Gly Pro
            900                 905                 910

Leu Phe Gly Lys Val Phe Phe Ala Met Trp Val Ile Met His Leu Tyr
        915                 920                 925

Pro Phe Leu Lys Gly Leu Met Gly Arg Gln Asn Arg Thr Pro Thr Ile
        930                 935                 940

Val Val Leu Trp Ser Val Leu Leu Ala Ser Val Phe Ser Leu Leu Trp
945                 950                 955                 960

Val Lys Ile Asp Pro Phe Val Gly Gly Thr Glu Thr Val Asn Thr Asn
                965                 970                 975
```

```
    Asn Cys Asn Thr His Leu Leu Ile His His Arg Ser Ala Ala Val Val
                    980                 985                 990

Pro Arg Arg Thr Cys Phe Trp Cys Cys Lys Arg Gly Leu Pro Ala
                995                 1000                1005

<210> SEQ ID NO 41
<211> LENGTH: 3028
<212> TYPE: DNA
<213> ORGANISM: Zea mays

<400> SEQUENCE: 41
cacgagttca acatcgacga cgagaatcag cagaggcagc tggagggcaa catgcagaac     60
agccagatca ccgaggcgat gctgcacggc aggatgagct acgggagggg ccccgacgac    120
ggcgacggca acaacacccc gcagatcccg cccatcatca ccggctcccg ctccgtgccg    180
gtgagcggtg agtttccgat taccaacggg tatggccacg gcgaggtctc gtcttccctg    240
cacaagcgca tccatccgta ccctgtgtct gagccaggga gtgccaagtg ggacgagaag    300
aaagaagtga gctggaagga gaggatggac gactggaagt ccaagcaggg catcctcggc    360
ggcggcgccg atcccgaaga catggacgcc gacgtggcac tgaacgacga ggcgaggcag    420
ccgctgtcga ggaaggtgtc gatcgcgtcg agcaaggtga acccgtaccg gatggtgatc    480
gtggtgcgtc tcgttgtgct cgccttcttc ctccggtacc gtatcctgca ccccgtcccg    540
gacgccatcg ggctgtggct cgtctccatc atctgcgaga tctggttcgc catctcctgg    600
atcctcgacc agttccccaa gtggttcccc atcgaccgcg agacgtacct cgaccgcctc    660
tccctcaggt acgagaggga aggggagccg tcgctgctgt cggcggtgga cctgttcgtg    720
agcacggtgg acccgctcaa ggagccgccg ctggtgaccg ccaacaccgt gctctccatc    780
ctcgccgtag actaccccgt ggacaaggtc tcctgctacg tctccgacga cggcgcgtcg    840
atgctgacgt tcgagtcgct gtcggagacg gccgagttcg cgcgcaagtg ggtgcccttc    900
tgcaagaagt tcggcatcga gccccgcgcc ccggagttct acttctcgct caaggtcgac    960
tacctcaagg acaaggtgca gcccaccttc gtgcaggagc gccgcgccat gaagagagag   1020
tatgaggagt tcaaggtccg gatcaacgcg ctggtggcca aggccatgaa ggtgccggca   1080 gagggggtgga tcatgaagga cggcacgccg tggcccggga caacacccg cgaccacccc   1140 ggcatgatcc aggtgttcct gggccacagc ggcgccacg acaccgaggg caacgagctg   1200
ccccgcctcg tgtacgtctc ccgtgagaag cgcccgggat ccagcacca caagaaggcc   1260 ggcgccatga acgctctgat tcgcgtctcc gccgtgctga ccaacgcgcc attcatgctc   1320
aacttggact gtgatcacta catcaacaac agcaaggcca tccgggaggc catgtgcttc   1380
ctcatggacc ctcaggtcgg ccggaaggtc tgctacgttc agttcccgca gaggttcgac   1440
ggcatcgacg tgcacgaccg atacgctaac aggaacaccg tcttcttcga catcaacatg   1500
aaggggctgg acggcatcca aggcccggtg tacgtcggga cagggtgcgt gttccggcgc   1560
caggcgctct acggctacaa ccctcccaag ggacccaaga gcccaagat ggtgacctgc   1620 gactgctgcc cgtgcttcgg ccgcaagaag cggaaacacg ccaaggacgg gctgccggag   1680
ggcaccgctg atatgggagt agatagcgac aaggagatgc tcatgtccca catgaacttc   1740
gagaagcggc tcgggcagtc cgcggcgttc gtcacgtcga cgctgatgga ggaaggcggc   1800
gtccctcctt cgtcgagccc cgccgcgctc tcaaggagg ccatccatgt catcagctgc   1860
ggctacgagg acaagaccga ctgggggctg agctggggt ggatctacgg gtcgatcacg   1920
gaggacatcc tgacgggggtt caagatgcac tgccgcgggt ggcgctccgt gtactgcatg   1980
```

-continued

```
ccgaagcggg cggcgttcaa ggggtcggcg ccgatcaatc tatcggaccg tctcaaccag      2040
gtgctccggt gggcgctggg gtccgtcgag atcttcttca gccggcacag ccccctgctg      2100
tacggctaca agaacggcaa cctcaagtgg ctggagcgct cgcctacat caacaccacc       2160 atctacccct tcacctcgct cccgctgctc gcctactgca ccctcccgc cgtctgcctc       2220 ctcaccggca agttcatcat gccgtcgatt agcacgttcg ccagcctctt cttcatcgcc      2280
ctcttcatgt ccatcttcgc gacgggcatc ctggagatgc ggtggagcgg ggtgagcatc      2340
gaggagtggt ggaggaacga gcagttctgg gtcatcggcg gcgtgtccgc gcatctcttc      2400
gccgtcgtgc agggcctgct caaggtcctc gccgggatcg acaccaactt caccgtcacc      2460
tccaaggcca ccgcgacga ggacgacgag ttcgccgagc tctacgcctt caagtggacc       2520
acgctcctca tcccgcccac cacgctgctc atcattaacg tcatcggcgt cgtggccggc      2580
atctccgacg ccatcaacaa cgggtaccag tcctgggggc ccctcttcgg caagctcttc      2640
ttcgccttct gggtcatcgt ccacctctac ccgttcctca aggggctcat ggggcgccag      2700
aacaggacgc ccaccgttgt tgtcatctgg tccattctgc tggcctccat cttctccctg      2760
ctctgggtca ggatcgaccc tttcatcgtc aggaccaagg gcccggacgt caggcagtgt      2820
ggcatcaatt gctgagctgt ttattaaggt tcaaaattct ggagcttgtg cataggga ga    2880 aaaaaacaat ttagaaattt tgtaaggttg ttgtgtctgt aatgttatgg tacccagaat     2940
tgtcggacga ggaattgaac aaaggacaag gtttgattgt taaatggcaa aaaaaaaaa     3000 aaaaaaaaaa aaaaaaaaa aaaaaaaa                                        3028
```

<210> SEQ ID NO 42
<211> LENGTH: 927
<212> TYPE: PRT
<213> ORGANISM: Zea mays

<400> SEQUENCE: 42

```
Met Gln Asn Ser Gln Ile Thr Glu Ala Met Leu His Gly Arg Met Ser
1               5                   10                  15

Tyr Gly Arg Gly Pro Asp Asp Gly Asp Gly Asn Asn Thr Pro Gln Ile
            20                  25                  30

Pro Pro Ile Ile Thr Gly Ser Arg Ser Val Pro Val Ser Gly Glu Phe
        35                  40                  45

Pro Ile Thr Asn Gly Tyr Gly His Gly Glu Val Ser Ser Ser Leu His
    50                  55                  60

Lys Arg Ile His Pro Tyr Pro Val Ser Glu Pro Gly Ser Ala Lys Trp
65                  70                  75                  80

Asp Glu Lys Lys Glu Val Ser Trp Lys Glu Arg Met Asp Asp Trp Lys
                85                  90                  95

Ser Lys Gln Gly Ile Leu Gly Gly Ala Asp Pro Glu Asp Met Asp
            100                 105                 110

Ala Asp Val Ala Leu Asn Asp Glu Ala Arg Gln Pro Leu Ser Arg Lys
        115                 120                 125

Val Ser Ile Ala Ser Ser Lys Val Asn Pro Tyr Arg Met Val Ile Val
    130                 135                 140

Val Arg Leu Val Val Leu Ala Phe Phe Leu Arg Tyr Arg Ile Leu His
145                 150                 155                 160

Pro Val Pro Asp Ala Ile Gly Leu Trp Leu Val Ser Ile Ile Cys Glu
                165                 170                 175

Ile Trp Phe Ala Ile Ser Trp Ile Leu Asp Gln Phe Pro Lys Trp Phe
```

-continued

```
            180                 185                 190
Pro Ile Asp Arg Glu Thr Tyr Leu Asp Arg Leu Ser Leu Arg Tyr Glu
            195                 200                 205
Arg Glu Gly Glu Pro Ser Leu Leu Ser Ala Val Asp Leu Phe Val Ser
            210                 215                 220
Thr Val Asp Pro Leu Lys Glu Pro Leu Val Thr Ala Asn Thr Val
225                 230                 235                 240
Leu Ser Ile Leu Ala Val Asp Tyr Pro Val Asp Lys Val Ser Cys Tyr
                245                 250                 255
Val Ser Asp Asp Gly Ala Ser Met Leu Thr Phe Glu Ser Leu Ser Glu
            260                 265                 270
Thr Ala Glu Phe Ala Arg Lys Trp Val Pro Phe Cys Lys Lys Phe Gly
            275                 280                 285
Ile Glu Pro Arg Ala Pro Glu Phe Tyr Phe Ser Leu Lys Val Asp Tyr
            290                 295                 300
Leu Lys Asp Lys Val Gln Pro Thr Phe Val Gln Glu Arg Arg Ala Met
305                 310                 315                 320
Lys Arg Glu Tyr Glu Glu Phe Lys Val Arg Ile Asn Ala Leu Val Ala
                325                 330                 335
Lys Ala Met Lys Val Pro Ala Glu Gly Trp Ile Met Lys Asp Gly Thr
            340                 345                 350
Pro Trp Pro Gly Asn Asn Thr Arg Asp His Pro Gly Met Ile Gln Val
            355                 360                 365
Phe Leu Gly His Ser Gly Gly His Asp Thr Glu Gly Asn Glu Leu Pro
            370                 375                 380
Arg Leu Val Tyr Val Ser Arg Glu Lys Arg Pro Gly Phe Gln His His
385                 390                 395                 400
Lys Lys Ala Gly Ala Met Asn Ala Leu Ile Arg Val Ser Ala Val Leu
                405                 410                 415
Thr Asn Ala Pro Phe Met Leu Asn Leu Asp Cys Asp His Tyr Ile Asn
            420                 425                 430
Asn Ser Lys Ala Ile Arg Glu Ala Met Cys Phe Leu Met Asp Pro Gln
            435                 440                 445
Val Gly Arg Lys Val Cys Tyr Val Gln Phe Pro Gln Arg Phe Asp Gly
            450                 455                 460
Ile Asp Val His Asp Arg Tyr Ala Asn Arg Asn Thr Val Phe Phe Asp
465                 470                 475                 480
Ile Asn Met Lys Gly Leu Asp Gly Ile Gln Gly Pro Val Tyr Val Gly
                485                 490                 495
Thr Gly Cys Val Phe Arg Arg Gln Ala Leu Tyr Gly Tyr Asn Pro Pro
                500                 505                 510
Lys Gly Pro Lys Arg Pro Lys Met Val Thr Cys Asp Cys Cys Pro Cys
            515                 520                 525
Phe Gly Arg Lys Lys Arg His Ala Lys Asp Gly Leu Pro Glu Gly
            530                 535                 540
Thr Ala Asp Met Gly Val Asp Ser Asp Lys Glu Met Leu Met Ser His
545                 550                 555                 560
Met Asn Phe Glu Lys Arg Phe Gly Gln Ser Ala Ala Phe Val Thr Ser
                565                 570                 575
Thr Leu Met Glu Glu Gly Gly Val Pro Pro Ser Ser Pro Ala Ala
            580                 585                 590
Leu Leu Lys Glu Ala Ile His Val Ile Ser Cys Gly Tyr Glu Asp Lys
            595                 600                 605
```

```
Thr Asp Trp Gly Leu Glu Leu Gly Trp Ile Tyr Gly Ser Ile Thr Glu
    610                 615                 620

Asp Ile Leu Thr Gly Phe Lys Met His Cys Arg Gly Trp Arg Ser Val
625                 630                 635                 640

Tyr Cys Met Pro Lys Arg Ala Ala Phe Lys Gly Ser Ala Pro Ile Asn
                645                 650                 655

Leu Ser Asp Arg Leu Asn Gln Val Leu Arg Trp Ala Leu Gly Ser Val
                660                 665                 670

Glu Ile Phe Phe Ser Arg His Ser Pro Leu Leu Tyr Gly Tyr Lys Asn
                675                 680                 685

Gly Asn Leu Lys Trp Leu Glu Arg Phe Ala Tyr Ile Asn Thr Thr Ile
                690                 695                 700

Tyr Pro Phe Thr Ser Leu Pro Leu Leu Ala Tyr Cys Thr Leu Pro Ala
705                 710                 715                 720

Val Cys Leu Leu Thr Gly Lys Phe Ile Met Pro Ser Ile Ser Thr Phe
                725                 730                 735

Ala Ser Leu Phe Phe Ile Ala Leu Phe Met Ser Ile Phe Ala Thr Gly
                740                 745                 750

Ile Leu Glu Met Arg Trp Ser Gly Val Ser Ile Glu Glu Trp Trp Arg
                755                 760                 765

Asn Glu Gln Phe Trp Val Ile Gly Gly Val Ser Ala His Leu Phe Ala
                770                 775                 780

Val Val Gln Gly Leu Leu Lys Val Leu Ala Gly Ile Asp Thr Asn Phe
785                 790                 795                 800

Thr Val Thr Ser Lys Ala Thr Gly Asp Glu Asp Glu Phe Ala Glu
                805                 810                 815

Leu Tyr Ala Phe Lys Trp Thr Thr Leu Leu Ile Pro Pro Thr Thr Leu
                820                 825                 830

Leu Ile Ile Asn Val Ile Gly Val Val Ala Gly Ile Ser Asp Ala Ile
                835                 840                 845

Asn Asn Gly Tyr Gln Ser Trp Gly Pro Leu Phe Gly Lys Leu Phe Phe
                850                 855                 860

Ala Phe Trp Val Ile Val His Leu Tyr Pro Phe Leu Lys Gly Leu Met
865                 870                 875                 880

Gly Arg Gln Asn Arg Thr Pro Thr Val Val Ile Trp Ser Ile Leu
                885                 890                 895

Leu Ala Ser Ile Phe Ser Leu Leu Trp Val Arg Ile Asp Pro Phe Ile
                900                 905                 910

Val Arg Thr Lys Gly Pro Asp Val Arg Gln Cys Gly Ile Asn Cys
                915                 920                 925
```